(12) United States Patent
Hunter

(10) Patent No.: US 6,689,803 B2
(45) Date of Patent: Feb. 10, 2004

(54) COMPOSITIONS AND METHODS FOR TREATING SURGICAL ADHESIONS

(75) Inventor: William L. Hunter, Vancouver (CA)

(73) Assignee: Angiotech Pharmaceuticals, Inc., Vancouver (CA)

(*) Notice: Subject to any disclaimer, the term of this patent is extended or adjusted under 35 U.S.C. 154(b) by 0 days.

(21) Appl. No.: 10/067,467

(22) Filed: Feb. 5, 2002

(65) Prior Publication Data

US 2002/0183380 A1 Dec. 5, 2002

Related U.S. Application Data

(63) Continuation of application No. 09/368,463, filed on Aug. 4, 1999, now abandoned, which is a division of application No. 09/088,546, filed on Jun. 1, 1998, now Pat. No. 6,495,579, which is a continuation-in-part of application No. 08/980,549, filed on Dec. 1, 1997, now Pat. No. 6,515,016.

(60) Provisional application No. 60/032,215, filed on Dec. 2, 1996, and provisional application No. 60/063,087, filed on Oct. 24, 1997.

(51) Int. Cl.$^7$ ............................................. A61K 31/425
(52) U.S. Cl. ....................................................... 514/365
(58) Field of Search .......................................... 514/365

(56) References Cited

U.S. PATENT DOCUMENTS

| | | | |
|---|---|---|---|
| 4,391,797 A | 7/1983 | Folkman et al. | 424/19 |
| 4,753,965 A | 6/1988 | Stemerick et al. | 514/647 |
| 4,863,968 A | 9/1989 | Edwards et al. | 514/646 |
| 4,904,697 A | 2/1990 | Sunkara et al. | 514/629 |
| 5,092,885 A | 3/1992 | Yamada et al. | 623/11 |
| 5,330,756 A | 7/1994 | Steuart et al. | 424/405 |
| 5,356,927 A | 10/1994 | Taraschi et al. | 514/449 |
| 5,411,947 A | 5/1995 | Hostetler et al. | 514/43 |
| 5,443,458 A | 8/1995 | Eury | 604/89.1 |
| 5,466,455 A | 11/1995 | Huffstutler, Jr. et al. | 424/401 |
| 5,476,954 A | 12/1995 | Bourzat et al. | 549/510 |
| 5,484,809 A | 1/1996 | Hostetler et al. | 514/449 |
| 5,496,846 A | 3/1996 | Wilson et al. | 514/449 |
| 5,532,388 A | 7/1996 | Bouchard et al. | 549/510 |
| 5,541,232 A | 7/1996 | Howell et al. | 514/731 |
| 5,550,261 A | 8/1996 | Bouchard et al. | 549/510 |
| 5,565,439 A | 10/1996 | Piazza et al. | 514/110 |
| 5,565,478 A | 10/1996 | Kohn et al. | 514/359 |
| 5,567,417 A | 10/1996 | Sasisekharan et al. | 424/94.5 |
| 5,571,917 A | 11/1996 | Bouchard et al. | 544/369 |
| 5,573,781 A | 11/1996 | Brown et al. | 424/484 |
| 5,576,345 A | 11/1996 | M.ang.nsson et al. | 514/449 |
| 5,576,450 A | 11/1996 | Bouchard et al. | 549/510 |
| 5,580,997 A | 12/1996 | Bouchard et al. | 549/510 |

(List continued on next page.)

FOREIGN PATENT DOCUMENTS

| | | |
|---|---|---|
| EP | 038567 A1 | 10/1981 |
| EP | 262681 A1 | 4/1988 |
| EP | 274846 B1 | 7/1988 |
| EP | 288794 A2 | 11/1988 |
| EP | 294905 B1 | 12/1988 |
| EP | 470246 B1 | 2/1992 |
| EP | 470569 A1 | 2/1992 |
| EP | 543653 A1 | 5/1993 |
| EP | 551182 A1 | 7/1993 |
| EP | 567816 A1 | 11/1993 |
| EP | 568310 A1 | 11/1993 |
| EP | 669916 B1 | 9/1995 |
| EP | 706376 B1 | 4/1996 |
| EP | 717041 A1 | 6/1996 |
| EP | 0747066 A2 * | 12/1996 |
| EP | 747385 A1 | 12/1996 |
| EP | 0 941 089 B1 | 5/2001 |
| JP | 61-063613 | 4/1986 |
| WO | WO 90/01969 | 3/1990 |
| WO | WO 91/07154 | 5/1991 |
| WO | WO 91/10424 | 7/1991 |
| WO | WO 91/11193 | 8/1991 |
| WO | WO 91/12779 | 9/1991 |
| WO | WO 92/00747 | 1/1992 |
| WO | WO 92/05200 | 4/1992 |
| WO | WO 92/12717 | 8/1992 |

(List continued on next page.)

OTHER PUBLICATIONS

Budavari et al. (eds.), *The Merck Index, 12th Edition*, Merck & Co., Whitehouse Station, NJ, 1996, only one page supplied, see Entry No. 7117 (Paclitaxel).*

Stearns et al., "Taxol Blocks Processes Essential for Prostate Tumor Cell (PC–3 ML) Invasion and Metastasis," *Cancer Research*, 52(13), 3776–3781 (Jul. 1, 1992).*

Schiff et al., "Taxol Stabilizes Microtubules in Mouse Fibroblast Cells," *Proc. National Academy of Sciences USA*, 77(3) 1561–1566 (Mar., 1980).*

Hunter et al., "Local Delivery of Chemotherapy: A Supplement to Existing Cancer Treatments—A Case for Surgical Pastes and Coated Stents," *Advanced Drug Delivery Reviews*, 26, 199–207 (1997).

Bollag et al., "Epothilones, a New Class of MicrotubuleStabilizing Agents with a Taxol–Like Mechanisms of Action," *Cancer Research*, 55(11), 2325–2333 (Jun. 1, 1995).

ter Haar et al., "Discodemolide, A Cytotoxic Marine Agent That Stabilizes Microtubules More Potently Than Taxol," *Biochemistry*, 35(1), 243–250 (Jan. 9, 1996).

Panda et al., "Suppression of Microtubule Dynamics by LY290181," *Journal of Biological Chemistry*, 272(12), 7681–7687 (Mar. 21, 1997).

(List continued on next page.)

Primary Examiner—James O. Wilson
Assistant Examiner—Lawrence E Crane
(74) Attorney, Agent, or Firm—Seed IP Law Group PLLC

(57) ABSTRACT

Methods and compositions for treating or preventing inflammatory diseases such as psoriasis or multiple sclerosis are provided, comprising the step of delivering to the site of inflammation an anti-microtubule agent, or analogue or derivative thereof.

16 Claims, 107 Drawing Sheets

U.S. PATENT DOCUMENTS

| | | | |
|---|---|---|---|
| 5,580,998 A | 12/1996 | Bouchard et al. | 549/510 |
| 5,583,153 A | 12/1996 | Brahn | 514/449 |
| 5,587,459 A | 12/1996 | Uckun | 530/391.1 |
| 5,587,493 A | 12/1996 | Bouchard et al. | 549/510 |
| 5,599,942 A | 2/1997 | Bouchard et al. | 548/215 |
| 5,606,083 A | 2/1997 | Bouchard et al. | 549/510 |
| 5,612,052 A * | 3/1997 | Shalaby | 424/426 |
| 5,614,587 A * | 3/1997 | Rhee et al. | 525/54.1 |
| 5,616,608 A | 4/1997 | Kinsella et al. | 514/449 |
| 5,620,971 A | 4/1997 | Armistead et al. | 514/212 |
| 5,621,001 A | 4/1997 | Canetta et al. | 514/449 |
| 5,626,862 A | 5/1997 | Brem et al. | 424/426 |
| 5,627,206 A | 5/1997 | Hupe et al. | 514/468 |
| 5,631,278 A | 5/1997 | Taraschi et al. | 514/449 |
| 5,635,531 A | 6/1997 | Chen | 514/471 |
| 5,641,803 A | 6/1997 | Carretta et al. | 514/449 |
| 5,651,986 A | 7/1997 | Brem et al. | 424/484 |
| 5,654,337 A | 8/1997 | Roentsch et al. | 514/570 |
| 5,654,449 A | 8/1997 | Bouchard et al. | 549/510 |
| 5,665,761 A | 9/1997 | Canetta et al. | 514/449 |
| 5,667,764 A | 9/1997 | Kopia et al. | 424/1.45 |
| 5,696,153 A | 12/1997 | Ainsworth et al. | 514/449 |
| 5,714,159 A * | 2/1998 | Shalaby | 424/426 |
| 5,716,981 A | 2/1998 | Hunter et al. | 514/449 |
| 5,733,925 A | 3/1998 | Kunz et al. | 514/449 |
| 5,770,609 A | 6/1998 | Grainger et al. | 514/319 |
| 5,773,464 A | 6/1998 | Walker et al. | 514/475 |
| 5,789,189 A | 8/1998 | Woo | 435/30 |
| 5,811,447 A | 9/1998 | Kunz et al. | 514/411 |
| 5,873,904 A | 2/1999 | Ragheb et al. | 623/1 |
| 5,882,881 A | 3/1999 | Woo | 435/30 |
| 5,886,026 A | 3/1999 | Hunter et al. | 514/449 |
| 5,916,913 A | 6/1999 | Joseph | 514/449 |
| 5,936,035 A * | 8/1999 | Rhee et al. | 525/54.1 |
| 5,958,741 A | 9/1999 | Stierle et al. | 435/123 |
| 5,972,992 A | 10/1999 | Carver et al. | 514/449 |
| 5,977,163 A | 11/1999 | Li et al. | 514/449 |
| 5,981,568 A | 11/1999 | Kunz et al. | 514/411 |
| 5,994,341 A | 11/1999 | Hunter et al. | 514/210 |
| 6,040,306 A | 3/2000 | Batts et al. | 514/236.8 |
| 6,074,659 A | 6/2000 | Kunz et al. | 424/423 |
| 6,096,331 A | 8/2000 | Desai et al. | 424/422 |
| 6,132,765 A | 10/2000 | DiCosmo et al. | 424/450 |
| 6,166,173 A | 12/2000 | Mao et al. | 528/398 |
| 6,322,797 B1 | 11/2001 | Mao et al. | 424/271 |
| 6,413,539 B1 * | 7/2002 | Shalaby | 424/426 |
| 6,465,427 B1 | 10/2002 | Blaschuk et al. | 514/9 |
| 6,495,579 B1 * | 12/2002 | Hunter | 514/365 |
| 6,515,016 B2 | 2/2003 | Hunter | 514/449 |
| 6,551,610 B2 * | 4/2003 | Shalaby et al. | 424/426 |

FOREIGN PATENT DOCUMENTS

| | | |
|---|---|---|
| WO | WO 92/15286 | 9/1992 |
| WO | WO 93/06792 | 4/1993 |
| WO | WO 93/11120 | 6/1993 |
| WO | WO 94/01425 | 1/1994 |
| WO | WO 94/07880 | 4/1994 |
| WO | WO 94/12158 | 6/1994 |
| WO | WO 94/12484 | 6/1994 |
| WO | WO 94/13654 | 6/1994 |
| WO | WO 94/21308 | 9/1994 |
| WO | WO 95/03036 | 2/1995 |
| WO | WO 95/03795 | 2/1995 |
| WO | WO 95/13270 | 5/1995 |
| WO | WO 95/13271 | 5/1995 |
| WO | WO 95/19769 | 7/1995 |
| WO | WO 95/21868 | 8/1995 |
| WO | WO 95/33736 | 12/1995 |
| WO | WO 95/35095 | 12/1995 |
| WO | WO 96/01259 | 1/1996 |
| WO | WO 96/03984 | 2/1996 |
| WO | WO 96/10912 | 4/1996 |
| WO | WO 96/13249 | 5/1996 |
| WO | WO 96/13494 | 5/1996 |
| WO | WO 96/30355 | 10/1996 |
| WO | WO 96/30356 | 10/1996 |
| WO | WO 96/31493 | 10/1996 |
| WO | WO 97/20842 | 6/1997 |
| WO | WO 97/42958 | 11/1997 |
| WO | WO 97/45105 | 12/1997 |
| WO | WO 98/13359 | 4/1998 |
| WO | WO 98/24427 | 6/1998 |
| WO | WO 99/21908 A1 * | 5/1999 |
| WO | WO 99/52889 | 10/1999 |
| WO | WO 00/07543 | 2/2000 |

OTHER PUBLICATIONS

Wood et al., "Inhibition of Mitosis and Microtubule Function Through Direct Tubulin Binding by a Novel Antiproliferative Naphthopyran LY290181," *Molecular Pharmacology*, 52(3), 437–444 (Sep., 1997).

Alberts et al., *The Molecular Biology of the Cell*, $2^{nd}$ edition revised and amended, in three volumes, vol. 1, Mir, Moscow, 1994, p. 445. (English Translation Attached).

Satoskar and Bandarkar, *Pharmacology and Pharmacotherapy*, vol. 1, Meditsina, Moscow, 1986, p 37. (English Translation Attached).

Belikov V.G., *Pharmaceutical Chemistry*, Part 1. General Pharmaceutical Chemistry, $2^{nd}$ Edition, Revised and Amended, vysshaya Shkola, Moscow, 1993, pp 43–47. (English Translation Attached).

Achiron et al., "Intravenous immunoglobulin treatment in multiple sclerosis," *Neurology 50*: 398–402, Feb. 1998.

Alberts et al., "Molecular Biology of the Cell," $2^{nd}$ Edition, Garland Publishing, New York, 1989, p. 653.

Bansil et al., "Multiple sclerosis: Immune mechanism and update on current therapies," *Ann. Neurol.* 37(S1): S87–S101, 1995.

Barrese et al., "Mechanism of Demyelination in DM20 Transgenic Mice Involves Increased Fatty Acylation," *Journal of Neuroscience Research* 53: 143–152, 1998.

Bartoli et al., "In vitro and in vivo antitumoral activity of free, and encapsulated taxol," *Journal of Microencapsulation* 7(2): 191–197, 1990.

Beranek, "Angiogenesis in Psoriasis," *Laboratory Investigation* 62(1): 131, 1990.

Cao et al., "Inhibition of Experimental Allergic Encephalomyelitis in Lewis Rats by Paclitaxel," *Annals of Neurology* 46(3): 470, Abstract No. 94, Sep. 1999.

Chandrasekhar et al., "Identification of a Novel Chemical Series that Blocks Interleukin–1–Stimulated Metalloprotease Activity in Chondrocytes," *Journal of Pharmacology and Experimental Therapeutics* 273(3): 1519–1528, 1995.

Chandrasekhar et al., "Identification of a Novel Chemical Series That Block Interleukin–1–Stimulated Metalloprotease Activity in Chondrocytes," *Journal of Pharmacology and Experimental Therapeutics* 273(3): 1519–1528, 1995.

Constable, "Biological And Therapeutic Aspects Of Proliferative Vitreoretinopathy," *Jpn. J. Ophthalmol.* 31: 513–520, 1987.

Coomber and Gotlieb, "In Vitro Endothelial Wound Repair. Interaction of Cell Migration and Proliferation," *Arteriosclerosis* 10(2): 215–222, 1990.

Cox et al., "Local Delivery of Heparin and Methotrexate Fails to Inhibit In Vivo Smooth Muscle Cell Proliferation," *Abstracts From the 64th Scientific Sessions, American Heart Assoc.*, Abstract No. 0284, 1991.

Currier et al., "Low Dose Oral Methotrexate Treatment of Multiple Sclerosis: A Pilot Study," *Journal of Neurology, Neurosurgery, and Psychiatry* 56: 1217–1218, 1993.

Detmar, "Molecular Regulation of Angiogenesis in the Skin," *The Journal of Investigative Dermatology*, pp. 207–208, 1996.

Detmar et al., "Overexpression of Vascular Permeability Factor/Vascular Endothelial Growth Factor and its Receptors in Psoriasis," *J. Exp. Med.* 180: 1141–1146, 1994.

EP 669916B1, Derwent WPI, Accession No. 1994–193767/199424, 1997.

EP 567816A1 A1, Derwent WPI, Accession No. 1993–346277–199344, 1993.

Gold et al., "Animal Models for Autoimmune Demyelinating Disorders of the Nervous System," *Molecular Medicine Today* 6: 88–91, 2000.

Goodkin et al., "Low–Dose (7.5 mg) Oral Methotrexate Reduces the Rate of Progression in Chronic Progressive Multiple Sclerosis," *Annals of Neurology* 37: 30–40, 1995.

Goodkin et al., "Low–Dose Oral Methotrexate in Chronic Progressive Multiple Sclerosis: Analysis of Serial MRIs," *Neurology* 47: 1153–1157, 1996.

Hermans et al., "Prevention of resenosis after percutaneous transluminal coronary angioplasty: The search for a "magic bullet"," *American Heart Journal* 122(No. 1, Pt. 1): 171–187, 1991.

Hirata et al., "Inhibition Of In Vitro Vascular Endothelial Cell Proliferation And In Vivo Neovascularization By Low-Dose Methotrexate," *Arthritis and Rheumatism* 32(9): 1065–1073, 1989.

Hui et al., "Inhibition of Activator Protein 1 Activity by Paclitaxel Supresses Interleukin–1–Induced Collagenase and Stromelysin Expression By Bovine Chondrocytes," *Arthritis & Rheumatism* 41(5): 869–876, 1998.

Jampel et al., "In Vitro Release of Hydrophobic Drugs From Polyanhydride Disks," *Ophthalmic Surgery* 33(11): 676–680, 1991.

Jeffes and Weinstein, "Methotrexate And Other Chemotherapeutic Agents Used To Treat Psoriasis," *Dermatologic Clinics* 13(4): 875–890, 1995.

Johnson et al., "Over–Expression of the DM–20 Myelin Proteolipid Causes Central Nervous System Demyelination in Transgenic Mice," *Journal of Neurochemistry* 64: 967–976, 1995.

Krupp, "Advances in the Treatment of Multiple Sclerosis," *WJM* 165(5): 320–321, 1996.

Kumar and West, "Psoriasis, Angiogenesis and Hyaluronic Acid," *Laboratory Investigation* 62(5): 664–665, 1990.

Lebwohl and Abel, "Topical Therapy For Psoriasis," *International Journal of Dermatology* 34(10): 673–684, 1995.

Lewis, "Therapeutic progress II: Treatment of psoriasis," *Journal of Clinical Pharmacy and Therapeutics* 19: 223–232, 1994.

Mastronardi et al., "Demyelination in a Transgenic Mouse: A Model for Multiple Sclerosis," *Journal of Neuroscience Research* 36: 315–324, 1993.

Mastronardi et al., "Modifications of Myelin Basic Protein in DM20 Transgenic Mice Are Similar to those in Myelin Basic Protein from Multiple Sclerosis," *J. Clin. Invest.* 97(2): 349–358, 1996.

Mastronardi et al., "Myelin Basic Protein in Experimental Allergic Encephalomyelitis Is No Affected at the Posttranslatinal Level: Implications for Demyelinating Disease," *Journal of Neuroscience Research* 44: 344–349, 1996.

Moscarello et al., "Paclitaxel Attenuates Demyelination in a Transgenic Spontaneously Demyelinating Model," *Annals of Neurology* 46(3): 469, Abstract No. 92, 1999.

Moses and Langer, "Inhibitors of Angiogenesis," *Bio/Technology* 9: 630–634, 1991.

Noseworthy and Miller, "Measurement of treatment efficacy and new trail results in multiple sclerosis," *Current Opinion in Neurology* 10: 201–210, 1997.

O'Connor et al., "A Phase Study of Micellar Paclitaxel in the Treatment of Secondary Progressive Multiple Sclerosis," *Annals of Neurology* 46(3): 470, Abstract No. 95, Sep. 1999.

O'Keefe et al., "Ineffectiveness of Colchicine for the Prevention of Restenosis After Coronary Angioplasty," *JACC* 19(7): 1597–1600, 1992.

PCT Written Opinion, PCT Patent Application No. PCT/CA97/00910, Aug. 14, 1998.

Pitt and Schindler, *Progress in Contraceptive Delivery Systems*, MTP Press, Lancaster, 1980, Chapter 2, "The design of controlled drug delivery systems based on biodegradable polymers," pp. 17–46.

Pritzker and Moscarello, "A Novel Microtubule Independent Effect of Paclitaxel: The Inhibition of Peptidylarginine Deiminase from Bovine Brain," *Biochemica et Biophysica Acta* 1388: 154–160, 1998.

Rompps Chemie–Lexicon, pp. 4129–4130, 2577, 1190, 1988.

Rote Liste, p. 85–088—85–092, 1995.

Rudick et al., "Management of Multiple Sclerosis," *The New England Journal of Medicine* 337(22): 1604–1611, 1997.

Schluep and Bogousslavsky, "Emerging treatments in multiple sclerosis: a clinical perspective," *Current Opinion in Neurology* 9: 187–198, 1996.

Seideman et al., "Psoriatic Arthritis Treated with Oral Colchicine," *Journal of Rheumatology* 14: 777–779, 1987.

Spuls et al., "A Systematic Review of Five Systemic Treatments for Severe Psoriasis," *British Journal of Dermatology* 137: 943–949, 1997.

Tang et al., "Regression Of Collagen–Induced Arthritis With Taxol, A Microtubule Stabilizer," *Arthritis Rheum.* 36(9): No. 42, 1993.

The Merck Index, Twelfth Edition, Merck, Whitehouse Station, New Jersey, 1996, pp. 1404, 1541, 1200.

Thompson and Noseworthy, "New treatments for multiple sclerosis: a clinical perspective," *Current Opinion in Neurology* 9: 187–198, 1996.

Van Oosten et al., "Choosing Drug Therapy for Multiple Sclerosis," *Drugs* 56(4): 555–569, 1998.

Verdoorn et al., "Cellular Migration, Proliferation, and Contraction. An In Vitro Approach to a Clinical Problem–Proliferative Vitreoretinopathy," *Arch. Ophthalmol.* 104: 1216–1219, 1986.

Wang et al., "Preparation and Characterization of Poly(lactic–co–glycolic acid) Microspheres for Targeted Delivery of a Novel Anticancer Agent, Taxol," *Chem. Pharm. Bull.* 44(10): 1935–1940, 1996.

Waubant et al., "Pathophysiology of Multiple Sclerosis Lesions," *Science and Medicine* Nov./Dec.: 32–41, 1997.

Weiner et al., "Therapy for Multiple Sclerosis," *Multiple Sclerosis* 13(1): 173–196, 1995.

Weinstein et al., "A Clinical Screening Program for Topical Chemotherapeutic Drugs in Psoriasis," *Arch. Dermatol. 117*: 388–393, 1981.

Weinstein and Kruger, Therapy of Moderate to Severe Psoriasis, Weinstein and Gottlieb (eds.), National Psoriasis Foundation, 1993, Chapter 1, "An Overview of Psoriasis," pp. 1–22.

Wolf, "Angiogenesis in Normal and Psoriatic Skin," *Laboratory Investigation 61*(2): 139–142, 1989.

Xi–ran et al., "Clinical Trial And Experimental Study On Treating Psoriasis With Camptothecine," *Chinese Medical Journal 101*(6): 427–430, 1988.

Zonneveld et al., "Ranitidine does not affect psoriasis: A multicenter, double–blind, placebo–controlled study," *J. Am. Acad. Dermatol. 36*: 932–934, 1997.

Notice of Opposition of Grant of European Patent 706376 by Biocompatibles Limited. Produced by Gill Jennings & Every. Dated Mar. 25, 1998.

Further Letter Concerning Notice of Opposition of Grant of European Patent 706376 by Biocompatibles Limited. Produced by Gill Jennings & Every. Dated Mar. 25, 1998.

Notice of Opposition of Grant of European Patent 706376 by Focal, Inc. Produced by Hoffman Eitle. Dated Mar. 25, 1998.

Notice of Opposition of Grant of European Patent 706376 by Schering AG. Produced by Frohwitter. Dated Mar. 25, 1998.

Supplement to Notice of Opposition of Grant of European Patent 706376 by Schering AG. Produced by Frohwitter. Dated Mar. 25, 1998.

Notice of Opposition of Grant of European Patent 706376 by Inflow Dynamics AG. Produced by Patentanwalt Uwe Czybilka. Dated Mar. 25, 1998. (English translation also provided).

Notice of Opposition of Grant of European Patent 706376 by STS Biopolymers, Inc. Produced by J.A. Kemp & Co. Dated Mar. 25, 1998.

\* cited by examiner

Epothilone B

Collagenase

GAPHD

| IL-1 (ng/mL) | 0 | 20 | 20 | 20 |
| Drug (M) | 0 | 0 | $10^{-9}$ | $10^{-7}$ |

Melting temperature, enthalpy, molecular weight ($M_n$), polydispersity ($M_w/M_n$), and intrinsic viscosity ($[\eta]$) of PDLLA-PEG-PDLLA

| PDLLA-PEG-PDLLA PEG content | Melting Temp.$^a$, °C | $\Delta H^a$, J/g | $M_n^b \times 10^{-4}$ | $M_w/M_n^b$ | $[\eta]^c$, dl/g |
|---|---|---|---|---|---|
| 100% | 61.8 | 184.8 | 0.8$^d$ | -- | -- |
| 70% | 50.2 | 72.2 | 2.1 | 1.21 | 0.27 |
| 40% | 46.3 | 42.8 | 4.5 | 3.5 | 0.29 |
| 30% | None | None | 5.9 | 2.95 | 1.0 |
| 20% | None | None | 5.1 | 2.96 | 1.45 |
| 10% | None | None | 11 | 2.38 | 1.5 |
| taxol | 212 | 59.3 | -- | -- | -- |
| 20% taxol loaded copolymer (30%PEG) | 212.1 | 5.6 | -- | -- | -- | a: measured by DSC.
b: measured by GPC, relative to polystyrene standard.
c: in $CHCl_3$ at 25°C
d: data supplied by manufacturer

*Fig. 25*

Mass loss and polymer composition change of PDLLA-PEG-PDLLA cylinders (loaded with 20% taxol) during the release into PBS albumin buffer at 37°C

| Sample[a] | Time, day | Dry wt. loss, % | 1.65/5.1[b] | 3.6/5.1[b] |
|---|---|---|---|---|
| 20% PEG-1mm | 0 | 0 | 3.51 | 1.65 |
| 20% PEG-1mm | 32 | 7.9 | – | – |
| 20% PEG-1mm | 69 | 19.2 | 3.63 | 0.68 |
| 30% PEG-1mm | 0 | 0 | 3.39 | 3.91 |
| 30% PEG-1mm | 32 | 28.9 | – | – |
| 30% PEG-1mm | 69 | 45.5 | 4.3 | 0.56 |
| 30% PEG-0.65mm | 0 | 0 | 3.39 | 3.91 |
| 30% PEG-0.65mm | 32 | 26.7 | – | – |
| 30% PEG-0.65mm | 69 | 57.5 | 5.8 | 0.21 | a: PDLLA-PEG-PDLLA copolymer cylinders showing PEG content and diameter of cylinder.
b: measured by $^1$H-NMR in CDCl$_3$; 1.65/5.1 represents the ratio of peak areas at 1.65ppm (due to -CHCH$_3$*- in PDLLA) and 5.1ppm (due to -CH*CH$_3$- in PDLLA); 3.6/5.1 represents the ratio of peak areas at 3.6ppm (due to -CH$_2$*CH$_2$*- in PEG) and 5.1ppm.

Fig. 29

Neointimal Hyperplasia
(14 days post-injury)

Paste applied to the Adventitia
(14 days post-injury)

*Fig. 78A*
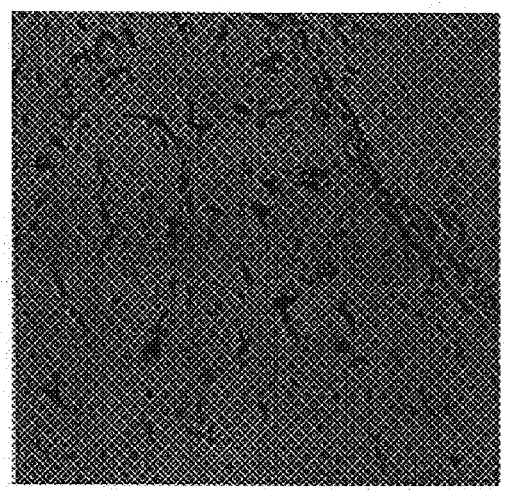
Normal Mice
*Fig. 78B*
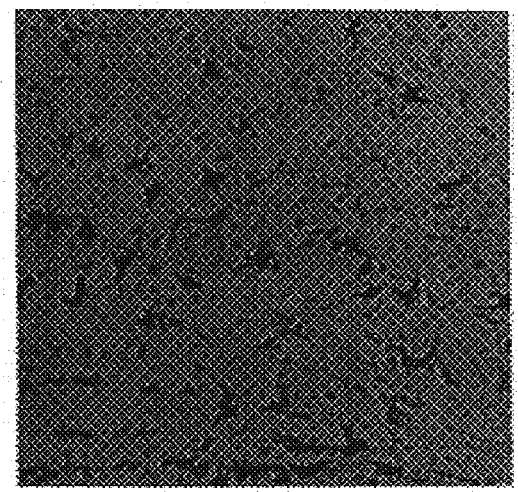
Transgenic Control
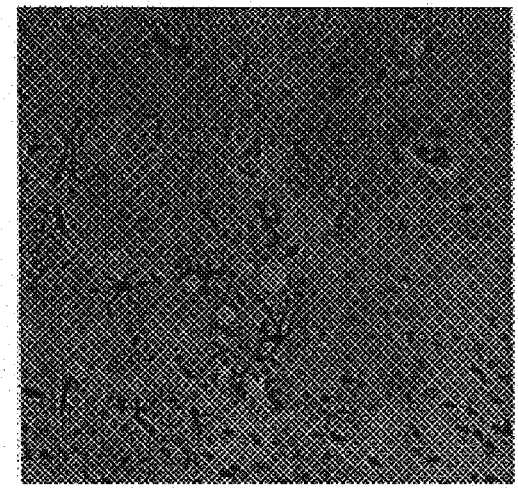
Transgenic Paclitaxel Treated
*Fig. 78C*

Values are mean ± SEM

Values are mean ± SEM. *Significant difference relative to control group, p<0.001.

COMPOSITIONS AND METHODS FOR TREATING SURGICAL ADHESIONS

CROSS REFERENCE TO RELATED APPLICATIONS

This application is a continuation of U.S. application Ser. No. 09/368,463, filed Aug. 4, 1999 now abandoned, which is a division of U.S. application Ser. No. 09/088,546, filed Jun. 1, 1998 now U.S. Pat. No. 6,495,579, which application is a continuation-in-part of U.S. application Ser. No. 08/980, 549, filed Dec. 1, 1997 now U.S. Pat. No. 6,515,016, which claims the benefit of Provisional Application No. 60/032, 215, filed Dec. 2, 1996, and Provisional Application No. 60/063,087, filed Oct. 24, 1997, which applications are incorporated by reference in their entirety.

TECHNICAL FIELD

The present invention relates generally to compositions and methods for treating or preventing inflammatory diseases.

BACKGROUND OF THE INVENTION

Inflammatory diseases, whether of a chronic or acute nature, represent a substantial problem in the healthcare industry. Briefly, chronic inflammation is considered to be inflammation of a prolonged duration (weeks or months) in which active inflammation, tissue destruction and attempts at healing are proceeding simultaneously (*Robbins Pathological Basis of Disease* by R. S. Cotran, V. Kumar, and S. L. Robbins, W. B. Saunders Co., p. 75, 1989). Although chronic inflammation can follow an acute inflammatory episode, it can also begin as an insidious process that progresses with time, for example, as a result of a persistent infection (e.g., tuberculosis, syphilis, fungal infection) which causes a delayed hypersensitivity reaction, prolonged exposure to endogenous (e.g., elevated plasma lipids) or exogenous (e.g., silica, asbestos, cigarette tar, surgical sutures) toxins, or, autoimmune reactions against the body's own tissues (e.g., rheumatoid arthritis, systemic lupus erythematosus, multiple sclerosis, psoriasis). Chronic inflammatory diseases therefore, include many common medical conditions such as rheumatoid arthritis, restenosis, psoriasis, multiple sclerosis, surgical adhesions, tuberculosis, chronic inflammatory lung diseases (e.g., asthma, pneumoconiosis, chronic obstructive pulmonary disease, nasal polyps and pulmonary fibrosis), periodontal disease (i.e., periodontitis) and polycystic kidney disease.

Psoriasis

Psoriasis is a common, chronic inflammatory skin disease characterized by raised, inflamed, thickened and scaly lesions, which itch, burn, sting and bleed easily. In approximately 10% of patients, psoriasis is accompanied by pronounced arthropathic symptoms that are similar to the changes seen in rheumatoid arthritis. Approximately 2 to 3% of the U.S. population suffers from psoriasis, with 250,000 new cases being diagnosed each year.

At present, the cause of psoriasis is unknown, although there is considerable evidence that it is a polygenic autoimmune disorder. In addition, there is currently no cure for psoriasis. Available treatments include topical therapies such as steroid creams and ointments, coal tar and anthralin, and systemic treatment such as steroids, ultra violet B, PUVA, methotrexate and cyclosporin. However, unsatisfactory remission rates and/or potentially serious side effects characterize most anti-psoriatic therapies. The overall cost of treating psoriasis in the United States is estimated at between $3 to $5 billion per year, making psoriasis a major health care problem.

Multiple Sclerosis

Multiple sclerosis (MS), affecting 350,000 people (women:men=2:1) in the United States, with 8,000 new cases reported each year, is the most common chronic inflammatory disease involving the nervous system. Typically, MS presents clinically as recurring episodes of adverse neurological deficits occurring over a period of several years. Roughly half of MS cases progress to a more chronic phase. Although the disease does not result in early death or impairment of cognitive functions, it cripples the patient by disturbing visual acuity; stimulating double vision; disturbing motor functions affecting walking and use of the hands; producing bowel and bladder incontinence; spasticity; and sensory deficits (touch, pain and temperature sensitivity).

The cause of MS is unknown, although there is considerable evidence that it is an autoimmune disease. Currently, there is no cure available for multiple sclerosis, and present therapeutic regimens have been only partially successful. For example, although chemotherapeutic agents such as methotrexate, cyclosporin and azathioprine, have been examined for the management of patients with treatment unresponsive progressive disease, minimal long-term beneficial effects have been demonstrated to date.

Other therapeutics which have been recently approved include interferon-β for use in ambulatory patients with relapsing-remitting MS (Paty et al., *Neurology* 43:662–667, 1993), specifically, Betaseron (recombinant interferon β-1β; human interferon beta substituted at position 17, Cys® Ser; Berlex/Chiron) or Avonex (recombinant interferon β-1α; glycosylated human interferon beta produced in mammalian cells; Biogen). Unfortunately, while Betaseron provides for an enhanced quality of life for MS patients, disease progression does not appear to be significantly improved. Adverse experiences associated with Betaseron therapy include: injection site reactions (inflammation, pain, hypersensitivity and necrosis), and a flu-like symptom complex (fever, chills, anxiety and confusion).

Rheumatoid Arthritis

Rheumatoid arthritis (RA) is a debilitating, chronic inflammatory disease affecting 1 to 2% of the world's population. This condition causes pain, swelling and destruction of multiple joints in the body and can also result in damage to other organs such as the lungs and kidneys. People with advanced disease have a mortality rate greater than some forms of cancer and because of this, treatment regimes have shifted towards aggressive early drug therapy designed to reduce the probability of irreversible joint damage. Recent recommendations of the American College of Rheumatology (*Arthritis and Rheumatism* 39(5):713–722, 1996) include early initiation of disease-modifying anti-rheumatic drug (DMARD) therapy for any patient with an established diagnosis and ongoing symptoms. Anticancer drugs have become the first line therapy for the vast majority of patients, with the chemotherapeutic drug, methotrexate, being the drug of choice for 60 to 70% of rheumatologists. The severity of the disease often warrants indefinite weekly treatment with this drug and, in those patients whose disease progresses despite methotrexate therapy (over 50% of patients), second line chemotherapeutic drugs such as cyclosporin and azathioprine (alone or in combination) are frequently employed.

Restenosis

Restenosis is a form of chronic vascular injury leading to vessel wall thickening and loss of blood flow to the tissue supplied by the blood vessel. It occurs in response to vascular reconstructive procedures, including virtually any manipulation which attempts to relieve vessel obstructions, and is the major factor limiting the effectiveness of invasive treatments for vascular diseases. Restenosis has been a major challenge to cardiovascular research for the past 15 years. According to 1994 estimates (U.S. Heart and Stroke Foundation), over 60 million Americans have one or more forms of cardiovascular disease. These diseases claimed approximately 1 million lives in the same year (41% of all deaths in the United States) and are considered the leading cause of death and disability in the developed world.

Currently, no existing, technically approved, treatments for the prevention of restenosis have been effective in humans. Systemic therapies which have been investigated include agents directed at treatment of endothelial loss, anti-platelet agents (e.g., aspirin), vasodilators (e.g., calcium channel blockers), antithrombotics (e.g., heparin), anti-inflammatory agents (e.g., steroids), agents which prevent vascular smooth muscle cell (VSMC) proliferation (e.g. colchicine) and promoters of re-endothelialization (e.g., vascular endothelial growth factor). Local treatments which have been investigated include local drug delivery (e.g. heparin) and beta and gamma radiation. All have been disappointing in human use, primarily because they appear to act on a limited portion of the restenotic process. Systemic treatments have also encountered the additional problem of achieving adequate absorption and retention of the drug at the site of the disease to provide a lasting biological effect, without causing unfavorable systemic complications and toxicities.

Inflammatory Bowel Disease

Inflammatory bowel disease (IBD) refers to chronic disorders (primarily Crohn's disease and ulcerative colitis) that cause inflammation or ulceration in the small and large intestines. Briefly, approximately 2 million people in the United States suffer from IBD with males and females affected equally. The peak incidence primarily occurs between the ages of 15 and 30 with a second peak often reported between 55 and 60 years of age. Although there are many documented patterns of prevalence, it is a disease of unknown cause.

IBD is often characterized with alternating periods of remission followed by periods of unpredictable relapse or flare of varying severity. About 50% of patients are in remission at any given time and the majority suffer at least one relapse in a 10 year period. In addition, there are many systemic complications that accompany this disease with the most common being arthritis. Symptoms of arthritis occur in one fourth of all people with IBD. Joint inflammation occurs most often when the colon is involved in the disease process and flares when the bowel disease is most active. This form of inflammatory arthritis does not cause permanent deformity and is often short lived. Other complications of this disease include eye inflammation (iritis, conjunctivitis and episcleritis), mouth inflammation (mucositis), skin inflammation (erythema nodosum and pyoderma gangrenosum), musculoskeletal abnormalities (ankylosing spondylitis), renal complications (kidney stones and fistulas to urinary tract), gallstones and other diseases of the liver (e.g. hepatitis) and biliary system (sclerosing cholangitis). Unfortunately, in many cases, long-term disease (>10 years) can lead to more severe complications such as colonic cancer and extraintestinal carcinomas.

At present, there is no cure for IBD. Many of the current therapeutic agents focus on controlling the disease symptoms by suppressing the inflammation associated with the disease. The principle drugs used to treat IBD are aminosalicylates and corticosteroids and for those individuals that do not respond well to these agents, antibiotics and immunosuppressive medications can also be used. Although drug treatment is effective for 70 to 80% of patients, surgery is often required for individuals having more active disease. Chronic symptoms and complications associated with active disease such as intestinal blockage, perforation, abscess, or bleeding can be relieved and corrected with invasive surgery. Although surgery does not cure the disease permanently and recurrence rate is high, it does relieve active symptoms.

Surgical Adhesions

Surgical adhesion formation, a complex process in which bodily tissues that are normally separate grow together, is most commonly seen to occur as a result of surgical trauma These post-operative adhesions occur in 60 to 90% of patients undergoing major gynaecologic surgery and represent one of the most common causes of intestinal obstruction in the industrialized world. These adhesions are a major cause of failed surgical therapy and are the leading cause of bowel obstruction and infertility. Other adhesion-treated complications include chronic pelvic pain, urethral obstruction and voiding dysfunction. Currently, preventative therapies, administered 4 to 5 days following surgery, are used to inhibit adhesion formation. Various modes of adhesion prevention have been examined, including (1) prevention of fibrin deposition, (2) reduction of local tissue inflammation and (3) removal of fibrin deposits. Fibrin deposition is prevented through the use of physical barriers that are either mechanical or comprised of viscous solutions. Although many investigators are utilizing adhesion prevention barriers, a number of technical difficulties exist. Inflammation is reduced by the administration of drugs such as corticosteroids and nonsteroidal anti-inflammatories. However, the results from the use of these drugs in animal models have not been encouraging due to the extent of the inflammatory response and dose restriction due to systemic side effects. Finally, the removal of fibrin deposits has been investigated using proteolytic and fibrinolytic enzymes. A potential complication to the clinical use of these enzymes is the possibility for excessive bleeding.

Inflammatory Lung Diseases

Chronic inflammatory lung diseases, including for example, asthma, pneumoconiosis, chronic obstructive pulmonary disease, nasal polyps and pulmonary fibrosis, affect many people worldwide. Typically such diseases are characterized by an invasive inflammatory process and thickening of the affected tissues.

For example, nasal polyps are characterized by thickened tissue of the nasal lining. Polyps may occur in respiratory diseases such as asthma, cystic fibrosis, primary ciliary diskinesia and immune deficiencies. Nasal polyps are thought to develop as a manifestation of chronic inflammatory processes involving the upper airways. They are found in 36% of patients with aspirin intolerance, 7% of those with asthma, 0.1% in children and about 20% in those with cystic fibrosis. Other conditions associated with nasal polyps are Churg-Strauss syndrome, allergic fungal sinusitis and cilia dyskinetic syndrome and Young's syndrome. About 40% of patients with surgical polypectomies have recurrences (Settipane, *Allergy Asthma Proc.* 17(5):231–236, 1996).

The main symptoms of nasal polyposis are nasal obstruction and disturbance of sense of smell. The objectives of medical treatment of nasal polyposis are (1) to eliminate nasal polyps and rhinitis symptoms, (2) to re-establish nasal breathing and olfaction and (3) to prevent recurrence. Occlusion of the nasal passage by a few large polyps can be treated by simple polypectomy to help the patient breathe through the nose. The aim of surgery is to restore the physiological properties of the nose by making the airway as free from polyps as possible and to allow drainage of infected sinuses. However, recurrent nasal polyposis is one of the most common unsolved problems of clinical rhinology. Complementary medical treatment of polyposis is always necessary, as surgery cannot treat the inflammatory component of the mucosal disease. Topical corticosteroids are the most widely utilized treatment to reduce the size of polyps and to prevent recurrence after surgery. Steroids reduce rhinitis, improve nasal breathing, reduce the size of the polyps and decrease recurrence rate but they have negligible effect on the sense of smell and on any sinus pathology. The use of steroids in polyposis, however, is associated with infectious complications that require antibiotics. Other drugs for the management of nasal polyposis include H1-receptor antagonists (e.g., azelastine HCL) and anti-diuretics (e.g., furosemide). These treatments are not always effective and recurrence rates are still very high. Current medical treatment of nasal polyposis utilizes corticosteroids to alleviate the symptoms of the disease but has no action against the underlying pathology of the disease. In addition, recurrence of the disease or resistance to steroid therapy has been observed in patients with nasal polyps.

Graft Rejection

Graft rejection is a complex process whereby the grafted tissue is recognized as foreign by the host's immune system. On the basis of morphology and the underlying mechanism, rejection reactions fit into three categories: hyperacute, acute and chronic. With the risks of infection eliminated and early (acute) rejection being managed by immunosuppressive therapy, chronic rejection has become an increasingly important cause of graft dysfunction and ultimate failure. Currently, chronic vascular rejection is the leading cause of death or graft failure in cardiac transplant recipients after the first year.

The present invention provides compositions and methods suitable for treating or preventing inflammatory diseases. These compositions and methods address the problems associated with the existing procedures, offer significant advantages when compared to existing procedures, and further provide other, related advantages.

SUMMARY OF THE INVENTION

Briefly stated, the present invention provides methods for treating or preventing inflammatory diseases, comprising delivering to a site of inflammation an anti-microtubule agent. Representative examples of such agents include taxanes (e.g., paclitaxel and docetaxel), campothecin, eleutherobin, sarcodictyins, epothilones A and B, discodermolide, deuterium oxide ($D_2O$), hexylene glycol (2-methyl-2,4-pentanediol), tubercidin (7-deazaadenosine), LY290181 (2-amino-4-(3-pyridyl)-4H-naphtho(1,2-b) pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Within other embodiments, the anti-microtubule agent is formulated to further comprise a polymer.

Representative examples of inflammatory diseases which may be treated include multiple sclerosis, psoriasis, arthritis, stenosis, graft rejection, surgical adhesions, inflammatory bowel disease and inflammatory lung disease.

Within certain embodiments of the invention, the anti-microtubule agents may be formulated along with other compounds or compositions, such as, for example, an ointment, cream, lotion, gel, spray, foam, mousse, coating, wrap, paste, barrier, implant, microsphere, microparticle, film or the like. Within certain embodiments, the compound or composition may function as a carrier, which may be either polymeric, or non-polymeric. Representative examples of polymeric carriers include poly(ethylene-vinyl acetate), copolymers of lactic acid and glycolic acid, poly (caprolactone), poly (lactic acid), copolymers of poly (lactic acid) and poly (caprolactone), gelatin, hyaluronic acid, collagen matrices, celluloses and albumen. Representative examples of other suitable carriers include, but are not limited to ethanol; mixtures of ethanol and glycols (e.g., ethylene glycol or propylene glycol); mixtures of ethanol and isopropyl myristate or ethanol, isopropyl myristate and water (e.g., 55:5:40); mixtures of ethanol and eineol or D-limonene (with or without water); glycols (e.g., ethylene glycol or propylene glycol) and mixtures of glycols such as propylene glycol and water, phosphatidyl glycerol, dioleoylphosphatidyl glycerol, Transcutol®, or terpinolene; mixtures of isopropyl myristate and 1-hexyl-2-pyrrolidone, N-dodecyl-2-piperidinone or 1-hexyl-2-pyrrolidone.

Within yet other aspects, the anti-microtubule agent may be formulated to be contained within, or, adapted to release by a surgical or medical device or implant, such as, for example, stents, sutures, indwelling catheters, prosthesis, and the like.

These and other aspects of the present invention will become evident upon reference to the following detailed description and attached drawings. In addition, various references are set forth below which describe in more detail certain procedures, devices or compositions, and are therefore incorporated by reference in their entirety.

BRIEF DESCRIPTION OF THE DRAWINGS

FIG. 14B is an underside view of the CAM shown in 15A. Briefly, this view demonstrates the radial appearance of the blood vessels which enter the tumor like the spokes of a wheel. Note that the blood vessel density is greater in the vicinity of the tumor than it is in the surrounding normal CAM tissue. FIG. 14D is taken from the underside of the CAM shown in 14C, and demonstrates the disruption of blood flow into the tumor when compared to control tumor tissue. Note that the blood vessel density is reduced in the vicinity of the tumor and is sparser than that of the normal surrounding CAM tissue.

FIG. 16D illustrates the typical "elbowing" effect (arrowheads) of both small and large vessels being redirected away from the periphery of the avascular zone.

FIG. 25 is a table which shows the melting temperature, enthalpy, molecular weight, polydispersity and intrinsic viscosity of a PDLLA-PEG-PDLLA composition.

FIG. 29 is a table which shows the mass loss and polymer composition change of PDLLA-PEG-PDLLA cylinders (loaded with 20% paclitaxel) during the release into PBS albumin buffer at 37° C.

Paclitaxel-loaded paste applied immediately adjacent to the perivascular region of the vessel prevented restenosis; however, when the paste was not directly adjacent to the vascular wall neointimal hyperplasia was evident.

FIGS. 78A, 78B and 78C show the effect of paclitaxel on astrocyte GFAP staining. Brain sections from normal animals and transgenic animals (who develop a neurological disease similar to multiple sclerosis) treated with vehicle or paclitaxel were stained with GFAP (a marker for activated astrocytes) and examined histologically. In control transgenic mice there was an increase in the number of astrocytes and total GFAP levels compared to normal brain sections. However, the morphology of the cells was similar. Brain sections of paclitaxel treated transgenic mice show decreased numbers of astrocytes and GFAP levels compared to untreated transgenic animals. Histologically there is cell rounding and thinning of stellate processes in astrocytes.

Figure 79A:
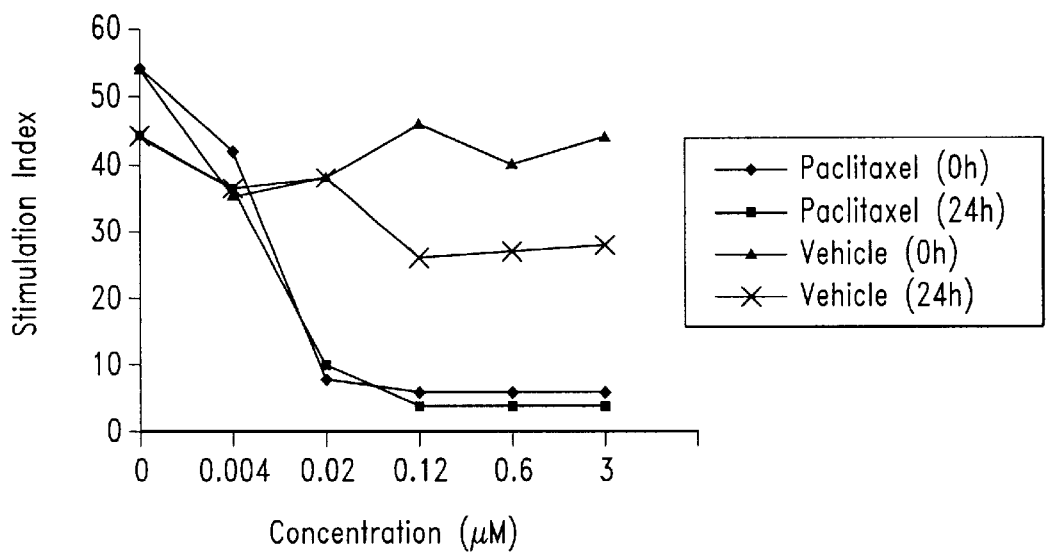
Figure 79B:
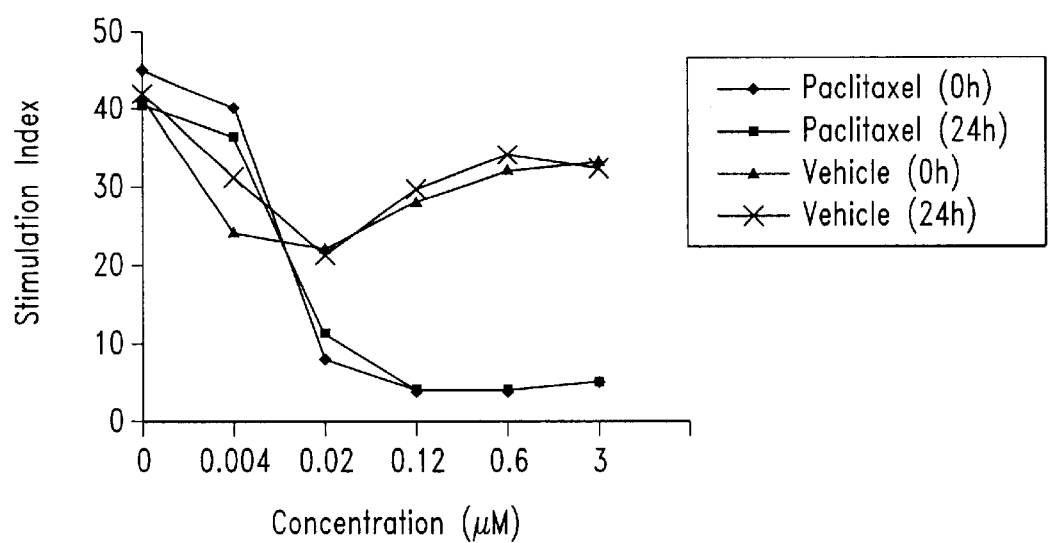
Figure 80A:
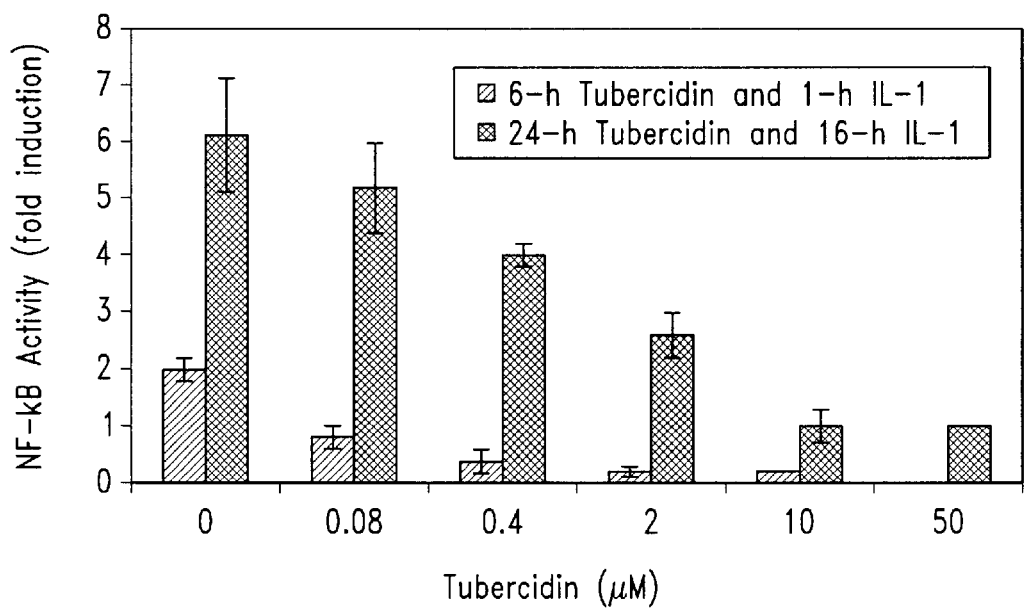
Figure 80B:
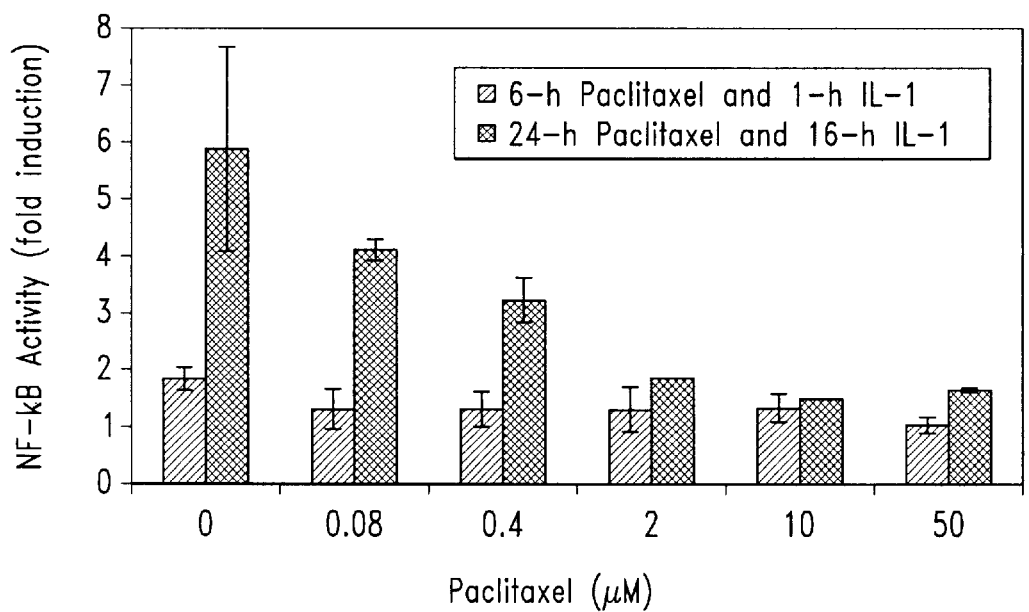
Figure 80C:
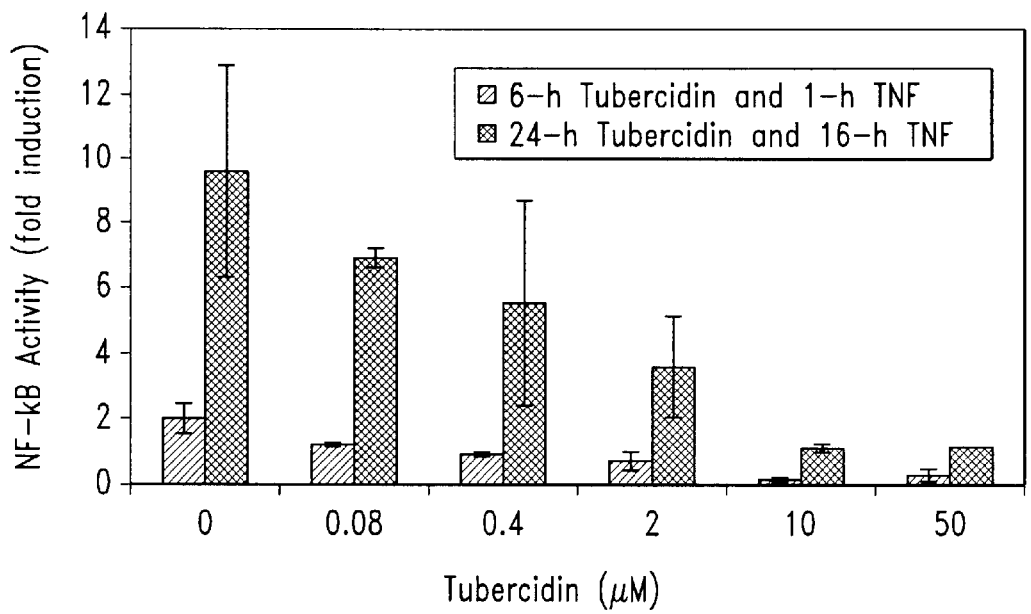
Figure 80D:
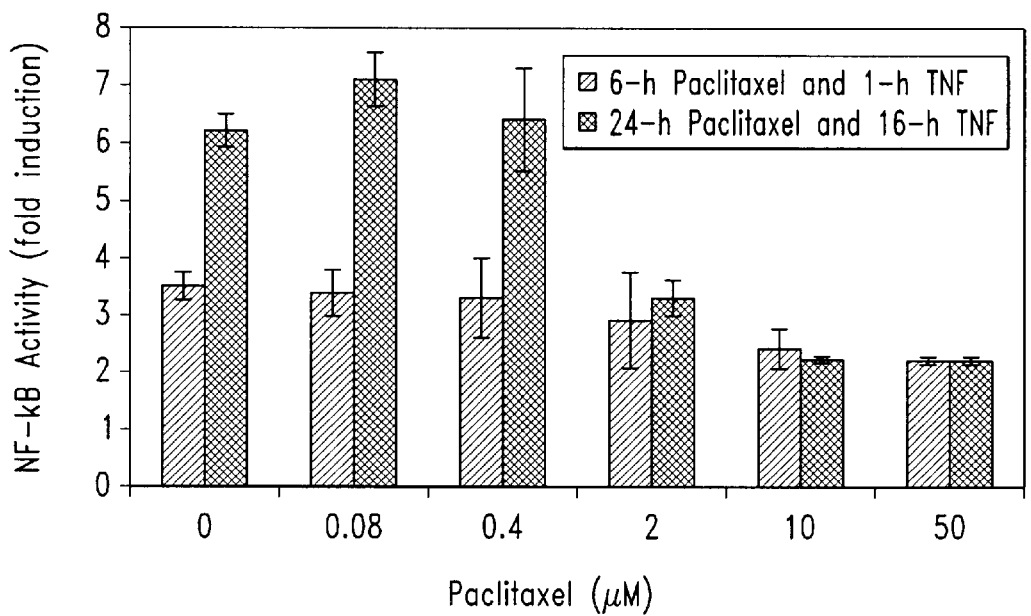

FIGS. 79A and 79B are graphs which show that paclitaxel inhibits T-cell stimulation in response to myelin basic protein peptide (GP68–88) and ConA. A 48-hour culture of T-cell proliferation of RT-1 was performed with GP68–88 (A) or ConA (B) as stimulagens. Paclitaxel and its vehicle (micelles) were added at graded concentrations at the beginning of antigen stimulation or 24 hours later. Paclitaxel inhibited T-cell proliferation at concentrations as low as 0.02 $\mu$M, regardless of the stimulagen.

FIGS. 80A, 80B, 80C and 80D, are graphs which show that tubercidin and paclitaxel inhibit both IL-1- and TNF-induced NF-$\kappa$B activity.

Figure 81A:
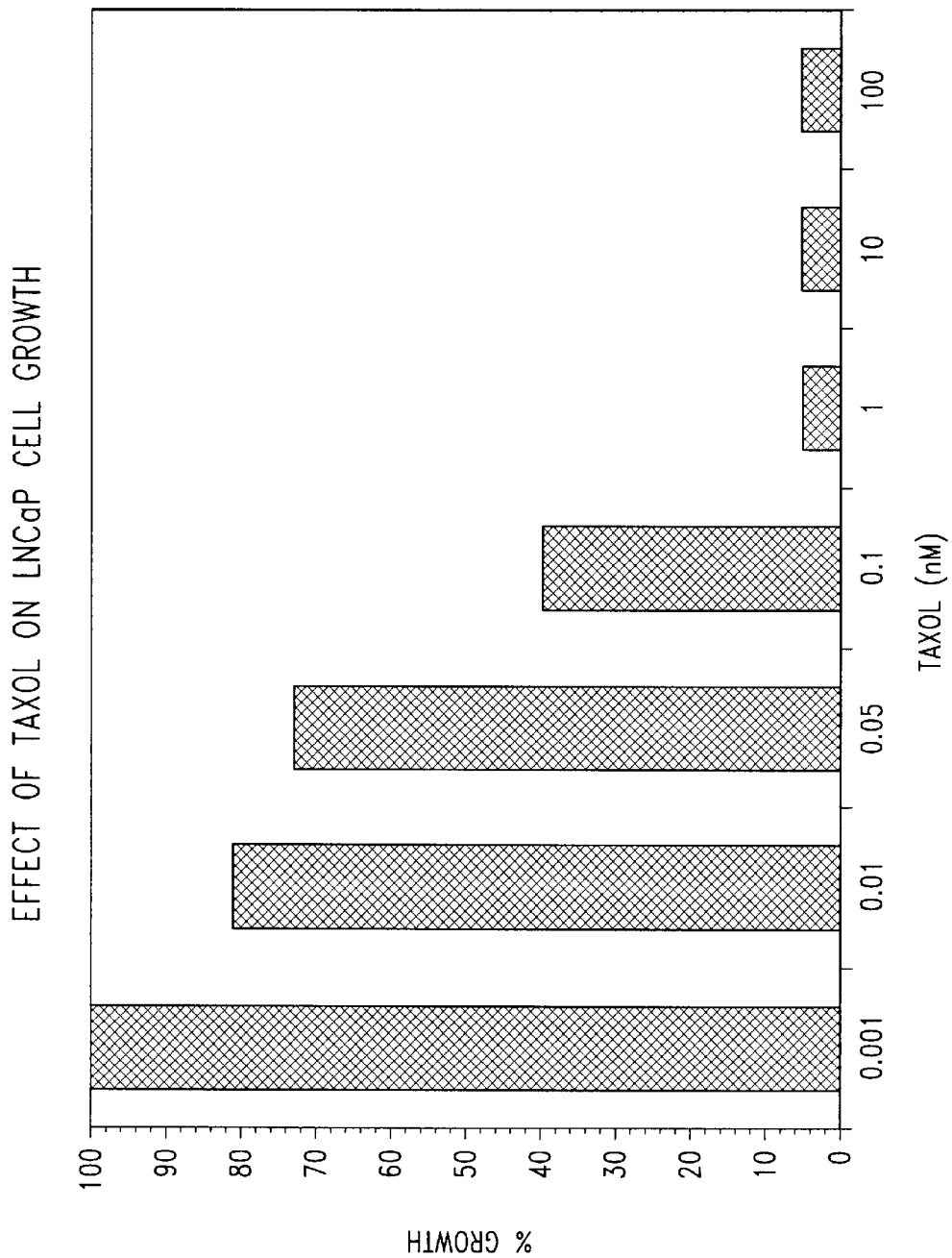
Figure 81B:
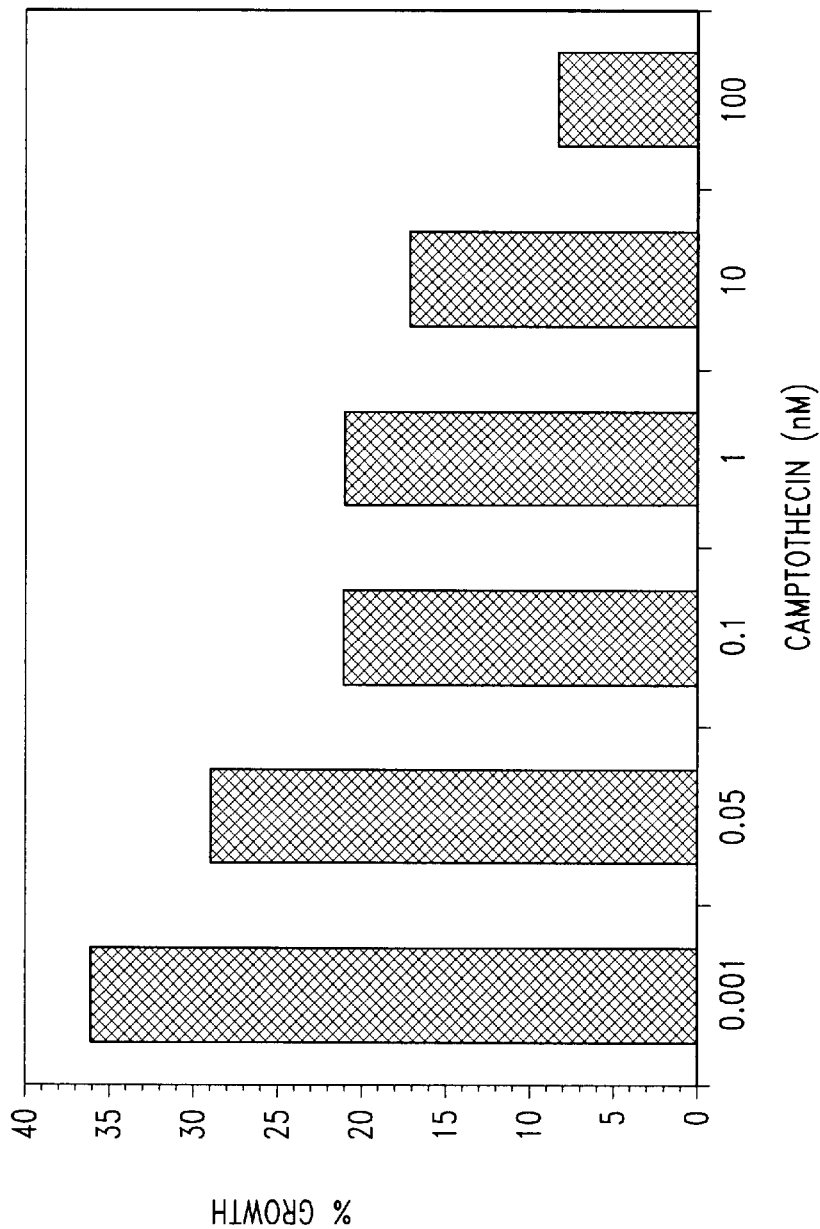

FIGS. 81A and 81B are graphs which show the effect of increasing concentrations of paclitaxel or camptothecin on the cell growth of human prostate cancer cells (LNCaP) ($2\times10^3$ cells/well) as measured by crystal violet (0.5%) staining and quantitation by absorbance at 492 nm. Percent growth is expressed as a % relative to controls and a mean of 8 results is given.

Figure 82A:
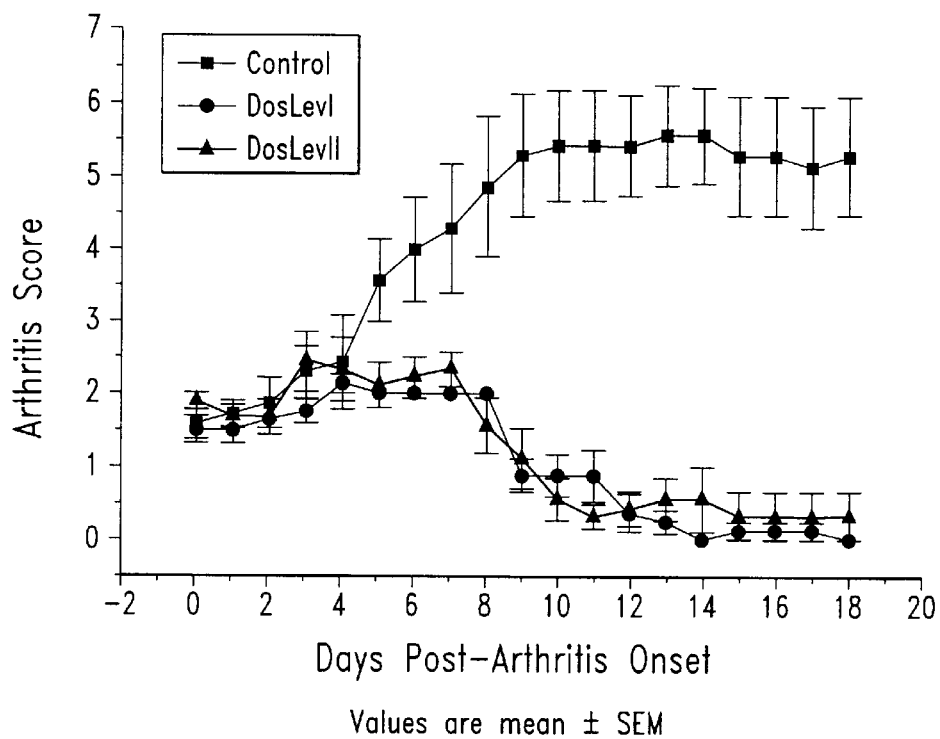
Figure 82B:
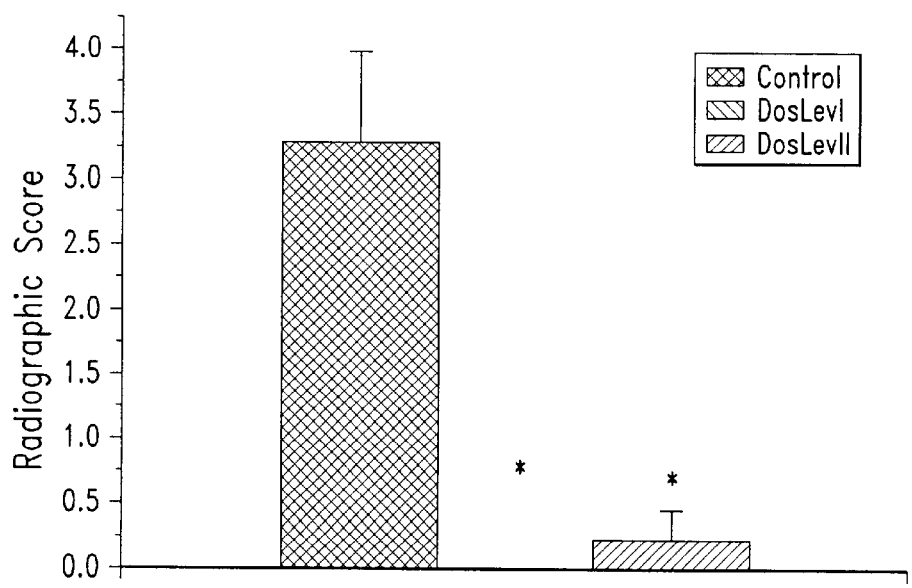

FIGS. 82A and 82B are graphs which show the effect of micellar paclitaxel on the collagen-induced arthritis (CIA) rat model. Micellar paclitaxel (low and high subsequent doses) significantly reduced mean arthritis scores in rats from Day 5 through Day 18 relative to control (p<0.001). In addition, micellar paclitaxel reduced radiographic scores of ankle joints in the animals.

FIGS. 83A, 83B, 83C and 83D are graphs which show the effect of micellar paclitaxel on the actively-induced (83A and 83B) and passively-induced (83C and 83D) experimental autoimmune encephalomyelitis (EAE) rat models of multiple sclerosis. Values are mean±SEM. A. Micellar paclitaxel-treated rats had minimal weight loss whereas rats in the control group suffered more severe weight loss. B. Micellar paclitaxel prevented clinical indices of MS. C. Rats treated with micellar paclitaxel did not show weight loss, however, rats in the control group lost weight during the study. N=3, 2 control animals died on Day 7. D. Micellar paclitaxel-treated animals showed no clinical signs of disease at the end of the study period. N=3, 2 control animals died on Day 7.

DETAILED DESCRIPTION OF THE INVENTION

Prior to setting forth the invention, it may be helpful to an understanding thereof to set forth definitions of certain terms that will be used hereinafter.

"Inflammatory Diseases" as used herein refers to any of a number of diseases which are characterized by vascular changes: edema and infiltration of neutrophils (e.g., acute inflammatory reactions); infiltration of tissues by mononuclear cells; tissue destruction by inflammatory cells, connective tissue cells and their cellular products; and attempts at repair by connective tissue replacement (e.g., chronic inflammatory reactions). Representative examples of such diseases include many common medical conditions such as arthritis, atherosclerosis, psoriasis, inflammatory bowel disease, multiple sclerosis, surgical adhesions, restenosis, tuberculosis, graft rejection and chronic inflammatory respiratory diseases (e.g., asthma, pneumoconiosis, chronic obstructive pulmonary disease, nasal polyps and pulmonary fibrosis).

"Anti-microtubule Agents" should be understood to include any protein, peptide, chemical, or other molecule which impairs the function of microtubules, for example, through the prevention or stabilization of polymerization. A wide variety of methods may be utilized to determine the anti-microtubule activity of a particular compound, including for example, assays described by Smith et al. (*Cancer Lett* 79(2):213–219, 1994) and Mooberry et al., (*Cancer Lett.* 96(2):261–266, 1995).

As noted above, the present invention provides methods for treating or preventing inflammatory diseases, comprising the step of delivering to the site of inflammation an anti-microtubule agent. Briefly, a wide variety of agents may be delivered to a site of inflammation (or potential site of inflammation), either with or without a carrier (e.g., a polymer or ointment), in order to treat or prevent an inflammatory disease. Representative examples of such agents include taxanes (e.g., paclitaxel (discussed in more detail below) and docetaxel) (Schiff et al., *Nature* 277: 665–667, 1979; Long and Fairchild, *Cancer Research* 54: 4355–4361, 1994; Ringel and Horwitz, *J. Natl. Cancer Inst.* 83(4): 288–291, 1991; Pazdur et al., *Cancer Treat. Rev.* 19(4): 351–386, 1993), campothecin, eleutherobin (e.g., U.S. Pat. No. 5,473,057), sarcodictyins (including sarcodictyin A), epothilones A and B (Bollag et al., *Cancer Research* 55: 2325–2333, 1995), discodermolide (ter Haar et al., *Biochemistry* 35: 243–250, 1996), deuterium oxide ($D_2O$) (James and Lefebvre, *Genetics* 130(2): 305–314, 1992; Sollott et al., *J. Clin. Invest.* 95: 1869–1876, 1995), hexylene glycol (2-methyl-2,4-pentanediol) (Oka et al., *Cell Struct. Funct.* 16(2): 125–134, 1991), tubercidin (7-deazaadenosine) (Mooberry et al., *Cancer Lett.* 96(2): 261–266, 1995), LY290181 (2-amino-4-(3-pyridyl)-4H-naphtho(1,2-b) pyran-3-cardonitrile) (Panda et al., *J. Biol. Chem.* 272(12): 7681–7687, 1997; Wood et al., *Mol. Pharmacol.* 52(3): 437–444, 1997), aluminum fluoride (Song et al., *J. Cell. Sci. Suppl.* 14: 147–150, 1991), ethylene glycol bis-(succinimidylsuccinate) (Caplow and Shanks, *J. Biol. Chem.* 265(15): 8935–8941, 1990), glycine ethyl ester (Mejillano et al., *Biochemistry* 31(13): 3478–3483, 1992), nocodazole (Ding et al., *J. Exp. Med.* 171(3): 715–727, 1990; Dotti et al., *J. Cell Sci. Suppl.* 15: 75–84, 1991; Oka et al., *Cell Struct. Funct.* 16(2): 125–134, 1991; Weimer et al., *J. Cell. Biol.* 136(1), 71–80, 1997), cytochalasin B (Illinger et al., *Biol. Cell* 73(2–3): 131–138, 1991), colchicine and CI 980 (Allen et al., *Am. J. Physiol.* 261(4 Pt. 1): L315–L321, 1991; Ding et al., *J. Exp. Med.* 171(3): 715–727, 1990; Gonzalez et al., *Exp. Cell. Res.* 192(1): 10–15, 1991; Stargell et al., *Mol. Cell. Biol.* 12(4): 1443–1450, 1992; Garcia et al., *Antican. Drugs* 6(4): 533–544, 1995), colcemid (Barlow et al., *Cell. Motil. Cytoskeleton* 19(1): 9–17, 1991; Meschini et al., *J. Microsc.* 176(Pt. 3): 204–210, 1994; Oka et al., *Cell Struct. Funct.* 16(2): 125–134, 1991), podophyllotoxin (Ding et al., *J. Exp. Med.* 171(3): 715–727, 1990), benomyl (Hardwick et al., *J. Cell. Biol.* 131(3): 709–720, 1995; Shero et al., *Genes*

Dev. 5(4): 549–560, 1991), oryzalin (Stargell et al., *Mol. Cell. Biol.* 12(4): 1443–1450, 1992), majusculamide C (Moore, *J. Ind. Microbiol.* 16(2): 134–143, 1996), demecolcine (Van Dolah and Ramsdell, *J. Cell. Physiol.* 166(1): 49–56, 1996; Wiemer et al., *J. Cell. Biol.* 136(1): 71–80, 1997), methyl-2-benzimidazolecarbamate (MBC) (Brown et al., *J. Cell. Biol.* 123(2): 387–403, 1993), LY195448 (Barlow & Cabral, *Cell Motil. Cytoskel.* 19: 9–17, 1991), subtilisin (Saoudi et al., *J. Cell Sci.* 108: 357–367, 1995), 1069C85 (Raynaud et al., *Cancer Chemother. Pharmacol.* 35: 169–173, 1994), steganacin (Hamel, *Med. Res. Rev.* 16(2): 207–231, 1996), combretastatins (Hamel, *Med. Res. Rev.* 16(2): 207–231, 1996), curacins (Hamel, *Med. Res. Rev.* 16(2): 207–231, 1996), estradiol (Aizu-Yokata et al., *Carcinogen.* 15(9): 1875–1879, 1994), 2-methoxyestradiol (Hamel, *Med. Res. Rev.* 16(2): 207–231, 1996), flavanols (Hamel, *Med. Res. Rev.* 16(2): 207–231, 1996), rotenone (Hamel, *Med. Res. Rev.* 16(2): 207–231, 1996), griseofulvin (Hamel, *Med. Res. Rev.* 16(2): 207–231; 1996), vinca alkaloids, including vinblastine and vincristine (Ding et al., *J. Exp. Med.* 171(3): 715–727, 1990; Dirk et al., *Neurochem. Res.* 15(11): 1135–1139, 1990; Hamel, *Med. Res. Rev.* 16(2): 207–231, 1996; Illinger et al., *Biol. Cell* 73(2–3): 131–138, 1991; Wiemer et al., *J. Cell. Biol.* 136(1): 71–80, 1997), maytansinoids and ansamitocins (Hamel, *Med. Res. Rev.* 16(2): 207–231, 1996), rhizoxin (Hamel, *Med. Res. Rev.* 16(2): 207–231, 1996), phomopsin A (Hamel, *Med. Res. Rev.* 16(2): 207–231, 1996), ustiloxins (Hamel, *Med. Res. Rev.* 16(2): 207–231, 1996), dolastatin 10 (Hamel, *Med Res. Rev.* 16(2): 207–231, 1996), dolastatin 15 (Hamel, *Med. Res. Rev.* 16(2): 207–231, 1996), halichondrins and halistatins (Hamel, *Med. Res. Rev.* 16(2): 207–231, 1996), spongistatins (Hamel, *Med. Res. Rev.* 16(2): 207–231, 1996), cryptophycins (Hamel, *Med. Res. Rev.* 16(2): 207–231, 1996), rhazinilam (Hamel, *Med. Res. Rev.* 16(2): 207–231, 1996), betaine (Hashimoto et al., *Zool. Sci.* 1: 195–204, 1984), taurine (Hashimoto et al., *Zool. Sci.* 1: 195–204, 1984), isethionate (Hashimoto et al., *Zool. Sci.* 1: 195–204, 1984), HO-221 (Ando et al., *Cancer Chemother. Pharmacol.* 37: 63–69, 1995), adociasulfate-2 (Sakowicz et al., *Science* 280: 292–295, 1998), estramustine (Panda et al., *Proc. Natl. Acad. Sci. USA* 94: 10560–10564, 1997), monoclonal anti-idiotypic antibodies (Leu et al., *Proc. Natl. Acad. Sci. USA* 91(22): 10690–10694, 1994), microtubule assembly promoting protein (taxol-like protein, TALP) (Hwang et al., *Biochem. Biophys. Res. Commun.* 208(3): 1174–1180, 1995), cell swelling induced by hypotonic (190 mosmol/L) conditions, insulin (100 nmol/L) or glutamine (10 mmol/L) (Haussinger et al., *Biochem. Cell. Biol.* 72(1–2): 12–19, 1994), dynein binding (Ohba et al., *Biochim. Biophys. Acta* 1158(3): 323–332, 1993), gibberelin (Mita and Shibaoka, *Protoplasma* 119(1/2): 100–109, 1984), XCHO1 kinesin-like protein) (Yonetani et al., *Mol. Biol. Cell* 7(suppl): 211A, 1996), lysophosphatidic acid (Cook et al., *Mol. Biol. Cell* 6(suppl): 260A, 1995), lithium ion (Bhattacharyya and Wolff, *Biochem. Biophys. Res. Commun.* 73(2): 383–390, 1976), plant cell wall components (e.g., poly-L-lysine and extensin) (Akashi et al., *Planta* 182(3): 363–369, 1990), glycerol buffers (Schilstra et al., *Biochem. J.* 277(Pt. 3): 839–847, 1991; Farrell and Keates, *Biochem. Cell. Biol.* 68(11): 1256–1261, 1990; Lopez et al., *J. Cell. Biochem.* 43(3): 281–291, 1990), Triton X-100 microtubule stabilizing buffer (Brown et al., *J. Cell Sci.* 104(Pt. 2): 339–352, 1993; Safiejko-Mroczka and Bell, *J. Histochem. Cytochem.* 44(6): 641–656, 1996), microtubule associated proteins (e.g., MAP2, MAP4, tau, big tau, ensconsin, elongation factor-1-alpha EF-1α) and E-MAP-115) (Burgess et al., *Cell Motil.*

*Cytoskeleton* 20(4): 289–300, 1991; Saoudi et al., *J. Cell. Sci.* 108(Pt. 1): 357–367, 1995; Bulinski and Bossler, *J. Cell. Sci.* 107(Pt. 10): 2839–2849, 1994; Ookata et al., *J. Cell Biol.* 128(5): 849–862, 1995; Boyne et al., *J. Comp. Neurol.* 358(2): 279–293, 1995; Ferreira and Caceres, *J. Neurosci.* 11(2): 392400, 1991; Thurston et al., *Chromosoma* 105(1): 20–30, 1996; Wang et al., *Brain Res. Mol. Brain Res.* 38(2): 200–208, 1996; Moore and Cyr, *Mol. Biol. Cell* 7(suppl): 221-A, 1996; Masson and Kreis, *J. Cell Biol.* 123(2), 357–371, 1993), cellular entities (e.g. histone H1, myelin basic protein and kinetochores) (Saoudi et al., *J. Cell. Sci.* 108(Pt. 1): 357–367, 1995; Simerly et al., *J. Cell Biol.* 111(4): 1491–1504, 1990), endogenous microtubular structures (e.g., axonemal structures, plugs and GTP caps) (Dye et al., *Cell Motil. Cytoskeleton* 21(3): 171–186, 1992; Azhar and Murphy, *Cell Motil. Cytoskeleton* 15(3): 156–161, 1990; Walker et al., *J. Cell Biol.* 114(1): 73–81, 1991; Drechsel and Kirschner, *Curr. Biol.* 4(12): 1053–1061, 1994), stable tubule only polypeptide (e.g., STOP145 and STOP220) (Pirollet et al., *Biochim. Biophys. Acta* 1160(1): 113–119, 1992; Pirollet et al., *Biochemistry* 31(37): 8849–8855, 1992; Bosc et al., *Proc. Natl. Acad. Sci. USA* 93(5): 2125–2130, 1996; Margolis et al., *EMBO J.* 9(12): 4095–4102, 1990) and tension from mitotic forces (Nicklas and Ward, *J. Cell Biol.* 126(5): 1241–1253, 1994), as well as any analogues and derivatives of any of the above. Such compounds can act by either depolymerizing microtubules (e.g., colchicine and vinblastine), or by stabilizing microtubule formation (e.g., paclitaxel).

Within one preferred embodiment of the invention, the therapeutic agent is paclitaxel, a compound which disrupts microtubule formation by binding to tubulin to form abnormal mitotic spindles. Briefly, paclitaxel is a highly derivatized diterpenoid (Wani et al., *J. Am. Chem. Soc.* 93:2325, 1971) which has been obtained from the harvested and dried bark of *Taxus brevifolia* (Pacific Yew) and *Taxomyces Andreanae* and *Endophytic Fungus* of the Pacific Yew (Stierle et al., *Science* 60:214–216,-1993). "Paclitaxel" (which should be understood herein to include prodrugs, analogues and derivatives such as, for example, TAXOL®, TAXOTERE®, Docetaxel, 10-desacetyl analogues of paclitaxel and 3'N-desbenzoyl-3'N-t-butoxy carbonyl analogues of paclitaxel) may be readily prepared utilizing techniques known to those skilled in the art (see e.g., Schiff et al., *Nature* 277:665–667, 1979; Long and Fairchild, *Cancer Research* 54:4355–4361, 1994; Ringel and Horwitz, *J. Natl. Cancer Inst.* 83(4):288–291, 1991; Pazdur et al., *Cancer Treat. Rev.* 19(4):351–386, 1993; WO 94/07882; WO 94/07881; WO 94/07880; WO 94/07876; WO 93/23555; WO 93/10076; WO94/00156; WO 93/24476; EP 590267; WO 94/20089; U.S. Pat. Nos. 5,294,637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,248,796; 5,422,364; 5,300,638; 5,294,637; 5,362,831; 5,440,056; 4,814,470; 5,278,324; 5,352,805; 5,411,984; 5,059,699; 4,942,184; *Tetrahedron Letters* 35(52):9709–9712, 1994; *J. Med. Chem.* 35:4230–4237, 1992; *J. Med. Chem.* 34:992–998, 1991; *J. Natural Prod.* 57(10):1404–1410, 1994; *J. Natural Prod.* 57(11):1580–1583, 1994; *J. Am. Chem. Soc.* 110:6558–6560, 1988), or obtained from a variety of commercial sources, including for example, Sigma Chemical Co., St. Louis, Mo. (T7402—from *Taxus brevifolia*).

Representative examples of such paclitaxel derivatives or analogues include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di (sodium 1,2-benzenedicarboxylate, 10-desacetoxy-11,12-dihydrotaxol-10,12(18)-diene derivatives, 10-desacetoxytaxol, Protaxol(2'- and/or 7-O-ester derivatives), (2'- and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol, Derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG(5000)carbamate taxol, 2'-benzoyl and 2',7-dibenzoyl taxol derivatives, other prodrugs (2'-acetyl taxol; 2',7-diacetyltaxol; 2'succinyltaxol; 2'-(beta-alanyl)-taxol); 2'gamma-aminobutyryltaxol formate; ethylene glycol derivatives of 2'-succinyltaxol; 2'-glutaryltaxol; 2'-(N,N-dimethylglycyl)taxol; 2'-(2-(N,N-dimethylamino) propionyl)taxol; 2'orthocarboxybenzoyl taxol; 2'aliphatic carboxylic acid derivatives of taxol, Prodrugs {2'(N,N-diethylaminopropionyl)taxol, 2'(N,N-dimethylglycyl)taxol, 7(N,N-dimethylglycyl)taxol, 2',7-di-(N,N-dimethylglycyl) taxol, 7(N,N-diethylaminopropionyl)taxol, 2',7-di(N,N-diethylaminopropionyl)taxol, 2'-(L-glycyl)taxol, 7-(L-glycyl)taxol, 2',7-di(L-glycyl)taxol, 2'-(L-alanyl)taxol, 7-(L-alanyl)taxol, 2',7-di(L-alanyl)taxol, 2'-(L-leucyl)taxol, 7-(L-leucyl)taxol, 2',7-di(L-leucyl)taxol, 2'-(L-isoleucyl) taxol, 7-(L-isoleucyl)taxol, 2',7-di(L-isoleucyl)taxol, 2'-(L-valyl)taxol, 7-(L-valyl)taxol, 2'7-di(L-valyl)taxol, 2'-(L-phenylalanyl)taxol, 7-(L-phenylalanyl)taxol, 2',7-di(L-phenylalanyl)taxol, 2'-(L-prolyl)taxol, 7-(L-prolyl)taxol, 2',7-di(L-prolyl)taxol, 2'-(L-lysyl)taxol, 7-(L-lysyl)taxol, 2',7-di(L-lysyl)taxol, 2'-(L-glutamyl)taxol, 7-(L-glutamyl) taxol, 2',7-di(L-glutamyl)taxol, 2'-(L-arginyl)taxol, 7-(L-arginyl)taxol, 2',7-di(L-arginyl)taxol}, Taxol analogs with modified phenylisoserine side chains, taxotere, (N-debenzoyl-N-tert-(butoxycaronyl)-10-deacetyltaxol, and taxanes (e.g., baccatin III, cephalomannine, 10-deacetylbaccatin III, brevifoliol, yunantaxusin and taxusin).

Formulations

As noted above, therapeutic anti-microtubule agents described herein may be formulated in a variety of manners, and thus may additionally comprise a carrier. In this regard, a wide variety of carriers may be selected of either polymeric or non-polymeric origin.

For example, within one embodiment of the invention a wide variety of polymeric carriers may be utilized to contain and/or deliver one or more of the therapeutic agents discussed above, including for example both biodegradable and non-biodegradable compositions. Representative examples of biodegradable compositions include albumin, collagen, gelatin, hyaluronic acid, starch, cellulose (methylcellulose, hydroxypropylcellulose, hydroxypropylmethylcellulose, hydroxyethylcellulose, carboxymethylcellulose, cellulose acetate phthalate, cellulose acetate succinate, hydroxypropylmethylcellulose phthalate), casein, dextrans, polysaccharides, fibrinogen, poly(D,L lactide), poly(D,L-lactide-co-glycolide), poly(glycolide), poly (hydroxybutyrate), poly(alkylcarbonate) and poly (orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) "Polymers in Controlled Drug Delivery" Wright, Bristol, 1987; Arshady, J. Controlled Release 17:1–22, 1991; Pitt, Int. J. Phar. 59:173–196, 1990; Holland et al., J. Controlled Release 4:155–0180, 1986). Representative examples of nondegradable polymers include poly(ethylene-vinyl acetate) ("EVA") copolymers, silicone rubber, acrylic polymers (polyacrylic acid, polymethylacrylic acid, polymethylmethacrylate, polyalkylcynoacrylate), polyethylene, polyproplene, polyamides (nylon 6,6), polyurethane, poly(ester urethanes), poly (ether urethanes), poly(ester-urea), polyethers (poly (ethylene oxide), poly(propylene oxide), Pluronics and poly (tetramethylene glycol)), silicone rubbers and vinyl polymers (polyvinylpyrrolidone, poly(vinyl alcohol), poly (vinyl acetate phthalate). Polymers may also be developed which are either anionic (e.g. alginate, carrageenin, carboxymethyl cellulose and poly(acrylic acid), or cationic (e.g., chitosan, poly-L-lysine, polyethylenimine, and poly (allyl amine)) (see generally, Dunn et al., J. Applied Polymer Sci. 50:353–365, 1993; Cascone et al., J. Materials Sci.: Materials in Medicine 5:770–774, 1994; Shiraishi et al., Biol. Pharm. Bull. 16(11):1164–1168, 1993; Thacharodi and Rao, Int'l J. Pharm. 120:115–118, 1995; Miyazaki et al., Int'l J. Pharm. 118:257–263, 1995). Particularly preferred polymeric carriers include poly(ethylenevinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) with a polyethylene glycol (e.g., MePEG), and blends thereof.

Polymeric carriers can be fashioned in a variety of forms, with desired release characteristics and/or with specific desired properties. For example, polymeric carriers may be fashioned to release a therapeutic agent upon exposure to a specific triggering event such as pH (see e.g., Heller et al., "Chemically Self-Regulated Drug Delivery Systems," in Polymers in Medicine III, Elsevier Science Publishers B. V., Amsterdam, 1988, pp. 175–188; Kang et al., J. Applied Polymer Sci. 48:343–354, 1993; Dong et al., J. Controlled Release 19:171–178, 1992; Dong and Hoffmnan, J. Controlled Release 15:141–152, 1991; Kim et al., J. Controlled Release 28:143–152, 1994; Cornejo-Bravo et al., J. Controlled Release 33:223–229, 1995; Wu and Lee, Pharm. Res. 10(10):1544–1547, 1993; Serres et al., Pharm. Res. 13(2):196–201, 1996; Peppas, "Fundamentals of pH- and Temperature-Sensitive Delivery Systems," in Gurny et al. (eds.), Pulsatile Drug Delivery, Wissenschaftliche Verlagsgesellschaft mbH, Stuttgart, 1993, pp. 41–55; Doelker, "Cellulose Derivatives," 1993, in Peppas and Langer (eds.), Biopolymers I, Springer-Verlag, Berlin). Representative examples of pH-sensitive polymers include poly(acrylic acid) and its derivatives (including for example, homopolymers such as poly(aminocarboxylic acid); poly(acrylic acid); poly(methyl acrylic acid), copolymers of such homopolymers, and copolymers of poly(acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water soluble polymer.

Likewise, polymeric carriers can be fashioned which are temperature sensitive (see e.g., Chen et al., "Novel Hydrogels of a Temperature-Sensitive Pluronic Grafted to a Bioadhesive Polyacrylic Acid Backbone for Vaginal Drug Delivery," in *Proceed. Intern. Symp. Control. Rel. Bioact. Mater.* 22:167–168, Controlled Release Society, Inc., 1995; Okano, "Molecular Design of Stimuli-Responsive Hydrogels for Temporal Controlled Drug Delivery," in *Proceed. Intern. Symp. Control. Rel. Bioact. Mater.* 22:111–112, Controlled Release Society, Inc., 1995; Johnston et al., *Pharm. Res.* 9(3):425–433, 1992; Tung, *Int'l J. Pharm.* 107:85–90, 1994; Harsh and Gehrke, *J. Controlled Release* 17:175–186, 1991; Bae et al., *Pharm. Res.* 8(4):531–537, 1991; Dinarvand and D'Emanuele, *J. Controlled Release* 36:221–227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820–821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822–823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829–830; Kim et al., *Pharm. Res.* 9(3):283–290, 1992; Bae et al., *Pharm. Res.* 8(5):624–628, 1991; Kono et al., *J. Controlled Release* 30:69–75, 1994; Yoshida et al., *J. Controlled Release* 32:97–102. 1994; Okano et al., *J. Controlled Release* 36:125–133, 1995; Chun and Kim, *J. Controlled Release* 38:39–47, 1996; D'Emanuele and Dinarvand, *Int'l J. Pharm.* 118:237–242, 1995; Katono et al., *J. Controlled Release* 16:215–228, 1991; Hoffman, "Thermally Reversible Hydrogels Containing Biologically Active Species," in Migliaresi et al. (eds.), *Polymers in Medicine III*, Elsevier Science Publishers B. V., Amsterdam, 1988, pp. 161–167; Hoffman, "Applications of Thermally Reversible Polymers and Hydrogels in Therapeutics and Diagnostics," in Third International Symposium on Recent Advances in Drug Delivery Systems, Salt Lake City, Utah, Feb. 24–27, 1987, pp. 297–305; Gutowska et al., *J. Controlled Release* 22:95–104, 1992; Palasis and Gehrke, *J. Controlled Release* 18:1–12, 1992; Paavola et al., *Pharm. Res.* 12(12):1997–2002, 1995).

Representative examples of thermogelling polymers, and their gelatin temperature (LCST (° C.)) include homopolymers such as poly(-methyl-N-n-propylacrylamide), 19.8; poly(N-n-propylacrylamide), 21.5; poly(N-methyl-N-isopropylacrylamide), 22.3; poly(N-n-propylmethacrylamide), 28.0; poly(N-isopropylacrylamide), 30.9; poly(N,n-diethylacrylamide), 32.0; poly(N-isopropylmethacrylamide), 44.0; poly(N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; poly(N-ethylacrylamide), 72.0. Moreover thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide).

Other representative examples of thermogelling polymers include cellulose ether derivatives such as hydroxypropyl cellulose, 41° C.; methyl cellulose, 55° C.; hydroxypropylmethyl cellulose, 66° C.; and ethylhydroxyethyl cellulose, and Pluronics such as F-127, 10–15° C.; L-122, 19° C.; L-92, 26° C.; L-81, 20° C.; and L-61, 24° C.

A wide variety of forms may be fashioned by the polymeric carriers of the present invention, including for example, rod-shaped devices, pellets, slabs, or capsules (see e.g., Goodell et al., *Am. J. Hosp. Pharm.* 43:1454–1461, 1986; Langer et al., "Controlled release of macromolecules from polymers", in *Biomedical Polymers, Polymeric Materials and Pharmaceuticals for Biomedical Use,* Goldberg, E. P., Nakagim, A. (eds.) Academic Press, pp. 113–137, 1980; Rhine et al., *J. Pharm. Sci.* 69:265–270, 1980; Brown et al., *J. Pharm. Sci.* 72:1181–1185, 1983; and Bawa et al., *J. Controlled Release* 1:259–267, 1985). Therapeutic agents may be linked by occlusion in the matrices of the polymer, bound by covalent linkages, or encapsulated in microcapsules. Within certain preferred embodiments of the invention, therapeutic compositions are provided in non-capsular formulations such as microspheres (ranging from nanometers to micrometers in size), pastes, threads of various size, films and sprays.

Preferably, therapeutic compositions of the present invention are fashioned in a manner appropriate to the intended use. Within certain aspects of the present invention, the therapeutic composition should be biocompatible, and release one or more therapeutic agents over a period of several days to months. For example, "quick release" or "burst" therapeutic compositions are provided that release greater than 10%, 20%, or 25% (w/v) of a therapeutic agent (e.g., paclitaxel) over a period of 7 to 10 days. Such "quick release" compositions should, within certain embodiments, be capable of releasing chemotherapeutic levels (where applicable) of a desired agent. Within other embodiments, "low release" therapeutic compositions are provided that release less than 1% (w/v) of a therapeutic agent over a period of 7 to 10 days. Further, therapeutic compositions of the present invention should preferably be stable for several months and capable of being produced and maintained under sterile conditions.

Within certain aspects of the present invention, therapeutic compositions may be fashioned in any size ranging from 50 nm to 500 µm, depending upon the particular use. Alternatively, such compositions may also be readily applied as a "spray", which solidifies into a film or coating. Such sprays may be prepared from microspheres of a wide array of sizes, including for example, from 0.1 µm to 3 µm, from 10 µm to 30 µm, and from 30 µm to 100 µm.

Therapeutic compositions of the present invention may also be prepared in a variety of "paste" or gel forms. For example, within one embodiment of the invention, therapeutic compositions are provided which are liquid at one temperature (e.g., temperature greater than 37° C., such as 40° C., 45° C., 50° C., 55° C. or 60° C.), and solid or semi-solid at another temperature (e.g., ambient body temperature, or any temperature lower than 37° C.). Such "thermopastes" may be readily made given the disclosure provided herein.

Within yet other aspects of the invention, the therapeutic compositions of the present invention may be formed as a film, wrap or barrier. Preferably, such films are generally less than 5, 4, 3, 2, or 1 mm thick, more preferably less than 0.75 mm or 0.5 mm thick, and most preferably less than 500 µm to 100 µm thick. Such films are preferably flexible with a good tensile strength (e.g., greater than 50, preferably greater than 100, and more preferably greater than 150 or 200 N/cm²), good adhesive properties (i.e., readily adheres to moist or wet surfaces), and have controlled permeability.

Within further aspects of the invention, the therapeutic compositions may be formulated for topical application. Representative examples include: ethanol; mixtures of ethanol and glycols (e.g., ethylene glycol or propylene glycol); mixtures of ethanol and isopropyl myristate or ethanol, isopropyl myristate and water (e.g., 55:5:40); mixtures of ethanol and eineol or D-limonene (with or without water); glycols (e.g., ethylene glycol or propylene glycol) and mixtures of glycols such as propylene glycol and water, phosphatidyl glycerol, dioleoylphosphatidyl glycerol, ethyldiglycol (i.e., Transcutole®), or terpinolene; mixtures of isopropyl myristate and 1-hexyl-2-pyrrolidone, N-dodecyl-2-piperidinone or 1-hexyl-2-pyrrolidone. Other excipients may also be added to the above, including for example, acids such as oleic acid and linoleic acid, and soaps such as sodium lauryl sulfate. A preferred embodiment would include buffered saline or water, antimicrobial agents (e.g., methylparaben, propylparaben), carrier polymer(s), such as celluloses (e.g., hydroxyethylcellulose) and (a) penetration or permeation enhancer(s) (e.g., ethoxydiglycol—Transcutol®, isopropyl myristate, ethylene glycol, 1-hexyl-2-pyrrolidone, D-limonene). For a more detailed description of the above, see generally, Hoelgaard et al., *J. Contr. Rel.* 2:111, 1985; Liu et al., *Pharm. Res.* 8:938, 1991; Roy et al., *J. Pharm. Sci.* 83:126, 1991; Ogiso et al., *J. Pharm. Sci.* 84:482, 1995; Sasaki et al., *J. Pharm. Sci.* 80:533, 1991; Okabe et al., *J. Contr. Rel.* 32:243, 1994; Yokomizo et al., *J. Contr. Rel.* 38:267, 1996; Yokomizo et al., *J. Contr. Rel.* 42:37, 1996; Mond et al., *J. Contr. Rel.* 33:72, 1994; Michniak et al., *J. Contr. Rel.* 32:147, 1994; Sasaki et al., *J. Pharm. Sci.* 80:533; 1991; Baker & Hadgraft, *Pharm. Res.* 12:993, 1995; Jasti et al., *AAPS Proceedings,* 1996; Lee et al., *AAPS Proceedings,* 1996; Ritschel et al., *Skin Pharmacol.* 4:235, 1991; and McDaid & Deasy, *Int. J. Pharm.* 133:71, 1996.

Within certain embodiments of the invention, the therapeutic compositions may also comprise additional ingredients such as surfactants (e.g., Pluronics such as F-127, L-122, L-92, L-81, and L-61).

Within further aspects of the present invention, polymeric carriers are provided which are adapted to contain and release a hydrophobic compound, the carrier containing the hydrophobic compound in combination with a carbohydrate, protein or polypeptide. Within certain embodiments, the polymeric carrier contains or comprises regions, pockets, or granules of one or more hydrophobic compounds. For example, within one embodiment of the invention, hydrophobic compounds may be incorporated within a matrix which contains the hydrophobic compound, followed by incorporation of the matrix within the polymeric carrier. A variety of matrices can be utilized in this regard, including for example, carbohydrates and polysaccharides such as starch, cellulose, dextran, methylcellulose, and hyaluronic acid, proteins or polypeptides such as albumin, collagen and gelatin. Within alternative embodiments, hydrophobic compounds may be contained within a hydrophobic core, and this core contained within a hydrophilic shell.

Other carriers that may likewise be utilized to contain and deliver the therapeutic agents described herein include: hydroxypropyl β cyclodextrin (Cserhati and Hollo, *Int. J. Pharm.* 108:69–75, 1994), liposomes (see e.g., Sharma et al., *Cancer Res.* 53:5877–5881, 1993; Sharma and Straubinger, *Pharm. Res.* 11(60):889–896, 1994; WO 93/18751; U.S. Pat. No. 5,242,073), liposome/gel (WO 94/26254), nanocapsules (Bartoli et al., *J. Microencapsulation* 7(2):191–197, 1990), micelles (Alkan-Onyuksel et al., *Pharm. Res.* 11(2):206–212, 1994), implants (Jampel et al., *Invest. Ophthalm. Vis. Science* 34(11):3076–3083, 1993; Walter et al., *Cancer Res.* 54:22017–2212, 1994), nanoparticles (Violante and Lanzafame PAACR), nanoparticles—modified (U.S. Pat. No. 5,145,684), nanoparticles (surface modified) (U.S. Pat. No. 5,399,363), taxol emulsion/solution (U.S. Pat. No. 5,407,683), micelle (surfactant) (U.S. Pat. No. 5,403,858), synthetic phospholipid compounds (U.S. Pat. No. 4,534,899), gas borne dispersion (U.S. Pat. No. 5,301,664), liquid emulsions, foam, spray, gel, lotion, cream, ointment, dispersed vesicles, particles or droplets solid- or liquid-aerosols, microemulsions (U.S. Pat. No. 5,330,756), polymeric shell (nano- and micro-capsule) (U.S. Pat. No. 5,439,686), taxoid-based compositions in a surface-active agent (U.S. Pat. No. 5,438,072), emulsion (Tarr et al., *Pharm. Res.* 4: 62–165, 1987), nanospheres (Hagan et al., *Proc. Intern. Symp. Control Rel. Bioact. Mater.* 22, 1995; Kwon et al., *Pharm Res.* 12(2):192–195; Kwon et al., *Pharm. Res.* 10(7):970–974; Yokoyama et al., *J. Contr. Rel.* 32:269–277, 1994; Gref et al., *Science* 263:1600–1603, 1994; Bazile et al., *J. Pharm. Sci.* 84:493–498, 1994), implants (U.S. Pat. No. 4,882,168), wraps, films and inhaled formulations.

As discussed in more detail below, therapeutic agents of the present invention, which are optionally incorporated within one of the carriers described herein to form a therapeutic composition, may be prepared and utilized to treat or prevent a wide variety of diseases.

Treatment or Prevention of Inflammatory Diseases

As noted above, the present invention provides methods for treating or preventing a wide variety of inflammatory diseases, comprising the step of administering to a patient an anti-microtubule agent. Representative examples of inflammatory diseases that may be treated include, for example, atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis, irritant dermatitis, allergic dermatitis), periodontal disease (i.e., periodontitis), polycystic kidney disease and type I diabetes.

Other examples of inflammatory diseases include vasculitis (e.g. Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

In order to further the understanding of such diseases, representative inflammatory diseases are discussed in more detail below.

1. Inflammatory Skin Diseases (e.g. Psoriasis and Eczema)

Utilizing the agents, compositions and methods provided herein, a wide variety of inflammatory skin diseases can be readily treated or prevented. For example, within one embodiment of the invention an inflammatory skin disease such as psoriasis or eczema may be treated or prevented by delivering to a site of inflammation (or a potential site of inflammation) an agent which inhibits microtubule function.

Briefly, skin cells are genetically programmed to follow two possible programs—normal growth or wound healing. In the normal growth pattern, skin cells are created in the basal cell layer and then move up through the epidermis to the skin surface. Dead cells are shed from healthy skin at the same rate new cells are created. The turnover time (i.e., time from cell birth to death) for normal skin cells is approximately 28 days. During wound healing, accelerated growth and repair is triggered resulting in rapid turnover of skin cells (to replace and repair the wound), increased blood supply (to meet the increased metabolic needs associated with growth) and localized inflammation.

In many respects, psoriasis is similar to an exaggerated wound healing process. Skin cells (called "keratinocytes") are created and pushed to the skin surface in as little as 2–4 days. The surface skin cannot shed the dead cells fast enough and excessive keratinocytes build up to form elevated, scaly lesions. This growth is supported by new blood vessels in the dermis (the support tissue beneath the epidermis) established to provide the nutrients necessary to support the hyperproliferating keratinocytes. At the same time, lymphocytes, neutrophils and macrophage invade the tissue, creating inflammation, swelling and soreness, and potentially producing growth factors which augment the rapid proliferation of the keratinocytes. All these cells (keratinocytes, vascular endothelial cells and white blood cells) produce tissue degrading enzymes or proteinases that aid in the progression of the disease and the destruction of surrounding tissue.

Utilizing the compositions provided above, inflammatory skin lesions may be readily treated. In particular, the anti-microtubule agent is administered directly to the site of inflammation (or a potential site of inflammation), in order to treat or prevent the disease. Suitable anti-microtubule agents are discussed in detail above, and include for example, taxanes (e.g., paclitaxel and docetaxel), campothecin, eleutherobin, sarcodictyins, epothilones A and B, discodermolide, deuterium oxide ($D_2O$), hexylene glycol (2-methyl-2,4-pentanediol), tubercidin(7-deazaadenosine), LY290181 (2-amino-4(3-pyridyl)-4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g. poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-MAP-115), cellular entities (e.g., histone H1, myelin basic protein and kinetochores), endogenous microtubular structures (e.g. axonemal structures, plugs and GTP caps), stable tubule only polypeptide (e.g. STOP145 and STOP220) and tension from mitotic forces, as well as any analogues and derivatives of any of the above. Within certain embodiments, the anti-microtubule agent is an agent other than a paclitaxel, campothecin, or an epothilone. Such agents may, within certain embodiments, be delivered as a composition along with a polymeric carrier, or in a liposome, cream or ointment formulation as discussed in more detail both above and below. Within preferred embodiments of the invention, the agents or compositions are delivered either topically, or by subcutaneous administration.

An effective anti-microtubule therapy for psoriasis will achieve at least one of the following: decrease the number and severity of skin lesions, decrease the frequency or duration of active disease exacerbations, increase the amount of time spent in remission (i.e., periods when the patient is symptom-free) and/or decrease the severity or duration of associated symptoms (e.g., joint pain and swelling, axial skeletal pain, bowel symptoms).

Clinically the treatment will result in a reduction in the size or number of skin lesions, diminution of cutaneous symptoms (pain, burning and bleeding of the affected skin) and/or a reduction in associated symptoms (e.g., joint redness, heat, swelling, diarrhea, abdominal pain). Pathologically an anti-microtubule agent will produce at least one of the following: inhibition of keratinocyte proliferation, reduction of skin inflammation (for example, by impacting on: attraction and growth factors, antigen presentation, production of reactive oxygen species and matrix metalloproteinases), and inhibition of dermal angiogenesis.

The anti-microtubule agent can be administered in any manner sufficient to achieve the above end points, but preferred methods include topical and systemic administration. Patients with localized disease can be administered a topical paclitaxel cream, ointment or emollient applied directly to the psoriatic lesions. For example, a topical cream containing 0.001% to 10% paclitaxel by weight can be administered depending upon severity of the disease and the patient's response to treatment: In a preferred embodiment, a topical preparation containing paclitaxel at 0.01% to 1% by weight would be administered to psoriatic lesions. Alternatively, direct intracutaneous injection of paclitaxel in a suitable pharmaceutical vehicle can be used for the management of individual lesions.

In patients with widespread disease or extracutaneous symptoms (e.g., psoriatic arthritis, Reiter's syndrome, associated spondylitis, associated inflammatory bowel disease) systemic paclitaxel treatment can be administered. For example, intermittent treatments with an intravenous paclitaxel formulation can be administered at a dose of 10 to 75 mg/m$^2$ depending upon therapeutic response and patient tolerance; an equivalent oral preparation would also be suitable for this indication. Other anti-microtubule agents would be administered at "paclitaxel equivalent" doses adjusted for potency and tolerability of the agent.

Other conditions can also benefit from topical anti-microtubule agents including: eczematous disease (atopic dermatitis, contact dermatitis, eczema), immunobullous disease, pre-malignant epithelial tumors, basal cell carcinoma, squamous cell carcinoma, keratocanthoma, malignant melanoma and viral warts. Topical creams, ointments, and emollients containing 0.001% to 10% paclitaxel by weight can be suitable for the management of these conditions.

2. Chronic Inflammatory Neurological Disorders (e.g., Multiple Sclerosis)

Within other aspects of the invention, anti-microtubule agents may be utilized to treat or prevent chronic inflammatory neurological disorders, such as multiple sclerosis. Briefly, multiple sclerosis (MS) is a devastating demyelinating disease of the human central nervous system. Although its etiology and pathogenesis is not known, genetic, immunological and environmental factors are believed to play a role. In the course of the disease, there is a progressive demyelination in the brain of MS patients resulting in the loss of motor function. Although the exact mechanisms involved in the loss of myelin are not understood, there is an increase in astrocyte proliferation and accumulation in the areas of myelin destruction. At these sites, there is macrophage-like activity and increased protease activity which is at least partially responsible for degradation of the myelin sheath.

The anti-microtubule agent can be administered to the site of inflammation (or a potential site of inflammation), in order to treat or prevent the disease. Suitable anti-microtubule agents are discussed in detail above, and include for example, taxanes (e.g., paclitaxel and docetaxel), campothecin, eleutherobin, sarcodictyins, epothilones A and B, discodermolide, deuterium oxide ($D_2O$), hexylene glycol (2-methyl-2,4-pentanediol), tubercidin(7-deazaadenosine), LY290181 (2-amino-4-(3-pyridyl)-4H-naphtho(1,2-b) pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g. poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1$\alpha$) and E-MAP-115), cellular entities (e.g., histone H1, myelin basic protein and kinetochores), endogenous microtubular structures (e.g. axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within certain embodiments of the invention, the agents or compositions may be administered orally, intravenously, or by direct administration (preferably with ultrasound, CT, fluoroscopic, MRI or endoscopic guidance) to the disease site.

An effective anti-microtubule therapy; for multiple sclerosis will accomplish one or more of the following: decrease the severity of symptoms; decrease the duration of disease exacerbations; increase the frequency and duration of disease remission/symptom-free periods; prevent fixed impairment and disability; and/or prevent/attenuate chronic progression of the disease. Clinically, this would result in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically the treatment reduces one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

The anti-microtubule agent can be administered in any manner sufficient to achieve the above endpoints. However, preferred methods of administration include intravenous, oral, or subcutaneous, intramuscular or intrathecal injection. The anti-microtubule agent can be administered as a chronic low dose therapy to prevent disease progression, prolong disease remission, or decrease symptoms in active disease. Alternatively, the therapeutic agent can be administered in higher doses as a "pulse" therapy to induce remission in acutely active disease. The minimum dose capable of achieving these endpoints can be used and can vary according to patient, severity of disease, formulation of the administered agent, and route of administration. For example, for paclitaxel, preferred embodiments include 10 to 75 mg/m$^2$ once every 1 to 4 weeks, 10 to 75 mg/m$^2$ daily, as tolerated, or 10 to 175 mg/m$^2$ once weekly, as tolerated or until symptoms subside. Other anti-microtubule agents can be administered at equivalent doses adjusted for the potency and tolerability of the agent.

3. Arthritis

Inflammatory arthritis is a serious health problem in developed countries, particularly given the increasing number of aged individuals. For example, one form of inflammatory arthritis, rheumatoid arthritis (RA) is a multisystem chronic, relapsing, inflammatory disease of unknown cause. Although many organs can be affected, RA is basically a severe form of chronic synovitis that sometimes leads to destruction and ankylosis of affected joints (*Robbins Pathological Basis of Disease,* by R. S. Cotran, V. Kumar, and S. L. Robbins, W. B. Saunders Co., 1989). Pathologically the disease is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and eventually the pannus grows to fill the joint space. The pannus develops an extensive network of new blood vessels through the process of angiogenesis which is essential to the evolution of the synovitis. Release of digestive enzymes (matrix metalloproteinases (e.g., collagenase, stromelysin)) and other mediators of the inflammatory process (e.g., hydrogen peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint.

It is generally believed, but not conclusively proven, that RA is an autoimmune disease, and that many different arthrogenic stimuli activate the immune response in the immunogenetically susceptible host. Both exogenous infectious agents (Ebstein-Barr virus, rubella virus, cytomegalovirus, herpes virus, human T-cell lymphotropic virus, Mycoplasma, and others) and endogenous proteins (collagen, proteoglycans, altered immunoglobulins) have been implicated as the causative agent which triggers an inappropriate host immune response. Regardless of the inciting agent, autoimmunity plays a role in the progression of the disease. In particular, the relevant antigen is ingested by antigen-presenting cells (macrophages or dendritic cells in the synovial membrane), processed, and presented to T lymphocytes. The T cells initiate a cellular immune response and stimulate the proliferation and differentiation of B lymphocytes into plasma cells. The end result is the production of an excessive inappropriate immune response directed against the host tissues (e.g. antibodies directed against type II collagen, antibodies directed against the Fc portion of autologous IgG (called "Rheumatoid Factor")). This further amplifies the immune response and hastens the destruction of the cartilage tissue. Once this cascade is initiated numerous mediators of cartilage destruction are responsible for the progression of rheumatoid arthritis.

Thus, within one aspect of the present invention, methods are provided for treating or preventing inflammatory arthritis (e.g., rheumatoid arthritis) comprising the step of administering to a patient a therapeutically effective amount of an anti-microtubule agent. Inflammatory arthritis includes a variety of conditions including, but not limited to, rheumatoid arthritis, systemic lupus erythematosus, systemic sclerosis (scleroderma), mixed connective tissue disease, Sjögren's syndrome, ankylosing spondylitis, Behcet's syndrome, sarcoidosis, and osteoarthritis—all of which feature inflamed, painful joints as a prominent symptom. Within a preferred embodiment of the invention, anti-microtubule agents may be administered directly to a joint by intra-articular injection, as a surgical paste, or administered by another route, e.g., systemically or orally.

Suitable anti-microtubule agents are discussed in detail above, and include for example, taxanes (e.g., paclitaxel and docetaxel), campothecin, eleutherobin, sarcodictyins, epothilones A and B, discodermolide, deuterium oxide ($D_2O$), hexylene gylcol(2-methyl-2,4-pentanediol), tubercidin(7-deazaadenosine), LY290181 (2-amino-4-(3-pyridyl)4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g. poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within certain embodiments, the anti-microtubule agent is an agent other than a paclitaxel, campothecin, or an epothilone.

An effective anti-microtubule therapy for inflammatory arthritis will accomplish one or more of the following: (i) decrease the severity of symptoms (pain, swelling and tenderness of affected joints; morning stiffness, weakness, fatigue, anorexia, weight loss); (ii) decrease the severity of clinical signs of the disease (thickening of the joint capsule, synovial hypertrophy, joint effusion, soft tissue contractures, decreased range of motion, ankylosis and fixed joint deformity); (iii) decrease the extra-articular manifestations of the disease (rheumatic nodules, vasculitis, pulmonary nodules, interstitial fibrosis, pericarditis, episcleritis, iritis, Felty's syndrome, osteoporosis); (iv) increase the frequency and duration of disease remission/symptom-free periods; (v) prevent fixed impairment and disability; and/or (vi) prevent/attenuate chronic progression of the disease. Pathologically, an effective anti-microtubule therapy for inflammatory arthritis will produce at least one of the following: (i) decrease the inflammatory response, (ii) disrupt the activity of inflammatory cytokines (such as IL-1, TNFα, FGF, VEGF), (iii) inhibit synoviocyte proliferation, (iv) block matrix metalloproteinase activity, and/or (v) inhibit angiogenesis. An anti-microtubule agent will be administered systemically (orally, intravenously, or by intramuscular or subcutaneous injection) in the minimum dose to achieve the above mentioned results. For patients with only a small number of joints affected, or with disease more prominent in a limited number of joints, the anti-microtubule agent can be directly injected (intraarticular injection) into the affected joints.

The anti-microtubule agent can be administered in any manner sufficient to achieve the above endpoints. However, preferred methods of administration include intravenous, oral, or subcutaneous, intramuscular or intra-articular injection. The anti-microtubule agent can be administered as a chronic low dose therapy to prevent disease progression, prolong disease remission, or decrease symptoms in active disease. Alternatively, the therapeutic agent can be administered in higher doses as a "pulse" therapy to induce remission in acutely active disease. The minimum dose capable of achieving these endpoints can be used and can vary according to patient, severity of disease, formulation of the administered agent, and route of administration. For example, for paclitaxel, preferred embodiments would be 10 to 75 mg/m$^2$ once every 1 to 4 weeks, 10 to 75 mg/m$^2$ daily, as tolerated, or 10 to 175 mg/m$^2$ once weekly, as tolerated or until symptoms subside. Other anti-microtubule agents can be administered at equivalent doses adjusted for the potency and tolerability of the agent.

4. Implants and Surgical or Medical Devices, Including Stents and Grafts

A variety of implants, surgical devices or stents, may be coated with or otherwise constructed to contain and/or release any of the anti-microtubule agents provided herein Representative examples include cardiovascular devices (e.g., implantable venous catheters, venous ports, tunneled venous catheters, chronic infusion lines or ports, including hepatic artery infusion catheters, pacemaker wires, implantable defibrillators); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, portosystemic shunts, shunts for ascites, peritoneal implants for drug delivery, peritoneal dialysis catheters, implantable meshes for hernias, suspensions or solid implants to prevent surgical adhesions, including meshes); genitourinary devices (e.g. uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy); ophthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to transtempanic drains); plastic surgery implants (e.g., prevention of fibrous contracture in response to gel- or saline-containing breast implants in the subpectoral or subglandular approaches or post-mastectomy, or chin implants), and orthopedic implants (e.g., cemented orthopedic prostheses).

Suitable anti-microtubule agents are discussed in detail above, and include for example, taxanes (e.g., paclitaxel and docetaxel), campothecin, eleutherobin, sarcodictyins, epothilones A and B, discodermolide, deuterium oxide ($D_2O$), hexylene gylcol(2-methyl-2,4-pentanediol), tubercidin(7-deazaadenosine), LY290181 (2-amino-4-(3-pyridyl)-4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (NBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g. poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within certain embodiments (e.g. in the case of stents), the anti-microtubule agent is an agent other than a paclitaxel, campothecin, or an epothilone.

Implants and other surgical or medical devices may be coated with (or otherwise adapted to release) anti-microtubule compositions or anti-microtubule factors of the present invention in a variety of manners, including for example: (a) by directly affixing to the implant or device an anti-microtubule agent or composition (e.g. by either spraying the implant or device with a polymer/drug film, or by dipping the implant or device into a polymer/drug solution, or by other covalent or noncovalent means); (b) by coating the implant or device with a substance such as a hydrogel which will in turn absorb the anti-microtubule composition (or anti-microtubule factor above); (c) by interweaving anti-microtubule composition coated thread (or the polymer itself formed into a thread) into the implant or device; (d) by inserting the implant or device into a sleeve or mesh which is comprised of or coated with an anti-microtubule composition; (e) constructing the implant or device itself with an anti-microtubule agent or composition; or (f) by otherwise adapting the implant or device to release the anti-microtubule agent. Within preferred embodiments of the invention, the composition should firmly adhere to the implant or device during storage and at the time of insertion. The anti-microtubule agent or composition should also preferably not degrade during storage, prior to insertion, or when warmed to body temperature after insertion inside the body (if this is required). In addition, it should preferably coat the implant or device smoothly and evenly, with a uniform distribution of anti-microtubule agent, while not changing the stent contour. Within preferred embodiments of the invention, the anti-microtubule agent or composition should provide a uniform, predictable, prolonged release of the anti-microtubule factor into the tissue surrounding the implant or device once it has been deployed. For vascular stents, in addition to the above properties, the composition should not render the stent thrombogenic (causing blood clots to form), or en cause significant turbulence in blood flow (more than the stent itself would be expected to cause if it was uncoated).

In the case of stents, a wide variety of stents may be developed to contain and/or release the anti-microtubule agents provided herein, including esophageal stents, gastrointestinal stents, vascular stents, biliary stents, colonic stents, pancreatic stents, ureteric and urethral stents, lacrimal stents, Eustachian tube stents, fallopian tube stents, nasal stents, sinus stents and tracheal/bronchial stents. Stents may be readily obtained from commercial sources, or constructed in accordance with well-known techniques. Representative examples of stents include those described in U.S. Pat. No. 4,768,523, entitled "Hydrogel Adhesive"; U.S. Pat. No. 4,776,337, entitled "Expandable Intraluminal Graft, and Method and Apparatus for Implanting and Expandable Intraluminal Graft"; U.S. Pat. No. 5,041,126 entitled "Endovascular Stent and Delivery System"; U.S. Pat. No. 5,052, 998 entitled "Indwelling Stent and Method of Use"; U.S. Pat. No. 5,064,435 entitled "Self-Expanding Prosthesis Having Stable Axial Length"; U.S. Pat. No. 5,089,606, entitled "Water-insoluble Polysaccharide Hydrogel Foam for Medical Applications"; U.S. Pat. No. 5,147,370, entitled "Nitinol Stent for Hollow Body Conduits"; U.S. Pat. No. 5,176,626, entitled "Indwelling Stent"; U.S. Pat. No. 5,213,580, entitled "Biodegradable Polymeric Endoluminal Sealing Process"; and U.S. Pat. No. 5,328,471, entitled "Method and Apparatus for Treatment of Focal Disease in Hollow Tubular Organs and Other Tissue Lumens."

Within other aspects of the present invention, methods are provided for expanding the lumen of a body passageway, comprising inserting a stent into the passageway, the stent having a generally tubular structure, the surface of the structure being coated with (or otherwise adapted to release) an anti-microtubule composition (or, an anti-microtubule factor alone), such that the passageway is expanded. A variety of embodiments are described below wherein the lumen of a body passageway is expanded in order to eliminate a biliary, gastrointestinal, esophageal, tracheal/bronchial, urethral or vascular obstruction.

Generally, stents are inserted in a similar fashion regardless of the site or the disease being treated. Briefly, a preinsertion examination, usually a diagnostic imaging procedure, endoscopy, or direct visualization at the time of surgery, is generally first performed in order to determine the appropriate positioning for stent insertion. A guidewire is then advanced through the lesion or proposed site of insertion, and over this is passed a delivery catheter which allows a stent in its collapsed form to be inserted. Typically, stents are capable of being compressed, so that they can be inserted through tiny cavities via small catheters, and then expanded to a larger diameter once they are at the desired location. Once expanded, the stent physically forces the walls of the passageway apart and holds them open. As such, they are capable of insertion via a small opening, and yet are still able to hold open a large diameter cavity or passageway. The stent may be self-expanding (e.g., the Wallstent and Gianturco stents), balloon expandable (e.g., the Palmaz stent and Strecker stent), or implanted by a change in temperature (e.g., the Nitinol stent).

Stents are typically maneuvered into place under radiologic or direct visual control, taking particular care to place the stent precisely across the narrowing in the organ being treated. The delivery catheter is then removed, leaving the stent standing on its own as a scaffold. A post-insertion examination, usually an x-ray, is often utilized to confirm appropriate positioning.

Within a preferred embodiment of the invention, methods are provided for eliminating biliary obstructions, comprising inserting a biliary stent into a biliary passageway, the stent having a generally tubular structure, the surface of the structure being coated with (or otherwise adapted to release) an agent or composition as described above, such that the biliary obstruction is eliminated. Briefly, tumor overgrowth of the common bile duct results in progressive cholestatic jaundice which is incompatible with life. Generally, the biliary system which drains bile from the liver into the duodenum is most often obstructed by (1) a tumor composed of bile duct cells (cholangiocarcinoma), (2) a tumor which invades the bile duct (e.g., pancreatic carcinoma), or (3) a tumor which exerts extrinsic pressure and compresses the bile duct (e.g., enlarged lymph nodes).

Both primary biliary tumors, as well as other tumors which cause compression of the biliary tree may be treated utilizing the stents described herein. One example of primary biliary tumors are adenocarcinomas (which are also called Klatskin tumors when found at the bifurcation of the common hepatic duct). These tumors are also referred to as biliary carcinomas, choledocholangiocarcinomas, or adenocarcinomas of the biliary system. Benign tumors which affect the bile duct (e.g. adenoma of the biliary system), and, in rare cases, squamous cell carcinomas of the bile duct and adenocarcinomas of the gallbladder, may also cause compression of the biliary tree and therefore, result in biliary obstruction.

Compression of the biliary tree is most commonly due to tumors of the liver and pancreas which compress and therefore obstruct the ducts. Most of the tumors from the pancreas arise from cells of the pancreatic ducts. This is a highly fatal form of cancer (5% of all cancer deaths; 26,000 new cases per year in the U.S.) with an average of 6 months survival and a 1 year survival rate of only 10%. When these tumors are located in the head of the pancreas they frequently cause biliary obstruction, and this detracts significantly from the quality of life of the patient. While all types of pancreatic tumors are generally referred to as "carcinoma of the pancreas" there are histologic subtypes including: adenocarcinoma, adenosquamous carcinoma, cystadeno carcinoma, and acinar cell carcinoma Hepatic tumors, as discussed above, may also cause compression of the biliary tree, and therefore cause obstruction of the biliary ducts.

Within one embodiment of the invention, a biliary stent is first inserted into a biliary passageway in one of several ways: from the top end by inserting a needle through the abdominal wall and through the liver (a percutaneous transhepatic cholangiogram or "PTC"); from the bottom end by cannulating the bile duct through an endoscope inserted through the mouth, stomach, and duodenum (an endoscopic retrograde cholangiogram or "ERCP"); or by direct incision during a surgical procedure. A preinsertion examination, PTC, ERCP, or direct visualization at the time of surgery should generally be performed to determine the appropriate position for stent insertion. A guidewire is then advanced through the lesion, and over this a delivery catheter is passed to allow the stent to be inserted in its collapsed form. If the diagnostic exam was a PTC, the guidewire and delivery catheter is inserted via the abdominal wall, while if the original exam was an ERCP the stent may be placed via the mouth. The stent is then positioned under radiologic, endoscopic, or direct visual control taking particular care to place it precisely across the narrowing in the bile duct. The delivery catheter is then removed leaving the stent standing as a scaffolding which holds the bile duct open. A further cholangiogram may be performed to document that the stent is appropriately positioned.

Within yet another embodiment of the invention, methods are provided for eliminating esophageal obstructions, comprising inserting an esophageal stent into an esophagus, the stent having a generally tubular structure, the surface of the structure being coated with (or otherwise adapted to release) an anti-microtubule agent or composition as described above, such that the esophageal obstruction is eliminated. Briefly, the esophagus is the hollow tube which transports food and liquids from the mouth to the stomach. Cancer of the esophagus or invasion by cancer arising in adjacent organs (e.g., cancer of the stomach or lung) results in the inability to swallow food or saliva Within this embodiment, a preinsertion examination; usually a barium swallow or endoscopy should generally be performed in order to determine the appropriate position for stent insertion. A catheter or endoscope may then be positioned through the mouth, and a guidewire is advanced through the blockage. A stent delivery catheter is passed over the guidewire under radiologic or endoscopic control, and a stent is placed precisely across the narrowing in the esophagus. A post-insertion examination, usually a barium swallow x-ray, may be utilized to confirm appropriate positioning.

Within yet another embodiment of the invention, methods are provided for eliminating colonic obstructions, comprising inserting a colonic stent into a colon, the stent having a generally tubular structure, the surface of the structure being coated with (or otherwise adapted to release) an anti-microtubule agent or composition as described above, such that the colonic obstruction is eliminated. Briefly, the colon is the hollow tube which transports digested food and waste materials from the small intestines to the anus. Cancer of the rectum and/or colon or invasion by cancer arising in adjacent organs (e.g., cancer of the uterus, ovary, bladder) results in the inability to eliminate feces from the bowel. Within this embodiment, a preinsertion examination, usually a barium enema or colonoscopy should generally be performed in order to determine the appropriate position for stent insertion. A catheter or endoscope may then be positioned through the anus, and a guidewire is advanced through the blockage. A stent delivery catheter is passed over the guidewire under radiologic or endoscopic control, and a stent is placed precisely across the narrowing in the colon or rectum. A post-insertion examination, usually a barium enema x-ray, may be utilized to confirm appropriate positioning.

Within other embodiments of the invention, methods are provided for eliminating tracheal/bronchial obstructions, comprising inserting a tracheal/bronchial stent into the trachea or bronchi, the stent having a generally tubular structure, the surface of which is coated with (or otherwise adapted to release) an anti-microtubule agent or composition as described above, such that the tracheal/bronchial obstruction is eliminated. Briefly, the trachea and bronchi are tubes which carry air from the mouth and nose to the lungs. Blockage of the trachea by cancer, invasion by cancer arising in adjacent organs (e.g., cancer of the lung), or collapse of the trachea or bronchi due to chondromalacia (weakening of the cartilage rings) results in inability to breathe. Within this embodiment of the invention, preinsertion examination, usually an endoscopy, should generally be performed in order to determine the appropriate position for stent insertion. A catheter or endoscope is then positioned through the mouth, and a guidewire advanced through the blockage. A delivery catheter is then passed over the guidewire in order to allow a collapsed stent to be inserted The stent is placed under radiologic or endoscopic control in order to place it precisely across the narrowing. The delivery catheter may then be removed leaving the stent standing as a scaffold on its own. A post-insertion examination, usually a bronchoscopy may be utilized to confirm appropriate positioning.

Within another embodiment of the invention, methods are provided for eliminating urethral obstructions, comprising inserting a urethral stent into a urethra, the stent having a generally tubular structure, the surface of the structure being coated with (or otherwise adapted to release) an anti-microtubule agent or composition as described above, such that the urethral obstruction is eliminated. Briefly, the urethra is the tube which drains the bladder through the penis. Extrinsic narrowing of the urethra as it passes through the prostate, due to hypertrophy of the prostate, occurs in virtually every man over the age of 60 and causes progressive difficulty with urination. Within this embodiment, a preinsertion examination, usually an endoscopy or urethrogram should generally first be performed in order to determine the appropriate position for stent insertion, which is above the external urinary sphincter at the lower end, and close to flush with the bladder neck at the upper end. An endoscope or catheter is then positioned through the penile opening and a guidewire advanced into the bladder. A delivery catheter is then passed over the guidewire in order to allow stent insertion. The delivery catheter is then removed, and the stent expanded into place. A post-insertion examination, usually endoscopy or retrograde urethrogram, may be utilized to confirm appropriate position.

Within another embodiment of the invention, methods are provided for eliminating vascular obstructions, comprising inserting a vascular stent into a blood vessel, the stent having a generally tubular structure, the surface of the structure being coated with (or otherwise adapted to release) an anti-microtubule agent or composition as described above, such that the vascular obstruction is eliminated. Briefly, stents may be placed in a wide array of blood vessels, both arteries and veins, to prevent recurrent stenosis at the site of failed angioplasties, to treat narrowings that would likely fail if treated with angioplasty, and to treat post-surgical narrowings (e.g., dialysis graft stenosis). Representative examples of suitable sites include the iliac, renal, and coronary arteries, the superior vena cava, and in dialysis grafts. Within one embodiment, angiography is first performed in order to localize the site for placement of the stent. This is typically accomplished by injecting radiopaque contrast through a catheter inserted into an artery or vein as an x-ray is taken. A catheter may then be inserted either percutaneously or by surgery into the femoral artery, brachial artery, femoral vein, or brachial vein, and advanced into the appropriate blood vessel by steering it through the vascular system under fluoroscopic guidance. A stent may then be positioned across the vascular stenosis. A post-insertion angiogram may also be utilized in order to confirm appropriate positioning.

A commonly used animal model for the study of restenosis is the rat carotid artery model in which the common carotid artery is denuded of endothelium by the intraluminal passage of a balloon catheter introduced through the external carotid artery (Clowes et al., *Lab. Invest.* 49(2) 208–215, 1983). At 2 weeks, the carotid artery is markedly narrowed due to smooth muscle cell constriction, but between 2 and 12 weeks the intimal doubles in thickness leading to a decrease in luminal size.

The anti-microtubule agent can be administered in any manner sufficient to achieve statistically significant results. The minimum dose capable of achieving such results can vary according to patient, severity of disease, formulation of the administered agent, and preferred embodiment. For example, for paclitaxel, stents can be coated with 1 $\mu$g to 1 mg of the drug, while the preferred range is 10 $\mu$g to 250 $\mu$g. Other anti-microtubule agents can be administered at equivalent doses adjusted for the potency and tolerability of the agent 5. Inflammatory Bowel Disease Utilizing the agent, compositions and methods provided herein, a wide variety of inflammatory diseases of the bowel can be treated or prevented. Inflammatory bowel disease is a general term for a group of chronic inflammatory disorders of unknown etiology involving the gastrointestinal tract. Chronic IBD is divided into 2 groups: ulcerative colitis and Crohn's disease. In Western Europe and the United States, ulcerative colitis has an incidence of 6 to 8 cases per 100,000.

While the cause of the disease remains unknown, genetic, infectious, immunological and psychological factors have all been proposed as causative. In ulcerative colitis, there is an inflammatory reaction involving the colonic mucosa leading to ulcerations of the surface. Neutrophil infiltration is common and repeated inflammatory episodes lead to fibrosis and shortening of the colon. With longstanding ulcerative colitis, the surface epithelium can become dysplastic and ultimately malignant. Crohn's disease is characterized by chronic inflammation extending through all layers of the intestinal wall. As the disease progresses, the bowel becomes thickened and stenosis of the lumen occurs. Ulceration of the mucosa occurs and the ulcerations can penetrate the submucosa and muscularis to form fistulae and fissures.

Anti-microtubule agents can be used to treat inflammatory bowel disease in several manners. In particular, the anti-microtubule agent can be administered to the site of inflammation (or a potential site of inflammation), in order to treat the disease. Suitable anti-microtubule agents are discussed in detail above, and include for example, taxanes (e.g. paclitaxel and docetaxel), campothecin, eleutherobin, sarcodictyins, epothilones A and B, discodermolide, deuterium oxide ($D_2O$), hexylene gylcol(2-methyl-2,4-pentanediol), tubercidin(7-deazaadenosine), LY290181 (2-amino-4-(3-pyridyl)-4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g. MAP2, MAP4, tau, big tau, ensconsin, elongation factor-1-alpha (EF-1α) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below.

The ideal model for the study of IBD should be a naturally occurring or inducible animal disease that is virtually identical to human disease. Presently, there are only two naturally occurring models, both in primate species, of intestinal inflammation in which no causal organism has been found. The first, the cotton-top tamarin, has a high prevalence of spontaneous colitis not associated with identifiable pathogens and, as in humans, the activity of the disease process spontaneously waxes and wanes (Madara et al, *Gastroenterology* 88:13–19, 1985). Another spontaneous chronic colitis also occurs in juvenile rhesus macaques (Adler et al., *Gastroenterology* 98:A436, 1990). There are many experimentally induced colitis animal models. In mice, rats, guinea pigs and rabbits, colitis can be induced by oral administration of sulfated polysaccarides (carrageenan amylopectin sulfate, dextran sulfate) (Marcus and Watt, *Lancet* 2:489–490, 1969), rectal injection of chemical irritants (diluted acetic acid) (MacPherson and Pfeiffer, *Digestion* 17:135–150, 1978) and delayed hypersensitivity reaction to dinitrochlorobenzene (Glick and Falchuk., *Gut* 22:120–125, 1981) or trinitrobenzene sulfonic acid (Rabin and Rogers, *Gastroenterology* 75:29–33, 1978).

As there are no pathogenomic features or specific diagnostic tests for IBD, effectiveness of an anti-microtubule agent in the management of the disease is determined clinically. An effective anti-microtubule therapy for IBD will achieve at least on of the following: decrease the frequency of attacks, increase the amount of time spent in remission (i.e., periods when the patient is symptom-free) and/or decrease the severity or duration of associated manifestations (abscess formation, fistula formation, colon cancer, intestinal perforation, intestinal obstruction, toxic megacolon, peripheral arthritis, ankylosing spondylitis, cholelithiasis, sclerosing cholangitis, cirrhosis, erythema nodosum, iritis, uveitis, episcleritis, venous thrombosis). Specifically symptoms such as bloody diarrhea, abdominal pain, fever, weight loss, rectal bleeding, tenesmus and abdominal distension will be reduced or alleviated.

The anti-microtubule agent can be administered in any manner sufficient to achieve a statistically significant improved clinical result. Nevertheless, preferred methods include oral, rectal or peritubular administration (preferably with ultrasound, CT, fluoroscopic, MRI or endoscopic guidance; this can also be accomplished by direct administration at the time of abdominal surgery). In some patients, intravenous, subcutaneous or intramuscular injection of the agent can also be used to treat the disease. In patients with widespread or extraintestinal symptoms, systemic treatment (e.g., oral, intravenous, subcutaneous, intramuscular injection) is appropriate. In preferred embodiments, paclitaxel can be administered orally at a dose of 10 to 75 $mg/m^2$ every 1 to 4 weeks, 10 to 75 $mg/m^2$ daily or 10 to 175 $mg/m^2$ weekly, depending upon therapeutic response and patient tolerance. To treat severe acute exacerbations, higher doses given orally (or intravenously) of 50 to 250 $mg/m^2$ of paclitaxel can be administered as a "pulse" therapy. In patients with localized rectal disease (the rectum is involved in 95% of ulcerative colitis patients), topical paclitaxel can be administered as a rectal cream or suppository. For example, a topical cream containing 0.001% to 10% paclitaxel by weight can be administered depending upon severity of the disease and the patient's response to treatment. In a preferred embodiment, a topical preparation containing 0.01% to 1% paclitaxel by weight could be administered per rectum daily as needed. Peritubular paclitaxel (i.e., administration of the drug to the outer or mesenteric surface of the bowel) can be administered to regions of the bowel with active disease. In a preferred embodiment, 0.5% to 20% paclitaxel by weight is loaded into a polymeric carrier (as described in the examples) and applied to the mesenteric surface as a "paste", "film" or "wrap" which releases the drug over a period of time. In all of the embodiments, other anti-microtubule agents would be administered at equivalent doses adjusted for potency and tolerability of the agent.

6. Surgical Procedures

As noted above, anti-microtubule agents and compositions may be utilized in a wide variety of surgical procedures. For example, within one aspect of the present invention an anti-microtubule agent or composition (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, anti-microtubule agents or compositions (e.g. in the form of a spray) may be delivered via endoscopic procedures in order to coat tumors, or inhibit disease in a desired locale. Within yet other aspects of the present invention, surgical meshes which have been coated with or adapted to release anti-microtubule agents or compositions of the present invention may be utilized in any procedure wherein a surgical mesh might be utilized. For example, within one embodiment of the invention a surgical mesh laden with an anti-microtubule composition may be utilized during abdominal cancer resection surgery (e.g., subsequent to colon resection) in order to provide support to the structure, and to release an amount of the anti-microtubule factor.

Within further aspects of the present invention, methods are provided for treating tumor excision sites, comprising administering an anti-microtubule agent or composition as described above to the resection margins of a tumor subsequent to excision, such that the local recurrence of cancer at the site is inhibited. Within one embodiment of the invention, the anti-microtubule composition(s) (or anti-microtubule factor(s) alone) are administered directly to the tumor excision site (e.g. applied by swabbing, brushing or otherwise coating the resection margins of the tumor with the anti-microtubule composition(s) or factor(s)). Alternatively, the anti-microtubule composition(s) or factor(s) may be incorporated into known surgical pastes prior to administration. Within particularly preferred embodiments of the invention, the anti-microtubule compositions are applied after partial mastectomy for malignancy, and after neurosurgical operations.

Within one aspect of the present invention, anti-microtubule agent or composition (as described above) may be administered to the resection margin of a wide variety of tumors, including for example, breast, head and neck tumors, colon, brain and hepatic tumors. For example, within one embodiment of the invention, anti-microtubule agents or compositions may be administered to the site of a neurological tumor subsequent to excision, such that recurrence of the tumor is inhibited. Briefly, the brain is highly functionally localized; i.e., each specific anatomical region is specialized to carry out a specific function. Therefore it is the location of brain pathology that is often more important than the type. A relatively small lesion in a key area can be far more devastating than a much larger lesion in a less important area Similarly, a lesion on the surface of the brain may be easy to resect surgically, while the same tumor located deep in the brain may not (one would have to cut through too many vital structures to reach it). Also, even benign tumors can be dangerous for several reasons: they may grow in a key area and cause significant damage; even though they would be cured by surgical resection this may not be possible; and finally, if left unchecked they can cause increased intracranial pressure. The skull is an enclosed space incapable of expansion. Therefore, if something is growing in one location, something else must be being compressed in another location—the result is increased pressure in the skull or increased intracranial pressure. If such a condition is left untreated, vital structures can be compressed, resulting in death. The incidence of central nervous system (CNS) malignancies is 8–16 per 100,000. The prognosis of primary malignancy of the brain is dismal, with a median survival of less than one year, even following surgical resection. These tumors, especially gliomas, are predominantly a local disease which recur within 2 centimeters of the original focus of disease after surgical removal.

Representative examples of brain tumors which may be treated utilizing the agents, compositions and methods described herein include glial tumors (such as anaplastic astrocytoma, glioblastoma multiform, pilocytic astrocytoma, oligodendroglioma, ependymoma, myxopapillary ependymoma, subependymoma, choroid plexus papilloma); neuron tumors (e.g., neuroblastoma, ganglioneuroblastoma, ganglioneuroma, and medulloblastoma); pineal gland tumors (e.g. pineoblastoma and pineocytoma); menigeal tumors (e.g., meningioma, meningeal hemangiopericytoma, meningeal sarcoma); tumors of nerve sheath cells (e.g., schwanoma (neurolemoma) and neurofibroma); lymphomas (e.g., Hodgkin's and non-Hodgkin's lymphoma (including numerous subtypes, both primary and secondary); malformative tumors (e.g., craniopharyngioma, epidermoid cysts, dermoid cysts and colloid cysts); and metastatic tumors (which can be derived from virtually any tumor, the most common being from lung, breast, melanoma, kidney, and gastrointestinal tract tumors).

Suitable anti-microtubule agents are discussed in detail above, and include for example, taxanes (e.g., paclitaxel and docetaxel), campothecin, eleutherobin, sarcodictyins, epothilones A and B, discodermolide, deuterium oxide ($D_2O$), hexylene gylcol(2-methyl-2,4-pentanediol), tubercidin(7-deazaadenosine), LY290181 (2-amino-4-(3-pyridyl)-4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g. poly-L-lysine and extensin), glycerol buffers, Triton X-100 microtubule stabilizing buffer, microtubule associated proteins (e.g. MAP2, MAP4, tau, big tau, ensconsin, elongation factor-1-alpha (EF-1α) and E-MAP-115), cellular entities (e.g. histone H1, myelin basic protein and kinetochores), endogenous microtubular structures (e.g. axonemal structures, plugs and GTP caps), stable tubule only polypeptide (e.g. STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within certain embodiments, the anti-microtubule agent is an agent other than a paclitaxel, campothecin, or an epothilone.

The anti-microtubule agent can be administered in any manner sufficient to achieve a statistically significant improved clinical result. Nevertheless, representative suitable methods include oral, rectal or peritubular administration (preferably with ultrasound, CT, fluoroscopic, MRI or endoscopic guidance; this can also be accomplished by direct administration at the time of abdominal surgery). In some patients, intravenous, subcutaneous or intramuscular injection of the agent can also be used to treat the disease. In patients who have undergone substantial surgical procedures, systemic treatment (e.g., oral, intravenous, subcutaneous, intramuscular injection) is appropriate. In preferred embodiments, paclitaxel can be administered orally at a dose of 10 to 75 mg/m$^2$ every 1 to 4 weeks, 10 to 75 mg/m$^2$ daily or 10 to 175 mg/m$^2$ weekly, depending upon therapeutic response and patient tolerance. To treat severe cases, higher doses given orally (or intravenously) of 50 to 250 mg/m$^2$ of paclitaxel can be administered as a "pulse" therapy. In patients undergoing localized topical surgical procedures, topical paclitaxel can be administered as a cream or ointment. For example, a topical cream containing 0.001% to 10% paclitaxel by weight can be administered depending upon the nature of the surgery and the patient's response to treatment. Direct administration of paclitaxel (i.e., administration of the drug to the outer or inner surface of vessel, organ, or other tissue or group of cells) can be accomplished directly to a vessel, organ, or site of surgery. In a one embodiment, 0.5% to 20% paclitaxel by weight is loaded into a polymeric carrier (as described in the examples) and applied to the mesenteric surface as a "paste", "film" or "wrap" which releases the drug over a period of time. In all of the embodiments, other anti-microtubule agents would be administered at equivalent doses adjusted for potency and tolerability of the agent.

7. Surgical Adhesions

Within other aspects of the invention, methods are provided for treating and/or preventing surgical adhesions by administering to the patient an anti-microtubule agent. Briefly, surgical adhesion formation is a complex process in which bodily tissues that are normally separate grow together. These post-operative adhesions occur in 60% to 90% of patients undergoing major gynecological surgery. Surgical trauma, as a result of tissue drying, ischemia, thermal injury, infection or the presence of a foreign body, has long been recognized as a stimulus for tissue adhesion formation. These adhesions are a major cause of failed surgical therapy and are the leading cause of bowel obstruction and infertility. Other adhesion-treated complications include chronic pelvic pain, urethral obstruction and voiding dysfunction.

Generally, adhesion formation is an inflammatory reaction in which factors are released, increasing vascular permeability and resulting in fibrinogen influx and fibrin deposition. This deposition forms a matrix that bridges the abutting tissues. Fibroblasts accumulate, attach to the matrix, deposit collagen and induce angiogenesis. If this cascade of events can be prevented within 4 to 5 days following surgery, then adhesion formation will be inhibited.

Thus, as noted above, the present invention provides methods for treating and/or preventing surgical adhesions. A wide variety of animal models may be utilized in order to assess a particular therapeutic composition or treatment regimen. Briefly, peritoneal adhesions occur in animals as a result of inflicted severe damage which usually involves two adjacent surfaces. Injuries may be mechanical, due to ischemia or as a result of the introduction of foreign material. Mechanical injuries include crushing of the bowel (Choate et al., *Arch. Surg.* 88:249–254, 1964) and stripping or scrubbing away the outer layers of bowel wall (Gustavsson et al., *Acta Chir. Scand.* 109:327–333, 1955). Dividing major vessels to loops of the intestine induces ischemia (James et al., *J. Path. Bact.* 90:279–287, 1965). Foreign material that may be introduced into the area includes talcum (Green et al., *Proc. Soc. Exp. Biol. Med.* 133:544–550, 1970), gauze sponges (Lehman and Boys, *Ann. Surg* 111:427435, 1940), toxic chemicals (Chancy, *Arch. Surg.* 60:1151–1153, 1950), bacteria (Moin et al., *Am. J. Med Sci.* 250:675–679, 1965) and feces (Jackson, *Surgery* 44:507–518,1958).

Presently, typical adhesion prevention models include the rabbit uterine horn model which involves the abrasion of the rabbit uterus (Linsky et al., *J. Reprod. Med.* 32(l):17–20, 1987), the rabbit uterine horn, devascularization modification model which involves abrasion and devascularization of the uterus (Wiseman et al., *J. Invest Surg.* 7:527–532, 1994) and the rabbit cecal sidewall model which involves the excision of a patch of parietal peritoneum plus the abrasion of the cecum (Wiseman and Johns, *Fertil. Steril. Suppl:* 25S, 1993).

Representative anti-microtubule agents for treating adhesions are discussed in detail above, and include taxanes (e.g., paclitaxel and docetaxel), campothecin, eleutherobin, sarcodictyins, epothilones A and B, discodermolide, deuterium oxide ($D_2O$), hexylene gylcol(2-methyl-2,4-pentanediol), tubercidin(7-deazaadenosine), LY290181 (2-amino-4-(3-pyridyl)4H-naphtho(1,2-b)pyran-3-cardonitrile), aluminum fluoride, ethylene glycol bis-(succinimidylsuccinate), glycine ethyl ester, monoclonal anti-idiotypic antibodies, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-5 MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within certain embodiments, the anti-microtubule agent is an agent other than a paclitaxel, campothecin, or an epothilone.

Utilizing the agents, compositions and methods provided herein a wide variety of surgical adhesions and complications of surgery can be treated or prevented. Adhesion formation or unwanted scar tissue accumulation/encapsulation complicates a variety of surgical procedures. As described above, surgical adhesions complicate virtually any open or endoscopic surgical procedure in the abdominal or pelvic cavity. Encapsulation of surgical implants also complicates breast reconstruction surgery, joint replacement surgery, hernia repair surgery, artificial vascular graft surgery, and neurosurgery. In each case, the implant becomes encapsulated by a fibrous connective tissue capsule which compromises or impairs the function of the surgical implant (e.g., breast implant, artificial joint, surgical mesh, vascular graft, dural patch). Chronic inflammation and scarring also occurs during surgery to correct chronic sinusitis or removal of other regions of chronic inflammation (e.g., foreign bodies, infections (fungal, mycobacterium)).

The anti-microtubule agent can be administered in any manner which achieves a statistically significant result. Preferred methods include peritubular administration (either direct application at the time of surgery or with endoscopic, ultrasound, CT, MRI, or fluoroscopic guidance); "coating" the surgical implant; and placement of a drug-eluting polymeric implant at the surgical site. In a preferred embodiment, 0.5% to 20% paclitaxel by weight is loaded into a polymeric carrier (as described in the following examples) and applied to the peritubular (mesenteric) surface as a "paste", "film", or "wrap" which releases the drug over a period of time such that the incidence of surgical adhesions is reduced. During endoscopic procedures, the paclitaxel-polymer preparation is applied as a "spray", via delivery ports in the endoscope, to the mesentery of the abdominal and pelvic organs manipulated during the operation. In a particularly preferred embodiment, the peritubular composition is 1% to 5% paclitaxel by weight. In another preferred embodiment, a polymeric coating containing 0.1% to 20% paclitaxel is applied to the surface of the surgical implant (e.g., breast implant, artificial joint, vascular graft) to prevent encapsulation/inappropriate scarring in the vicinity of the implant. In yet another preferred embodiment, a polymeric implant containing 0.1% to 20% paclitaxel by weight is applied directly to the surgical site (e.g., directly into the sinus cavity, chest cavity, abdominal cavity, or at the operative site during neurosurgery) such that recurrence of inflammation, adhesion formation, or scarring is reduced. In another embodiment, lavage fluid containing 1 to 75 mg/m$^2$ (preferably 10 to 50 mg/m$^2$) paclitaxel, would be used at the time of or immediately following surgery and administered during surgery or intraperitoneally, by a physician. In all of the embodiments, other anti-microtubule agents would be administered at equivalent doses adjusted for potency and tolerability of the agent.

8. Chronic Inflammatory Diseases of the Respiratory Tract

Within other aspects of the invention, anti-microtubule agents (and compositions) may be utilized to treat or prevent diseases such as chronic inflammatory disease of the respiratory tract. In particular, the anti-microtubule agent can be administered to the site of inflammation (or a potential site of inflammation), in order to treat the disease. Suitable anti-microtubule agents are discussed in detail above, and include for example, taxanes (e.g., paclitaxel and docetaxel), campothecin, eleutherobin, sarcodictyins, epothilones A and B, discodermolide, deuterium oxide ($D_2O$), hexylene gylcol (2-methyl-2,4-pentanediol), tubercidin(7-deazaadenosine), LY290181 (2-amino-4-(3-pyridyl)-4H-naphtho(1,2-b) pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1$\alpha$) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within preferred embodiments of the invention, the agents or compositions may be administered intranasally, systemically, by inhalation, topically (e.g., in the case of nasal polyps), or into the sinus cavities in order to achieve statistically significant clinical results.

Asthma

In certain aspects of the invention, anti-microtubule agents can by utilized to treat or prevent asthma. Briefly, asthma is a condition characterized by recurrent episodes of airway obstruction that can resolve spontaneously or in response to treatment. Although its exact etiology is not known, the condition is an exaggerated bronchoconstrictor and inflammatory response to stimuli which affects 5% of the population. An effective anti-microtubule therapy for asthma would alter one or more of the pathological features of the condition, such as decreasing inflammatory cell (T-cells, mast cells, eosinophils) infiltration and activity, reducing proliferation and thickening of the airway epithelium, inhibiting smooth muscle cell proliferation and hypertrophy in the airway wall, decreasing mucus secretion in to the airway lumen, blocking the activity of inflammatory cytokines (IL-3, IL4, IL-5, GMSF) which induce and perpetuate inflammation and inhibit hyperplasia and hypertrophy of airway secretory glands.

Clinically, an effective anti-microtubule therapy for asthma would accomplish one or more of the following endpoints: decrease the severity of symptoms, decrease the duration of exacerbations, increase the frequency and duration of disease remission periods, prevent fixed impairment and disability and prevent chronic progression of dyspnea, cough and wheezing; while improving hypoxia, $FEV_1$ (forced expiration volume in one second), resistance to airflow and hypocapnea/respiratory alkalosis and decreasing V:Q (ventilation:perfusion) mismatch.

The anti-microtubule agent can be administered in any manner sufficient to achieve the above endpoints. Preferred methods of administration include inhaled (e.g., by metered-dose inhaler, nebulizer, via an endothacheal tube, inhalation of microparticles) and systemic (intravenous, subcutaneous or intramuscular injection or oral preparation) treatments. Systemic treatment would be administered to patients with severe exacerbations or in those in which inhaled therapy was not suitable. The minimum dose capable of producing clinical or pathological improvement would be used. For example, for paclitaxel, preferred embodiments would be 10 to 75 mg/m² once every 1 to 4 weeks, 10 to 75 mg/m² daily, as tolerated, or 10 to 175 mg/m² once weekly, as tolerated or until symptoms subside. Other anti-microtubule agents can be administered at equivalent doses adjusted for the potency and tolerability of the agent. For inhaled therapy, 0.01% to 1% paclitaxel can be directly inhaled via the above mentioned delivery vehicles/formulations. This would result in delivery of 1 to 50 mg/m² of paclitaxel directly to the respiratory tract. This dose would be titrated according to response. Other anti-microtubule agents can be administered at equivalent doses adjusted for potency and tolerability of the agent.

Chronic Obstructive Pulmonary Disease (COPD)

COPD includes a variety of conditions (chronic bronchitis, asthmatic bronchitis, chronic obstructive bronchitis and emphysema) which lead to chronic airway obstruction. These conditions can cause severe disability and are the fourth leading cause of death in the U.S. Clinically, all are characterized by dyspnea, cough, wheezing and recurrent infections of the respiratory tract. Signs of the disease include a decreased $FEV_1$, increased residual volume, V:Q mismatch and hypoxemia Pathologically, there is increased mucus production, hyperplasia of mucus glands, increased protease (principally elastase) activity, inflammation of the airways and destruction of the alveolar wall. Despite a wide range of etiologies (smoking being the most common), improving any of the above symptoms, signs or pathological processes would favorably impact on the condition; an effective anti-microtubule therapy for COPD would, therefore, alter at least one of the aforementioned. Treatment with an anti-microtubule agent can be accomplished as described previously for asthma: inhaled paclitaxel would be given at 1 to 50 mg/m² repeated as required, for systemic paclitaxel therapy 10 to 50 mg/m² would be given every 1 to 4 weeks in chronic administration or 50 to 250 mg/m² given as a "pulse" in the acutely ill patient. Other anti-microtubule agents would be administered at clinically equivalent doses.

9. Stenosis, Neoplastic Diseases and Obstructions

As noted above, the present invention provides methods for treating or preventing a wide variety of diseases associated with the obstruction of body passageways, including for example, vascular diseases, neoplastic obstructions, inflammatory diseases, and infectious diseases.

For example, within one aspect of the present invention a wide variety of anti-microtubule agents and compositions as described herein may be utilized to treat vascular diseases that cause obstruction of the vascular system. Representative examples of such diseases include artherosclerosis of all vessels (around any artery, vein or graft) including, but not restricted to: the coronary arteries, aorta, iliac arteries, carotid arteries, common femoral arteries, superficial femoral arteries, popliteal arteries, and at the site of graft anastomosis; vasospasms (e.g., coronary vasospasms and Raynaud's disease); restenosis (obstruction of a vessel at the site of a previous intervention such as balloon angioplasty, bypass surgery, stent insertion and graft insertion); inflammatory and autoimmune conditions (e.g. temporal arteritis, vasculitis).

Briefly, in vascular diseases such as atherosclerosis, white cells, specifically monocytes and T lymphocytes adhere to endothelial cells, especially at locations of arterial branching. After adhering to the endothelium, leukocytes migrate across the endothelial cell lining in response to chemostatic stimuli, and accumulate in the intima of the arterial wall, along with smooth muscle cells. This initial lesion of atherosclerosis development is known as the "fatty streak". Monocytes within the fatty streak differentiate into macrophages; and the macrophages and smooth muscle cells progressively take up lipids and lipoprotein to become foam cells.

As macrophages accumulate, the overlying endothelium becomes mechanically disrupted and chemically altered by oxidized lipid, oxygen-derived free radicals and proteases which are released by macrophages. Foam cells erode through the endothelial surface causing micro-ulcerations of the vascular wall. Exposure of potentially thrombogenic subendothelial tissues (such as collagen and other proteins) to components of the bloodstream results in adherence of platelets to regions of disrupted endothelium. Platelet adherence and other events triggers the elaboration and release of growth factors into this milieu, including PDGF, platelet activating factor (PAF), IL-1 and IL-6. These paracrine factors are thought to stimulate vascular smooth muscle cell (VSMC) migration and proliferation.

In the normal (non-diseased) blood vessel wall, VSMCs have a contractile phenotype and low index of mitotic activity. However, under the influence of cytokines and growth factors released by platelets, macrophages and endothelial cells, VSMC undergo phenotypic alteration from mature contractile cells to immature secretory cells. The transformed VSMC proliferate in the media of the blood vessel wall, migrate into the intima, continue to proliferate in the intima and generate large quantities of extracellular matrix. This transforms the evolving vascular lesion into a fibrous plaque. The extracellular matrix elaborated by secretory VSMC includes collagen, elastin, glycoprotein and glycosaminoglycans, with collagen comprising the major extracellular matrix component of the atherosclerotic plaque. Elastin and glycosaminoglycans bind lipoproteins and also contribute to lesion growth. The fibrous plaque consists of a fibrous cap of dense connective tissue of varying thickness containing smooth muscle cells and overlying macrophages, T cells and extracellular material.

In addition to PDGF, IL-1 and IL-6, other mitogenic factors are produced by cells which infiltrate the vessel wall including: TGFβ; FGF, thrombospondin, serotonin, thromboxane $A_2$, norepenephrine, and angiotension II. This results in the recruitment of more cells, elaboration of further extracellular matrix and the accumulation of additional lipid. This progressively enlarges the atherosclerotic lesion until it significantly encroaches upon the vascular lumen. Initially, obstructed blood flow through the vascular tube causes ischemia of the tissues distal to the atherosclerotic plaque only when increased flow is required—later as the lesion further blocks the artery, ischemia occurs at rest.

Macrophages in the enlarging atherosclerotic plaque release oxidized lipids, free radicals, elastases, and collagenases that cause cell injury and necrosis of neighboring tissues. The lesion develops a necrotic core and is transformed into a complex plaque. Complex plaques are unstable lesions that can break off causing embolization; local hemorrhage (secondary to rupture of the vasa vasorum supplying the plaque which results in lumen obstruction due to rapid expansion of the lesion); or ulceration and fissure formation (this exposes the thrombogenic necrotic core to the blood stream producing local thrombosis or distal embolization). Even should none of the above sequela occur, the adherent thrombus may become organized and incorporated into the plaque, thereby accelerating its growth. Furthermore, as the local concentrations of fibrinogen and thrombin increase, proliferation of vascular smooth muscle cells within the media and intima is stimulated; a process which also ultimately leads to additional narrowing of the vessel.

The intima and media of normal arteries are oxygenated and supplied with nutrition from the lumen of the artery or from the vasa vasorum in the adventitia. With the development of atherosclerotic plaque, microvessels arising from the adventitial vasa vasorum extend into the thickened intima and media. This vascular network becomes more extensive as the plaque worsens and diminishes with plaque regression.

Hemorrhage from these microvessels may precipitate sudden expansion and rupture of plaque in association with arterial dissection, ulceration, or thrombosis. It has also been postulated that the leakage of plasma proteins from these microvessels may attract inflammatory infiltrates into the region and these inflammatory cells may contribute to the rapid growth of atherosclerotic plaque and to associated complications (through local edema and inflammation).

In order to treat vascular diseases, such as those discussed above, an anti-microtubule agent (either with or without a carrier) may be delivered to the external portion of the body passageway, or to smooth muscle cells via the adventia of the body passageway. Particularly preferred anti-microtubule agents in this regard, and include for example, taxanes (e.g., paclitaxel and docetaxel), campothecin, eleutherobin, sarcodictyins, epothilones A and B, discodermolide, deuterium oxide ($D_2O$), hexylene gylcol(2-methyl-2,4-pentanediol), tubercidin(7-deazaadenosine), LY290181 (2-amino-4-(3-pyridyl)-4H-naphtho(1,2-b) pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-MAP-115), cellular entities (e.g. histone H1, myelin basic protein and kinetochores), endogenous microtubular structures (e.g. axonemal structures, plugs and GTP caps), stable tubule only polypeptide (e.g., STOP145 and STOP220) and tension from mitotic forces, as well as any analogues and derivatives of any of the above. Within certain embodiments, the anti-microtubule agent is an agent other than a paclitaxel, campothecin, or an epothilone. Such agents may, within certain embodiments, be delivered as a composition along with a polymeric carrier, or in a liposome formulation as discussed in more detail both above and below. Within preferred embodiments of the invention, the agents or compositions may be administered by balloon catheter, orally, perivascularly, by stent, to systemically.

Within other aspects of the invention, the anti-microtubule therapeutic agents or compositions described herein may be utilized to treat neoplastic obstructions. Briefly, as utilized herein, a "neoplastic obstruction" should be understood to include any neoplastic (benign or malignant) obstruction of a bodily tube regardless of tube location or histological type of malignancy present. Representative examples include gastrointestinal diseases (e.g., oral-pharyngeal carcinoma adenocarcinoma, esophageal carcinoma (squamous cell, adenocarcinoma, lymphoma, melanoma), gastric carcinoma (adenocarcinoma, linitis plastica, lymphoma, leiomyosarcoma), small bowel tumors (adenomas, leiomyomas, lipomas, adenocarcinomas, lymphomas, carcinoid tumors), colon cancer (adenocarcinoma) and anorectal cancer); biliary tract diseases (e.g., neoplasms resulting in biliary obstruction such as pancreatic carcinoma (ductal adenocarcinoma, islet cell tumors, cystadenocarcinoma), cholangiocarcinoma and hepatocellular carcinoma); pulmonary diseases (e.g., carcinoma of the lung and/or tracheal/bronchial passageways (small cell lung cancer, non-small cell lung cancer)); female reproductive diseases (e.g., malignancies of the fallopian tubes, uterine cancer, cervical cancer, vaginal cancer); male reproductive diseases (e.g., testicular cancer, cancer of the epididymus, tumors of the vas deferens, prostatic cancer, benign prostatic hypertrophy); and urinary tract diseases (e.g., renal cell carcinoma, tumors of the renal pelvis, tumors of the urinary collection system such as transitional cell carcinoma, bladder carcinoma, and urethral obstructions due to benign strictures, or malignancy).

As an example, benign prostatic hyperplasia (BPH) is the enlargement of the prostate, particularly the central portion of the gland which surrounds the urethra, which occurs in response to prolonged androgenic stimulation. It affects more than 80% of the men over 50 years of age. This enlargement can result in compression of the portion of the urethra which runs through the prostate, resulting in bladder outflow tract obstruction, i.e., an abnormally high bladder pressure is required to generate urinary flow. In 1980, 367,000 transurethral resections of the prostate were performed in the United States as treatment for BPH. Other treatments include medication, transurethral sphincterotomy, transurethral laser or microwave, transurethral hyperthermia, transurethral ultrasound, transrectal microwave, transrectal hyperthermia, transrectal ultrasound and surgical removal. All have disadvantages including interruption of the sphincter mechanism resulting in incontinence and stricture formation.

In order to treat neoplastic diseases, such as those discussed above, a wide variety of therapeutic agents (either with or without a polymeric carrier) may be delivered to the external portion of the body passageway, or to smooth muscle cells via the adventia of the body passageway. For example, within one preferred embodiment a needle or catheter is guided into the prostate gland adjacent to the urethra via the transrectal route (or alternatively transperineally) under ultrasound guidance and through this deliver a therapeutic agent, preferably in several quadrants of the gland, particularly around the urethra. The needle or catheter can also be placed under direct palpation or under endoscopic, fluoroscopic, CT or MRI guidance, and administered at intervals. As an alternative, the placement of pellets via a catheter or trocar can also be accomplished. The above procedures can be accomplished alone or in conjunction with a stent placed in the prostatic urethra. By avoiding urethral instrumentation or damage to the urethra, the sphincter mechanism would be left intact, avoiding incontinence, and a stricture is less likely.

Within other aspects of the invention, methods are provided for preventing or treating inflammatory diseases which affect or cause the obstruction of a body passageway.

Inflammatory diseases include both acute and chronic inflammation which result in obstruction of a variety of body tubes. Representative examples include vasculitis (e.g., Giant cell arteritis (temporal arteritis, Takayasu's arteritis), polyarteritis nodosa, allergic angiitis and granulomatosis (Churg-Strauss disease), polyangiitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system), Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon)); respiratory tract diseases (e.g., asthma, hypersensitivity pneumonitis, asbestosis, silicosis, and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

In order to treat inflammatory diseases, such as those discussed above, an anti-microtubule agents (either with or without a carrier) may be delivered to the external portion of the body passageway, or to smooth muscle cells via the adventia of the body passageway.

Within yet other aspects of the present invention, methods are provided for treating or preventing infectious diseases that are associated with, or causative of, the obstruction of a body passageway. Briefly, infectious diseases include several acute and chronic infectious processes can result in obstruction of body passageways including for example, obstructions of the male reproductive tract (e.g., strictures due to urethritis, epididymitis, prostatitis); obstructions of the female reproductive tract (e.g., vaginitis, cervicitis, pelvic inflammatory disease (e.g., tuberculosis, gonococcus, chlamydia, enterococcus and syphilis)); urinary tract obstructions (e.g., cystitis, urethritis); respiratory tract obstructions (e.g., chronic bronchitis, tuberculosis, other mycobacterial infections (MAI, etc.), anaerobic infections, fungal infections and parasitic infections); and cardiovascular obstructions (e.g., mycotic aneurysms and infective endocarditis).

In order to treat infectious diseases, such as those discussed above, a wide variety of therapeutic agents (either with or without a carrier) may be delivered to the external portion of the body passageway, or to smooth muscle cells via the adventia of the body passageway. Particularly preferred therapeutic agents in this regard include the anti-microtubule agents discussed above.

The anti-microtubule agent can be administered in any manner sufficient to achieve a statistically significant clinical result. However, preferred methods of administration include systemic (i.e., intravenous) or local injection. The anti-microtubule agent can be administered as a chronic low dose therapy to prevent disease progression, prolong disease remission, or decrease symptoms in active disease. Alternatively, the therapeutic agent can be administered in higher doses as a "pulse" therapy to induce remission in acutely active disease. The minimum dose capable of achieving these endpoints can be used and can vary according to patient, severity of disease, formulation of the administered agent, and route of administration. For example, for paclitaxel, preferred embodiments would be 10 to 75 mg/m$^2$ once every 1 to 4 weeks, 10 to 75 mg/m$^2$ daily, as tolerated, or 10 to 175 mg/m$^2$ once weekly, as tolerated or until symptoms subside. Peritubular paclitaxel (i.e., administration of the drug to the outer or mesenteric surface of the bowel) can be administered to regions of the bowel with active disease. In a preferred embodiment, 0.5% to 20% paclitaxel by weight is loaded into a polymeric carrier (as described in the examples) and applied to the mesenteric surface as a "paste", "film" or "wrap" which releases the drug over a period of time. In all of the embodiments, other anti-microtubule agents would be administered at equivalent doses adjusted for potency and tolerability of the agent.

10. Graft Rejection

The above-described anti-microtubule agents and compositions can likewise be utilized to treat or prevent graft rejection. Briefly, the two major histological manifestations of chronic graft/organ rejection are inflammation and artherosclerosis. This neointimal hyperplasia has been observed in long-surviving renal allograts (Hume et al., *J. Clin. Invest.* 34:327, 1955; Busch et al., *Human Pathol.* 2:253, 1971) as well as cardiac (Johnson et al., *J. Heart Transplantation* 8:349, 1989), hepatic (Demetris et al., *Am. J. Pathol* 118:151, 1985) and lung grafts (Burke et al., *Lancet* I: 517: 1986). Cardiac grafts are extremely sensitive to this luminal narrowing because of the myocardial dependence on coronary blood flow.

Many animal models have been used to study chronic cardiac allograft rejection. The Lewis-F344 rat cardiac transplantation model produces cardiac allografts with chronic rejection characterized by arteriosclerotic lesion formation. This model is useful because over 80% of recipients survive for more than 3 weeks, with 90% of these exhibiting coronary intimal lesions (Adams et al., *Transplantation* 53:1115–1119, 1992). In addition to showing a high incidence and severity of lesions, the inflammatory stage of lesion development is quite recognizable since this system does not require immunosuppression. Although the degree of mononuclear infiltration and necrosis is more severe, the arterial lesions in this model strongly resemble clinical graft artherosclerosis.

An effective anti-microtubule therapy for graft rejection would accomplish at least one of the following: (i) prolong the life of the graft, (ii) decrease the side effects associated with immunosuppressive therapy, and (iii) decrease accelerated atherosclerosis associated with transplants.

Suitable anti-microtubule agents for treating graft rejection include for example, taxanes (e.g., paclitaxel and docetaxel), camptothecin, epothilones A and B, discodermolide, deuterium oxide ($D_2O$), hexylene gylcol(2-methyl-2,4-pentanediol), tubercidin(7-deazaadenosine), LY290181 (2-amino-4-(3-pyridyl)-4H-naphtho(1,2-b) pyran-3-cardonitrile), aluminum fluoride, ethylene glycol bis-(succinimidylsuccinate), glycine ethyl ester, monoclonal anti-idiotypic antibodies, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymer, or in a liposome formulation as discussed in more detail both above and below.

The anti-microtubule agent can be administered with transplants in any manner sufficient to achieve a statistically significant clinical result. However preferred methods include oral administration or intravenous, subcutaneous, or intramuscular injection. The anti-microtubule agent can be administered as a chronic low dose therapy to prevent chronic graft rejection or in higher doses to prevent acute graft rejection. For example, for paclitaxel, preferred embodiments would be 10 to 75 mg/m$^2$ once every 1 to 4 weeks, 10 to 75 mg/m$^2$ daily, as tolerated, or 10 to 175 mg/m$^2$ once weekly, as tolerated or until symptoms subside. Peritubular paclitaxel (i.e., administration of the drug to the outer or mesenteric surface of the bowel) can be administered to regions of the bowel with active disease. In a preferred embodiment, 0.5% to 20% paclitaxel by weight is loaded into a polymeric carrier (as described in the examples) and applied to the mesenteric surface as a "paste", "film" or "wrap" which releases the drug over a period of time. In all of the embodiments, other anti-microtubule agents would be administered at equivalent doses adjusted for potency and tolerability of the agent.

11. Systemic Lupus Erythematosus

Systemic lupus erythematosus (SLE) is a disease of unknown etiology characterized by inflammation in many different organ systems associated with the production of antibodies reactive with nuclear, cytoplasmic and cell membrane antigens. SLE is a fairly common disease, with a prevalence that may be as high as 1 in 2500 in some populations (Michet et al., *Mayo Clini. Proc.* 60:105, 1985). SLE is predominantly a disease of women, with a frequency of 1 in 700 among women between the ages of 10 and 64 and a female-to-male ratio of 9:1. The overall annual incidence of SLE is about 6 to 35 new cases per 100,000 population per year depending on risk of population.

SLE appears to be a complex disorder of multifactorial origin resulting from interactions among genetic, hormonal and environmental factors acting in concert to cause activation of helper T and B cells that results in the secretion of several species of autoantibodies. SLE is often classified as an autoimmune disorder, characterized by an increased number of autoantibodies, directed especially against nuclear antigens (antinuclear antibodies—ANAs) and phospholipids. Antiphospholipid antibodies are present in 20 to 40% of lupus patients and have been found to react with a number of anionic phospholipids.

The morphologic changes in SLE are extremely variable, reflecting the variability of the clinical manifestations and the course of the disease in individual patients. The most characteristic lesions result from the deposition of immune complexes and are found in the blood vessels, kidneys, connective tissue and skin. An acute necrotizing vasculitis involving small arteries and arterioles may be present in any tissue although skin and muscles are most commonly affected. In organs affected by small vessel vasculitis, the first lesions are usually characterized by granulocytic infiltration and periarteriolar edema. Fibrinoid deposits in the vessel walls also characterize the arteritis. In chronic stages, vessels undergo fibrous thickening with luminal narrowing. In the spleen, these vascular lesions involve the central arteries and are characterized by marked perivascular fibrosis, producing so-called onionskin lesions.

Suitable anti-microtubule agents for treating SLE include for example, taxanes (e.g., paclitaxel and docetaxel), camptothecin, epothilones A and B, discodermolide, deuterium oxide ($D_2$), hexylene gylcol(2-methyl-2,4-pentanediol), tubercidin(7-deazaadenosine), LY290181 (2-amino-4-(3-pyridyl)-4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g., MAP2, MAP4, tau, big tau, ensconsin, elongation factor-1-alpha (EF-1α) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within preferred embodiments of the invention, the agents or compositions may be administered intranasally, systemically, by inhalation, or topically (e.g., in the case of nasal polyps).

The anti-microtubule agent can be administered in any manner sufficient to achieve a statistically significant clinical result. However, preferred methods of administration include intravenous, oral, intramuscular or subcutaneous injection. The anti-microtubule agent can be administered as a chronic low dose therapy to prevent disease progression, prolong disease remission, or decrease symptoms in active disease. Alternatively, the therapeutic agent can be administered in higher doses as a "pulse" therapy to induce remission in acutely active disease. The minimum dose capable of achieving these endpoints can be used and can vary according to patient, severity of disease, formulation of the administered agent, and route of administration. For example, for paclitaxel, preferred embodiments would be 10 to 75 mg/m$^2$ once every 1 to 4 weeks, 10 to 75 mg/m$^2$ daily, as tolerated, or 10 to 175 mg/m$^2$ once weekly, as tolerated or until symptoms subside.

12. Periodontal Disease

Periodontal disease is a general term for all inflammatory diseases associated with the periodontium. Strongly correlated with age, periodontal disease targets the tooth's supporting structures, including the gingiva, cementum, alveolar bone and periodontal membrane. Periodontal disease evolves over time, beginning initially with gingivitis, and when left untreated, develops into gingivitis and then into periodontitis which subsequently evolves into edentulism. Inflammatory periodontal disease results from the interaction between dental plaque and the dentogingival junction. Host tissue destruction through periodontitis occurs only when the dental plaque and host conditions are out of balance, otherwise periodontal stability or homeostasis exists. Gingivitis is characteristically marked by the presence of motile gram negative microorganisms. Researchers have found a direct correlation between the degree of inflammation and the population size of motile organisms.

Untreated periodontal disease is characterized by varying levels of disease activity that is distributed in a somewhat symmetrical fashion throughout the mouth. In a healthy individual, the supporting connecting tissue is composed primarily of collagen bundle fibres and endothelium lined blood vessels. There is also the presence few inflammatory cells (lymphocytes, neutrophils and macrophages). The accumulation of dental plaque leads initially to gingivitis. At the cellular level, this is characterized by the accumulation of inflammatory exudates and leukocytes. As well, some of the collagen fibers are destroyed and replaced by inflammatory infiltrate and enlarged blood vessels. As gingivitis evolves, the inflammatory response consists mainly of neutrophils in the junctional epithelium and T lymphocytes in the connective tissue. At this stage the junctional epithelium remains a protective barrier between the plaque irritants and the periodontal membrane. As gingivitis progresses, the majority of the collagen fibers are replaced by inflamed connective tissue, extracellular white blood cells, larger and more numerous blood vessels, ulceration of the pocket epithelium and increased crevicular fluid production. Eventually the junctional epithelium extends apically as the primary periodontal membrane fibers are destroyed, and supporting alveolar bone is lost.

Periodontitis is a chronic, multifactorial disease where local etiological factors and host defense systems play a primary role. Disease activity is generally characterized by shifts from host tissue and microorganism homeostasis. Presently, periodontitis can only be diagnosed by the presence of increasing periodontal attachment loss, increasing pocket depth, bone loss and tooth loss. Chronic periodontitis can be treated in four stages: systemic (factors such as diabetes mellitus or premedication), initial or hygiene (patient education to eliminate local factors), corrective (periodontal surgery) and maintenance phases (prevention).

Suitable anti-microtubule agents for treating periodontitis include for example, taxanes (e.g., paclitaxel and docetaxel), camptothecin, epothilones A and B, discodermolide, deuterium oxide ($D_2O$), hexylene gylcol(2-methyl-2,4-pentanediol), tubercidin(7-deazaadenosine), LY290181 (2-amino-4-(3-pyridyl)-4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g. MAP2, MAP4, tau, big tau, ensconsin, elongation factor-1-alpha (EF-1$\alpha$) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within preferred embodiments of the invention, the agents or compositions may be administered intranasally, systemically, by inhalation, or topically (e.g. in the case of nasal polyps).

The anti-microtubule agent can be administered in any manner sufficient to achieve a statistically significant clinical result. However, preferred methods of administration include topical, dental/surgical implant or low-dose systemic. The anti-microtubule agent can be administered as a chronic low dose therapy to prevent disease progression, prolong disease remission, or decrease symptoms in active disease. The minimum dose capable of achieving these endpoints can be used and can vary according to patient, severity of disease, formulation of the administered agent, and route of administration. For example, for paclitaxel, preferred embodiments would be 10 to 75 mg/m$^2$ once every 1 to 4 weeks, 10 to 75 mg/m$^2$ daily, as tolerated, or 10 to 175 mg/m$^2$ once weekly, as tolerated or until symptoms subside. A topical cream containing 0.001% to 10% paclitaxel by weight can be administered depending upon severity of the disease and the patient's response to treatment. In a preferred embodiment, a topical preparation containing 0.01% to 1% paclitaxel by weight could be administered daily as needed. In a preferred embodiment of a paclitaxel-loaded dental/surgical implant, 0.5% to 20% paclitaxel by weight is loaded into a polymeric carrier which releases the drug over a period of time. In all of the embodiments, other anti-microtubule agents would be administered at equivalent doses adjusted for potency and tolerability of the agent.

13. Polycystic Kidney Disease

Polycystic kidney disease is a progressive kidney disease characterized by the formation of multiple cysts of varying size scattered diffusely throughout the kidneys, resulting in the compression and destruction of kidney parenchyma Cyst formation or outpouchings may also occur in other organs, particularly in the liver, but also in the pancreas, ovaries, gastrointestinal tract, and vascular tree.

The pathogenetic mechanism of renal parenchymal injury in polycystic kidney disease patients, typically characterized by renal cystic changes paralleled by interstitial inflammation and gradual fibrotic changes that cause the kidneys to enlarge several-fold greater than normal. This enlargement is owing to the proliferation of epithelial cells in tubule segments, to the accumulation of fluid within the dilated tubule segment created by the proliferating cells, and to remodeling of the extracellular matrix. The focal beginning of polycystic kidney disease in a relatively few renal tubules suggests that the cells in the walls of cysts may reflect clonal growth and that this aberrant proliferation may be secondary to a somatic "second hit" process. The rate at which the cysts enlarge appears to depend on endocrine, paracrine and autocrine factors that drive cellular proliferation and transepithelial fluid secretion within the cysts. The presence of the renal cysts within certain kidneys appears to provoke interstitial inflammation and apoptosis that contribute to fibrosis and renal insufficiency in approximately one-half of persons with the disease.

Suitable anti-microtubule agents for treating periodontitis include for example, taxanes (e.g., paclitaxel and docetaxel), camptothecin, epothilones A and B, discodermolide, deuterium oxide ($D_2O$), hexylene gylcol(2-methyl-2,4-pentanediol), tubercidin(7-deazaadenosine), LY290181 (2-amino4(3-pyridyl)4H-naphtho(1,2-b)pyran-3-cardonitrile), aluminum fluoride, ethylene glycol bis-(succinimidylsuccinate), glycine ethyl ester, nocodazole, cytochalasin B, colchicine, colcemid, podophyllotoxin, benomyl, oryzalin, majusculamide C, demecolcine, methyl-2-benzimidazolecarbamate (MBC), LY195448, subtilisin, 1069C85, steganacin, combretastatin, curacin, estradiol, 2-methoxyestradiol, flavanol, rotenone, griseofulvin, vinca alkaloids, including vinblastine and vincristine, maytansinoids and ansamitocins, rhizoxin, phomopsin A, ustiloxins, dolastatin 10, dolastatin 15, halichondrins and halistatins, spongistatins, cryptophycins, rhazinilam, betaine, taurine, isethionate, HO-221, adociasulfate-2, estramustine, monoclonal anti-idiotypic antibodies, microtubule assembly promoting protein (taxol-like protein, TALP), cell swelling induced by hypotonic (190 mosmol/L) conditions, insulin (100 nmol/L) or glutamine (10 mmol/L), dynein binding, gibberelin, XCHO1 (kinesin-like protein), lysophosphatidic acid, lithium ion, plant cell wall components (e.g., poly-L-lysine and extensin), glycerol buffers, Triton X-100 microtubule stabilizing buffer, microtubule associated proteins (e.g. MAP2, MAP4, tau, big tau, ensconsin, elongation factor-1-alpha (EF-1$\alpha$) and E-MAP-115), cellular entities (e.g., histone H1, myelin basic protein and kinetochores), endogenous microtubular structures (e.g., axonemal structures, plugs and GTP caps), stable tubule only polypeptide (e.g., STOP145 and STOP220) and tension from mitotic forces, as well as any analogues and derivatives of any of the above. Such agents may, within certain embodiments, be delivered as a composition along with a polymeric carrier, or in a liposome formulation as discussed in more detail both above and below. Within preferred embodiments of the invention, the agents or compositions may be administered intranasally, systemically, by inhalation, or topically (e.g. in the case of nasal polyps).

The anti-microtubule agent can be administered in any manner, which achieves a statistically significant clinical result. Representative methods include intravenous, subcutaneous or intraperitoneal. The anti-microtubule agent can be administered as a chronic low dose therapy to prevent disease progression, prolong disease remission, or decrease symptoms in active disease. Alternatively, the therapeutic agent can be administered in higher doses as a "pulse" therapy to induce remission in acutely active disease. The minimum dose capable of achieving these endpoints can be used and can vary according to patient, severity of disease, formulation of the administered agent, and route of administration. For example, for paclitaxel, preferred embodiments would be 10 to 75 mg/m$^2$ once every 1 to 4 weeks, 10 to 75 mg/m$^2$ daily, as tolerated, or 10 to 175 mg/m$^2$ once weekly, as tolerated or until symptoms subside. In a preferred embodiment, 0.5% to 20% paclitaxel by weight is loaded into a polymeric carrier (as described in the following examples) and applied to the organ surface as a "paste", "film", or "wrap" which releases the drug over a period of time such that the incidence of cysts is reduced. In a particularly preferred embodiment, the composition is 1% to 5% paclitaxel by weight. In another preferred embodiment, a polymeric implant containing 0.1% to 20% paclitaxel by weight is applied directly to the surgical site such that recurrence of disease is reduced. In another embodiment, lavage fluid containing 1 to 75 mg/m$^2$ (preferably 10 to 50 mg/m$^2$) paclitaxel, would be used at the time of or immediately following surgery and administered during surgery or intraperitoneally, by a physician. In all of the embodiments, other anti-microtubule agents would be administered at equivalent doses adjusted for potency and tolerability of the agent. Other anti-microtubule agents can be administered at equivalent doses adjusted for the potency and tolerability of the agent.

Formulation and Administration

As noted above, anti-microtubule agents of the present invention may be formulated in a variety of forms (e.g., microspheres, pastes, films, sprays, ointments, creams, gels and the like). Further, the compositions of the present invention may be formulated to contain more than one anti-microtubule agents, to contain a variety of additional compounds, to have certain physical properties (e.g., elasticity, a particular melting point, or a specified release rate). Within certain embodiments of the invention, compositions may be combined in order to achieve a desired effect (e.g., several preparations of microspheres may be combined in order to achieve both a quick and a slow or prolonged release of one or more anti-microtubule agents).

Anti-microtubule agents may be administered either alone, or in combination with pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

As noted above, anti-microtubule agents, compositions, or pharmaceutical compositions provided herein may be prepared for administration by a variety of different routes, including for example, topically to a site of inflammation, orally, rectally, intracranially, intrathecally, intranasally, intraocularly, intravenously, subcutaneously, intraperitoneally, intramuscularly, sublingually and intravesically. Other representative routes of administration include direct administration (preferably with ultrasound, CT, fluoroscopic, MRI or endoscopic guidance) to the disease site.

The therapeutic agents, therapeutic compositions and pharmaceutical compositions provided herein may be placed within containers, along with packaging material which provides instructions regarding the use of such materials. Generally, such instructions include a tangible expression describing the reagent concentration, as well as within certain embodiments, relative amounts of excipient ingredients or diluents (e.g., water, saline or PBS) which may be necessary to reconstitute the anti-microtubule agent, anti-microtubule composition, or pharmaceutical composition.

The following examples are offered by way of illustration, and not by way of limitation.

EXAMPLES

As discussed above, chronic inflammation is a process characterized by tissue infiltration with white blood cells (macrophages, lymphocytes, neutrophils, and plasma cells), tissue destruction by inflammatory cells and cell products (reactive oxygen species, tissue degrading enzymes such as matrix metalloproteinases), and repeated attempts at repair by connective tissue replacement (angiogenesis and fibrosis).

In order to assess anti-microtubule agents for their ability to effect chronic inflammatory the following pathological/biological endpoints: (1) inhibition of the white blood cell response (macrophages, neutrophils and T cells) which initiates the inflammatory cascade; (2) inhibition of mesenchymal cell (fibroblasts, synoviocytes, etc.) hyperproliferation that leads to the development of fibrosis and loss of organ function; (3) inhibition of matrix metalloproteinase production/activity which causes tissue damage; (4) disruption of angiogenesis which may enhance the inflammatory response and provide the metabolic support necessary for the growth and development of the fibrous tissue; and (5) all of this must be achieved without substantial toxicity to normal parenchymal cells or impairing the normal synthesis of the matrix components (e.g., collagen and proteoglycans).

As set forth in more detail below, the activity of agents which stabilize microtubules such as, for example, paclitaxel has been examined in several tissues and inflammatory disease states. These agents demonstrate an ability to alter many of the above disease parameters.

Example 1

Effect of Anti-Microtubule Agents on Neutrophil Activity

The example describes the effect of anti-microtubule agents on the response of neutrophils stimulated with opsonized CPPD crystals or opsonized zymosan. As shown by experiments set forth below, anti-microtubule agents are strong inhibitors of particulate-induced neutrophil activation as measured by chemiluminescence, superoxide anion production and degranulation in response to plasma opsonized microcrystals or zymosan.

A. Materials and Methods

Hanks buffered saline solution (HBSS) pH 7.4 was used throughout this study. All chemicals were purchased from Sigma Chemical Co (St. Louis, Mo.) unless otherwise stated. All experiments were performed at 37° C. unless otherwise stated.

1. Preparation and Characterization of Crystals

CPPD (triclinic) crystals were prepared. The size distribution of the crystals was approximately 33% less than 10 $\mu$m, 58% between 10 and 20 $\mu$m and 9% greater than 20 $\mu$m. Crystals prepared under the above conditions are pyrogen-free and crystals produced under sterile, pyrogen-free conditions produced the same magnitude of neutrophil response as crystals prepared under normal, non-sterile laboratory conditions.

2. Opsonization of Crystals and Zymosan

All experiments that studied neutrophil responses to crystals or zymosan in the presence of paclitaxel were performed using plasma opsonized CPPD or zymosan. Opsonization of crystals or zymosan was done with 50% heparinized plasma at a concentration of 75 mg of CPPD or 12 mg of zymosan per ml of 50% plasma Crystals or zymosan were incubated with plasma for 30 minutes at 37° C. and then washed in excess HBSS.

3. Neutrophil Preparation

Neutrophils were prepared from freshly collected human citrated whole blood. Briefly, 400 ml of blood were mixed with 80 ml of 4% dextran T500 (Phamacia LKB, Biotechnology AB Uppsala, Sweden) in HBSS and allowed to settle for 1 hour. Plasma was collected continuously and 5 ml applied to 5 ml of Ficoll Paque (Pharmacia) in 15 ml polypropylene tubes (Corning, N.Y.). Following centrifugation at 500 g for 30 minutes, the neutrophil pellets were washed free of erythrocytes by 20 seconds of hypotonic shock. Neutrophils were resuspended in HBSS, kept on ice and used for experiments within 3 hours. Neutrophil viability and purity was always greater than 90%.

4. Incubation of Neutrophils With Anti-microtubule Agents (a) Paclitaxel

A stock solution of paclitaxel at 12 mM in dimethylsulfoxide (DMSO) was freshly prepared before each experiment. This stock solution was diluted in DMSO to give solutions of paclitaxel in the 1 to 10 mM concentration range. Equal volumes of these diluted paclitaxel solutions was added to neutrophils at 5,000,000 cells per ml under mild vortexing to achieve concentrations of 0 to 50 $\mu$M with a final DMSO concentration of 0.5%. Cells were incubated for 20 minutes at 33° C. then for 10 minutes at 37° C. before addition to crystals or zymosan.

(b) Aluminum Fluoride

A stock solution of aluminum fluoride ($AlF_3$) at 1 M in HBSS was freshly prepared. This stock solution was diluted in HBSS to give solutions of $AlF_3$ in the 5 to 100 mM concentration range. Equal volumes (50 $\mu$l) of these diluted $AlF_3$ solutions was added to neutrophils at 5,000,000 cells per ml and incubated for 15 minutes at 37° C. Luminol (1 $\mu$M) was added and then 20 $\mu$l of opsonized zymosan (final concentration=1 mg/ml) to activate the cells.

(c) Glycine Ethyl Ester

A stock solution of glycine ethyl ester at 100 mM in HBSS was freshly prepared. This stock solution was diluted in HBSS to give solutions of glycine ethyl ester in the 0.5 to 10 mM concentration range. Equal volumes (50 $\mu$l) of these diluted glycine ethyl ester solutions was added to neutrophils at 5,000,000 cells per ml and incubated for 15 minutes at 37° C. Luminol (1 $\mu$M) was added and then 20 $\mu$l of opsonized zymosan (final concentration=1 mg/ml) to activate the cells.

(d) LY290181

A stock solution of LY290181 at 100 $\mu$M in HBSS was freshly prepared. This stock solution was diluted in HBSS to give solutions of LY290181 in the 0.5 to 50 $\mu$M concentration range. Equal volumes (50 $\mu$l) of these diluted LY290181 solutions was added to neutrophils at 5,000,000 cells per ml and incubated for 15 minutes at 37° C. Luminol (1 $\mu$M) was added and then 20 $\mu$l of opsonized zymosan (final concentration=1 mg/ml) to activate the cells.

5. Chemiluminescence Assay

All chemiluminescence studies were performed at a cell concentration of 5,000,000 cells/ml in HBSS with CPPD (50 mg/ml). In all experiments 0.5 ml of cells was added to 25 mg of CPPD or 0.5 mg of zymosan in 1.5 ml capped Eppendorf tubes. 10 $\mu$l of luminol dissolved in 25% DMSO in HBSS was added to a final concentration of 1 $\mu$M and the samples were mixed to initiate neutrophil activation by the crystals or zymosan. Chemiluminescence was monitored using an LKB Luminometer (Model 1250) at 37° C. for 20 minutes with shaking immediately prior to measurements to resuspend the crystals or zymosan. Control tubes contained cells, drug and luminol (crystals absent).

6. Superoxide Anion Generation

Superoxide anion concentrations were measured using the superoxide dismutase inhibitable reduction of cytochrome C assay. Briefly, 25 mg of crystals or 0.5 mg of zymosan was placed in a 1.5 ml capped Eppendorf tube and warmed to 37° C. 0.5 ml of cells at 37° C. were added together with ferricytochrome C (final concentration 1.2 mg/ml) and the cells were activated by shaking the capped tubes. At appropriate times tubes were centrifuged at 10,000 g for 10 seconds and the supernatant collected for assay be measuring the absorbance of 550 nm. Control tubes were set up under the same conditions with the inclusion of superoxide dismutase at 600 units per ml.

7. Neutrophil Degranulation Assay

One and a half milliliter Eppendorf tubes containing either 25 mg of CPPD or 1 mg of zymosan were preheated to 37° C. 0.5 ml of cells at 37° C. were added followed by vigorous shaking to initiate the reactions. At appropriate times, tubes were centrifuged at 10,000 g for 10 seconds and 0.4 ml of supernatant was stored at −20° C. for later assay.

Lysozyme was measured by the decrease in absorbance at 450 nm of a *Micrococcus lysodeikticus* suspension. Briefly, *Micrococcus lysodeikticus* was suspended at 0.1 mg/ml in 65 mM potassium phosphate buffer, pH 6.2 and the absorbance at 450 nm was adjusted to 0.7 units by dilution. The crystal (or zymosan) and cell supernatant (100 $\mu$l) was added to 2.5 ml of the Micrococcus suspension and the decrease in absorbance was monitored. Lysozyme standards (chicken egg white) in the 0 to 2000 units/ml range were prepared and a calibration graph of lysozyme concentration against the rate of decrease in the absorbance at 450 nm was obtained.

Myeloperoxidase (MPO) activity was measured by the increase in absorbance at 450 nm that accompanies the oxidation of dianisidine. 7.8 mg of dianisidine was dissolved in 100 ml of 0.1 M citrate buffer, pH 5.5 at 3.2 mM by sonication. To a 1 ml cuvette, 0.89 ml of the dianisidine solution was added, followed by 50 $\mu$l of 1% Triton x 100, 10 $\mu$l of a 0.05% hydrogen peroxide in water solution and 50 $\mu$l of crystal-cell supernatant. MPO activity was determined from the change in absorbance (450 nm) per minute, Delta Å 450, using the following equation:

$$\text{Dianisidine oxidation (nmol/min)}=50\times\text{Delta Å 450}$$

8. Neutrophil Viability

To determine the effect of the anti-microtubule agents on neutrophil viability the release of the cytoplasmic marker enzyme, lactate dehydrogenase (LDH) was measured. Control tubes containing cells with drug (crystals absent) from degranulation experiments were also assayed for LDH.

B. Results

In all experiments statistical significance was determined using Students' t-test and significance was claimed at p<0.05. Where error bars are shown they describe one standard deviation about the mean value for the n number given.

1. Neutrophil Viability (a) Paclitaxel

Neutrophils treated with paclitaxel at 46 for one hour at 37° C. did not show any increased level of LDH release (always less than 5% of total) above controls indicating that paclitaxel did not cause cell death.

(b) Aluminum Fluoride

Neutrophils treated with aluminum fluoride at a 5 to 100 mM concentration range for 1 hour at 37° C. did not show any increased level of LDH release above controls indicating that aluminum fluoride did not cause cell death.

(c) Glycine Ethyl Ester

Neutrophils treated with glycine ethyl ester at a 0.5 to 20 mM concentration range for 1 hour at 37° C. did not show any increased level of LDH release above controls indicating that glycine ethyl ester did not cause cell death.

2. Chemiluminescence (a) Paclitaxel

Figure 1A:
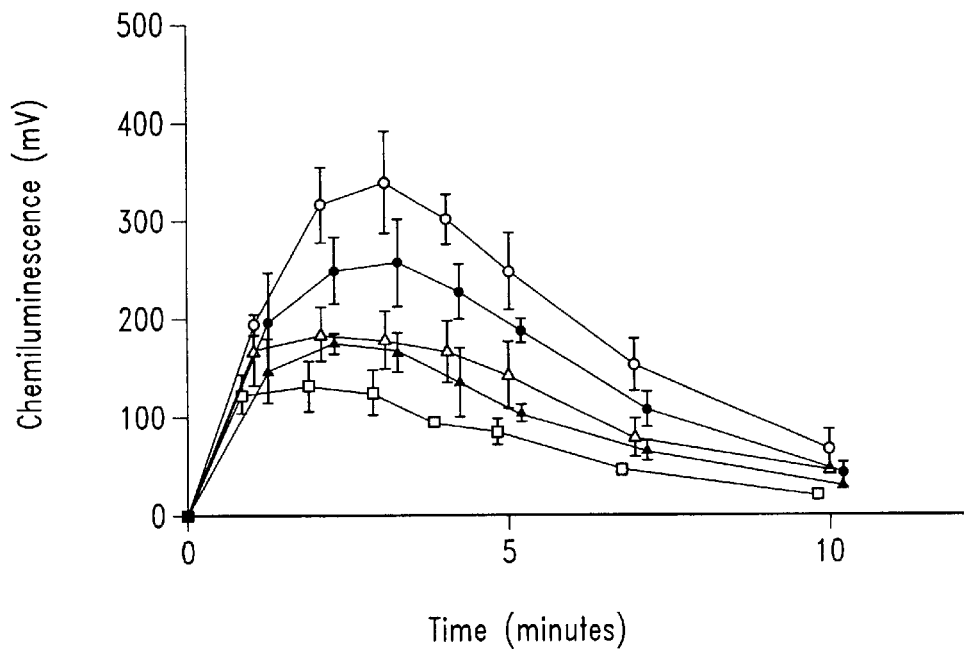
FIG. 1A is a graph which shows the chemiluminescence response of neutrophils ($5\times10^6$ cells/ml) to plasma opsonized CPPD crystals (50 mg/ml). Effect of paclitaxel (also referred to as "taxol") at (○) no paclitaxel, (●) 4.5 µM, (Δ) 14 µM, (▲) 28 µM, (□) 46 µM; n=3.
Figure 1B:
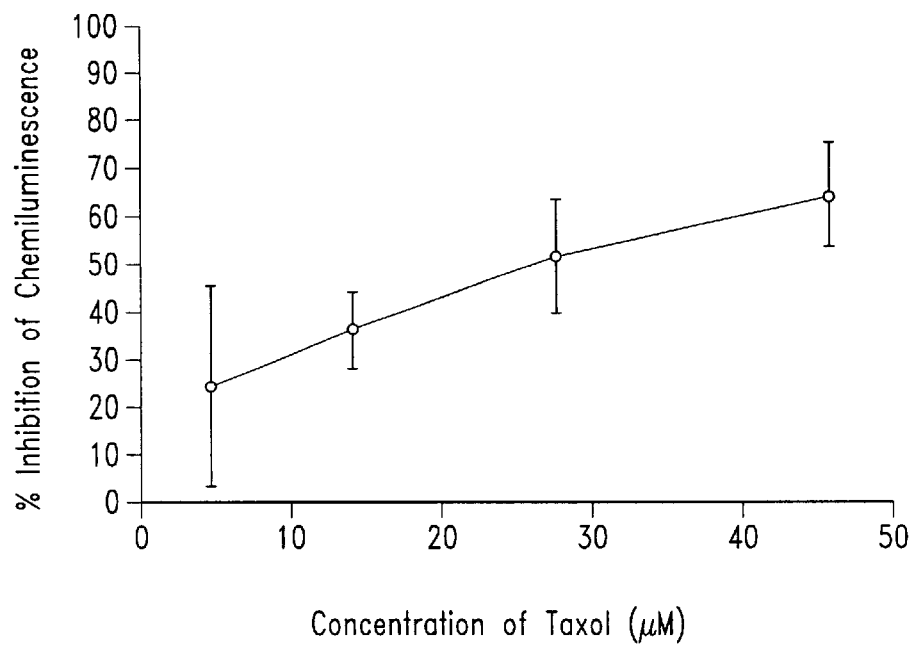
FIG. 1B is a graph which shows the time course concentration dependence of paclitaxel inhibition of plasma opsonized CPPD crystal-induced neutrophil chemiluminescence.
Figure 4A:
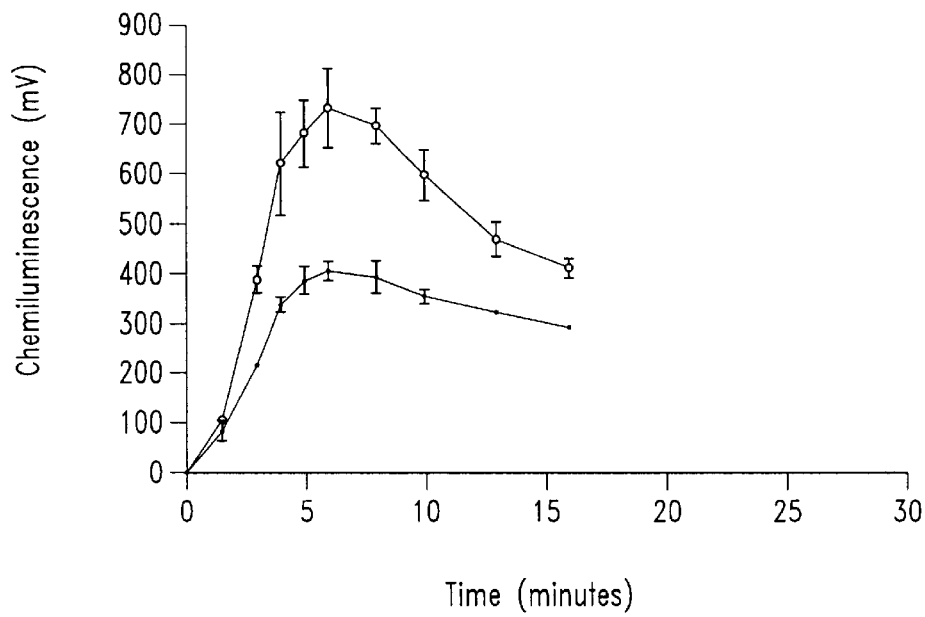
FIG. 4A is a graph which shows the chemiluminescence response of neutrophils ($5 \times 10^6$ cells/ml) in response to plasma opsonized zymosan (1 mg/ml). Effect of paclitaxel at (○) no paclitaxel, (●) 28 $\mu$M; n=3.

Paclitaxel at 28 $\mu$M produced strong inhibition of both plasma opsonized CPPD and plasma opsonized zymosan-induced neutrophil chemiluminescence as shown in FIGS. 1A, 1B and 2A respectively. The inhibition of the peak chemiluminescence response was 52% (+/−12%) and 45% (+/−11%) for CPPD and zymosan respectively. The inhibition by paclitaxel at 28 $\mu$M of both plasma opsonized CPPD and plasma opsonized zymosan-induced chemiluminescence was significant at all times from 3 to 16 minutes (FIGS. 1 and 4A). FIGS. 1A and 1B show the concentration dependence of paclitaxel inhibition of plasma opsonized CPPD-induced neutrophil chemiluminescence. In all experiments control samples never produced chemiluminescence values of greater than 5 mV and the addition of paclitaxel at all concentrations used in this study had no effect on the chemiluminescence values of controls.

(b) Aluminum Fluoride

Figure 1C:
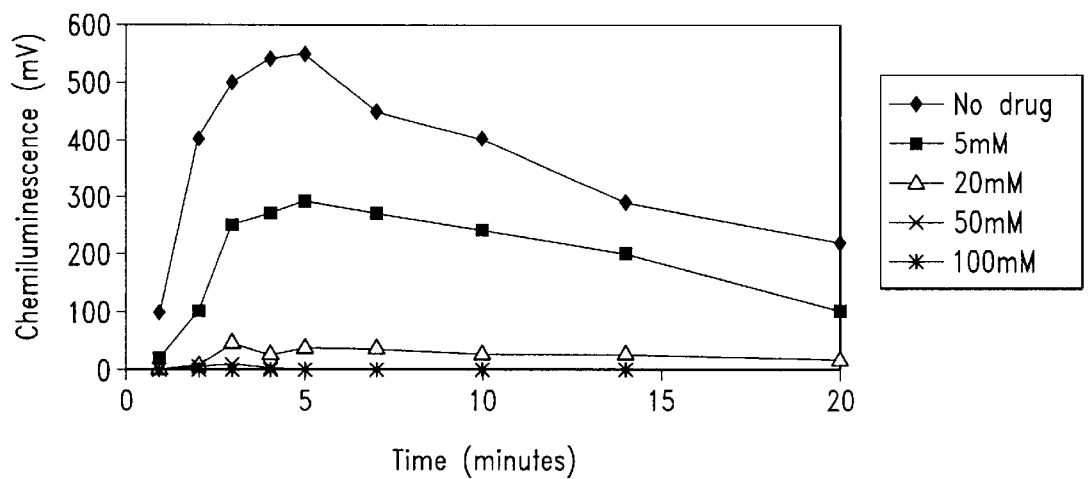
FIG. 1C is a graph which shows the effect of aluminum fluoride on opsonized zymozan-induced neutrophil activation as measured by chemiluminescence.

Aluminum fluoride at concentrations of 5 to 100 mM produced strong inhibition of plasma opsonized zymosan-induced neutrophil chemiluminescence as shown in FIG. 1C. This figure shows the concentration dependence of $AlF_3$ inhibition of plasma opsonized zymosan-induced neutrophil chemiluminescence. The addition of $AlF_3$ at all concentrations used in this study had no effect on the chemiluminescence values of controls.

(c) Glycine Ethyl Ester

Figure 1D:
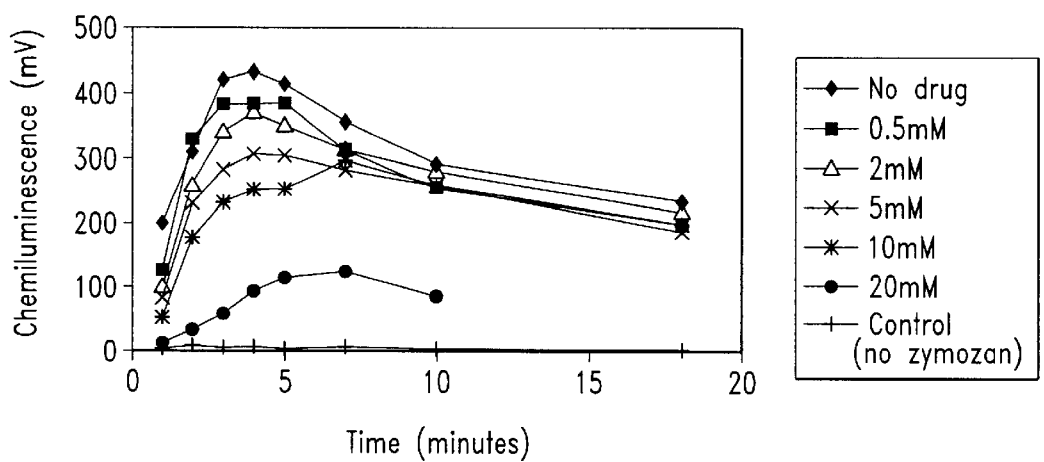
FIG. 1D is a graph which shows the effect of glycine ethyl ester on opsonized zymozan induced neutrophil activation as measured by chemiluminescence.

Glycine ethyl ester at concentrations of 0.5 to 20 mM produced strong inhibition of plasma opsonized zymosan-induced neutrophil chemiluminescence as shown in FIG. 1D. This figure shows the concentration dependence of glycine ethyl ester inhibition of plasma opsonized zymosan-induced neutrophil chemiluminescence. The addition of glycine ethyl ester at all concentrations used in this study had no effect on the chemiluminescence values of controls.

(d) LY290181

Figure 1E:
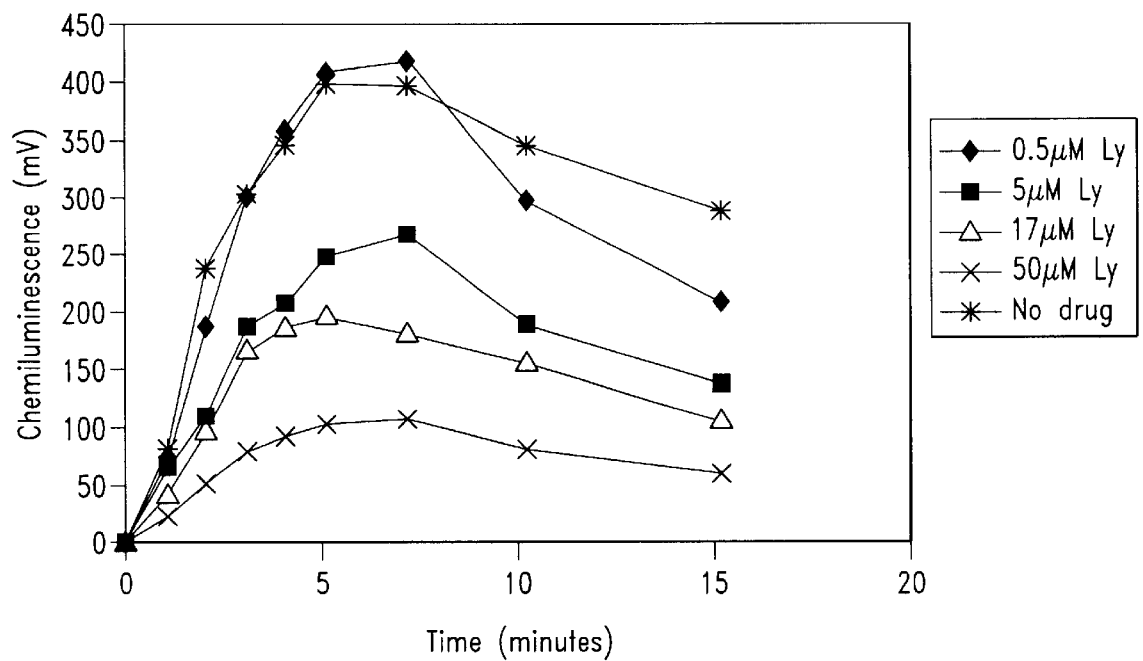
FIG. 1E is a graph which shows the effect of LY290181 on opsonized zymozan induced neutrophil chemiluminescence.

LY290181 at concentrations of 0.5 to 50 $\mu$M produced strong inhibition of plasma opsonized zymosan-induced neutrophil chemiluminescence as shown in FIG. 1E. This figure shows the concentration dependence of LY290181 inhibition of plasma opsonized zymosan-induced neutrophil chemiluminescence. The addition of LY290181 at all concentrations used in this study had no effect on the chemiluminescence values of controls.

3. Superoxide Generation

Figure 3A:
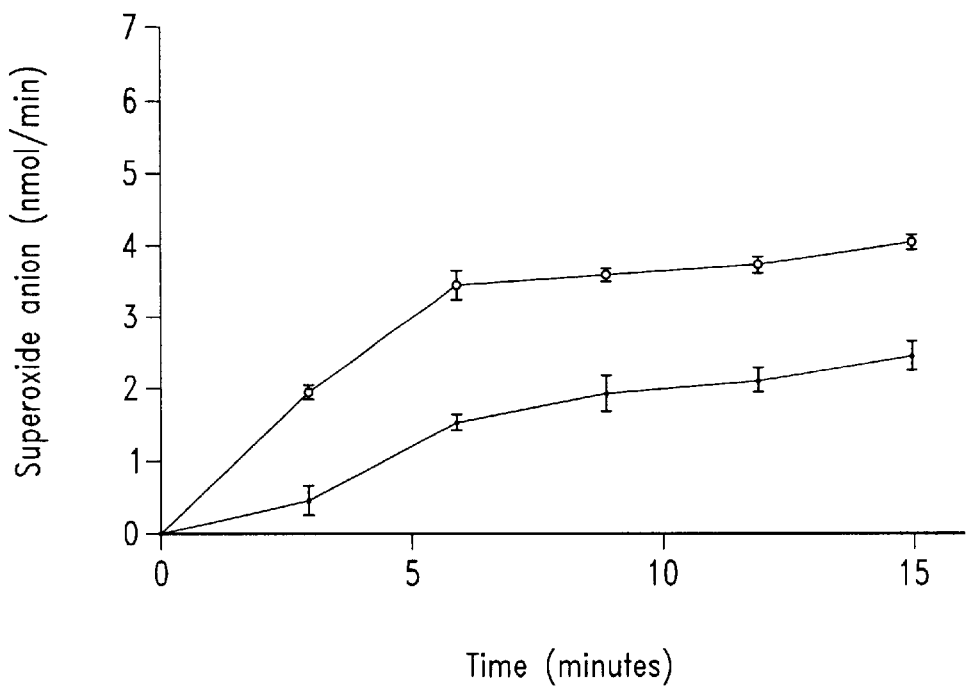
FIG. 3A is a graph which shows superoxide anion production by neutrophils ($5 \times 10^6$ cells/ml) in response to plasma opsonized CPPD crystals (50 mg/ml). Effect of paclitaxel at (○) no paclitaxel, (●) 28 $\mu$M, (Δ) Control (cells alone); n=3.
Figure 3B:
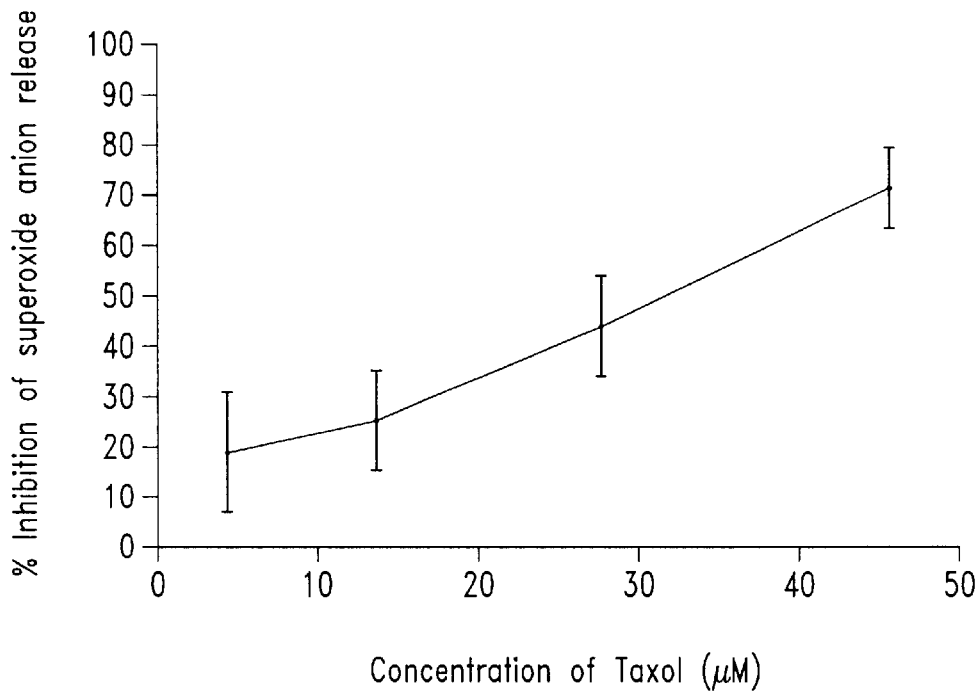
FIG. 3B is a graph which shows the time course concentration dependence of paclitaxel inhibition of plasma opsonized CPPD crystal-induced neutrophil superoxide anion production; n=3.

The time course of plasma opsonized CPPD crystal-induced superoxide anion production, as measured by the superoxide dismutase (SOD) inhibitable reduction of cytochrome C, is shown in FIG. 3. Treatment of the cells with paclitaxel at 28 $\mu$M produced a decrease in the amount of superoxide generated at all times. This decrease was significant at all times shown in FIG. 3A. The concentration dependence of this inhibition is shown in FIG. 3B. Stimulation of superoxide anion production by opsonized zymosan (FIG. 4B) showed a similar time course to CPPD-induced activation. The inhibition of zymosan-induced superoxide anion production by paclitaxel at 28 μM was less dramatic than the inhibition of CPPD activation but was significant at all times shown in FIG. 4B.

Figure 3C:
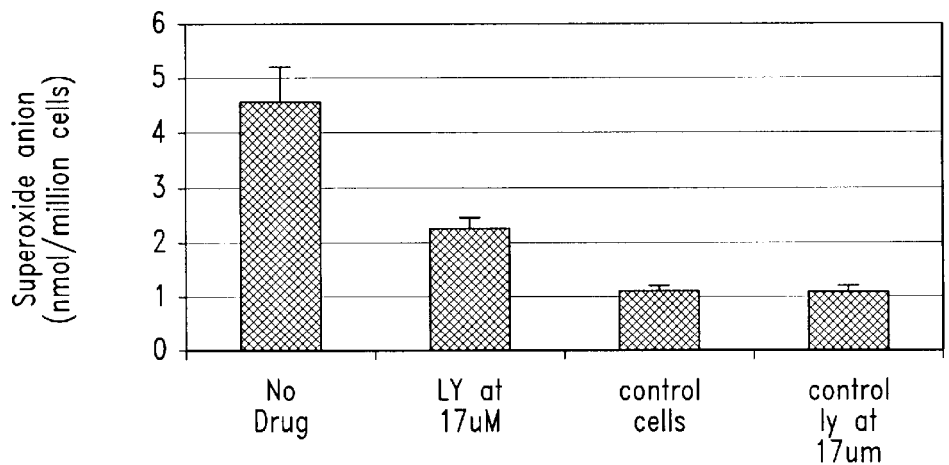
FIG. 3C is a graph which depicts the effect of LY290181 on CPPD crystal induced neutrophil superoxide anion generation.
Figure 4B:
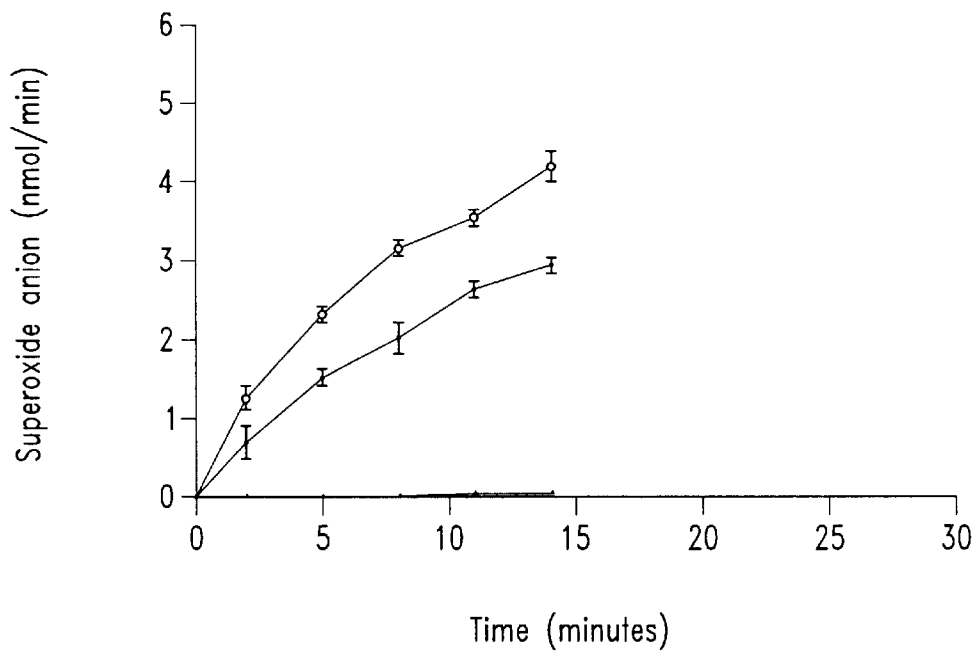
FIG. 4B is a graph which shows plasma opsonized zymosan-induced neutrophil superoxide anion production. Effect of paclitaxel at (○) no paclitaxel, (●) 28 $\mu$M, (Δ) Control (cells alone); n=3.

Treatment of CPPD crystal-induced neutrophils with LY290181 at 17 μM also produced a decrease in the amount of superoxide generated (FIG. 3C).

4. Neutrophil Degranulation

Figure 2:
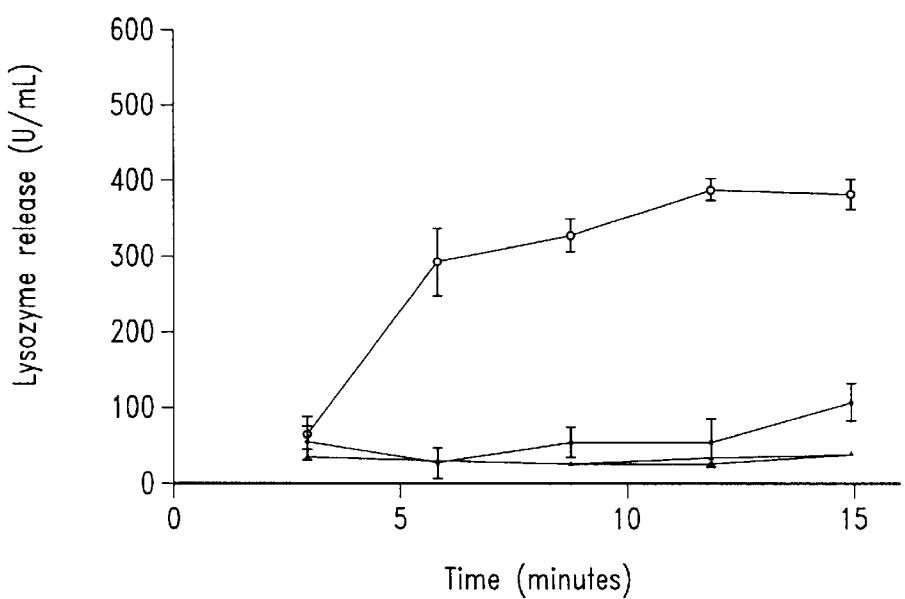
FIG. 2 is a graph which shows lysozyme release from neutrophils ($5 \times 10^6$/ml) in response to plasma opsonized CPPD crystals (50 mg/ml). Effect of paclitaxel at (○) no paclitaxel, (●) 28 $\mu$M, (Δ) Control (cells alone), (▲) Control (cells and paclitaxel at 28 $\mu$M); n=3.
Figure 5A:
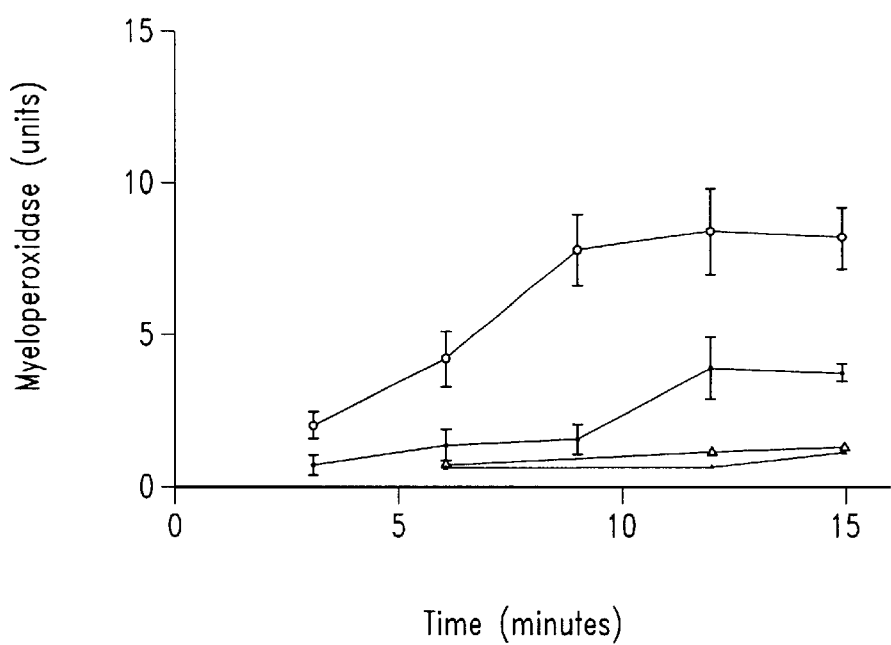
FIG. 5A is a graph which shows myeloperoxidase release from neutrophils ($5 \times 10^6$ cells/ml) in response to plasma opsonized CPPD crystals (50 mg/ml). Effect of paclitaxel at (○) no paclitaxel, (●)28 $\mu$M, (Δ) Control (cells alone), (▲) Control (cells with paclitaxel at 28 $\mu$M); n=3.
Figure 5B:
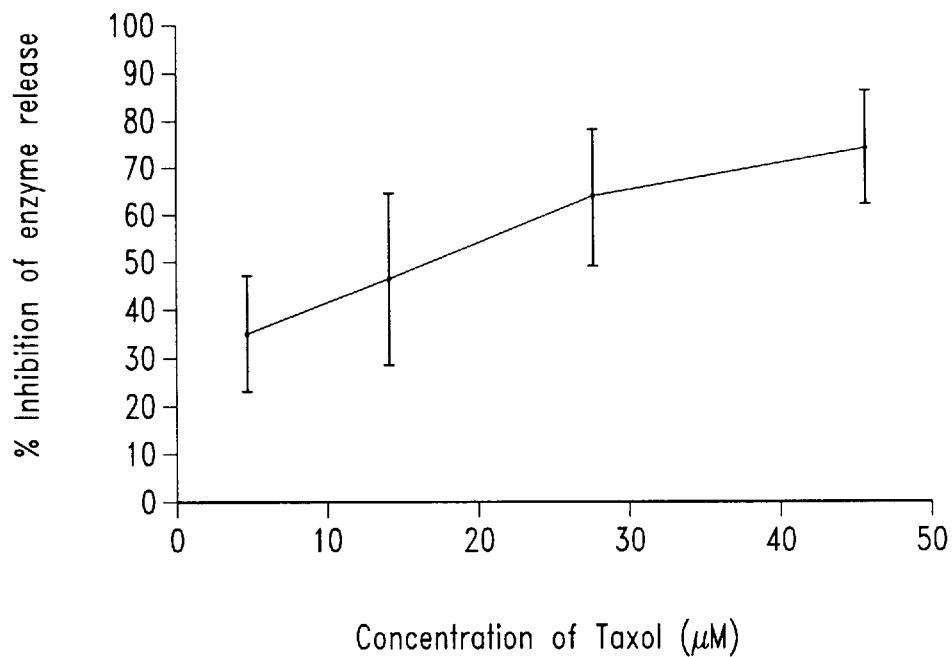
FIG. 5B is a graph which shows the concentration dependence of paclitaxel inhibition of myeloperoxidase release from neutrophils in response to plasma opsonized CPPD crystals; n 3.

Neutrophil degranulation was monitored by the plasma opsonized CPPD crystal-induced release of myeloperoxidase and lysozyme or the plasma opsonized zymosan-induced release of myeloperoxidase. It has been shown that sufficient amounts of these two enzymes are released into the extracellular media when plasma coated CPPD crystals are used to stimulate neutrophils without the need for the addition of cytochalasin B to the cells. FIGS. 5 and 2 show the time course of the release of MPO and lysozyme respectively, from neutrophils stimulated by plasma-coated CPPD. FIG. 5A shows that paclitaxel inhibits myeloperoxidase release from plasma opsonized CPPD activated neutrophils in the first 9 minutes of the crystal-cell incubation. Paclitaxel significantly inhibited CPPD-induced myeloperoxidase release at all times as shown in FIG. 5A. FIG. 5B shows the concentration dependence of paclitaxel inhibition of CPPD-induced myeloperoxidase release.

Paclitaxel at 28 μM reduced lysozyme release and this inhibition of degranulation was significant at all times as shown in FIG. 2.

Figure 5C:
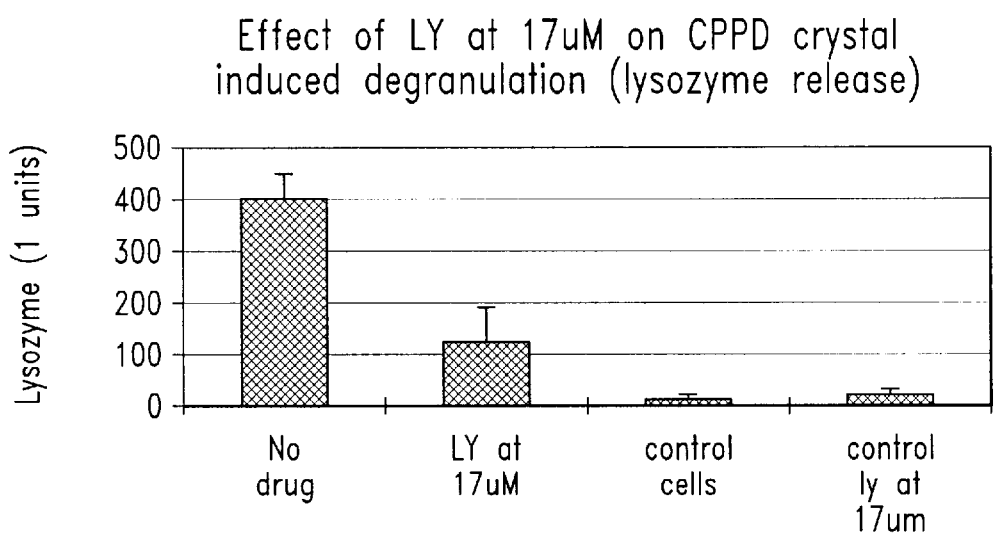
FIGS. 5C and 5D are graphs which show that LY290181 decreases both lysozyme and myeloperoxidase release in CPPD crystal-induced neutrophils.
Figure 5D:
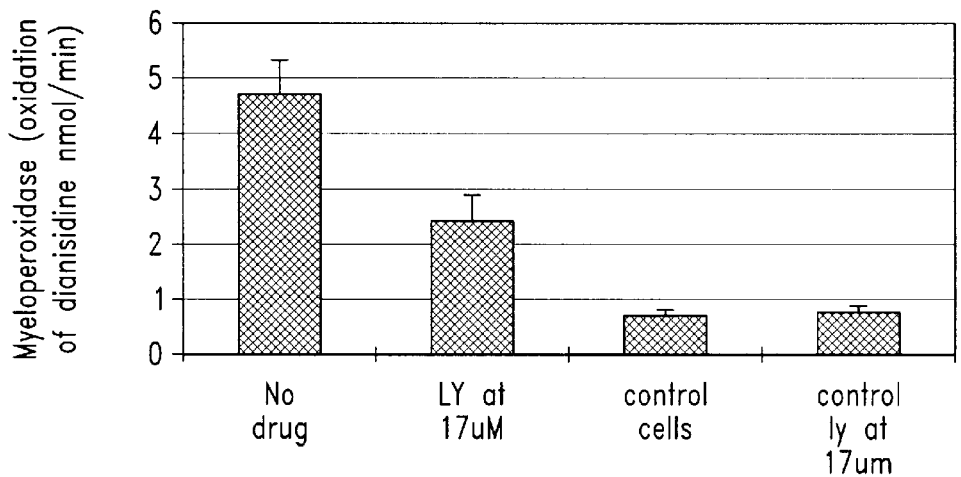
Figure 6:
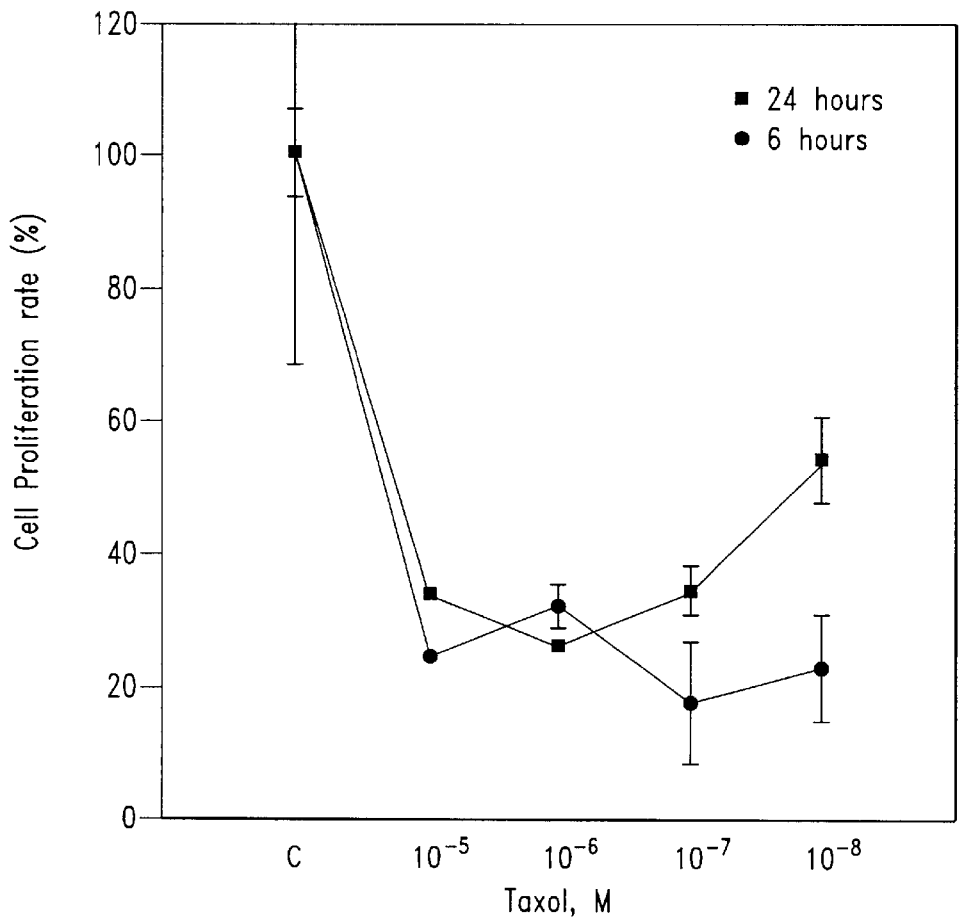
FIG. 6 is a graph which depicts proliferation of synoviocytes at various concentrations of paclitaxel.

Only minor amounts of MPO and lysozyme were released when neutrophils were stimulated with opsonized zymosan. Despite these low levels it was possible to monitor 50% inhibition of MPO release after 9 minutes Incubation in the presence of paclitaxel at 28 μM that was statistically significant ($p<0.05$) (data not shown). Treatment of CPPD crystal-induced neutrophils with LY290181 at 17 μM decreased both lysozyme and myeloperoxidase release from the cells (FIGS. 5C and 5D).

C. Discussion

These experiments demonstrate that paclitaxel and other anti-microtubule agents are strong inhibitors of crystal-induced neutrophil activation. In addition, by showing similar levels of inhibition in neutrophil responses to another form of particulate activator, opsonized zymosan, it is evident that the inhibitory activity of paclitaxel and other anti-microtubule agents are not limited to neutrophil responses to crystals. Paclitaxel, aluminum fluoride, glycine ethyl ester and LY290181 were also shown to be strong inhibitors of zymosan-induced neutrophil activation without causing cell death. LY290181 was shown to decrease superoxide anion production and degranulation of CPDD crystal-induced neutrophils.

Example 2

T Cell Response to Antigenic Stimulus

In order to determine whether paclitaxel affects T-cell activation in response to stimulagens, TR1 T-cell clones were stimulated with either the myelin basic protein peptide, GP68–88, or the lectin, conA, for 48 hours in the absence or presence of increasing concentrations of paclitaxel in a micellar formulation. Paclitaxel was added at the beginning of the experiment or 24 hours following the stimulation of cells with peptide or conA. Tritiated thymidine incorporation was determined as a measure of T-cell proliferation in response to peptide or conA stimulation.

The results demonstrated that T-cell stimulation increased in response to the peptide GP68–88 and conA. In the presence of control polymeric micelles, T-cell stimulation in response to both agonists was not altered. However, treatment with paclitaxel micelles, either at the beginning of the experiment or 24 hours following the stimulation, decreased T-cell response in a concentration dependent manner. Under both conditions, T-cell proliferation was completely inhibited by 0.02 μM paclitaxel (FIG. 79).

These data indicate that paclitaxel is a potent inhibitor of T-cell proliferation in response to antigen-induced stimulation.

Example 3

Effect of Paclitaxel on Synoviocyte Cell Proliferation In Vitro

Two experiments were conducted in order to assess the effect of differing concentrations of paclitaxel on tritiated thymidine incorporation (a measurement of synoviocyte DNA synthesis) and cell proliferation in vitro.

A. Materials and Methods

1. $^3$H-thymidine Incorporation into Synoviocytes

Synoviocytes were incubated with different concentrations of paclitaxel ($10^{-5}$ M, $10^{-6}$ M, $10^{-7}$ M, and $10^{-8}$ M) continuously for 6 or 24 hours in vitro. At these times, $1\times10^{-6}$ cpm of $^3$H-thymidine was added to the cell culture and incubated for 2 hours at 37° C. The cells were placed through a cell harvester, washed through a filter, the filters were cut, and the amount of radiation contained in the filter sections determined. Once the amount of thymidine incorporated into the cells was ascertained, it was used to determine the rate of cell proliferation. This experiment was repeated three times and the data collated.

2. Synoviocyte Proliferation

Bovine synovial fibroblasts were grown in the presence and absence of differing concentrations ($10^{-5}$ M, $10^{-6}$ M, $10^{-7}$ M, and $10^{-8}$ M) of paclitaxel for 24 hours. At the end of this time period the total number of viable synoviocyte cells was determined visually by dye exclusion counting using trypan blue staining. This experiment was conducted 4 times and the data collated.

B. Results

1. $^3$H-thymidine Incorporation into Synoviocytes

Figure 8A:
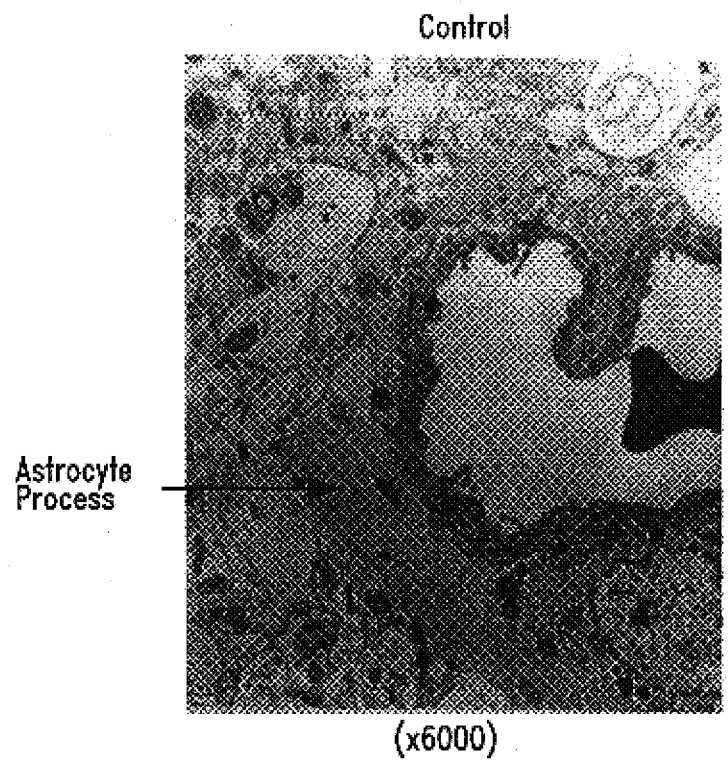
FIGS. 8A and 8B show the effect of paclitaxel on astrocyte morphology. Electron microscopic images revealed thick, well-organized filamentous processes in astrocytes of transgenic control animals, whereas transgenic animals treated with paclitaxel had morphologically altered astrocytes. Paclitaxel induced astrocyte cell rounding, thinned cellular processes and reduced cytoplasmic filaments relative to untreated animals.
Figure 8B:
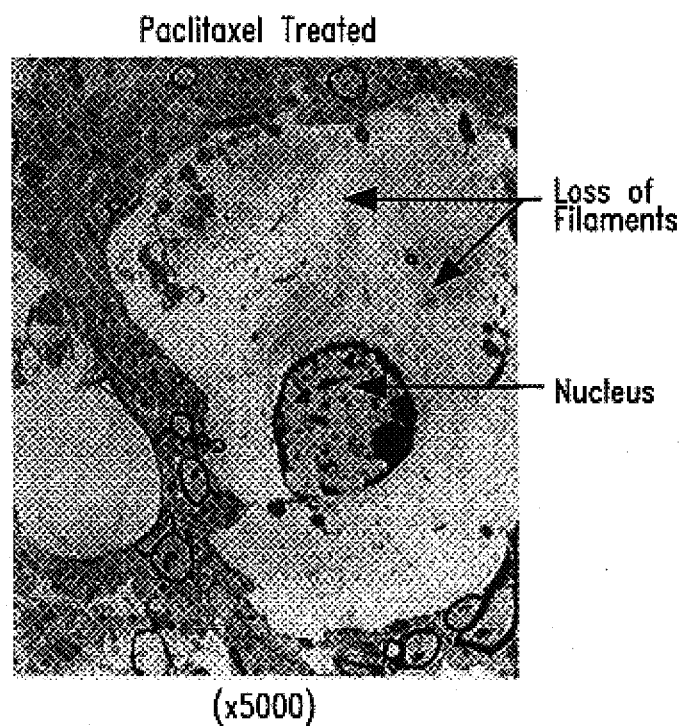

This study demonstrated that paclitaxel at low concentrations inhibits the incorporation of $^3$H-thymidine (and by extension DNA synthesis) in synoviocytes at concentrations as low as $10^{-8}$ M. At six hours there was no significant difference between the degree of inhibition produced by the higher versus the lower concentrations of paclitaxel (FIG. 8). However, by 24 hours some of the effect was lost at lower concentrations of the drug ($10^{-8}$ M), but was still substantially lower than that seen in control animals.

2. Synoviocyte Proliferation

Figure 9:
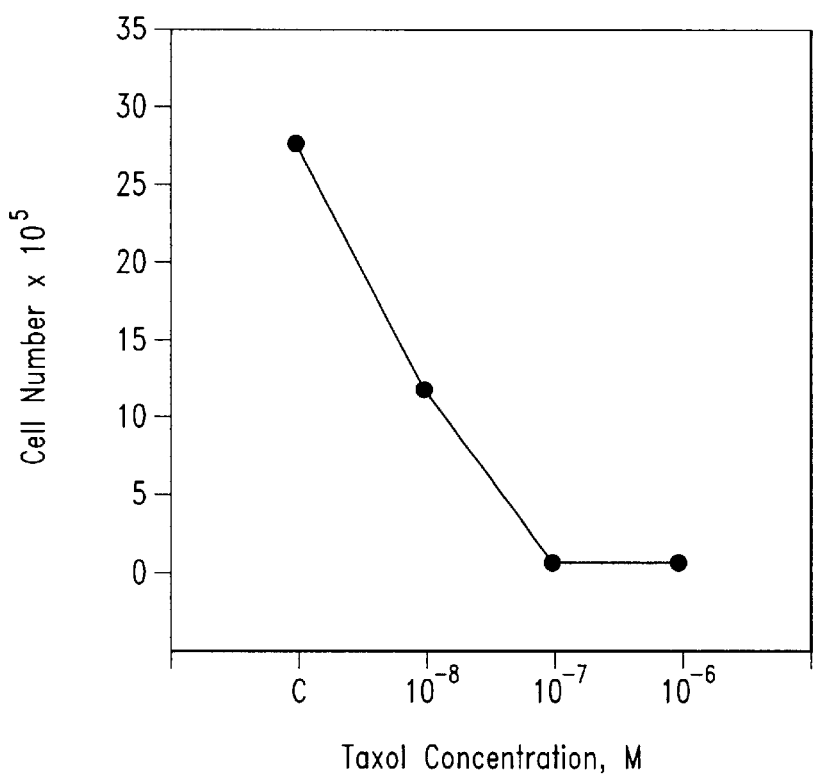
FIG. 9 is a graph which depicts the viability of EOMA cells treated with paclitaxel concentrations of greater than $10^{-8}$ M.

This study demonstrated that paclitaxel was cytotoxic to proliferating synovial fibroblasts in a concentration dependent manner. Paclitaxel at concentrations as low as $10^{-7}$ M is capable of inhibiting proliferation of the synoviocytes (FIG. 9). At higher concentrations of paclitaxel ($10^{-6}$ M and $10^{-5}$ M) the drug was toxic to the synovial fibroblasts in vitro.

C. Discussion

The above study demonstrates that paclitaxel is capable of inhibiting the proliferation of fibroblasts derived from synovium at relatively low concentrations in vitro. Therefore, given the role of connective tissue in the development of chronic inflammation and their behavior during the pathogenesis of inflammatory disease, blocking cell proliferation will favorably affect the outcome of the disease in vivo.

Example 4

Characterization of Paclitaxel's Activity on Human Epidermal Keratinocytes In Vitro The time and dose-dependent effects of paclitaxel on actively proliferating normal human keratinocytes and HaCAT keratinocytes (spontaneously immortalized human epidermal keratinocytes) was investigated.

A. Materials and Methods

The effect of paclitaxel on keratinocytes was assessed by determining the cell number and $^3$H-thymidine incorporation by the cells. For thymidine incorporation, keratinocytes plated at low density (in DMEM, supplemented with 10% FCS, glutamine, antibiotics) were treated with paclitaxel concentrations of 0 to $10^{-4}$ M for 6 hours during logarithmic growth. $^3$H-thymidine was added to the cells and incubated for a further 6 hours. The cells were harvested and radioactivity determined. To determine the total cell numbers, keratinocytes were plated as described and incubated in the presence and absence of paclitaxel for 4 days. Following incubation, cells were collected and counted by the trypan blue exclusion assay.

B. Results

Figure 7:
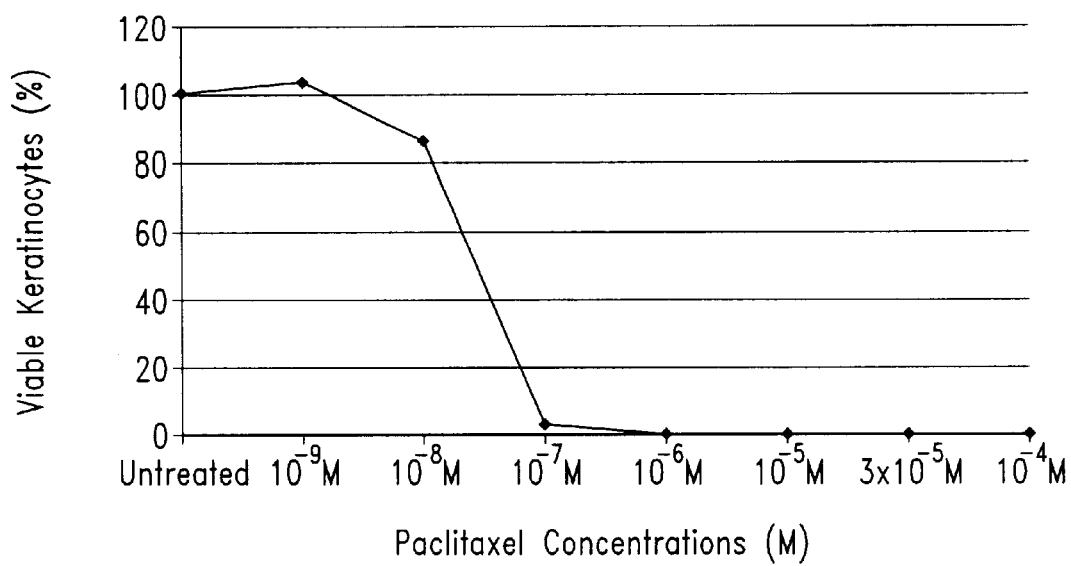
FIG. 7 is a graph which depicts the effects of paclitaxel on keratinocytes in vitro.

The number of viable cells as a percentage of untreated controls was determined. At a paclitaxel concentration of $10^{-9}$ M, cell viability was greater than 100% of untreated controls, while at $10^{-8}$ M viability was slightly less at 87% (FIG. 7). There was a significant drop in cell viability at a paclitaxel concentration of $10^{-7}$ M or higher.

C. Discussion

Paclitaxel was extremely cytotoxic to human keratinocytes at concentrations as low as $10^{-7}$ M. In psoriasis, keratinocytes are abnormally proliferating cells and since paclitaxel stabilizes microtubules, its effect in this mitotically active system is expected. In other studies, paclitaxel was found to be cytotoxic to proliferating synoviocytes, but to have no effect on non-proliferating chondrocytes. Thus, paclitaxel may act on the hyperproliferating cells in psoriatic lesions, while being non-toxic to normal epidermal cells.

Example 5

Effect of Paclitaxel on Astrocyte Proliferation

It is well established that there is an increase in the numbers of fibrous astrocytes in MS lesions, which are thought to be involved in the destruction of myelin through the production of cytokines and matrix metalloproteinases (Mastronardi et al., *J. Neurosci. Res.* 36:315–324, 1993; Chandler et al., *J. Neuroimmunol.* 72:155–161, 1997). Fibrous astrocytes have high levels of glial fibrillary acidic protein (GFAP) which serves as a biochemical marker for fibrous astrocyte proliferation. The ability of paclitaxel micelles to inhibit astrocyte proliferation was assessed in a transgenic mouse model of demyelinating disease (Mastronardi et al., *J. Neurosci. Res.* 36:315–324, 1993).

A. Materials and Methods

Subcutaneous administration of continuous paclitaxel therapy (2 mg/kg; 3× per week, total of 10 injections) was initiated at clinical onset of disease (approximately 4 months of age). Five animals received micellar paclitaxel, two mice were used as controls; one mouse was an untreated normal and one was an untreated transgenic littermate. Only one transgenic mouse was used as a control because the course of the disease has been well established in the laboratory. Four month old animals were injected with micellar paclitaxel, after the initial signs of neurological pathology of MS were evident.

Three days following the tenth injection, the experimental study was terminated and the brain tissues processed for histological analysis. For light microscopy, tissues were fixed in formalin and embedded in paraffin. Sections were stained with anti-GFAP antibody (DACO), washed and then reacted with secondary antibody conjugated with HPP. The sections were stained for HPP and counter-stained with haematoxylin. For electron microscopy, tissues were fixed in 2.5% glutaraldehyde and phosphate buffered saline (pH 7.2), and post-fixed with 1% osmium tetroxide. Sections were prepared and viewed with a JEOL 1200 EX II transmission EM.

B. Results

As the neurological pathology progresses, levels of GFAP are elevated in the transgenic mouse brains; this is thought to reflect an increase in the number of fibrous astrocytes present. In contrast, transgenic mice treated with paclitaxel have near normal levels of GFAP (Table 1). These data suggest that paclitaxel may inhibit astrocyte proliferation in vivo which may contribute to the prevention of demyelination in MS.

TABLE 1

Quantification of GFAP in Brain Homogenate

| Group | GFAP (ng) | GFAP (ng/μg homogenate protein) |
|---|---|---|
| Normal Mice | 0.64 ± 0.02 | 12.8 |
| Transgenic Mice | 1.80 +/− 0.10 | 36.0 |
| Transgenic Mice Treated with Paclitaxel | 0.69 +/− 0.05 | 13.8 |

Further analysis of GFAP in brain tissue was assessed histologically. FIG. 78 illustrates brain sections from normal mice, control transgenic mice not treated with paclitaxel and transgenic mice treated with paclitaxel.

Although control transgenic mice have higher numbers of fibrous astrocytes, the morphology of the astrocytes is similar to that seen in normal animals (thick stellate processes spreading from the cell body). However, in transgenic mice treated with paclitaxel the number of fibrous astrocytes decreased significantly. Further, two morphological changes are observed: the cell body of the fibrous astrocytes appears to round up (which has been shown to lead to apoptosis in culture) and the cellular processes become very thin around the cell body.

Further ultrastructural analysis using electron microscopy has shown that astrocytes of transgenic mice were characterized by densely stained astrocytic processes originating from the cell body. These broad processes contain a well-organized array of filaments indicating a viable, activated cell. However, the morphology of the astrocytes in transgenic animals treated with paclitaxel was characterized by cell rounding, thin filamentous processes and intracellular depletion and disorganization of filamentous proteins (FIG. 80).

C. Conclusions

These data demonstrate that paclitaxel causes changes to fibrous astrocytes in vivo, the most proliferative cell type in MS lesions. It is likely that paclitaxel is also inhibiting the function of astrocytic processes and, thus, may alter cellular events involved in myelin destruction.

Example 6

Effect of Paclitaxel on Endothelial Cell Proliferation

In order to determine whether paclitaxel inhibits endothelial cell proliferation, EOMA cells (an endothelial cell line) were plated at low density and incubated in the absence and presence of increasing concentrations of paclitaxel for 48 hours. Following the incubation, the number of viable cells were determined using the trypan blue exclusion assay. The results (provided in FIG. 9) show that paclitaxel at concentrations of $10^{-8}$M inhibited endothelial cell proliferation by over 50% and concentrations of $10^{-7}$M or greater completely inhibited cell proliferation. These data demonstrate that paclitaxel is a potent inhibitor of endothelial cell proliferation. All cell toxicity assays were performed three times, and each individual measurement was made in triplicate.

Figure 10:
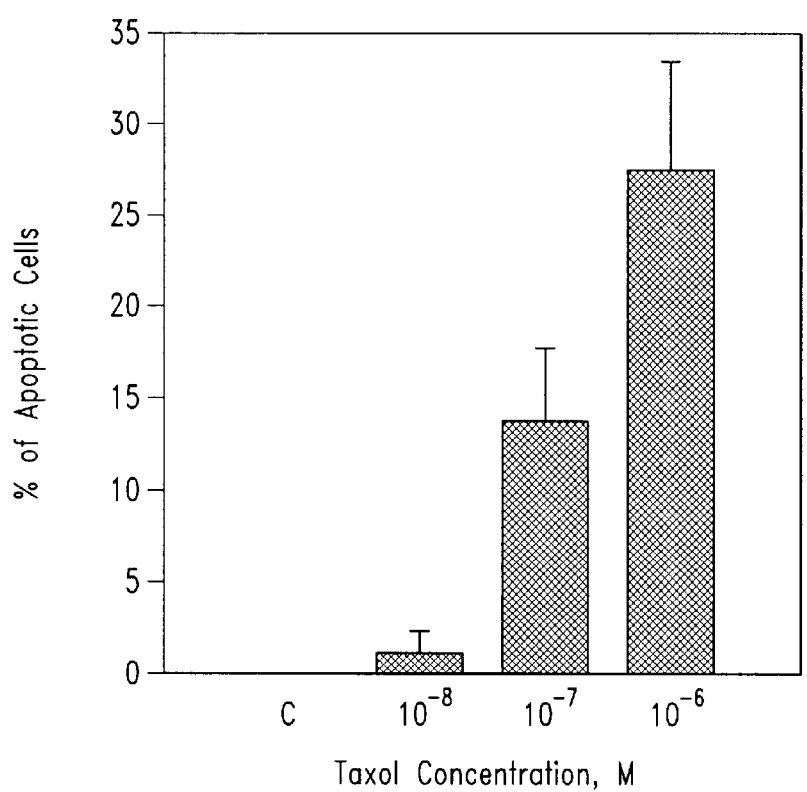
FIG. 10 is a bar graph which depicts the percentage of apoptotic EOMA cells in culture treated with increasing concentrations of paclitaxel.
Figure 11A:
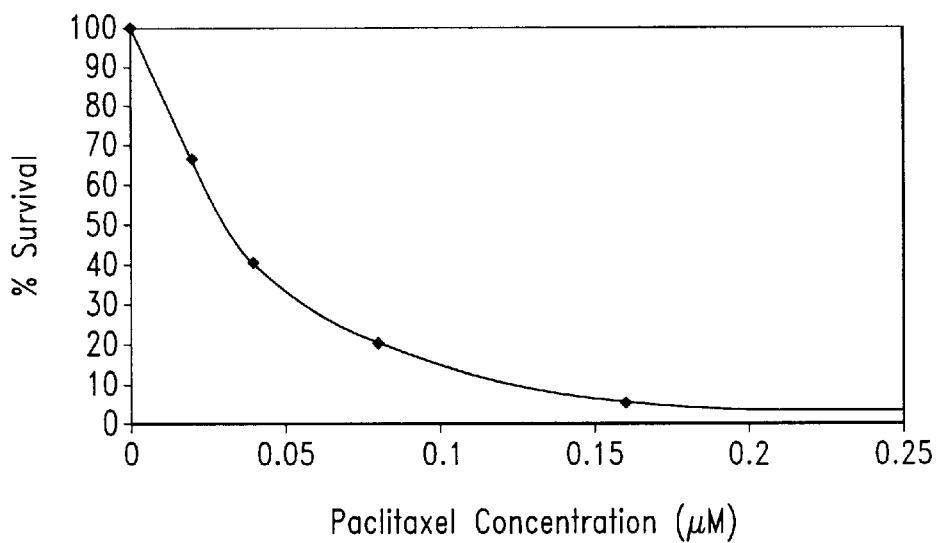
FIGS. 11A–11E are graphs which depict the effect of various anti-microtubule agents on synoviocytes after a period of 24 hours.
Figure 11B:
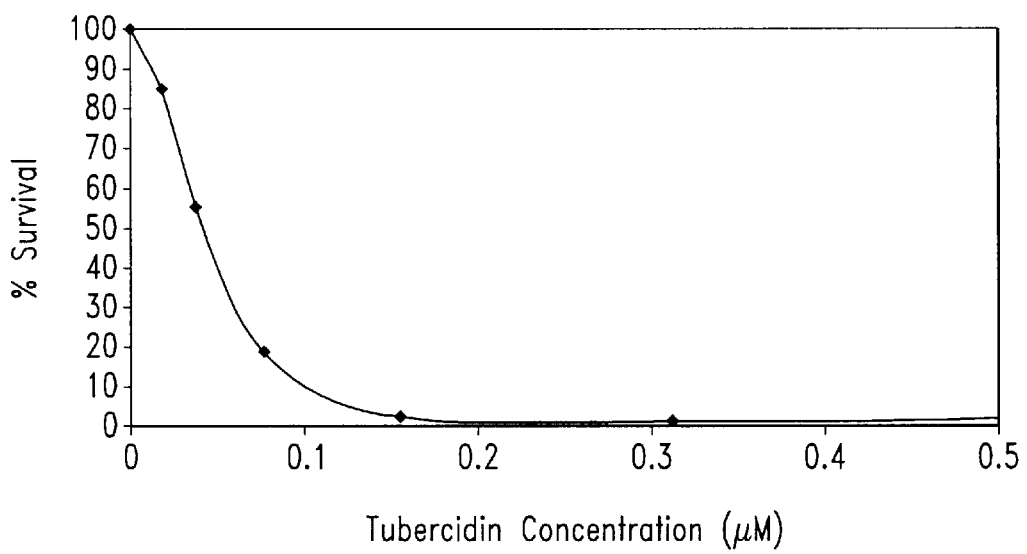
Figure 11C:
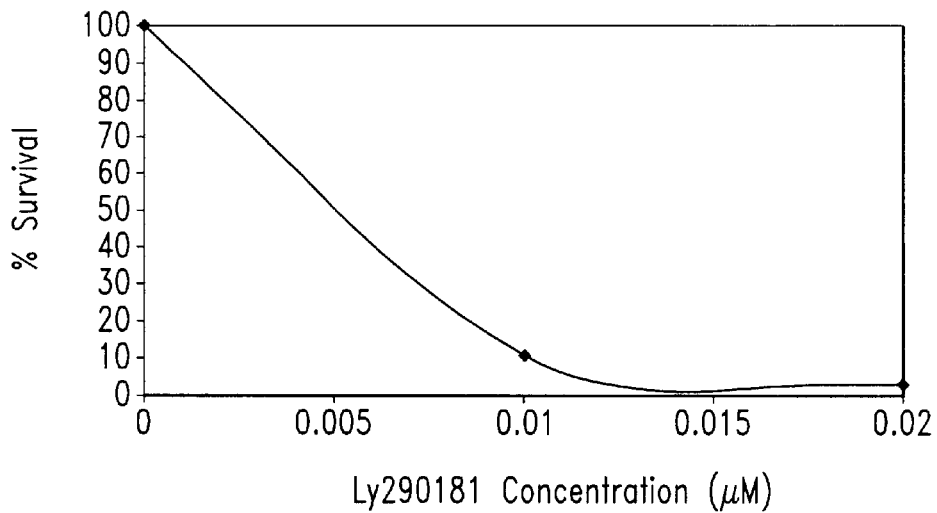
Figure 11D:
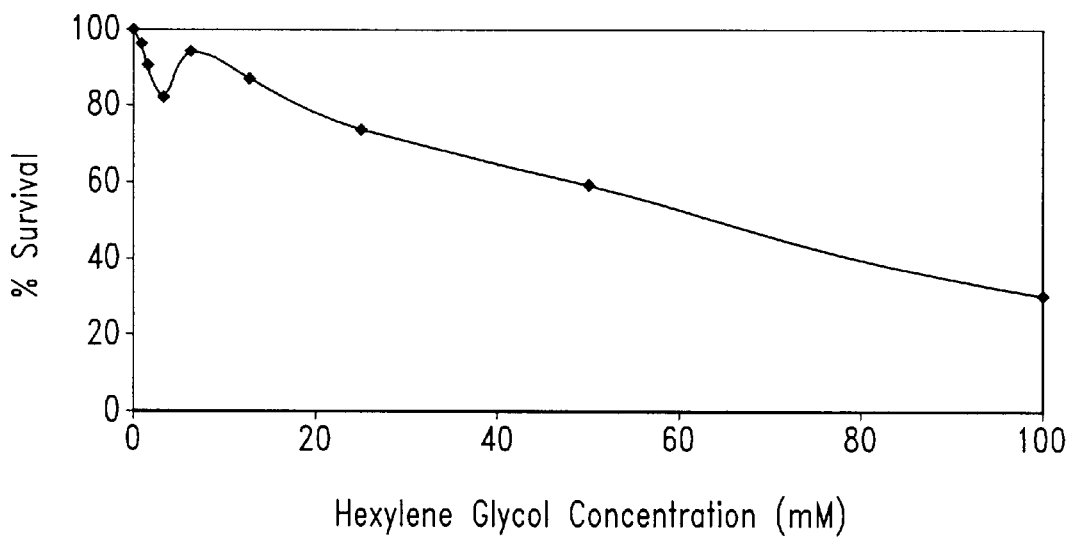
Figure 11E:
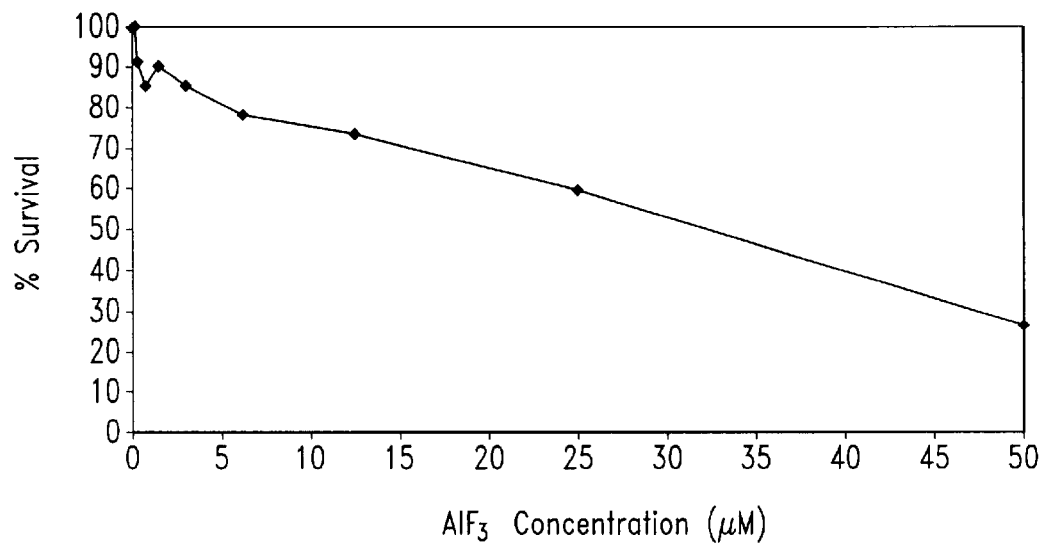
Figure 11F:
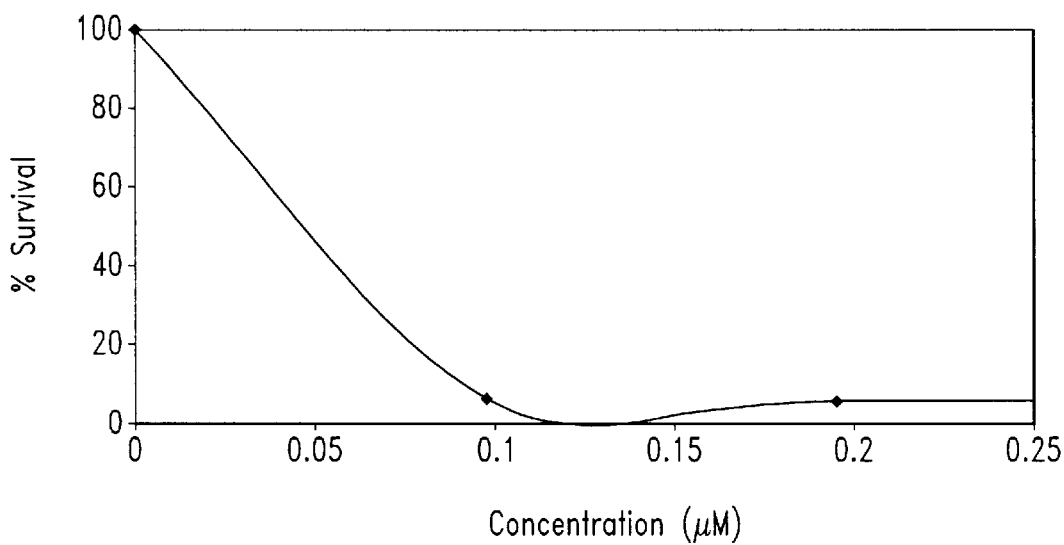
Figure 12A:
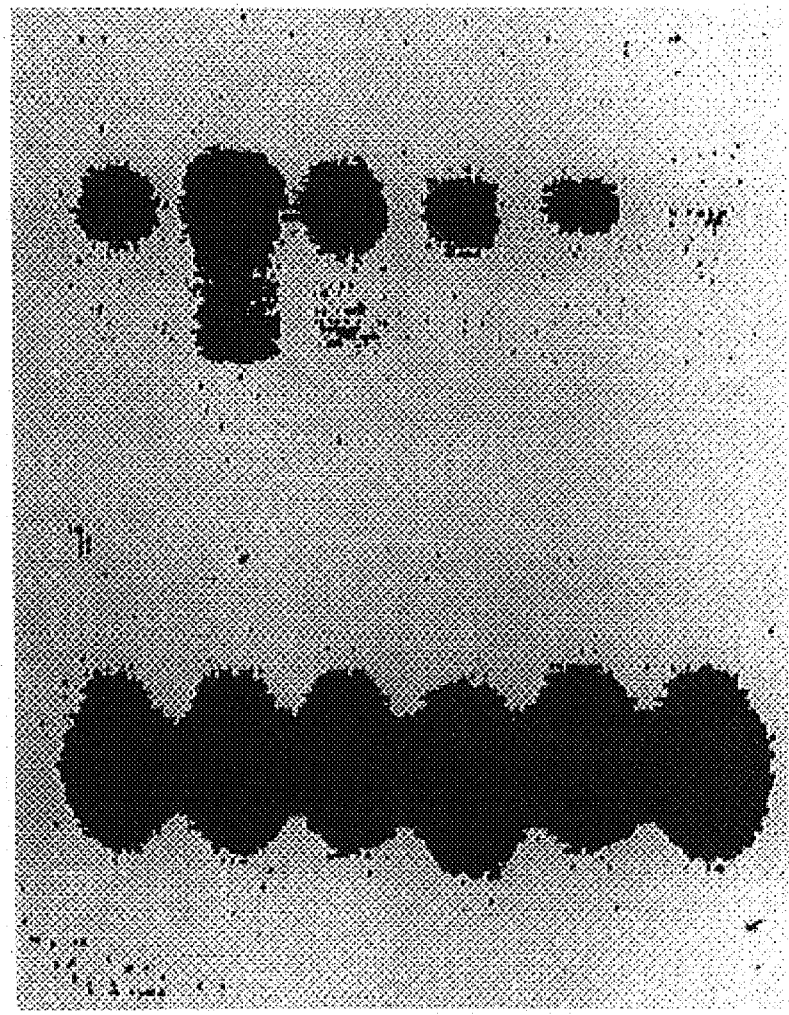
FIGS. 12A–12H are blots which show the effect of various anti-microtubule agents in inhibiting collagenase expression.
Figure 12B:
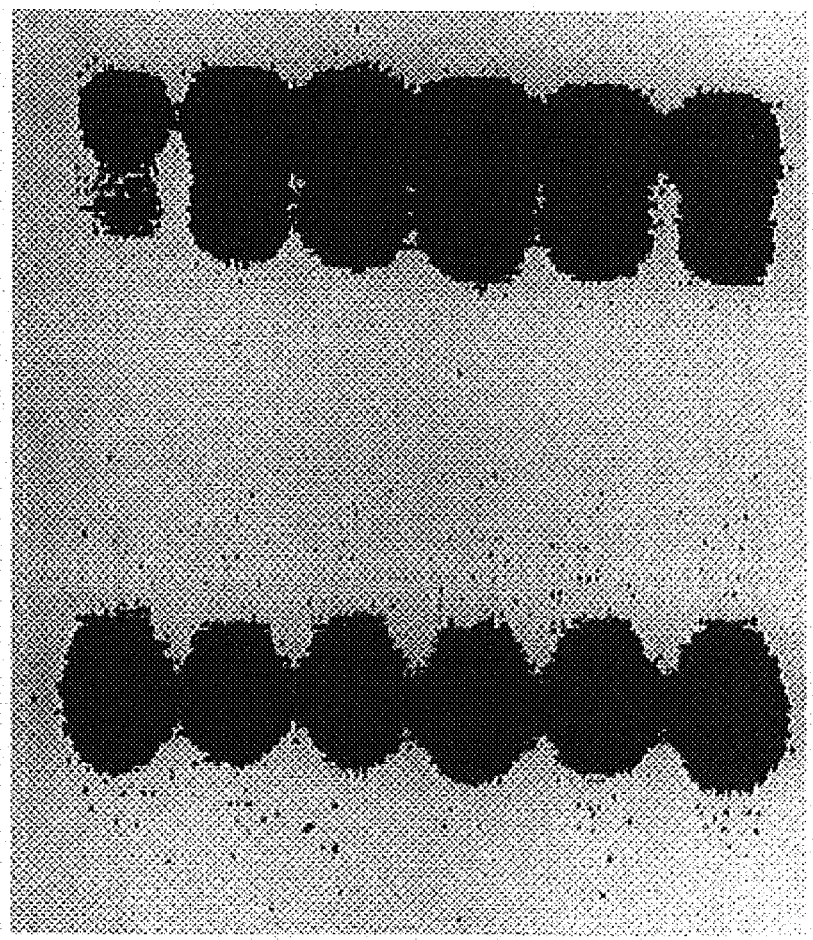
Figure 12C:
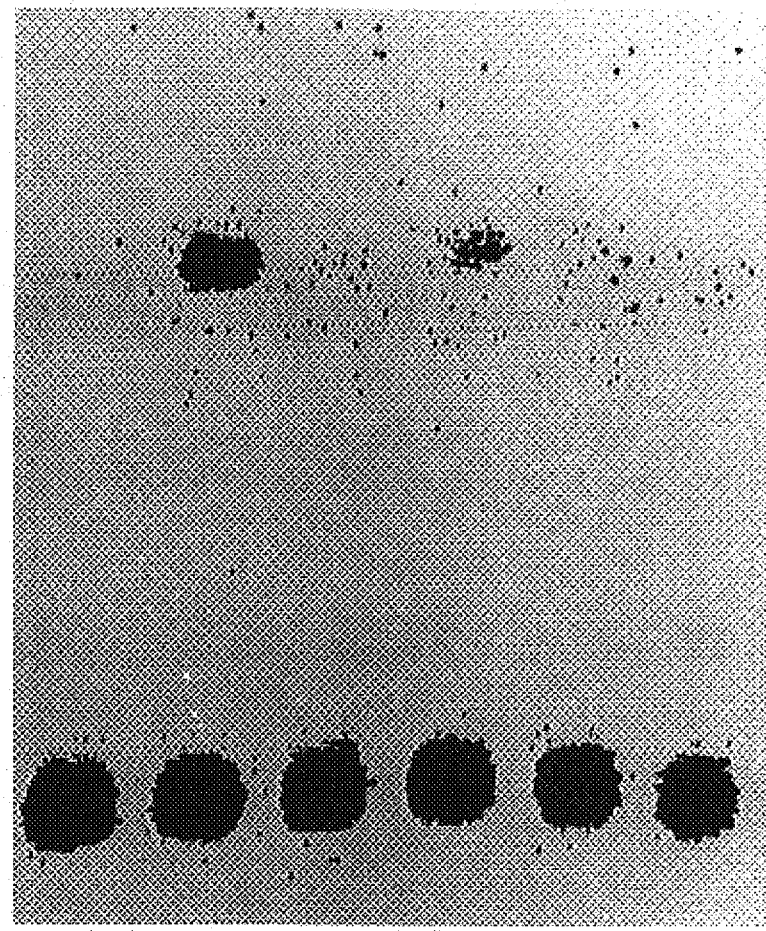
Figure 12D:
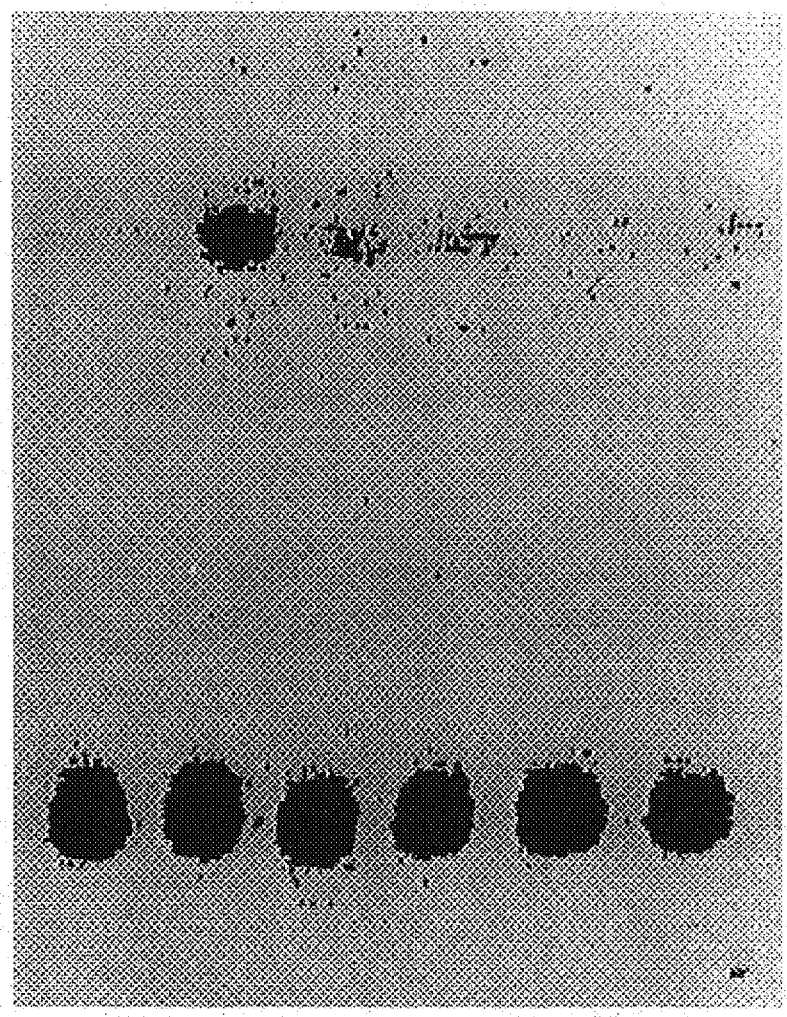
Figure 12E:
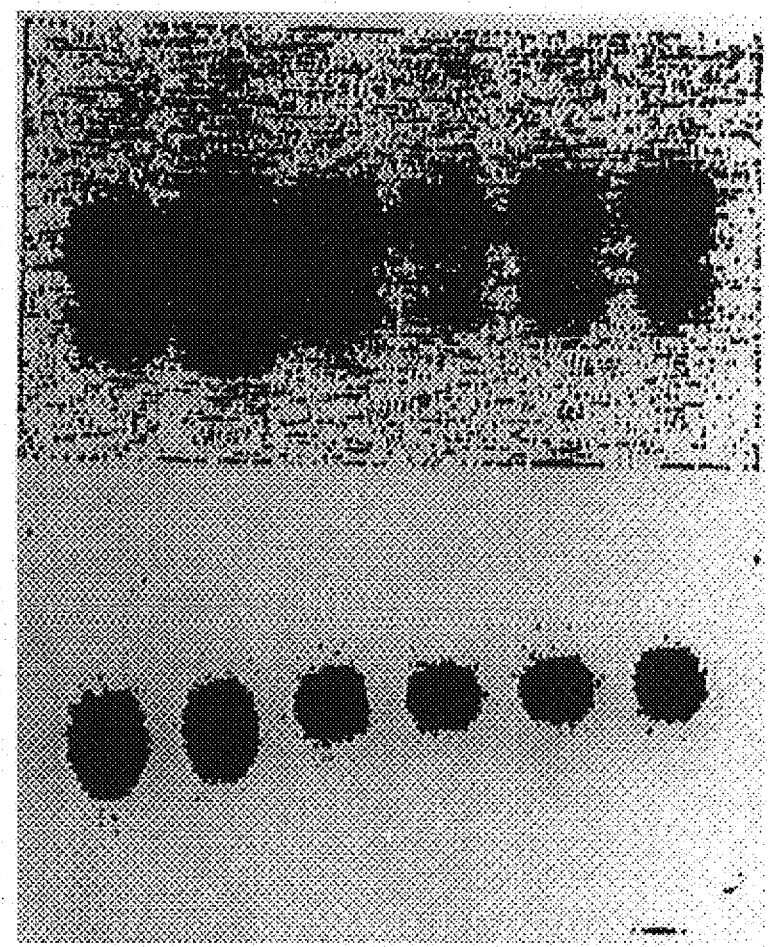
Figure 12F:
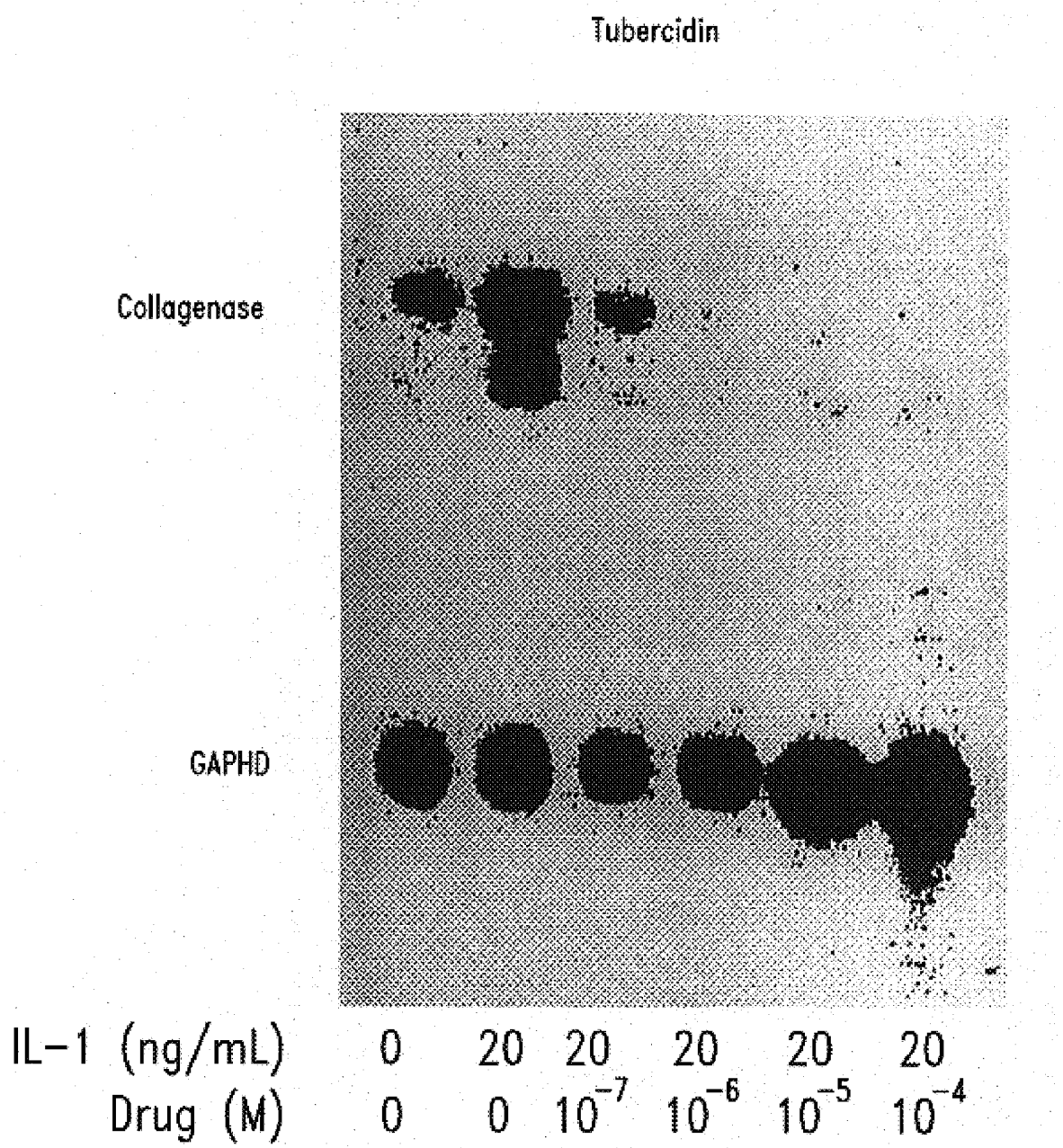
Figure 12G:
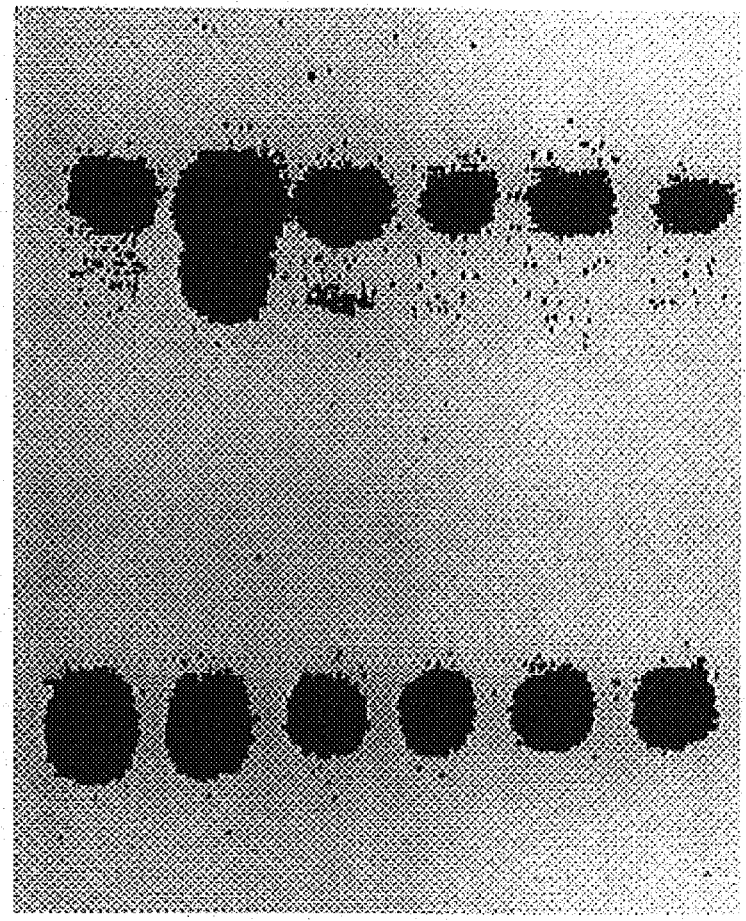
Figure 12H:
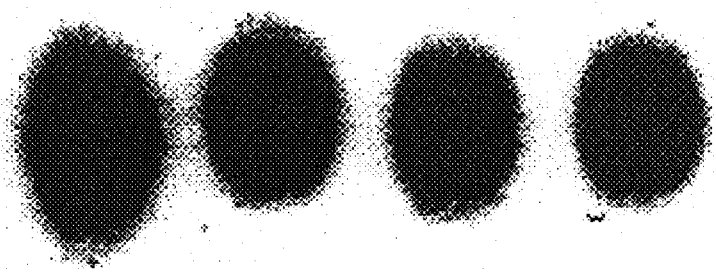
Figure 13A:
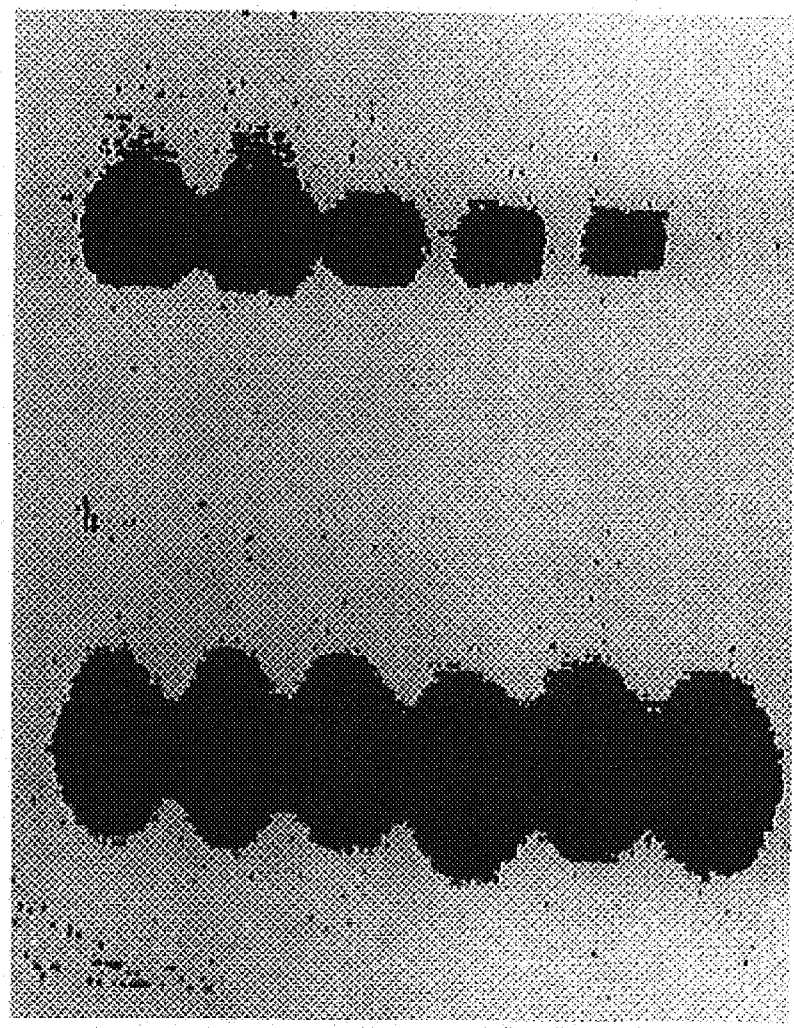
FIGS. 13A–13H are blots which show the effect of various anti-microtubule agents on proteoglycan expression.
Figure 13B:
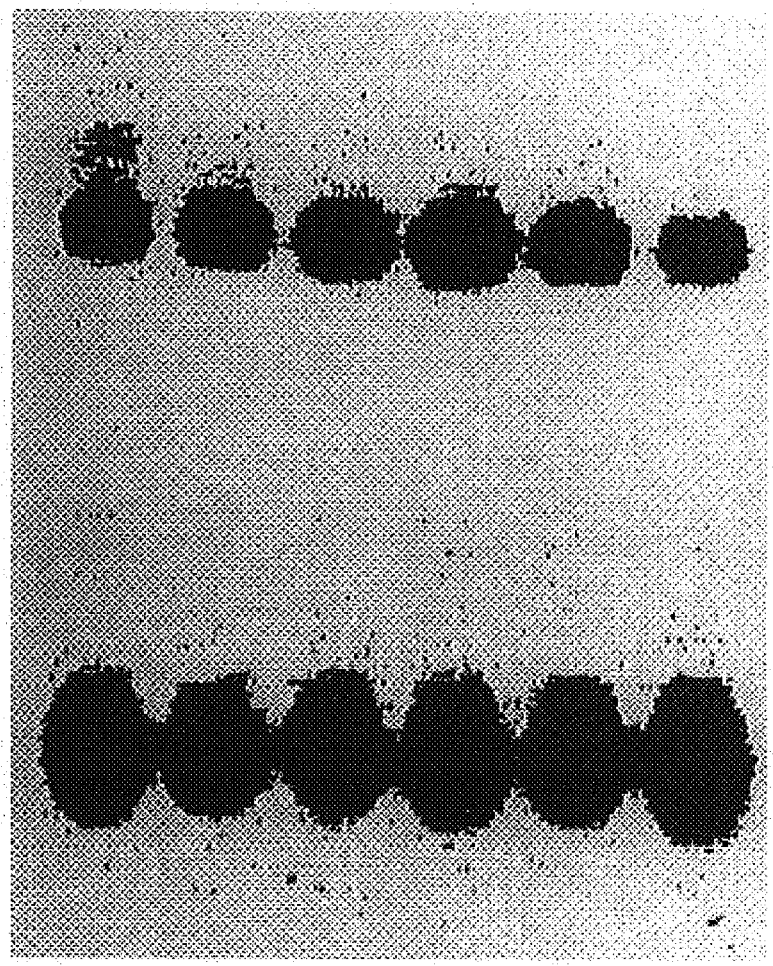
Figure 13C:
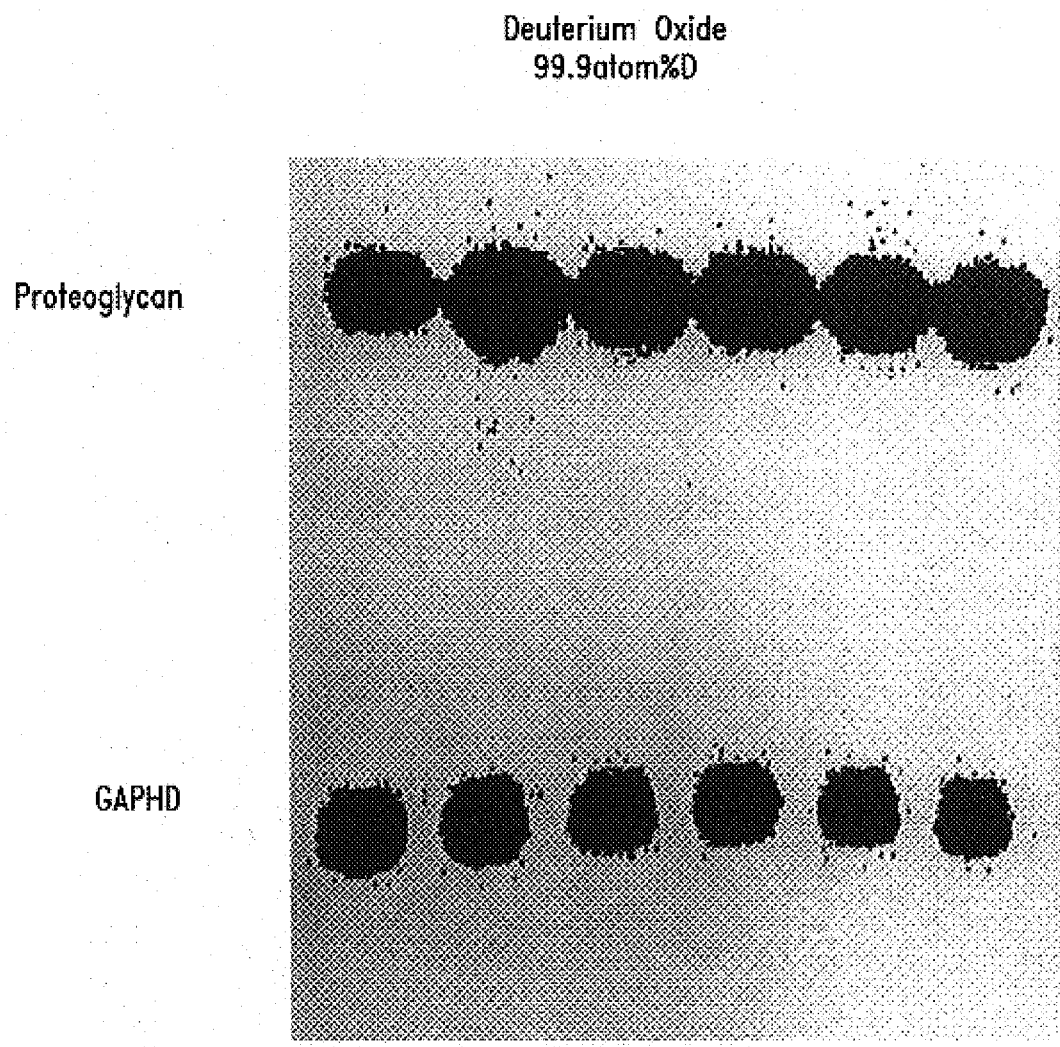
Figure 13D:
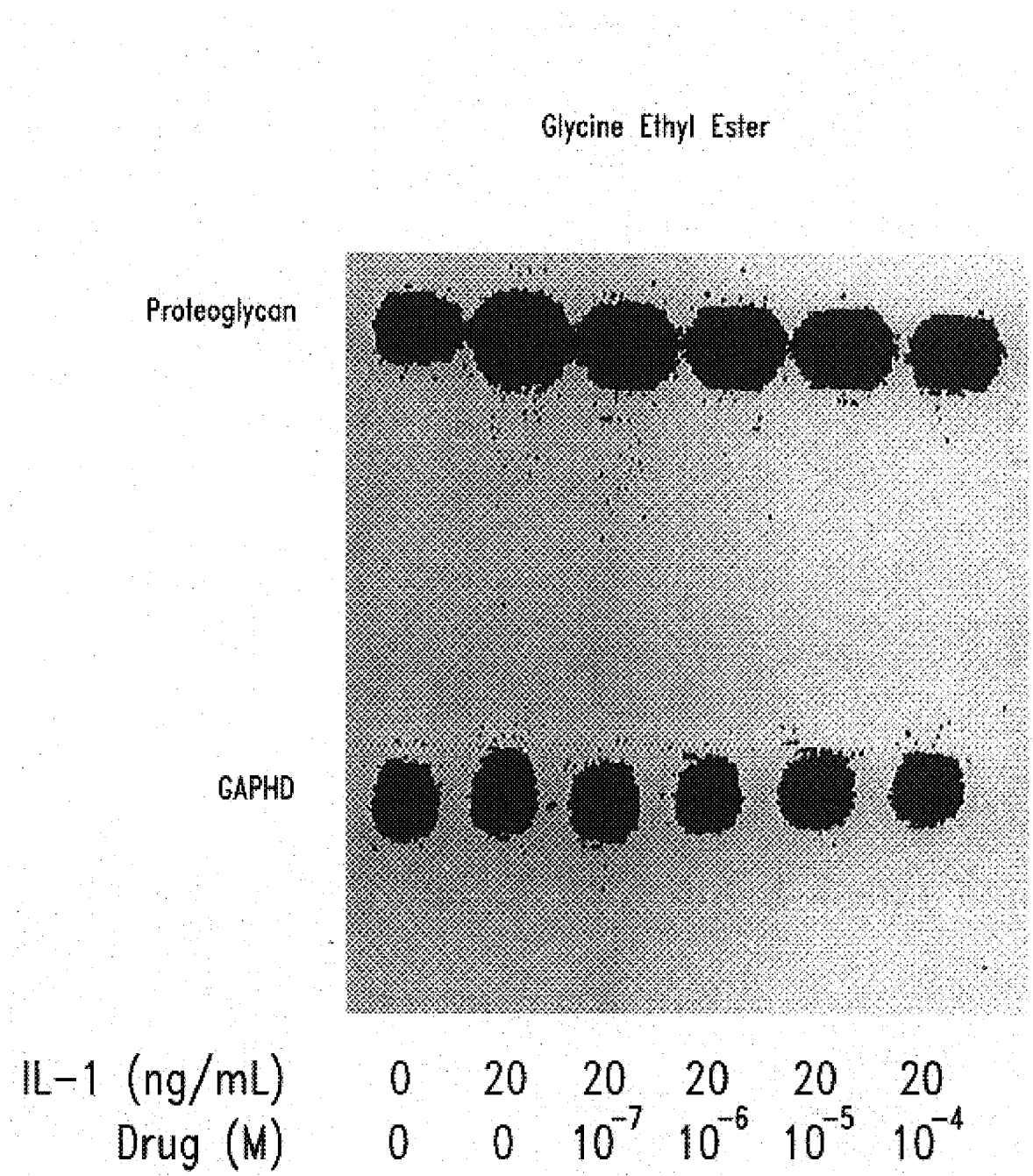
Figure 13E:
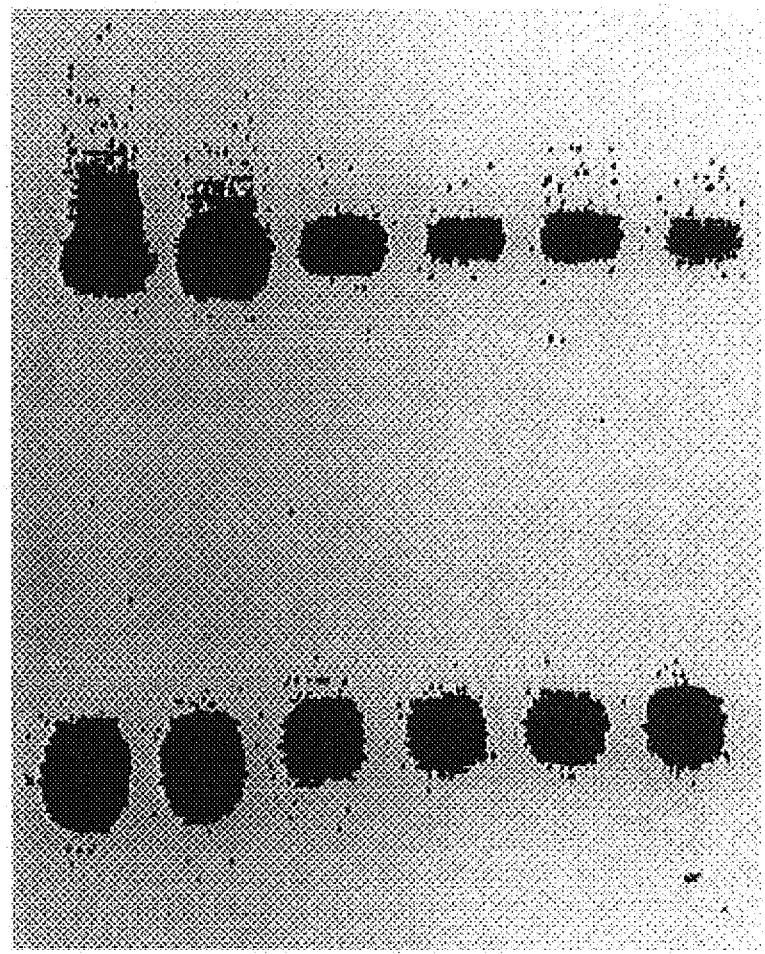
Figure 13F:
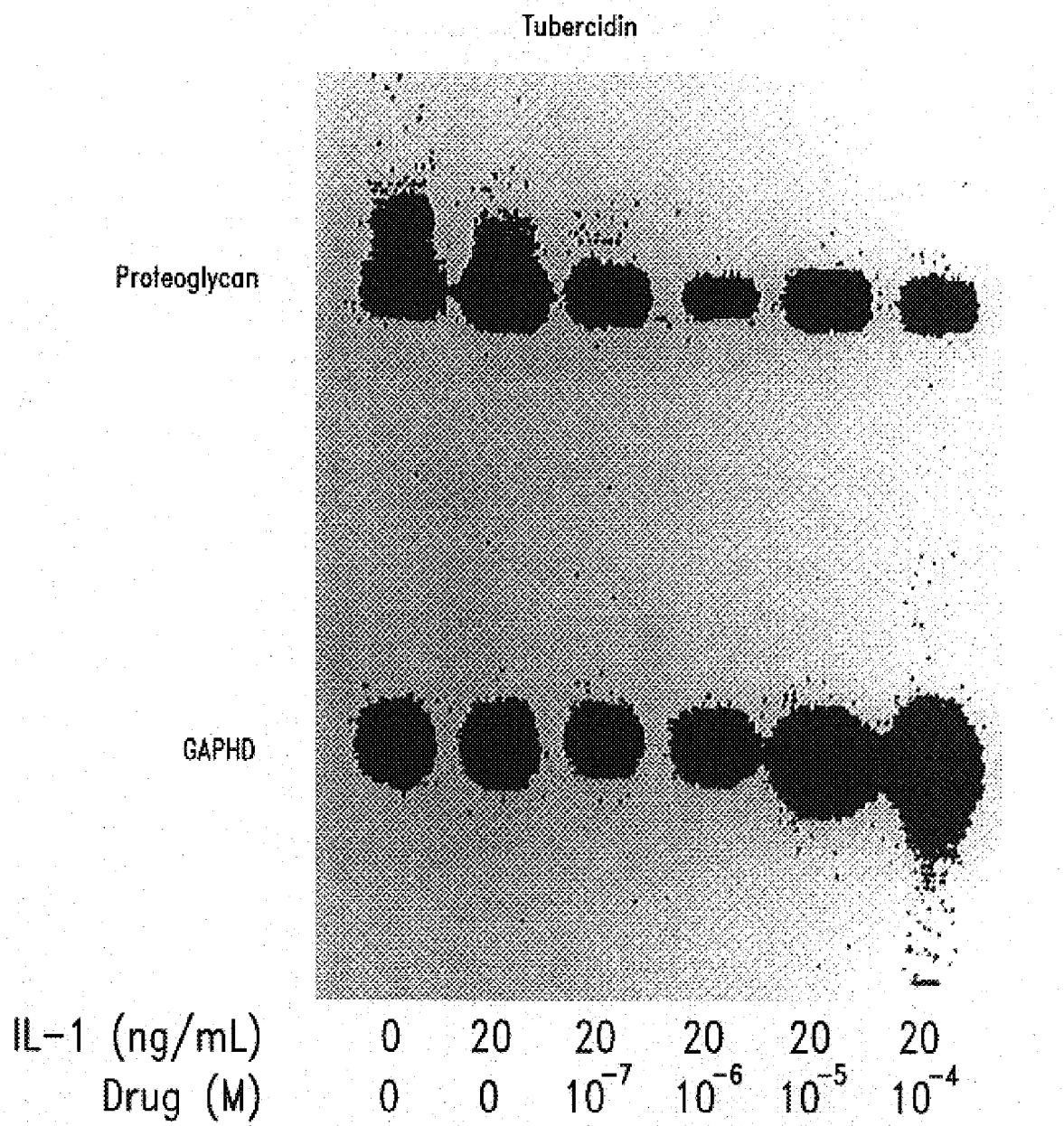
Figure 13G:
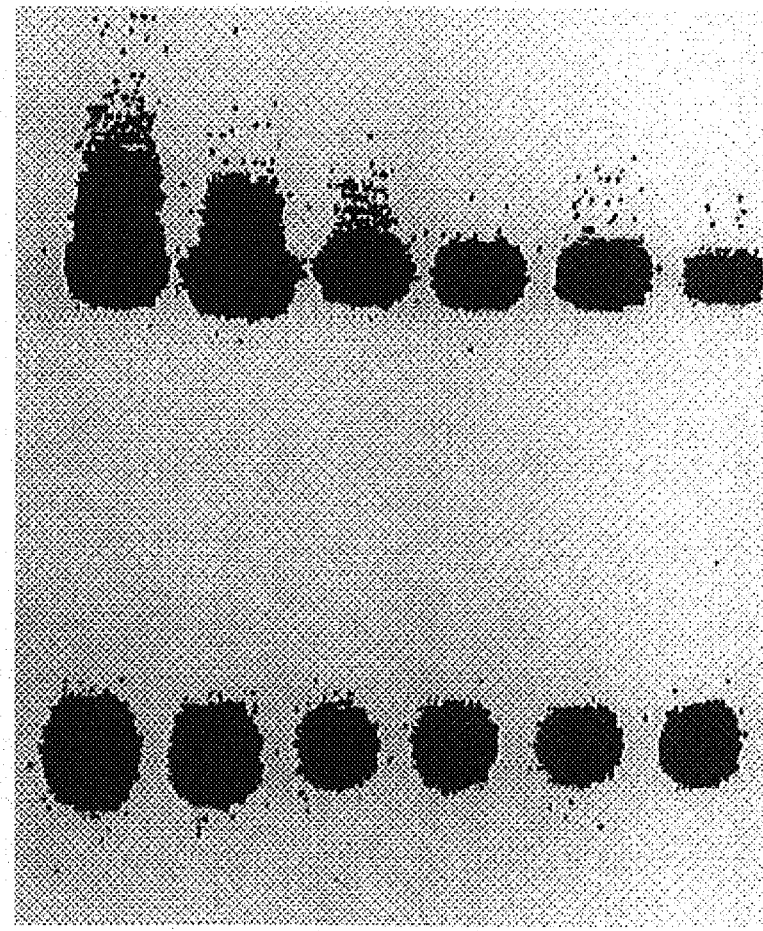
Figure 13H:
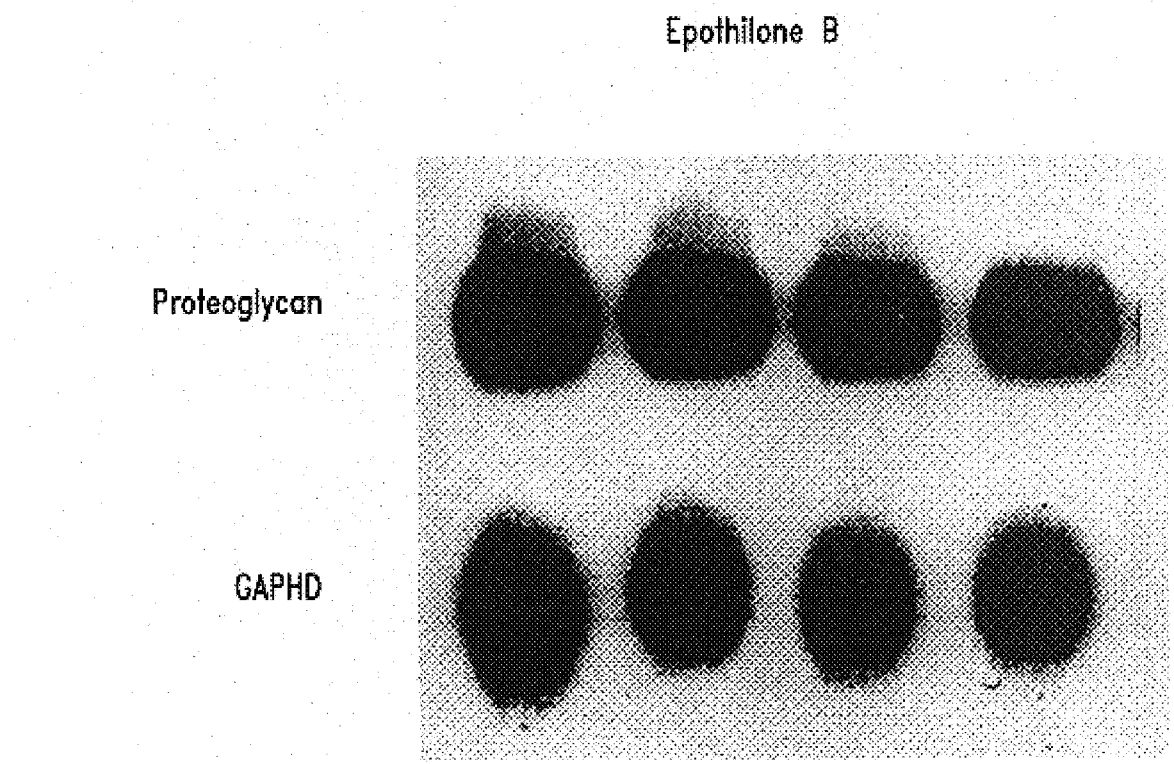

In order to determine the effect of paclitaxel on endothelial cell cycling and apoptosis, EOMA cells were incubated in the absence and presence of increasing concentrations of paclitaxel for 24 hours. The cells were fixed with 3.7% formaldehyde in phosphate buffered saline for 20 minutes, stained with DAPI (4'-6-diaminido-2-phenylindole), 1 ug/ml, and examined with a 40×objective under epifluorescent optics. Apoptotic cells were evaluated by scoring cells for fragmented nuclei and condensed chromatin. The data show that concentrations of paclitaxel greater than $10^{-8}$M induced endothelial cell apoptosis (FIG. 10).

Example 7

Proliferation Assay Protocol (MTT)

On day one, $5$–$10\times10^4$ synoviocytes were plated per well (96-well plate). Column #1 was kept free of cells (blank). On day 2, the plate was flicked to discard the medium and 200 $\mu l$ of medium containing various concentrations of drug was added. The cells were exposed for 6 hours, 24 hours or 4 days. There was no drug added to columns #1 and #2 (blank and untreated control, respectively). The medium containing the drug was discarded and 200 $\mu l$ of fresh complete medium was added. The cells were then left to grow for an additional 3 to 4 days. On day five, 20 $\mu l$ of dimethylthiazol diphenyltetrazolium bromide salt (MTT) (5 mg/ml PBS) was added and allowed to incubate for 4 hours at 37° C. The medium was decanted and 200 $\mu l$ of DMSO was added. The plate was agitated for 30 minutes and the absorbance read at 562 nm.

Results

The data were expressed as the % of survival which was obtained by dividing the number of cells remaining after treatment by the number of cells in the untreated control column #2 (the number of cells was obtained from a standard done prior to the assay). The $IC_{50}$, the concentration of drug that kills 50% of the population, can be interpolated from FIGS. 11A–E. For a 24-hour exposure, the LY290181 compound was found to be the most potent anti-microtubule agents to reduce and inhibit cell proliferation with an $IC_{50}$ of less than 5 nM (FIG. C). Paclitaxel, epothilone B and tubercidin were slightly less potent with $IC_{50}$s around 30 nM (FIG. A), 45 nM (FIG. F) and 45 nM (FIG. B), respectively. Finally, the $IC_{50}$s for aluminum fluoride ($AlF_3$) and hexylene glycol were significantly higher with values around 32 $\mu M$ (FIG. E) and 64 mM (FIG. D), respectively.

Example 8

Effect of Paclitaxel and Other Anti-Microtubule Agents on Matrix Metalloproteinase Production A. Materials and Methods 1. IL-1 Stimulated AP-1 Transcriptional Activity is Inhibited by Paclitaxel Chondrocytes were transfected with constructs containing at AP-1 driven CAT reporter gene, and stimulated with IL-1, IL-1 (50 ng/ml) was added and incubated for 24 hours in the absence and presence of paclitaxel at various concentrations. Paclitaxel treatment decreased CAT activity in a concentration dependent manner (mean±SD). The data noted with an asterisk (*) have significance compared with IL-1-induced CAT activity according to a t-test, P<0.05. The results shown are representative of three independent experiments.

2. Effect of Paclitaxel on IL-1 Induced AP-1 DNA Binding Activity, AP-1 DNA

Binding activity was assayed with a radiolabeled human AP-1 sequence probe and gel mobility shift assay. Extracts from chondrocytes untreated or treated with various amounts of paclitaxel ($10^{-7}$ to $10^{-5}$ M) followed by IL-1β (20 ng/ml) were incubated with excess probe on ice for 30 minutes, followed by non-denaturing gel electrophoresis. The "com" lane contains excess unlabeled AP-1 oligonucleotide. The results shown are representative of tree independent experiments.

3. Effect of Paclitaxel on IL-1 Induced MMP-1 and MMP-3 mRNA Expression

Cells were treated with paclitaxel at various concentrations ($10^{-7}$ to $10^{-5}$ M) for 24 hours. Then, treated with IL-1 (20 ng/ml) for additional 18 hours in the presence of paclitaxel. Total RNA was isolated, and the MMP-1 mRNA levels were determined by Northern blot analysis. The blots were subsequently stripped and reprobed with $^{32}$P-radiolabeled rat GAPDH cDNA, which was used as a housekeeping gene. The results shown are representative of four independent experiments. Quantitation of collagenase-1 and stromelysin-expression mRNA levels. The MMP-1 and MMP-3 expression levels were normalized with GAPDH.

4. Effect of Other Anti-microtubules on Collagenase Expression

Primary chondrocyte cultures were freshly isolated from calf cartilage. The cells were plated at $2.5\times10^6$ per ml in 100×20 mm culture dishes and incubated in Ham's F12 medium containing 5% FBS overnight at 37° C. The cells were starved in serum-free medium overnight and then treated with anti-microtubule agents at various concentrations for 6 hours. IL-1 (20 ng/ml) was then added to each plate and the plates incubated for an additional 18 hours. Total RNA was isolated by the acidified guanidine isothiocyanate method and subjected to electrophoresis on a denatured gel. Denatured RNA samples (15 $\mu g$) were analyzed by gel electrophoresis in a 1% denatured gel, transferred to a nylon membrane and hydridized with the $^{32}$P-labeled collagenase cDNA probe. $^{32}$P-labeled glyceraldehyde phosphate dehydrase (GAPDH) cDNA as an internal standard to ensure roughly equal loading. The exposed films were scanned and quantitatively analyzed with ImageQuant.

B. Results

1. Promoters on the Family of Matrix Metalloproteinases

Figure 19A:
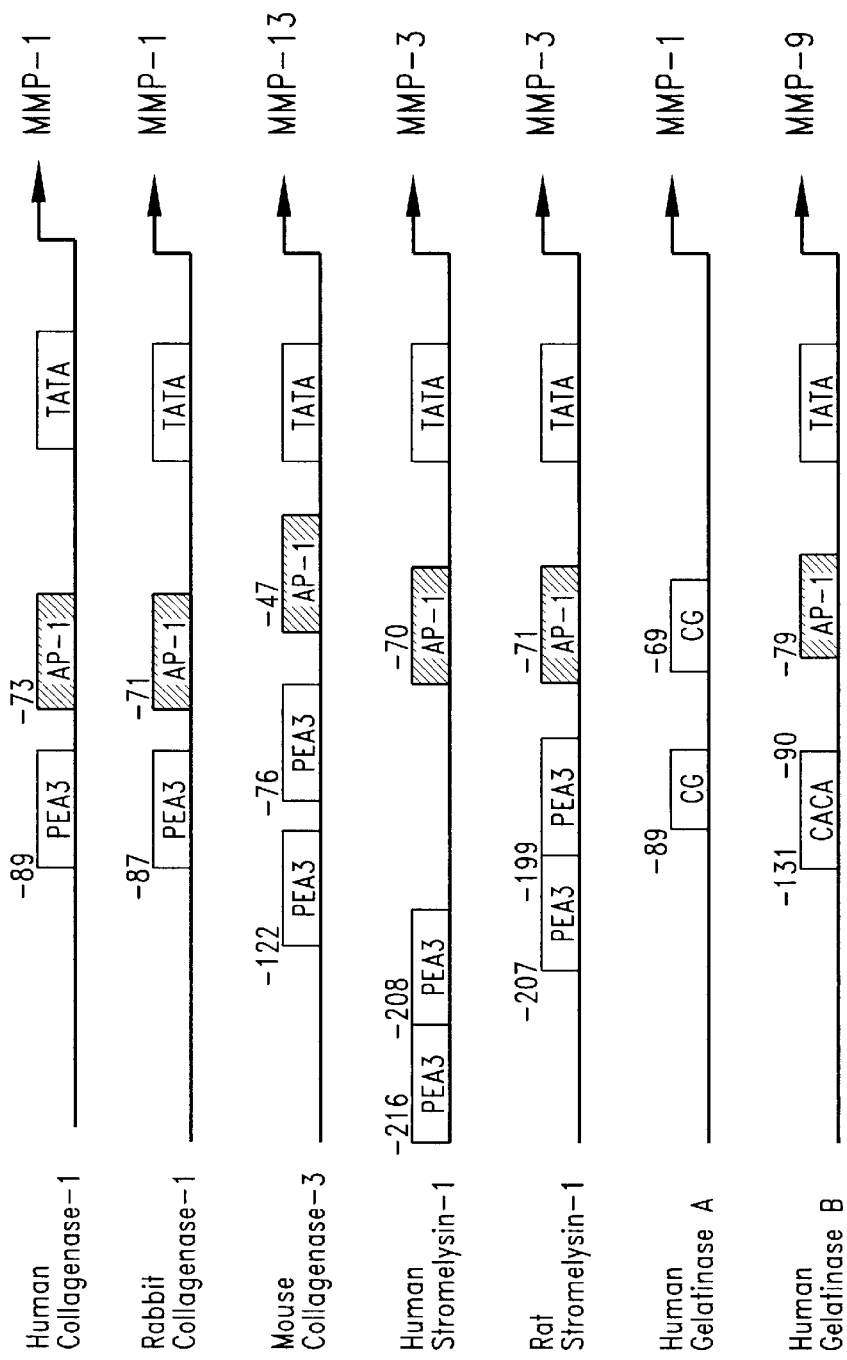
FIG. 19A schematically depicts the transcriptional regulation of matrix metalloproteinases.

FIG. 19A shows that all matrix metalloproteinases contained the transcriptional elements AP-1 and PEA-3 with the exception of Gelatinase B. It has been well established that expression of matrix metalloproteinases such as collagenases and stromelysins are dependent on the activation of the transcription factors AP-1. Thus inhibitors of AP-1 would inhibit the expression of matrix metalloproteinases.

2. Effect of Paclitaxel on AP-1 Transcriptional Activity

Figure 19B:
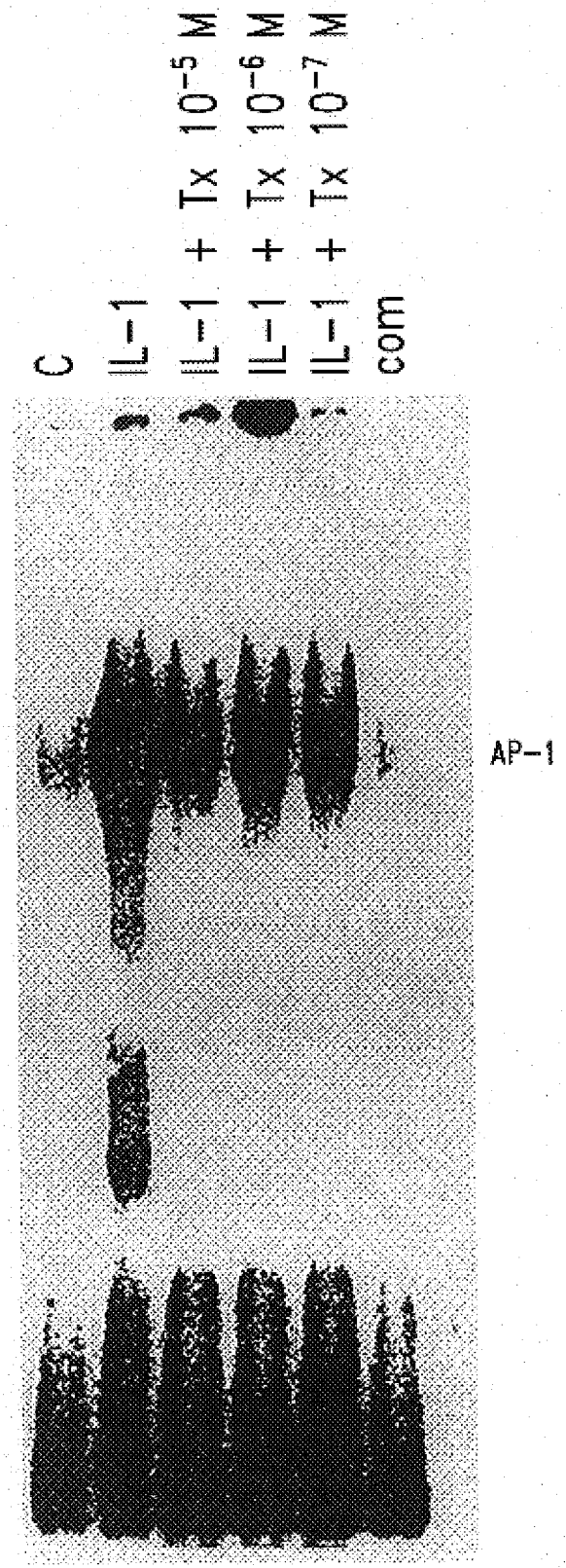
FIG. 19B is a blot which demonstrates that IL-1 stimulates AP-1 transcriptional activity.

As demonstrated in FIG. 19B, IL-1 stimulated AP-1 transcriptional activity 5-fold. Pretreatment of transiently transfected chondrocytes with paclitaxel reduced IL-1 induced AP-1 reporter gene CAT activity. Thus, IL-1 induced AP-1 activity was reduced in chondrocytes by paclitaxel in a concentration dependent manner ($10^{-7}$ to $10^{-5}$ M). These data demonstrated that paclitaxel was a potent inhibitor of AP-1 activity in chondrocytes.

3. Effect of Paclitaxel on AP-1 DNA Binding Activity

Figure 19C:
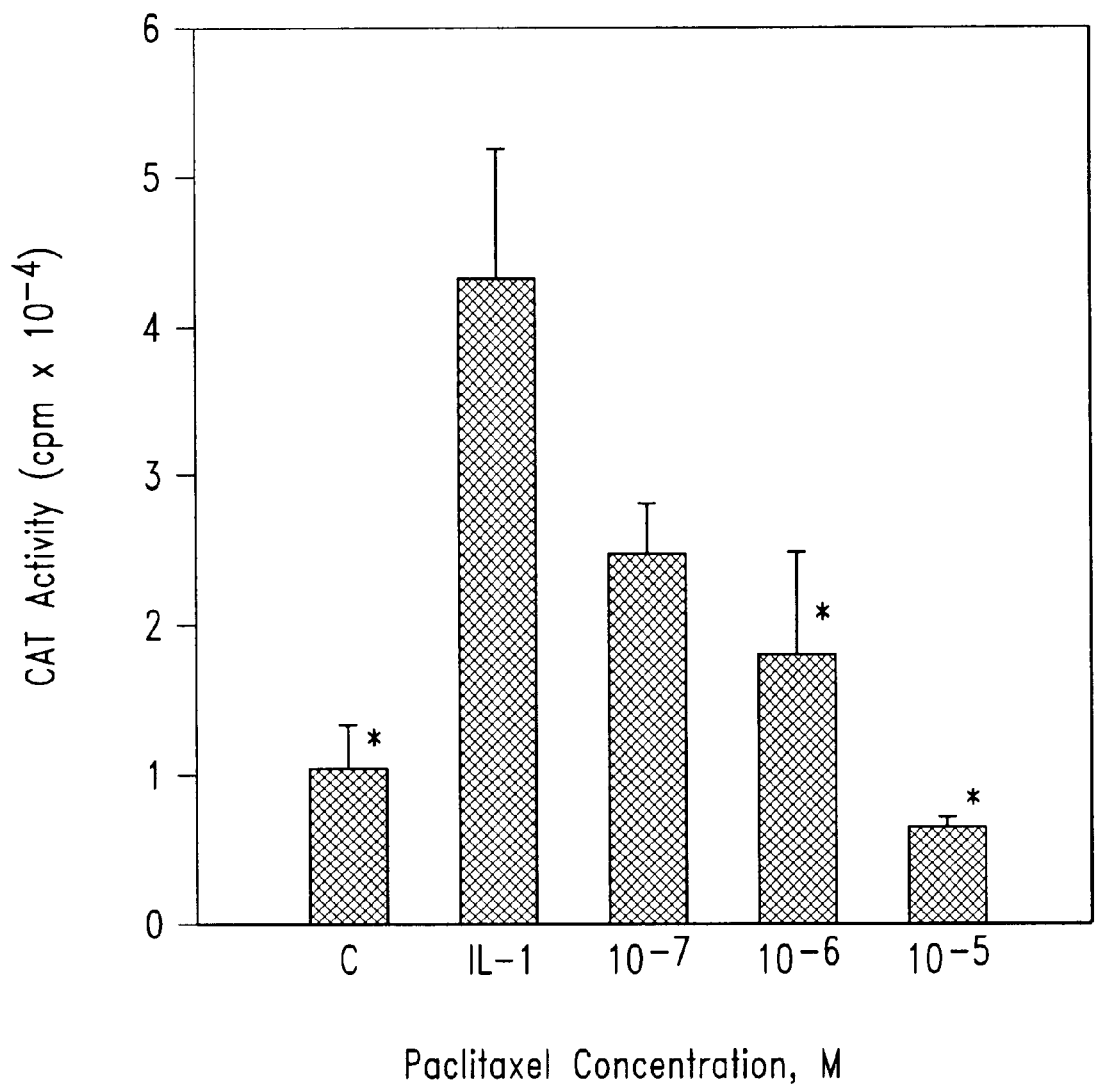
FIG. 19C is a graph which shows that IL-1 induced binding activity decreased in lysates from chondrocytes which were pretreated with paclitaxel.

To confirm that paclitaxel inhibition of AP-1 activity was not due to nonspecific effects, the effect of paclitaxel on IL-1 induced AP-1 binding to oligonucleotides using chondrocyte nuclear lysates was examined. As shown in FIG. 19C, IL-1 induced binding activity decreased in lysates from chondrocyte which have been pretreated with paclitaxel at concentration $10^{-7}$ to $10^{-5}$ M for 24 hours. Paclitaxel inhibition of AP-1 transcriptional activity closely correlated with the decrease in AP-1 binding to DNA.

4. Effect of Paclitaxel on Collagenase and Stromelysin Expression

Figure 20:
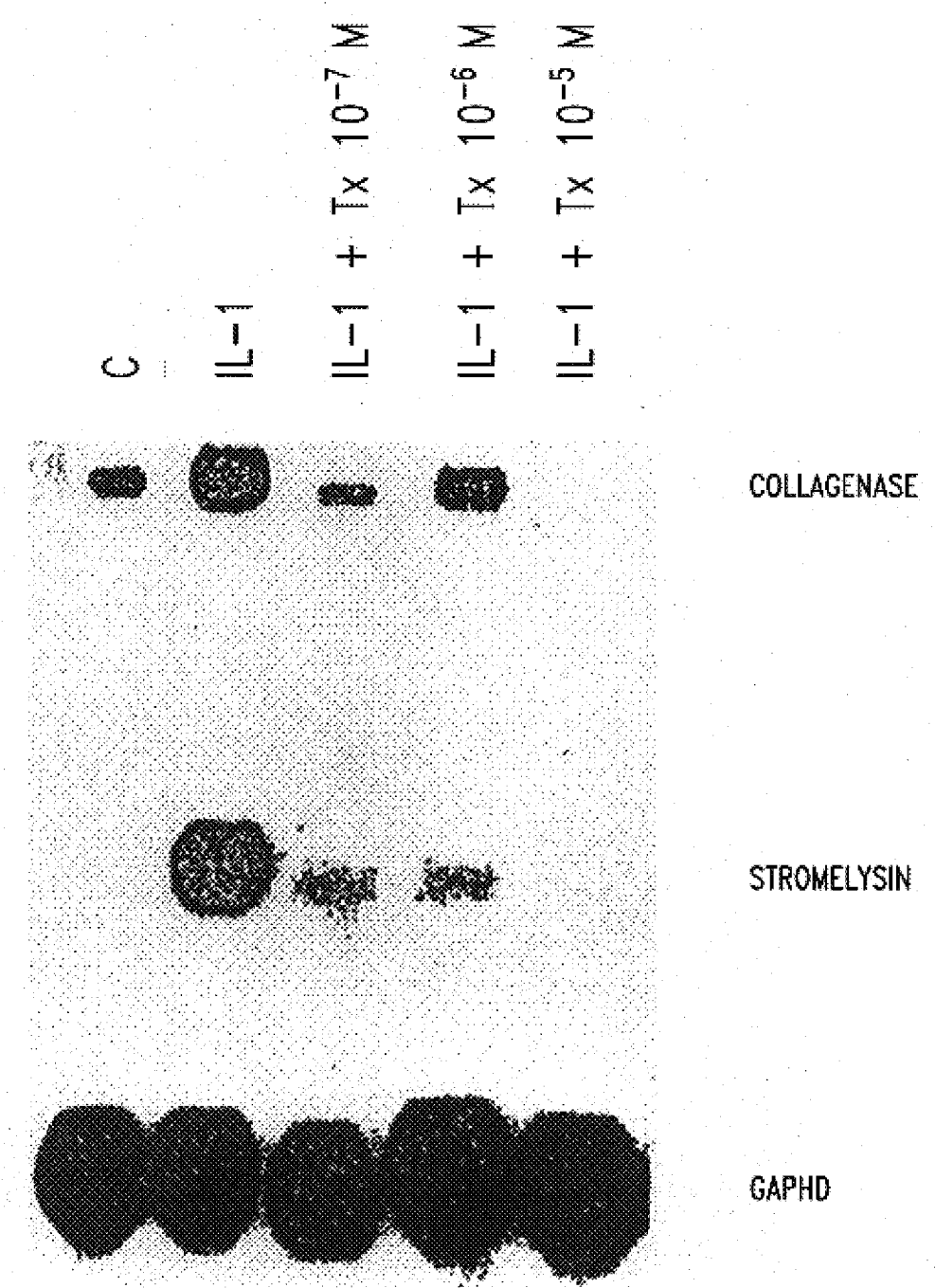
FIG. 20 is a blot which shows that IL-1 induction increases collagenase and stromelysin in RNA levels in chondrocytes, and that this induction can be inhibited by pretreatment with paclitaxel.

Since paclitaxel was a potent inhibitor of AP-1 activity, the effect of paclitaxel or IL-1 induced collagenase and stromelysin expression, two important matrix metalloproteinases involved in inflammatory diseases was examined. Briefly, as shown in FIG. 20, IL-1 induction increases collagenase and stromelysin mRNA levels in chondrocytes. Pretreatment of chondrocytes with paclitaxel for 24 hours significantly reduced the levels of collagenase and stromelysin mRNA. At $10^{-5}$ M paclitaxel, there was complete inhibition. The results show that paclitaxel completely inhibited the expression of two matrix metalloproteinases at concentrations similar to which it inhibits AP-1 activity.

5. Effect of Other Anti-microtubules on Collagenase Expression

FIGS. 12A–H demonstrate that anti-microtubule agents inhibited collagenase expression. Expression of collagenase was stimulated by the addition of IL-1 which is a proinflammatory cytokine. Pre-incubation of chondrocytes with various anti-microtubule agents, specifically LY290181, hexylene glycol, deuterium oxide, glycine ethyl ester, $AlF_3$, tubercidin epothilone, and ethylene glycol bis-(succinimidylsuccinate), all prevented IL-1-induced collagenase expression at concentrations as low as $1 \times 10^{-7}$ M.

C. Discussion

Paclitaxel was capable of inhibiting collagenase and stromelysin expression in vitro at concentrations of $10^{-6}$ M. Since this inhibition can be explained by the inhibition of AP-1 activity, a required step in the induction of all matrix metalloproteinases with the exception of gelatinase B, it is expected that paclitaxel would inhibit other matrix metalloproteinases which are AP-1 dependent. The levels of these matrix metalloproteinases are elevated in all inflammatory diseases and play a principle role in matrix degradation, cellular migration and proliferation, and angiogenesis. Thus, paclitaxel inhibition of expression of matrix metalloproteinases such as collagenase and stromelysin will have a beneficial effect in inflammatory diseases.

In addition to paclitaxel's inhibitory effect on collagenase expression, LY290181, hexylene glycol, deuterium oxide, glycine ethyl ester, $AlF_3$, tubercidin epothilone, and ethylene glycol bis-(succinimidylsuccinate), all prevented IL-1-induced collagenase expression at concentrations as low as $1 \times 10^{-7}$ M. Thus, anti-microtubule agents are capable of inhibiting the AP-1 pathway at varying concentrations.

Example 9

Effect of Anti-Microtubule Agents on the Expression of Proteoglycans

Primary chondrocyte cultures were freshly isolated from calf cartilage. The cells were plated at $2.5 \times 10^6$ per ml in 100×20 mm culture dishes and incubated in Ham's F12 medium containing 5% FBS overnight at 37° C. The cells were starved in serum-free medium overnight and then treated with anti-microtubule agents at various concentrations ($10^{-7}$ M, $10^{-6}$ M, $10^{-5}$ M and $10^{-4}$ M) for 6 hours. IL-1 (20 ng/ml) was then added to each plate and the plates incubated for an additional 18 hours. Total RNA was isolated by the acidified guanidine isothiocyanate method and subjected to electrophoresis on a denatured gel. Denatured RNA samples (15 μg) were analyzed by gel electrophoresis in a 1% denatured gel, transferred to a nylon membrane and hydridized with the $^{32}$P-labeled proteoglycan (aggrecan) cDNA probe. $^{32}$P-labeled glyceraldehyde phosphate dehydrase (GAPDH) cDNA as an internal standard to ensure roughly equal loading. The exposed films were scanned and quantitatively analyzed with ImageQuant.

Results

FIGS. 13A–H show that the anti-microtubule agents which had an inhibitory effect on collagenase expression (Example 8), specifically LY290181, hexylene glycol, deuterium oxide, glycine ethyl ester, $AlF_3$, tubercidin epothilone and ethylene glycol bis-(succinimidylsuccinate), did not affect the expression of aggrecan, a major component of cartilage matrix, at all concentrations evaluated.

Example 10

NF-κB Activity (Cell-Based) Assay

IL-1 and TNF were both identified as being proinflammatory cytokines that activate the transcription of genes driven by a transcription factor named NF-κB also involved in inflammatory processes. The inflammatory effect of IL-1 and TNF can therefore be indirectly assessed by means of a reporter gene assay (NF-κB) responding to IL-1 and TNF stimulation.

On day one, $5 \times 10^4$ NIH-3T3 (murine fibroblast), stably transfected with a NF-κB reporter construct (Luciferase, Promega Corp.), were plated per well (24-well plate). Once confluent (on day 3–4), cells were starved by replacing the complete medium with 1 ml of serum-free medium. Following a 24-hour starvation, cells were treated with various concentrations of anti-microtubule agents 6 hours prior to the addition of IL-1 (20 ng/ml) and TNF (20 ng/ml). Cells were exposed to IL-1 and TNF for 1 hour and 16 hours and NF-κB activity measured 24 hours later. On day five, the medium was discarded and the cells were rinsed once with PBS. Cells were then extracted for 15 minutes with 250 μl of lysis buffer (Promega Corp., Wisconsin). NF-κB transcriptional activity was assessed by adding 25 μl of luciferase substrate to a tube containing 2.5 μl of cell extract. The tube was immediately inserted in a luminometer (Turner Designs) and light emission measured for 10 seconds. The luciferase data were then normalized for protein concentration.

Results

The data were expressed by showing the interference that the anti-microtubule agents exhibited on NF-κB induction (fold induction). As shown in FIGS. 80A, 80B, 80C and 80D, tubercidin and paclitaxel inhibited both IL-1- and TNF-induced NF-κB activity. The inhibitory effect of tubercidin and paclitaxel for the 6-hour and 24-hour treatments were around 10 μM and 2 μM, respectively.

Example 11

Inhibition of Tumor Angiogenesis by Paclitaxel

Fertilized domestic chick embryos are incubated for 4 days prior to having their shells removed. The egg contents are emptied by removing the shell located around the airspace, severing the interior shell membrane, perforating the opposite end of the shell and allowing the egg contents to gently slide out from the blunted end. The contents are emptied into round-bottom sterilized glass bowls, covered with petri dish covers and incubated at 90% relative humidity and 3% carbon dioxide.

MDAY-D2 cells (a murine lymphoid tumor) are injected into mice and allowed to grow into tumors weighing 0.5–1.0 g. The mice are sacrificed, the tumor sites wiped with alcohol, excised, placed in sterile tissue culture media, and diced into 1 mm pieces under a laminar flow hood. Prior to placing the dissected tumors onto the 9-day old chick embryos, CAM surfaces are gently scraped with a 30 gauge needle to ensure tumor implantation. The tumors are then placed on the CAMs after 8 days of incubation (4 days after deshelling), and allowed to grow on the CAM for four days to establish a vascular supply. Four embryos are prepared utilizing this method, each embryo receiving 3 tumors. On day 12, each of the 3 tumors on the embyros received either 20% paclitaxel-loaded thermopaste, unloaded thermopaste, or no treatment. The treatments were continued for two days before the results were recorded.

The explanted MDAY-D2 tumors secrete angiogenic factors which induce the ingrowth of capillaries (derived from the CAM) into the tumor mass and allow it to continue to grow in size. Since all the vessels of the tumor are derived from the CAM, while all the tumor cells are derived from the explant, it is possible to assess the effect of therapeutic interventions on these two processes independently. This assay has been used to determine the effectiveness of paclitaxel-loaded thermopaste on: (a) inhibiting the vascularization of the tumor and (b) inhibiting the growth of the tumor cells themselves.

Figure 14A:
FIGS. 14A and 14B are two photographs of a CAM having a tumor treated with control (unloaded) thermopaste. Briefly, in FIG. 14A the central white mass is the tumor tissue. Note the abundance of blood vessels entering the tumor from the CAM in all directions. The tumor induces the ingrowth of the host vasculature through the production of "angiogenic factors." The tumor tissue expands distally along the blood vessels which supply it.
Figure 14B:
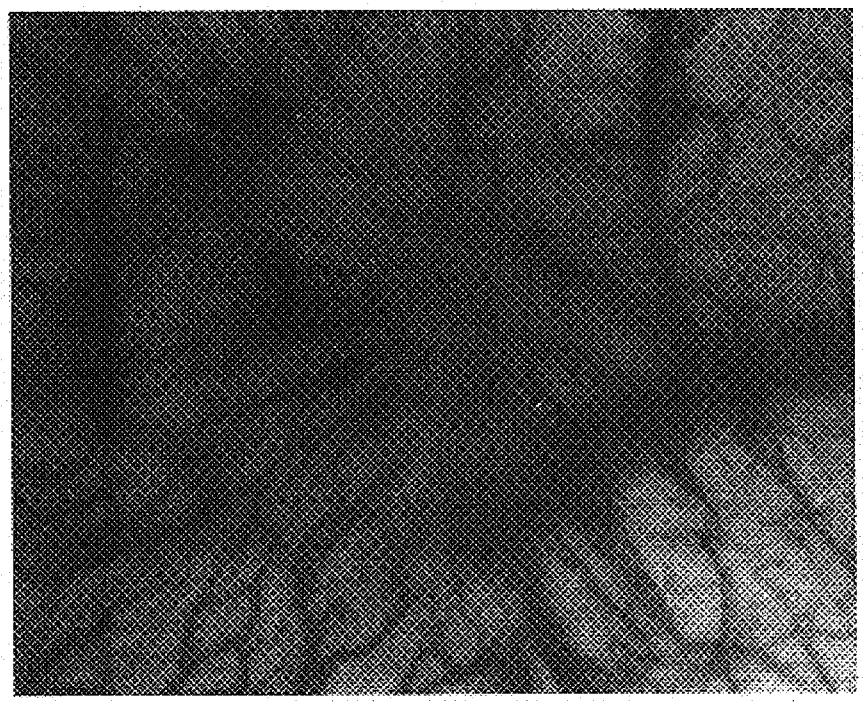
Figure 14C:
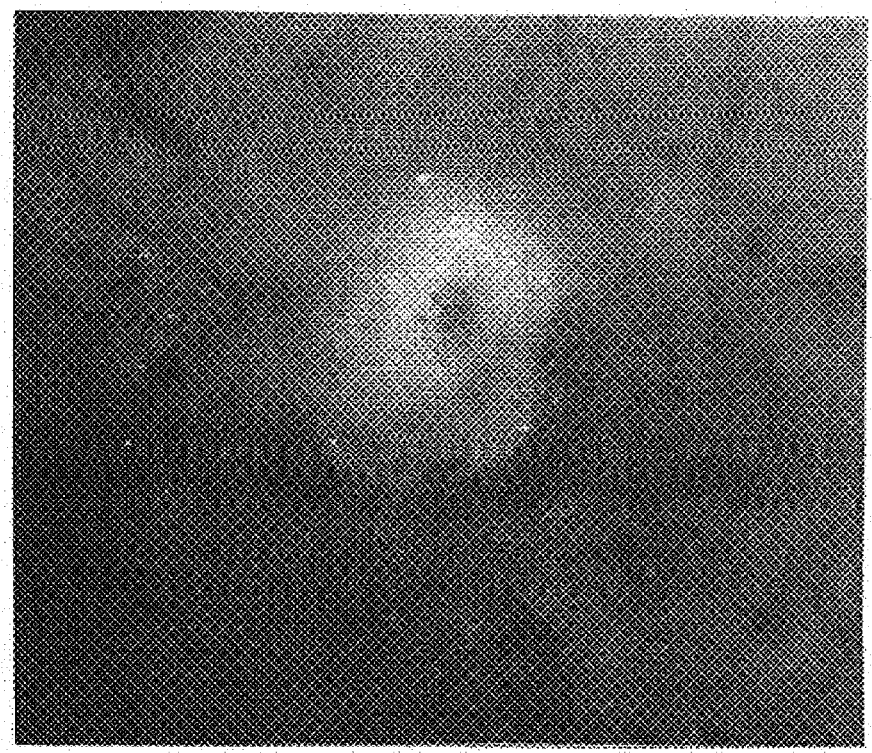
FIGS. 14C and 14D are two photographs of a CAM having a tumor treated with 20% paclitaxel-loaded thermopaste. Briefly, in FIG. 14C the central white mass is the tumor tissue. Note the paucity of blood vessels in the vicinity of the tumor tissue. The sustained release of the anti-microtubule agent is capable of overcoming the angiogenic stimulus produced by the tumor. The tumor itself is poorly vascularized and is progressively decreasing in size.
Figure 14D:

Direct in vivo stereomicroscopic evaluation and histological examination of fixed tissues from this study demonstrated the following. In the tumors treated with 20% paclitaxel-loaded thermopaste, there was a reduction in the number of the blood vessels which supplied the tumor (FIGS. 14C and 14D), a reduction in the number of blood vessels within the tumor, and a reduction in the number of blood vessels in the periphery of the tumor (the area which is typically the most highly vascularized in a solid tumor) when compared to control tumors (FIGS. 14A and 14B). The tumors began to decrease in size and mass during the two days the study was conducted. Additionally, numerous endothelial cells were seen to be arrested in cell division indicating that endothelial cell proliferation had been affected. Tumor cells were also frequently seen arrested in mitosis. All 4 embryos showed a consistent pattern with the 20% paclitaxel-loaded thermopaste suppressing tumor vascularity while the unloaded thermopaste had no effect.

By comparison, in CAMs treated with unloaded thermopaste, the tumors were well vascularized with an increase in the number and density of vessels when compared to that of the normal surrounding tissue, and dramatically more vessels than were observed in the tumors treated with paclitaxel-loaded paste. The newly formed vessels entered the tumor from all angles appearing like spokes attached to the center of a wheel (FIGS. 14A and 14B). The control tumors continued to increase in size and mass during the course of the study. Histologically, numerous dilated thin-walled capillaries were seen in the periphery of the tumor and few endothelial cells were seen to be in cell division. The tumor tissue was well vascularized and viable throughout.

As an example, in two similarly-sized (initially, at the time of explantation) tumors placed on the same CAM the following data was obtained. For the tumor treated with 20% paclitaxel-loaded thermopaste the tumor measured 330 mm×597 mm; the immediate periphery of the tumor has 14 blood vessels, while the tumor mass has only 3–4 small capillaries. For the tumor treated with unloaded thermopaste the tumor size was 623 mm×678 mm; the immediate periphery of the tumor has 54 blood vessels, while the tumor mass has 12–14 small blood vessels. In addition, the surrounding CAM itself contained many more blood vessels as compared to the area surrounding the paclitaxel-treated tumor.

This study demonstrates that thermopaste releases sufficient quantities of paclitaxel to inhibit the pathological angiogenesis which accompanies tumor growth and development. Under these conditions angiogenesis is maximally stimulated by the tumor cells which produce angiogenic factors capable of inducing the ingrowth of capillaries from the surrounding tissue into the tumor mass. The 20% paclitaxel-loaded thermopaste is capable of blocking this process and limiting the ability of the tumor tissue to maintain an adequate blood supply. This results in a decrease in the tumor mass both through a cytotoxic effect of the drug on the tumor cells themselves and by depriving the tissue of the nutrients required for growth and expansion.

Example 12

Inhibition of Angiogenesis by Paclitaxel

A. Chick Chorioallantoic Membrane ("CAM") Assays

Fertilized, domestic chick embryos were incubated for 3 days prior to shell-less culturing. In this procedure, the egg contents were emptied by removing the shell located around the air space. The interior shell membrane was then severed and the opposite end of the shell was perforated to allow the contents of the egg to gently slide out from the blunted end. The egg contents were emptied into round-bottom sterilized glass bowls and covered with petri dish covers. These were then placed into an incubator at 90% relative humidity and 3% $CO_2$ and incubated for 3 days.

Paclitaxel (Sigma, St. Louis, Mo.) was mixed at concentrations of 0.25, 0.5, 1, 5, 10, 30 $\mu$g per 10 ul aliquot of 0.5% aqueous methylcellulose. Since paclitaxel is insoluble in water, glass beads were used to produce fine particles. Ten microliter aliquots of this solution were dried on parafilm for 1 hour forming disks 2 mm in diameter. The dried disks containing paclitaxel were then carefully placed at the growing edge of each CAM at day 6 of incubation. Controls were obtained by placing paclitaxel-free methylcellulose disks on the CAMs over the same time course. After a 2 day exposure (day 8 of incubation) the vasculature was examined with the aid of a stereomicroscope. Liposyn II, a white opaque solution, was injected into the CAM to increase the visibility of the vascular details. The vasculature of unstained, living embryos were imaged using a Zeiss stereomicroscope which was interfaced with a video camera (Dage-MTI Inc., Michigan City, Ind.). These video signals were then displayed at 160×magnification and captured using an image analysis system (Vidas, Kontron; Etching, Germany). Image negatives were then made on a graphics recorder (Model 3000; Matrix Instruments, Orangeburg, N.Y.).

The membranes of the 8 day-old shell-less embryo were flooded with 2% glutaraldehyde in 0.1M sodium cacodylate buffer; additional fixative was injected under the CAM. After 10 minutes in situ, the CAM was removed and placed into fresh fixative for 2 hours at room temperature. The tissue was then washed overnight in cacodylate buffer containing 6% sucrose. The areas of interest were postfixed in 1% osmium tetroxide for 1.5 hours at 4° C. The tissues were then dehydrated in a graded series of ethanols, solvent exchanged with propylene oxide, and embedded in Spurr resin. Thin sections were cut with a diamond knife, placed on copper grids, stained, and examined in a Joel 1200EX electron microscope. Similarly, 0.5 mm sections were cut and stained with toluene blue for light microscopy.

At day 11 of development, chick embryos were used for the corrosion casting technique. Mercox resin (Ted Pella, Inc., Redding, Calif.) was injected into the CAM vasculature using a 30-gauge hypodermic needle. The casting material consisted of 2.5 grams of Mercox CL-2B polymer and 0.05 grams of catalyst (55% benzoyl peroxide) having a 5 minute polymerization time. After injection, the plastic was allowed to sit in situ for an hour at room temperature and then overnight in an oven at 65° C. The CAM was then placed in 50% aqueous solution of sodium hydroxide to digest all organic components. The plastic casts were washed extensively in distilled water, air-dried, coated with gold/palladium, and viewed with the Philips 501B scanning electron microscope.

Results of the above experiments are shown in FIGS. 15–18. Briefly, the general features of the normal chick shell-less egg culture are shown in FIG. 15A. At day 6 of incubation, the embryo is centrally positioned to a radially expanding network of blood vessels; the CAM develops adjacent to the embryo. These growing vessels lie close to the surface and are readily visible making this system an idealized model for the study of angiogenesis. Living, unstained capillary networks of the CAM can be imaged noninvasively with a stereomicroscope. FIG. 15B illustrates such a vascular area in which the cellular blood elements within capillaries were recorded with the use of a video/computer interface. The 3-dimensional architecture of such CAM capillary networks is shown by the corrosion casting method and viewed in the scanning electron microscope (FIG. 15C). These castings revealed underlying vessels which project toward the CAM surface where they form a single layer of anastomotic capillaries.

Figure 15A:
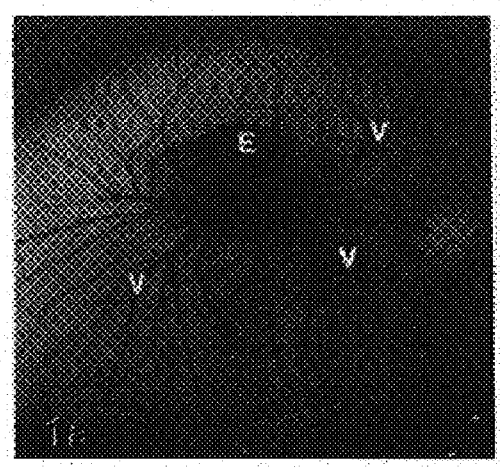
FIG. 15A is a photograph which shows a shell-less egg culture on day 6.
Figure 15B:
FIG. 15B is a digitized computer-displayed image taken with a stereomicroscope of living, unstained capillaries (1040×).
Figure 15C:
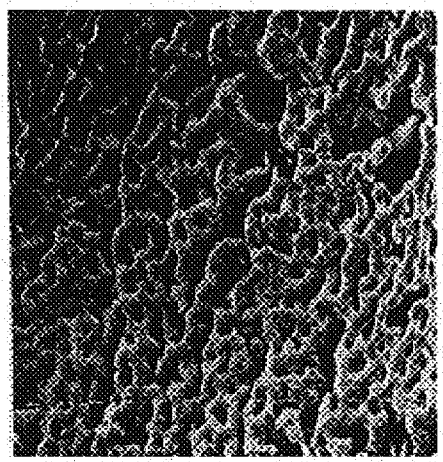
FIG. 15C is a photograph of a corrosion casting which shows chorioallenteic membrane (CAM) microvasculature that are fed by larger, underlying vessels (arrows; 1300×).
Figure 15D:
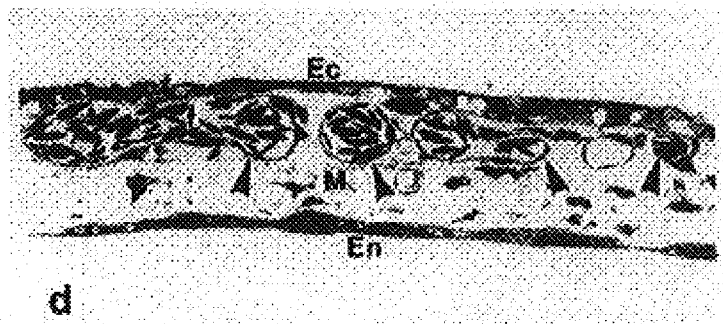
FIG. 15D is a photograph which depicts a 0.5 mm thick plastic section cut transversely through the CAM, and recorded at the light microscope level. This photograph shows the composition of the CAM, including an outer double-layered ectoderm (Ec), a mesoderm (M) containing capillaries (arrows) and scattered adventitial cells, and a single layered endoderm (En) (400×).
Figure 15E:
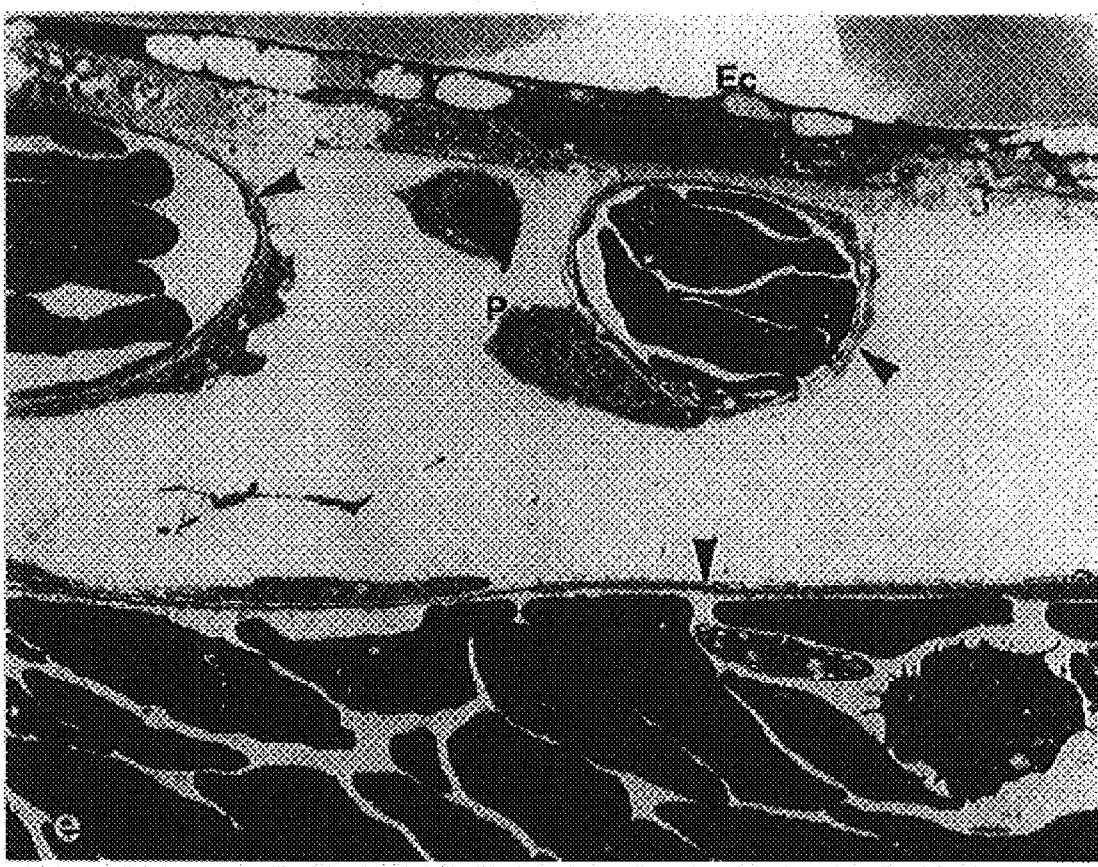
FIG. 15E is a photograph at the electron microscope level (3500×) wherein typical capillary structure is presented showing thin-walled endothelial cells (arrowheads) and an associated pericyte.

Transverse sections through the CAM show an outer ectoderm consisting of a double cell layer, a broader mesodermal layer containing capillaries which lie subjacent to the ectoderm, adventitial cells, and an inner, single endodermal cell layer (FIG. 15D). At the electron microscopic level, the typical structural details of the CAM capillaries are demonstrated. Typically, these vessels lie in close association with the inner cell layer of ectoderm (FIG. 15E).

After 48 hours exposure to paclitaxel at concentrations of 0.25, 0.5, 1, 5, 10, or 30 µg, each CAM was examined under living conditions with a stereomicroscope equipped with a video/computer interface in order to evaluate the effects on angiogenesis. This imaging setup was used at a magnification of 160×which permitted the direct visualization of blood cells within the capillaries; thereby blood flow in areas of interest could be easily assessed and recorded. For this study, the inhibition of angiogenesis was defined as an area of the CAM (measuring 2–6 mm in diameter) lacking a capillary network and vascular blood flow. Throughout the experiments, avascular zones were assessed on a 4 point avascular gradient (Table 1). This scale represents the degree of overall inhibition with maximal inhibition represented as a 3 on the avascular gradient scale. Paclitaxel was very consistent and induced a maximal avascular zone (6 mm in diameter or a 3 on the avascular gradient scale) within 48 hours depending on its concentration.

TABLE 1

AVASCULAR GRADIENT

| | |
|---|---|
| 0 | normal vascularity |
| 1 | lacking some microvascular movement |
| 2* | small avascular zone approximately 2 mm in diameter |
| 3* | avascularity extending beyond the disk (6 mm in diameter) |

*indicates a positive antiangiogenesis response

The dose-dependent, experimental data of the effects of a various therapeutic agents at different concentrations are shown in Table 2.

TABLE 2

| Agent | Delivery Vehicle | Concentration | Inhibition/n |
|---|---|---|---|
| paclitaxel | methylcellulose (10 ul) | 0.25 ug | 2/11 |
| | methylcellulose (10 ul) | 0.5 ug | 6/11 |
| | methylcellulose (10 ul) | 1 ug | 6/15 |
| | methylcellulose (10 ul) | 5 ug | 20/27 |
| | methylcellulose (10 ul) | 10 ug | 16/21 |
| | methylcellulose (10 ul) | 30 ug | 31/31 |
| | PCL paste (3 mg) | 0.05% | 0/9 |
| | PCL paste (3 mg) | 0.10% | 1/8 |
| | PCL paste (3 mg) | 0.25% | 5/7 |
| | PCL paste (3 mg) | 0.5% | 4/4 |
| | PCL paste (3 mg) | 1% | 8/8 |
| | PCL paste (3 mg) | 2% | 10/10 |
| | PCL paste (3 mg) | 5% | 10/10 |
| | PCL paste (3 mg) | 10% | 9/9 |
| | PCL paste (3 mg) | 20% | 6/6 |
| | 20% gelatin:60% PCL paste (3 mg) | 20% | 5/6 |
| | gelatin (1 mg) | 20% | 17/17 |
| | ophthalmic suspension (2 × 10 ul) | 0.3% | 1/12 |
| | ophthalmic suspension (2 × 15 ul) | 0.3% | 3/3 |
| | ophthalmic suspension (1 × 15 ul) | 0.3% | 15/15 |
| | ophthalmic microsphere suspension (15 ul) | 10% | 4/4 |
| | stent coating (~1 mg) | 2.5% | 5/5 |
| | stent coating (~1 mg) | 10% | 1/1 |
| | stent coating (~1 mg) | 33% | 3/3 |
| | cyclodextrin solution (10 ul) | 10% | 5/5 |
| | micellar formulation dry (1 mg) | 10% | too toxic |
| | micellar solution (10 ul) | 10% | too toxic |
| | micellar solution (10 ul) | 4 ug | 1/1- too toxic |
| | Cremophor Taxol (10 ul) | 4 ug | 1/1- too toxic |
| | 4PCL:1MePEG flakes (1 mg) | 20% | 10/13 |
| | PCL:MePEG paste (3 mg) | 20% | 6/9 |
| | microspheres (muco-adhesive) | 20% | 7/7 |
| | microspheres (EVA) | 0.6% | 2/2 |
| | microspheres (30–100 um)—slow release | 20% | 11/11 |
| | microspheres (30–100 um)—slow release | 10% | 1/8 |
| | microspheres (10–30 um)—med release | 20% | 5/6 |
| | microspheres (10–30 um)—med release | 10% | 5/9 |
| | microspheres (1–10 um)—fast release | 20% | 8/11 |
| | microspheres (1–10 um)—fast release | 10% | 9/9 |
| baccatin | paste (2 mg) | 2 ug | 2/3 |
| | methylcellulose (5 ul) | 5 ug | 4/7 |
| methotrexate | PCL paste (3 mg) | 1% | 0/13 |
| | PCL paste (3 mg) | 2% | 0/3 |

TABLE 2-continued

| Agent | Delivery Vehicle | Concentration | Inhibition/n |
|---|---|---|---|
| | PCL paste (3 mg) | 20% | 0/1 |
| | PCL:MePEG paste (3 mg) | 2% | 1/1 |
| | 95PCL:5MePEG paste (3 mg) | 1% | 0/6 |
| | 95PCL:5MePEG paste (3 mg) | 10% | 0/5 |
| | methylcellulose (10 ul) | 2 ug | 0/8 |
| prednisolone acetate | ophthalmic suspension (2 × 10 ul) | 1% | 3/4 |
| | ophthalmic suspension (2 × 15 ul) | 1% | 1/1 |
| pycnogenol (proantho-cyanidin) | methylcellulose (10 ul) | 10 ug | 1/18 |
| | PCL paste (3 mg) | 15% | 1/2 |
| | PCL paste (3 mg) | 30% | too toxic |
| verotoxin | methylcellulose (10 ul) | 10 ng | 0/8 |
| | methylcellulose (10 ul) | 675 ng | 0/2 |
| heparan sulphate fragment (1) | methylcellulose (10 ul) | 0.2 ug | 0/6 |
| heparan sulphate fragment (2) | methylcellulose (10 ul) | 0.4 ug | 0/7 |
| vanadate | microspheres (1 mg) | 5% | 0/5 |
| vanadyl sulphate | PCL paste (3 mg) | 2.5% | 0/3 |
| BMOV | PCL paste (3 mg) | 10% | too toxic |
| | PCL paste (3 mg) | 25% | too toxic |
| | PCL paste (3 mg) | 35% | too toxic |
| BEOV | PCL paste (3 mg) | 10% | too toxic |
| s-phosphonate | 80% PLA:20% MePEG paste (1 mg) | 20% | too toxic |
| | PCL paste (1 mg) | 2% | 2/7 |
| | PCL paste (3 mg) | 1% | 0/9 |
| | PCL paste (3 mg) | 2% | 0/6 |
| | PCL paste (3 mg) | 4% | 0/3 |
| | PCL paste (3 mg) | 8% | 1/9 |
| tamoxifen | methylcellulose (10 ul) | 5 ug | 0/2 |
| shark cartilage powder | N/A | 1 mg | 0/5 |
| estramustine sodium phosphate | PCL paste (3 mg) | 5% | 0/6 |
| | PCL paste (3 mg) | 10% | 0/6 |
| vinblastine | methylcellulose (10 ul) | 9 ug | too toxic |
| | methylcellulose (10 ul) | 2 ug | too toxic |
| | PCL paste (3 mg) | 0.25% | 4/6 |
| | PCL paste (3 mg) | 0.5% | 0/4 |
| | PCL paste (3 mg) | 1% | 2/3 |
| | PCL paste (3 mg) | 2% | too toxic |
| vincristine | methylcellulose (10 ul) | 9 ug | too toxic |
| | methylcellulose (10 ul) | 1 ug | too toxic |
| | PCL paste (3 mg) | 0.05% | 1/1-too toxic |
| | PCL paste (3 mg) | 0.1% | 2/2-too toxic |
| | PCL paste (3 mg) | 0.25% | 1/1-too toxic |
| | PCL paste (3 mg) | 0.5% | too toxic |
| | PCL paste (3 mg) | 1% | too toxic |
| | PCL paste (3 mg) | 2% | too toxic |
| diterpene-1 | methylcellulose (10 ul) | 3 ug | 0/5 |
| diterpene-2 | methylcellulose (10 ul) | 3 ug | 0/5 |
| lavendustine-c | PCL paste (3 mg) | 10% | 0/14 |
| | PCL paste (3 mg) | 20% | 0/10 |
| MDHC (tyrosine inhibitor) | PCL paste (3 mg) | 20% | 0/8 |
| erbstatin | PCL paste (3 mg) | 20% | 0/5-too toxic |
| genistein | PCL paste (3 mg) | 10% | 0/7 |
| | PCL paste (3 mg) | 20% | 0/4 |
| herbimysin | PCL paste (3 mg) | 2% | 3/4 |
| | PCL paste (3 mg) | 0.5% | 1/1 |
| camptothecin | PCL paste (3 mg) | 0.25% | 3/4 |
| | PCL paste (3 mg) | 1% | 2/3 |
| | PCL paste (3 mg) | 5% | 4/5 |
| suramin and | methylcellulose (10 ul) | 20 ug/70 ug | 2/4 |
| cortisone acetate | methylcellulose (10 ul) | 50 ug/40 ug | 5/14 |
| | methylcellulose (10 ul) | 50 ug/50 ug | 3/26 |
| | methylcellulose (10 ul) | 20 ug/50 ug | 0/24 |
| | methylcellulose (10 ul) | 70 ug/70 ug | 0/9 |
| suramin and tetrahydo S | methylcellulose (10 ul) | 50 ug/50 ug | 0/6 |
| | methylcellulose (10 ul) | 50 ug | 0/10 |
| protamine sulphate | methylcellulose (10 ul) | 100 ul | 1/10 |
| TIMP | methylcellulose (10 ul) | 15 ug | 0/5 |
| colchicine | methylcellulose (10 ul) | 3 ug | 1/1-too toxic |

Figure 16A:
FIGS. 16A, 16B, 16C and 16D are a series of digitized images of four different, unstained CAMs taken after a 48 hour exposure to 10 $\mu$g paclitaxel per 10 ml of methylcellulose. The transparent methylcellulose disk (*) containing paclitaxel is present on each CAM and is positioned over a singular avascular zone (A) with surrounding blood islands (Is). These avascular areas extend beyond the disk and typically have a diameter of approximately 6 mm.
Figure 16B:
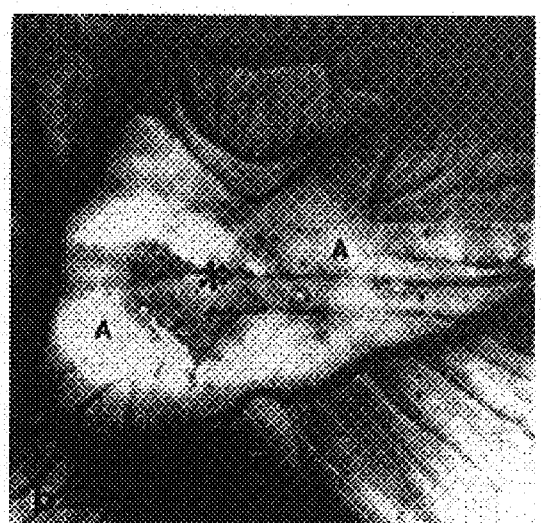
Figure 16C:
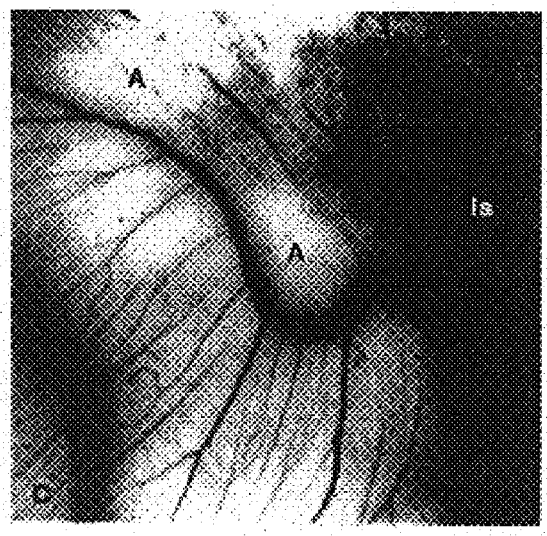
Figure 16D:
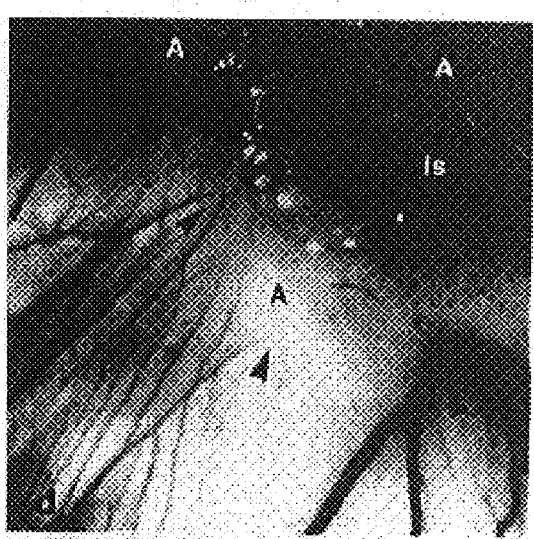

Typical paclitaxel-treated CAMs are also shown with the transparent methylcellulose disk centrally positioned over the avascular zone measuring 6 mm in diameter. At a slightly higher magnification, the periphery of such avascular zones is clearly evident (FIG. 16C); the surrounding functional vessels were often redirected away from the source of paclitaxel (FIGS. 16C and 16D). Such angular redirecting of blood flow was never observed under normal conditions. Another feature of the effects of paclitaxel was the formation of blood islands within the avascular zone representing the aggregation of blood cells.

Figure 17A:
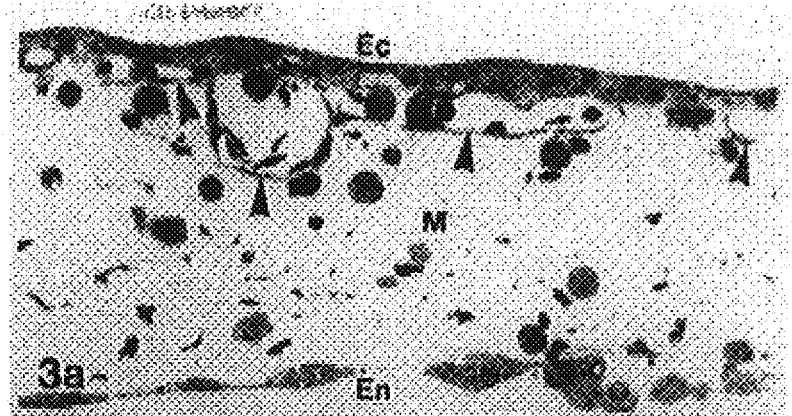
FIG. 17A is a photograph (=400×) which shows that the capillaries (arrowheads) immediately peripheral to the avascular zone exhibit numerous endothelial cells arrested in mitosis. Ectoderm (Ec); Mesoderm (M); Endoderm (En).
Figure 17B:
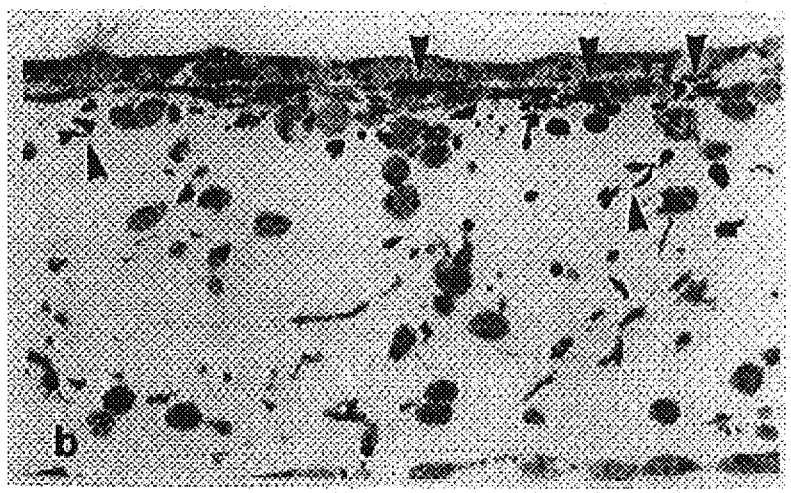
FIG. 17B (=400×) shows that within the avascular zone proper the typical capillary structure has been eliminated and there are numerous extravasated blood cells (arrowheads).
Figure 17C:
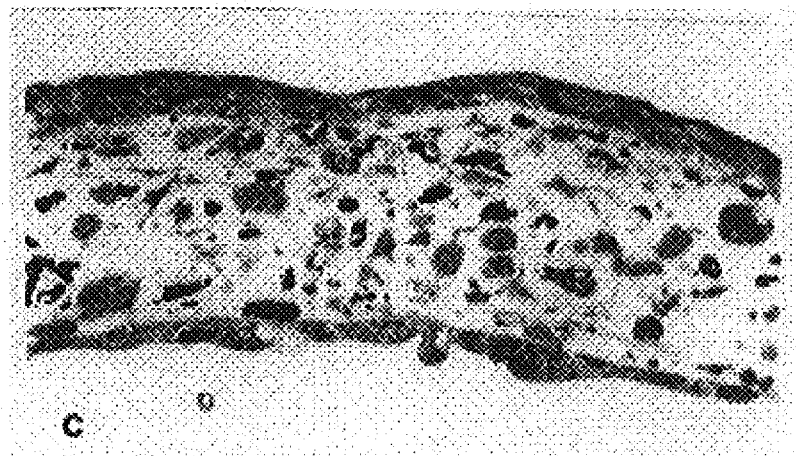
FIG. 17C (=400×) shows that in the central area of the avascular zone, red blood cells are dispersed throughout the mesoderm.
Figure 18A:
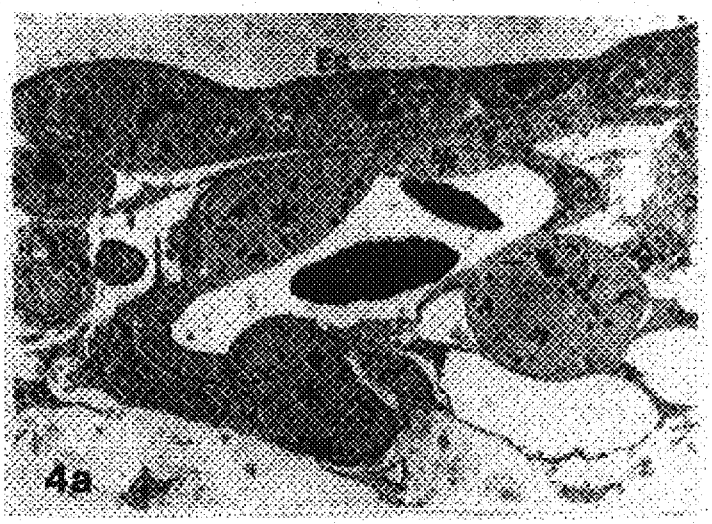
FIG. 18A (=2,200×) shows a small capillary lying subjacent to the ectodermal layer (Ec) possessing three endothelial cells arrested in mitosis (*). Several other cell types in both the ectoderm and mesoderm are also arrested in mitosis.
Figure 18B:
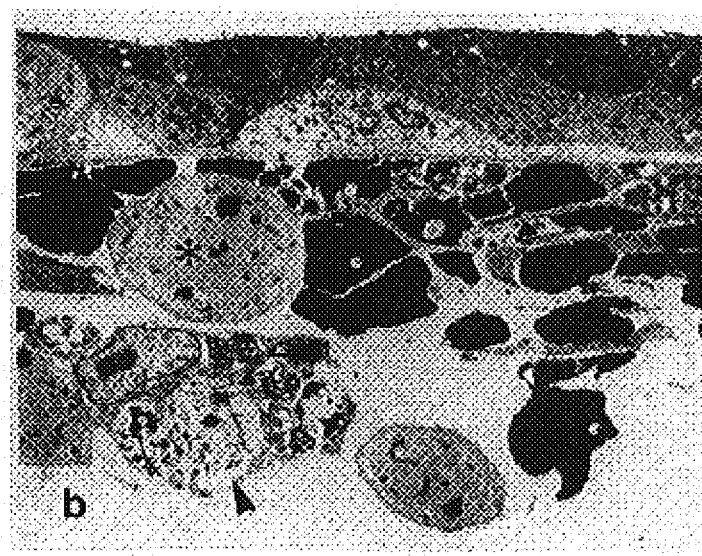
FIG. 18B (=2,800×) shows the early avascular phase contains extravasated blood cells subjacent to the ectoderm; these blood cells are intermixed with presumptive endothelial cells (*) and their processes. Degradative cellular vacuoles (arrowhead).
Figure 18C:
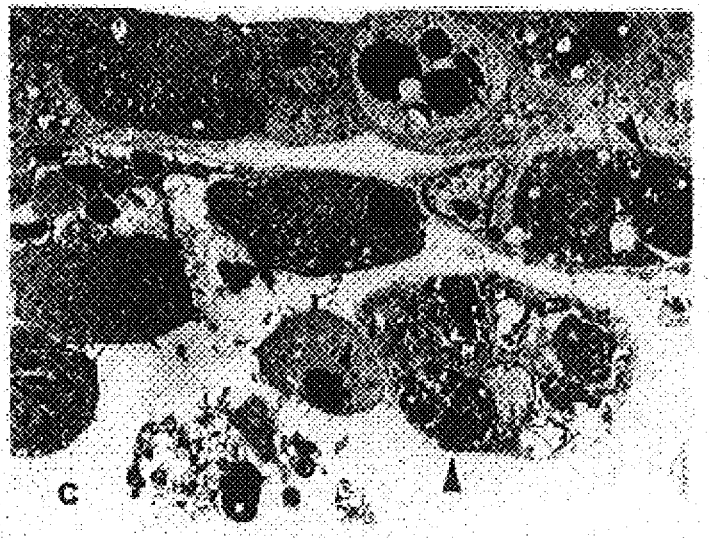
FIG. 18C (=2,800×) shows that in response to paclitaxel, the ecto-mesodermal interface has become populated with cells in various stages of degradation containing dense vacuoles and granules (arrowheads).

The associated morphological alterations of the paclitaxel-treated CAM are readily apparent at both the light and electron microscopic levels. For the convenience of presentation, three distinct phases of general transition from the normal to the avascular state are shown. Near the periphery of the avascular zone the CAM is hallmarked by an abundance of mitotic cells within all three germ layers (FIGS. 17A and 18A). This enhanced mitotic division was also a consistent observation for capillary endothelial cells. However, the endothelial cells remained junctionally intact with no extravasation of blood cells. With further degradation, the CAM is characterized by the breakdown and dissolution of capillaries (FIGS. 17B and 18B). The presumptive endothelial cells, typically arrested in mitosis, still maintain a close spatial relationship with blood cells and lie subjacent to the ectoderm; however, these cells are not junctionally linked. The most central portion of the avascular zone was characterized by a thickened ectodermal and endodermal layer (FIGS. 17C and 18C). Although these layers were thickened, the cellular junctions remained intact and the layers maintained their structural characteristics. Within the mesoderm, scattered mitotically arrested cells were abundant; these cells did not exhibit the endothelial cell polarization observed in the former phase. Also, throughout this avascular region, degenerating cells were common as noted by the electron dense vacuoles and cellular debris (FIG. 18C).

In summary, this study demonstrated that 48 hours after paclitaxel application to the CAM, angiogenesis was inhibited. The blood vessel inhibition formed an avascular zone which was represented by three transitional phases of paclitaxel's effect. The central, most affected area of the avascular zone contained disrupted capillaries with extravasated red blood cells; this indicated that intercellular junctions between endothelial cells were absent. The cells of the endoderm and ectoderm maintained their intercellular junctions and therefore these germ layers remained intact; however, they were slightly thickened. As the normal vascular area was approached, the blood vessels retained their junctional complexes and therefore also remained intact. At the periphery of the paclitaxel-treated zone, further blood vessel growth was inhibited which was evident by the typical redirecting or "elbowing" effect of the blood vessels (FIG. 16D).

Paclitaxel-treated avascular zones also revealed an abundance of cells arrested in mitosis in all three germ layers of the CAM; this was unique to paclitaxel since no previous study has illustrated such an event. By being arrested in mitosis, endothelial cells could not undergo their normal metabolic functions involved in angiogenesis. In comparison, the avascular zone formed by suramin and cortisone acetate do not produce mitotically arrested cells in the CAM; they only prevented further blood vessel growth into the treated area. Therefore, even though these agents are anti-angiogenic, there are many points in which the angiogenesis process may be targeted.

The effects of paclitaxel over the 48 hour duration were also observed. During this period of observation it was noticed that inhibition of angiogenesis occurs as early as 9 hours after application. Histological sections revealed a similar morphology as seen in the first transition phase of the avascular zone at 48 hours illustrated in FIGS. 17A and 18A. Also, we observed in the revascularization process into the avascular zone previously observed. It has been found that the avascular zone formed by heparin and angiostatic steroids became revascularized 60 hours after application. In one study, paclitaxel-treated avascular zones did not revascularize for at least 7 days after application implying a more potent long-term effect.

Example 13

Effect of Paclitaxel and Camptothecin on LNCaP Cell Proliferation

Materials and Methods

LNCaP cells were seeded at concentrations of $2\times10^3$ and $1\times10^3$ cells/well respectively in 96 well plates. After 48 hours, different concentrations of paclitaxel or camptothecin (25 µl) were added in each culture well and the plates were incubated at 37° C. for 5 days. After incubation, the cells were fixed with 1% glutaraldehyde solution, and stained for 5 minutes with 0.5% crystal violet. The dye was successively eluted with 100 µl of buffer solution and the absorbance was read on a Titertek Multiskan microplate reader using a wavelength of 492 nm Absorbance. Cell growth was expressed as a percentage relative to control wells in the absence of the compound (set at 100%).

Results

Paclitaxel inhibited LNCaP cell growth with an $EC_{50}$ of approximately 0.09 nM. Apoptosis experiments were performed on the cells in the wells after paclitaxel treatment using DNA fragmentation assays. Extensive apoptosis of cells was observed indicating that paclitaxel was cytotoxic by an apoptotic mechanism.

Camptothecin was extremely potent in its cytotoxic action against LNCaP cells. Concentrations as low as 0.001 nM were toxic to over 60% of cells. Therefore, $EC_{50}$ for this drug against LNCaP cells must lie in the femtomolar concentration range.

TABLE 1

| N | Paclitaxel (nM) | 492 nm Absorbance | % Growth |
|---|---|---|---|
| 16 | 0.001 | 0.049 ± 0.05 | 100 |
| 16 | 0.01 | 0.40 ± 0.03 | 81 |
| 8 | 0.05 | 0.36 ± 0.02 | 73 |
| 8 | 0.1 | 0.20 ± 0.03 | 40 |
| 8 | 1 | 0.025 ± 0.01 | 5 |
| 8 | 10 | 0.027 ± 0.01 | 5 |
| 8 | 100 | 0.033 ± 0.01 | 6 |

492 nm Absorbance of controls = 0.49 ± 0.06

TABLE 2

| N | Camptothecin (nM) | 492 nm Absorbance | % Growth |
|---|---|---|---|
| 16 | 0.001 | 0.169 ± 0.05 | 36 |
| 8 | 0.05 | 0.14 ± 0.04 | 29 |
| 8 | 0.1 | 0.10 ± 0.02 | 21 |
| 8 | 1 | 0.10 ± 0.02 | 21 |
| 8 | 10 | 0.088 ± 0.02 | 17 |
| 15 | 100 | 0.038 ± 0.01 | 8 |

492 nm Absorbance of controls = 0.47 ± 0.05

Example 14

Anti-Angiogenesis Activity of Additional Anti-Microtubule Agents

In addition to paclitaxel, other anti-microtubule agents can likewise be incorporated within polymeric carriers. Representative examples which are provided below include campothecin and vinca alkaloids such as vinblastine and vincristine, and microtubule stabilizing agents such as tubercidin, aluminum fluoride and LY290181.

A. Incorporation of Agents into PCL

Agents were ground with a mortar and pestle to reduce the particle size to below 5 microns. This was then mixed as a dry powder with polycaprolactone (molecular wt. 18,000 Birmingham Polymers, AL USA). The mixture was heated to 65° C. for 5 minutes and the molten polymer/agent mixture was stirred into a smooth paste for 5 minutes. The molten paste was then taken into a 1 ml syringe and extruded to form 3 mg pellets. These pellets were then placed onto the CAM on day 6 of gestation to assess their anti-angiogenic properties.

B. Effects of Camptothecin-Loaded PCL Paste on the CAM

Camptothecin-loaded thermopaste was effective at inhibiting angiogenesis when compared to control PCL pellets. At 5% drug loading, 4/5 of the CAMs tested showed potent angiogenesis inhibition. In addition, at 1% and 0.25% loading, 2/3 and 3/4 of the CAMs showed angiogenesis inhibition respectively. Therefore, it is evident from these results that camptothecin was sufficiently released from the PCL thermopaste and it has therapeutic anti-angiogenic efficacy.

C. Effects of Vinblastine- and Vincristine-Loaded PCL Paste on the CAM

When testing the formulations on the CAM, it was evident that the agents were being released from the PCL pellet in sufficient amounts to induce a biological effect. Both vinblastine and vincristine induced anti-angiogenic effects in the CAM assay when compared to control PCL thermopaste pellets.

At concentrations of 0.5% and 0.1% drug loading, vincristine induced angiogenesis inhibition in all of the CAMs tested. When concentrations exceeding 2% were tested, toxic drug levels were achieved and unexpected embryonic death occurred.

Vinblastine was also effective in inhibiting angiogenesis on the CAM at concentrations of 0.25%, 0.5% and 1%. However, at concentrations exceeding 2%, vinblastine was toxic to the embryo.

D. Effects of Tubercidin-Loaded PCL Paste on the CAM

Tubercidin-loaded paste was effective at inhibiting angiogenesis when compared to control pellets. At 1% drug loading, tubercidin induced angiogenesis inhibition in 1/3 CAMs tested. However, at greater drug concentrations of 5% drug loading, tubercidin potently inhibited angiogenesis in 2/3 CAMs. Therefore, it was evident from these results that tubercidin was sufficiently released from the PCL paste and it has potent anti-angiogenic activity.

E. Effects of Aluminum Fluoride-Loaded PCT Paste on the CAM

PCL pastes loaded with aluminum fluoride (AlF3) were effective at inhibiting angiogenesis at a 20% drug loading when compared to control pellets. At 20% drug loading, 2/4 CAMs showed angiogenesis inhibition as evident by an avascular zone measuring between 2 to 6 mm in diameter. However, at lower drug loading, 1% and 5%, angiogenesis inhibition was not evident (0/5 and 0/5 CAMs, respectively). Therefore, aluminum fluoride was effective at inducing angiogenesis inhibition only at higher drug concentrations.

F. Effect of LY290181-Loaded PCL Paste on the CAM

Assessment of PCL paste loaded with 5% LY290181 on the CAM, revealed that LY290181 induced angiogenesis inhibition in 1/3 CAMs tested. However, at 1% drug loading, LY290181 did not induce an anti-angiogenesis response (n=2).

Example 15

Effect of Paclitaxel on Viability of Non-Proliferating Cells

While it is important that a disease-modifying agent be capable of strongly inhibiting a variety of inappropriate cellular activities (proliferation, inflammation, proteolytic enzyme production) which occur in excess during the development of chronic inflammation, it must not be toxic to the normal tissues. It is particularly critical that normal cells not be damaged, as this would lead to progression of the disease. In this example, the effect of paclitaxel on normal non-dividing cell viability in vitro was examined, utilizing cultured chondrocytes grown to confluence.

Briefly, chondrocytes were incubated in the presence ($10^{-5}$ M, $10^{-7}$ M, and $10^{-9}$ M) or absence (control) of paclitaxel for 72 hours. At the end of this time period, the total number of viable cells was determined visually by trypan blue dye exclusion. This experiment was conducted 4 times and the data collated.

Figure 21:
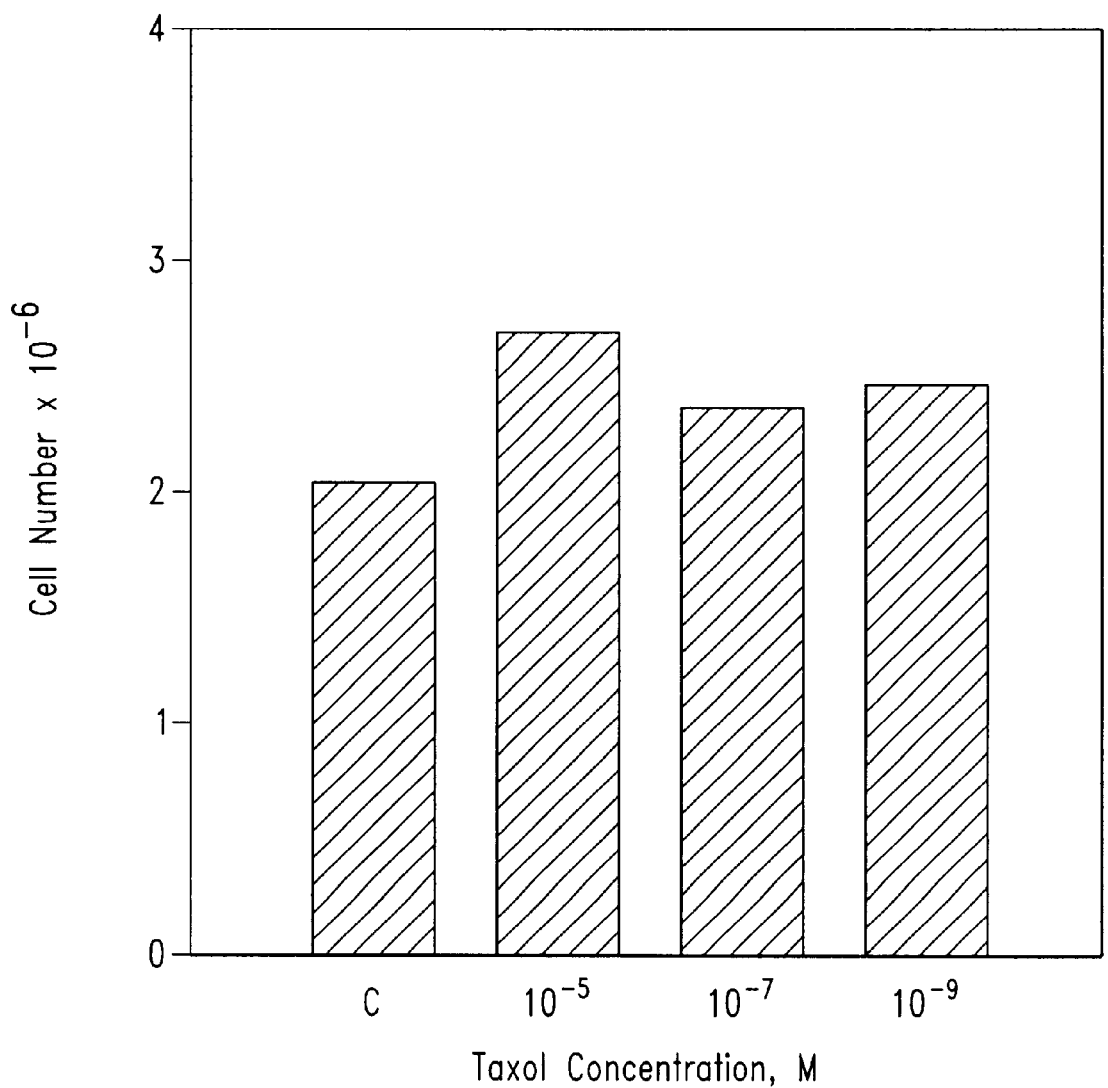
FIG. 21 is a bar graph which depicts the effects of paclitaxel on viability of normal chondrocytes in vitro.

Results of this experiment are shown in FIG. 21. Briefly, as is evident from FIG. 21, paclitaxel does not affect the viability of normal non-proliferating cells in vitro even at high concentrations ($10^{-5}$ M) of paclitaxel. More specifically, even at drug concentrations sufficient to block the pathological processes described in the preceding examples, there is no cytotoxicity to normal chondrocytes.

Example 16

Selection of Permeation Enhancer for Topical Paclitaxel Formulation

A. Paclitaxel Solubility in Various Enhancers

The following permeation enhancers were examined: Transcutol®, ethanol, propylene glycol, isopropyl myristate, oleic acid and Transcutol:isopropyl myristate (9:1 v:v). One milliliter of each enhancer in glass vials was pre-heated to 37° C. and excess paclitaxel was added. A sample of 0.5 ml of the fluid from each vial was centrifuged at 37° C. and 13000 rpm for 2 minutes. Aliquots (0.1 ml) of supernatant from the centrifuge tubes were transferred to volumetric flasks and diluted with methanol. Paclitaxel content was assessed by high pressure liquid chromatography (HPLC).

B. Partition Coefficient

A specific quantity of paclitaxel was dissolved in a volume of enhancer heated to 37° C. Aliquots (1 ml) of this solution were added to 1 ml of octanol in a 4 ml glass vial. Phosphate buffered saline (1 ml) (pH 7.4) was then added and the vials vortexed to create an emulsion. The vials were placed in a 37° C. oven for 16 hours, after which 0.1 ml of octanol phase was removed from each vial and diluted with 9.9 ml methanol. For the water phases, 0.5 ml was sampled from the oleic acid and isopropyl myristate vials and 0.5 ml was sampled from the propylene glycol vials and diluted with 0.5 ml methanol. From the Transcutol vials, 0.1 ml was sampled and diluted with 9.9 ml 50:50 Transcutol:PBS and 0.1 ml from the ethanol vials was sampled and diluted with 50:50 ethanol:PBS. Paclitaxel content was determined by HPLC. Each determination was performed in triplicate.

C. Results

The solubility of paclitaxel in each enhancer at 37° C. is listed in Table 1.

TABLE 1

Concentration of Paclitaxel at Saturation in Various Permeation Enhancers

| Enhancer | Paclitaxel concentration (mg/ml) | |
|---|---|---|
|  | Average | Standard deviation |
| Transcutol ® | 346.85 | 2.59 |
| Ethanol | 68.91 | 3.49 |
| Propylene glycol | 21.56 | 0.11 |
| Isopropyl myristate | 0.43 | 0.01 |
| Oleic acid | 0.31 | 0.01 |
| Transcutol ®:isopropyl myristate (9:1 v:v) | 353.93 | 0.42 |

The octanol/water partition coefficients, $K_{o/w}$, are listed in Table 2.

TABLE 2

Octanol/Water Partition Coefficient of Paclitaxel in Various Enhancer Solutions

| Enhancer | $K_{o/w}$ | Standard deviation |
|---|---|---|
| Transcutol ® | 25.25 | 0.27 |
| Ethanol | 6.88 | 0.13 |
| Propylene glycol | 37.13 | 2.48 |
| Isopropyl myristate | ∞ | — |
| Oleic acid | ∞ | — |

To act effectively, paclitaxel must penetrate the skin to the lower strata of the viable epidermis. It has been established that for drugs to penetrate the viable epidermis, they must possess an octanol/water partition coefficient of close to 100 (Hadgraft J. H. and Walters K., Drug absorption enhancements, A. G. de Boers Ed., Harwood Publishers, 1994). Based on the results in Tables 1 and 2, propylene glycol and Transcutol show the best combination of solubilizing paclitaxel and enhancing its partitioning from an oil phase to an aqueous phase.

However, the $K_{o/w}$ produced by both Transcutol and propylene glycol may be somewhat low, therefore they were combined with isopropyl myristate which has an infinite $K_{o/w}$ in an attempt to increase the solubility of paclitaxel in the octanol phase. Isopropyl myristate and Transcutol were mixed in a 1:9 volume ratio. The isopropyl myristate dissolved readily at room temperature in the Transcutol. In order to form a homogeneous phase, the propylene glycol and isopropyl myristate were also mixed with ethanol in a ratio of 4:3.5:0.5 propylene glycol:ethanol:isopropyl myristate. The $K_{o/w}$ results are shown in Table 3.

TABLE 3

Octanol/Water Partition Coefficients of
Paclitaxel in Enhancer Combinations

| Enhancer | $K_{o/w}$ | Standard deviation |
|---|---|---|
| Transcutol ®:isopropyl myristate (9:1) | 43.45 | 0.43 |
| Propylene glycol:ethanol:isopropyl myristate (4.0:3.5:0.5) | 42.39 | 1.66 |

The addition of isopropyl myristate to the Transcutol resulted in a significant increase in the partition coefficient. However, the propylene glycol:ethanol:isopropyl myristate solution did not result in a significant improvement in the partition coefficient over that of propylene glycol alone. This last result, and the fact that ethanol has been found to exacerbate the psoriatic condition, effectively eliminated this enhancer combination from further consideration. Furthermore, the addition of isopropyl myristate actually increased the solubility of paclitaxel over its solubility in Transcutol alone. The solubility of paclitaxel in Transcutol was 346.9 mg/ml whereas in Transcutol:isopropyl myristate combination the solubility increased to 353.9 mg/ml. Therefore, this enhancer combination was chosen in the skin studies.

Example 17

Preparation and Analysis of Topical Paclitaxel Formulations

A. Preparation of Paclitaxel Ointment A

Transcutol (3.2 g), isopropyl myristate (0.3 g), labrasol (2.5 g), paclitaxel (0.01 g) and 0.5 mCi/ml $^3$H-paclitaxel (0.3 ml) were combined in a 20 ml scintillation vial. In a separate scintillation vial, labrafil (2.5 g), arlacel 165 (1.2 g) and compritol (0.3 g) were combined and heated to 70° C. until completely melted. The contents of the first scintillation vial are added to the melt, vortexed until homogeneous and allowed to cool.

B. Preparation of Paclitaxel Ointment B

Transcutol (2.5 g), isopropyl myristate (1.0 g), labrasol (2.5 g), paclitaxel (0.01 g) and 0.5 mCi/ml $^3$H-paclitaxel (0.3 ml) were combined in a 20 ml scintillation vial. In a separate scintillation vial, labrafil (2.5 g), arlacel 165 (1.2 g) and compritol (0.3 g) were combined and heated to 70° C. until completely melted. The contents of the first scintillation vial are added to the melt, vortexed until homogeneous and allowed to cool.

C. Skin Preparation and Penetration Study

Frozen, excised Yucatan mini-pig skin was stored at −70° C. until used. Skin samples were prepared using a no. 10 cork borer to punch disks from the frozen skin. Samples were rinsed with a streptomyocin-penicillin solution and placed into freezer bags and stored at −70° C.

Skin sections were mounted on Franz diffusion cells, stratum corneum side up. The bottom receptor solution was a 0.05% amoxicillin solution in R.O. water. A donor cell was clamped on to each skin surface. The paclitaxel ointment was heated until melted (40 to 50° C.) and drawn into a syringe. While still molten, 0.1 ml was extruded onto each skin surface. The donor cells were covered with a glass disk and the assembly left for 24 hours.

After 24 hours, the cells were disassembled, excess ointment removed and stored in a scintillation vial. The skin surface was quickly washed with 3 ml dichloromethane (DCM) and dried. The wash DCM was stored in the same vial as the excess ointment. The skin sections and the receptor solution were placed into separate scintillation vials. The skin was cryotomed at −30° C. into 30 μm sections and collected in separate vials. The initial shavings and remaining skin were also collected in separate glass vials. The sectioned skin samples were dissolved by adding 0.5 ml of tissue solubilizer to each vial. The samples were left overnight to dissolve at room temperature. The following day, 3 ml of scintillation cocktail was added to the vials. For the DCM wash solutions, 100 μl was transferred to 1 ml of acetonitrile and then 3 ml of scintillation cocktail was added. The radioactivity of all the solutions was measured using a beta counter.

Skin samples were mounted on the Franz diffusion cells and separated into three groups. Each sample was treated accordingly (no treatment or ointment B with or without paclitaxel). After 24 hours, the samples were removed and processed using standard histological techniques.

D. Results

From the histological sections, the stratum corneum section of untreated skin was found to be between 50 to 120 μm thick while the viable epidermis was between 400 to 700 μm thick For the ointment which contained 3% w/w isopropyl myristate (ointment A), the concentration of paclitaxel in the skin was essentially constant at 1 μg/ml ($1.2 \times 10^{-6}$ M) in the stratum corneum and throughout the viable epidermis. For the ointment which contained 10% w/wisopropyl myristate (ointment B), the paclitaxel concentration was constant in the stratum corneum and the viable epidermis, but higher in the stratum corneum (6 μg/ml versus 2 μg/ml). There was no radioactivity in the receptor solution for each ointment investigation, indicating that paclitaxel did not pass completely through the skin section.

No gross differences were noted when the ointment containing paclitaxel was applied.

Example 18

Manufacture of Topical Formulations of Paclitaxel for the Treatment of Psoriasis As noted above, compositions for treating psoriasis may be administered via a variety of routes, including, for example, topically. For example, within one embodiment of the invention, a topical formulation for treating psoriasis was manufactured by first separately generating an active phase (containing one or more anti-microtubule agents) and a gum or polymer phase. The active phase was prepared by mixing 250 g ethoxydiglycol with 250 mg propylparaben and 500 mg methylparaben. The mixture was stirred until both components were completely dissolved, and mixing was continued for an additional 20 minutes to simulate the addition of paclitaxel. The final mixture was left to sit overnight covered with parafilm.

The gum phase was prepared by sprinkling 7.5 g hydroxyethylcellulose into water and continuously stirred at 65 rpm. Once all of the hydroxyethylcellulose was added, the rotation speed is gradually increased to 100 and mixing continued for an additional 40 minutes, ensuring that all hydroxyethylcellulose was dissolved. A small portion of ethoxydigylcol(82.3 g) was added to hydroxyethylcellulose/water and mixed manually for 5 minutes with a spatula. Mixing with a mixer was continued until approximately 20 ml of ethoxydiglycol had been added. The remainder was added and the mixture stirred at 100 rpm for 45 minutes. This gum was allowed to sit overnight (covered with parafilm).

To form the gel, approximately 20 ml of the active phase was added to the gum phase over a 15 minute time interval, mixing continuously at 50 rpm, interspersed with periods of manual mixing, until the mixer was able to continue independently. The remaining portion of the active phase was added to the gum phase over a 15 minute interval and stirred at 50. Once all of the active phase was added, stirring speed was increased to 100 and mixing continued for 5 hours. The final product was viscous, clear and syringeable with very little air dispensed in the gel itself.

An anti-microtubule agent (e.g., paclitaxel) was incorporated into the topical gel as follows. The active phase was produced by initially mixing 250 g ethoxydiglycol with 500 mg methylparaben and 250 mg propylparaben, while continuously stirring at a stirrer setting of 65. When all components were dispersed well and completely dissolved, 5.020 g of paclitaxel GMP was added and mixed for an additional 20 minutes at 65. Paclitaxel dissolved in 15 minutes, and the final product was a light amber color. The mixture was covered with parafilm and set aside.

To prepare the gum phase, water was mixed at a stirrer setting of 65 and 7.5 g hydroxyethylcellulose added slowly over a 5 minute period. Once the hydroxyethylcellulose was added, mixing speed was increased to 100 for 40 minutes. 20 ml of 82.3 g ethoxydiglycol was added and manually mixed with rotator blade until the substance was thoroughly mixed and softened. The remaining ethoxydiglycol was added over a 5 minute interval, while mixing at 100 for 45 minutes. Mixing speed was reduced to 50 and continued for 10 minutes.

To prepare the gel, 20 ml of active phase was added to the gum phase while mixing at a stirrer setting of 50 over 15 minute time interval. The remaining active phase was added over 45 minutes, while mixing at 50. The speed was increased to 100 and mixing continued for 5 hours. This process yielded approximately 429 g (approximately 86%) of a 1% paclitaxel-loaded gel.

Example 19

Manufacture of Systemic Formulations of Paclitaxel for the Treatment of Psoriasis In severe cases of psoriasis, more aggressive treatments are deemed acceptable and therefore the toxicities associated with systemic treatment with paclitaxel may be acceptable.

Figure 22:
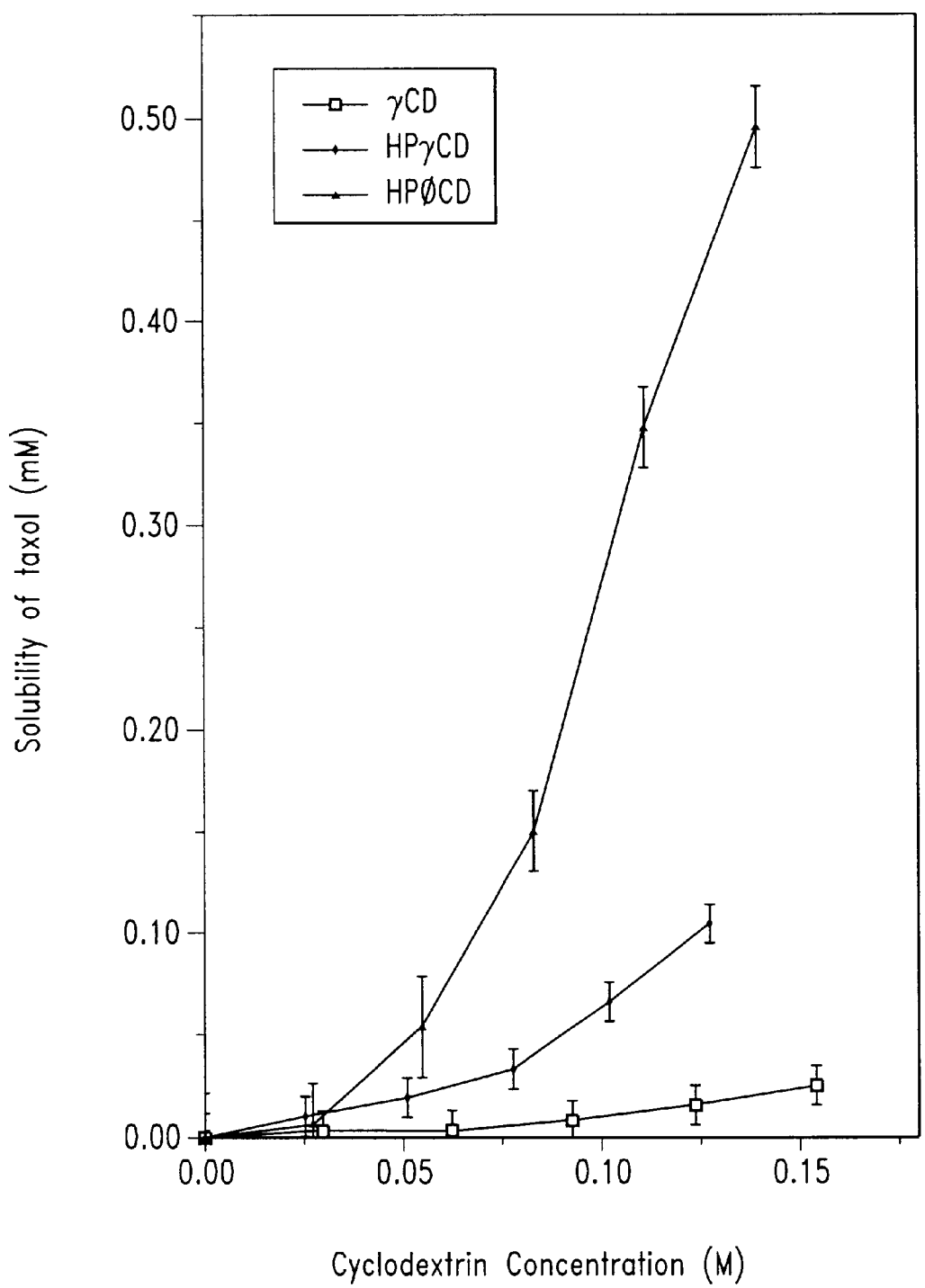
FIG. 22 is a graph which plots the observed pseudo first order kinetic degradation of paclitaxel (20 $\mu$g ml$^{-1}$ in 10% HPβCD and 10% HPγCD solutions at 37° C. and pH of 3.7 and 4.9, respectively.
Figure 23:
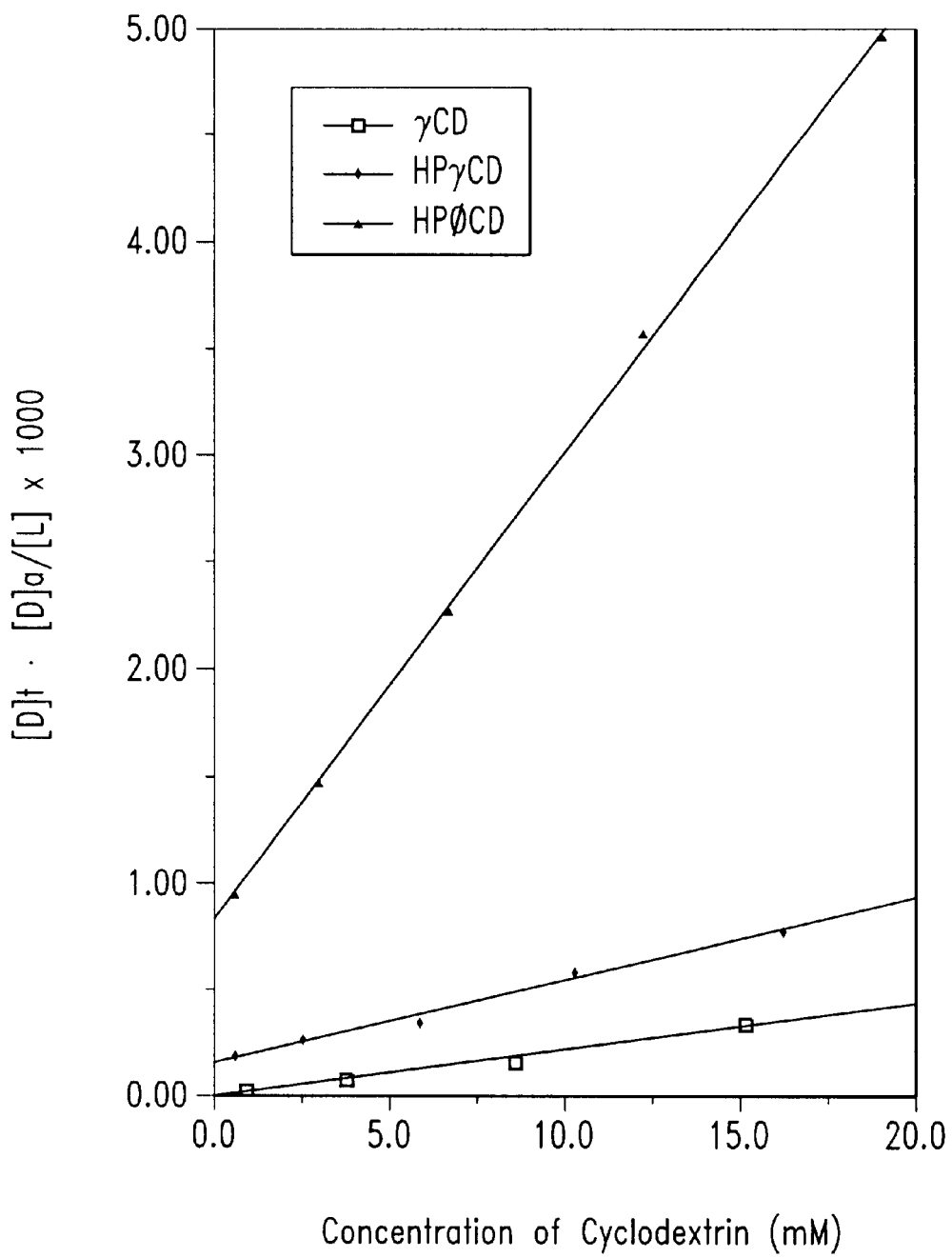
FIG. 23 is a graph which shows the phase solubility for cyclodextrins and paclitaxel in water at 37° C.
Figure 24:
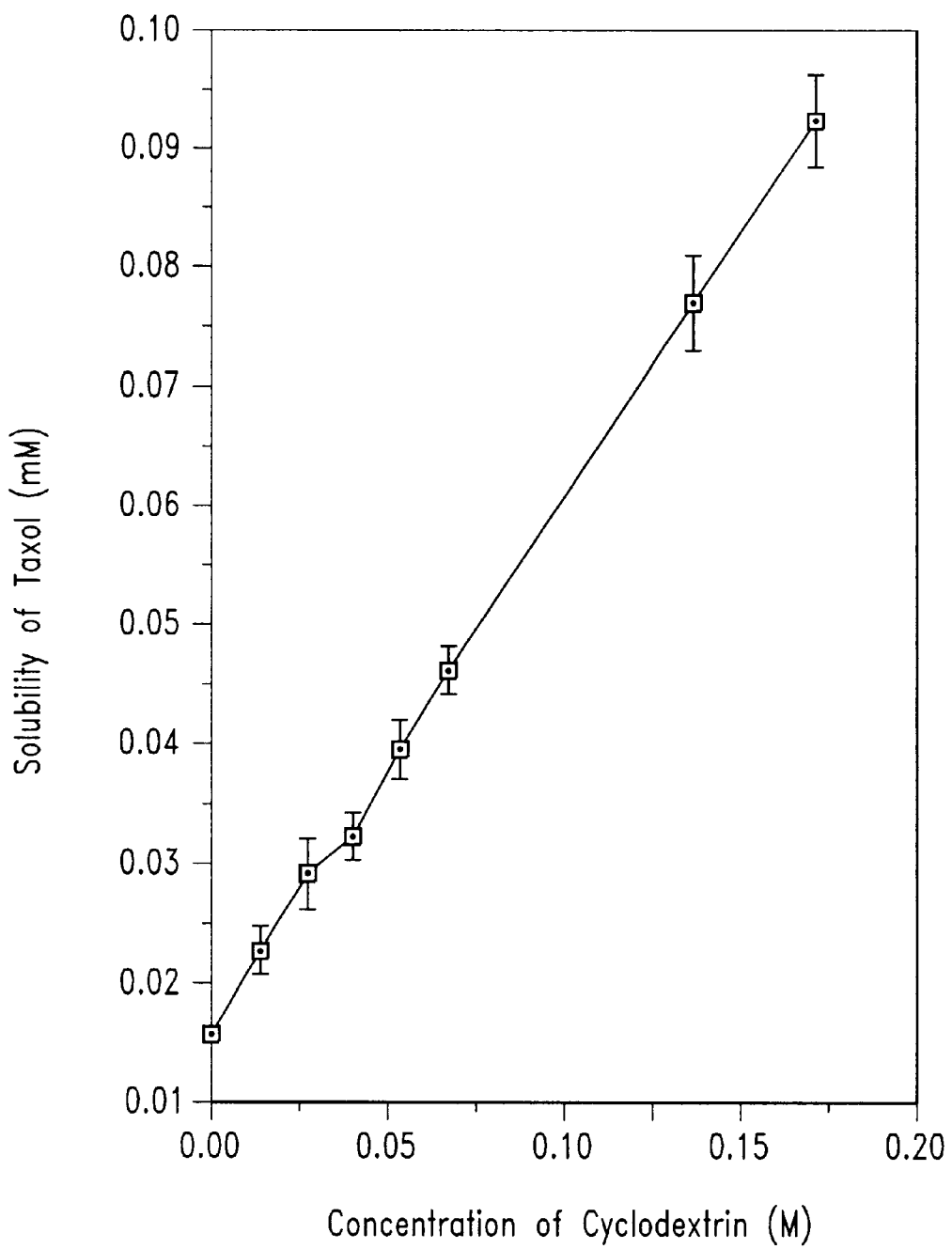
FIG. 24 is a graph which shows second order plots of the complexation of paclitaxel and γCD, HPβCD or HPγCD at 37° C.

The systemic formulation for paclitaxel is comprised of amphiphilic diblock copolymers which in aqueous solutions form micelles consisting of a hydrophobic core and a hydrophilic shell in water. Diblock copolymers of poly(DL-lactide)-block-methoxy polyethylene gylcol(PDLLA-MePEG), polycaprolactone-block methoxy polyethylene gylcol(PCL-MePEG) and poly(DL-lactide-co-caprolactone)-block-methoxy polyethylene gylcol (PDLLACL-MePEG) can be synthesized using a bulk melt polymerization procedure, or similar methods. Briefly, given amounts of monomers DL-lactide, caprolactone and methoxy polyethylene glycols with different molecular weights were heated (130° C.) to melt under the bubbling of nitrogen and stirred. The catalyst stannous octoate (0.2% w/w) was added to the molten monomers. The polymerization was carried out for 4 hours. The molecular weights, critical micelle concentrations and the maximum paclitaxel loadings were measured with GPC, fluorescence, and solubilization testing, respectively (FIG. 22). High paclitaxel carrying capacities were obtained. The ability of solubilizing paclitaxel depends on the compositions and concentrations of the copolymers (FIGS. 22 and 23). PDLLA-MePEG gave the most stable solubilized paclitaxel (FIGS. 23 and 24).

The strong association within the internal core of the polymeric micelles presents a high capacity environment for carrying hydrophobic drugs such as paclitaxel. The drugs can be covalently coupled to block copolymers to form a micellar structure or can be physically incorporated within the hydrophobic cores of the micelles. The mechanisms of drug release from the micelles include diffusion from the core and the exchange between the single polymer chains and the micelles. The small size of the micelles (normally less than 100 nm) will eliminate the difficulties associated with injecting larger particles.

Example 20

Procedure for Producing Thermopaste

Five grams of polycaprolactone mol. wt. 10,000 to 20,000; (Polysciences, Warrington, Pa. USA) a 20 ml glass scintillation vial which was placed into a 600 ml beaker containing 50 ml of water weighed. The beaker was gently heated to 65° C. and held at that temperature for 20 minutes until the polymer melted. A known weight of paclitaxel, or other angiogenesis inhibitor was thoroughly mixed into the melted polymer at 65° C. The melted polymer was poured into a prewarmed (60° C. oven) mould and allowed to cool until the polymer solidified. The polymer was cut into small pieces (approximately 2 mm by 2 mm in size) and was placed into a 1 ml glass syringe.

The glass syringe was then placed upright (capped tip downwards) into a 500 ml glass beaker containing distilled water at 65° C. (corning hot plate) until the polymer melted completely. The plunger was then inserted into the syringe to compress the melted polymer into a sticky mass at the tip end of the barrel. The syringe was capped and allowed to cool to room temperature.

For application, the syringe was reheated to 60° C. and administered as a liquid which solidified when cooled to body temperature.

Example 21

Modification of Paclitaxel Release from Thermopaste Using PDDLA-PEG-PDLLA and Low Molecular Weight Poly(D,L, Lactic Acid)

A. Preparation of PDLLA-PEG-PDLLA and Low Molecular Weight PDLLA

DL-lactide was purchased from Aldrich. Polyethylene gylcol (PEG) with molecular weight 8,000, stannous octoate, and DL-lactic acid were obtained from Sigma. Poly-ϵ-caprolactone (PCL) with molecular weight 20,000 was obtained from Birmingham Polymers (Birmingham, Ala.). Paclitaxel was purchased from Hauser Chemicals (Boulder, Colo.). Polystyrene standards with narrow molecular weight distributions were purchased from Polysciences (Warrington, Pa.). Acetonitrile and methylene chloride were HPLC grade Fisher Scientific).

The triblock copolymer of PDLLA-PEG-PDLLA was synthesized by a ring opening polymerization. Monomers of DL-lactide and PEG in different ratios were mixed and 0.5 wt % stannous octoate was added. The polymerization was carried out at 150° C. for 3.5 hours. Low molecular weight PDLLA was synthesized through polycondensation of DL-lactic acid. The reaction was performed in a glass flask under the conditions of gentle nitrogen purge, mechanical stirring, and heating at 180° C. for 1.5 hours. The PDLLA molecular weight was about 800 measured by titrating the carboxylic acid end groups.

B. Manufacture of Paste Formulations

Paclitaxel at loadings of 20% or 30% was thoroughly mixed into either the PDLLA-PEG-PDLLA copolymers or blends of PDLLA:PCL 90:10, 80:20 and 70:30 melted at about 60° C. The paclitaxel-loaded pastes were weighed into 1 ml syringes and stored at 4° C.

C. Characterization of PDLLA-PEG-PDLLA and the Paste Blends

The molecular weights and distributions of the PDLLA-PEG-PDLLA copolymers were determined at ambient temperature by GPC using a Shimadzu LC-10 AD HPLC pump and a Shimadzu RID-6A refractive index detector (Kyoto, Japan) coupled to a $10^4$ Å Hewlett Packard P1 gel column. The mobile phase was chloroform with a flow rate of 1 ml/minute. The injection volume of the sample was 20 μl at a polymer concentration of 0.2% (w/v). The molecular weights of the polymers were determined relative to polystyrene standards. The intrinsic viscosity of PDLLA-PEG-PDLLA in $CHCl_3$ at 25° C. was measured with a Cannon-Fenske viscometer.

Thermal analysis of the copolymers was carried out by differential scanning calorimetry (DSC) using a TA Instruments 2000 controller and DuPont 910S DSC (Newcastle, Del.). The heating rate was 10° C./min and the copolymer and paclitaxel/copolymer matrix samples were weighed (3–5 mg) into crimped open aluminum sample pans.

$^1H$ nuclear magnetic resonance (NMR) was used to determine the chemical composition of the polymer. $^1H$ NMR spectra of paclitaxel-loaded PDLLA-PEG-PDLLA were obtained in $CDCl_3$ using an NMR instrument (Bruker, AC-200E) at 200 MHz. The concentration of the polymer was 1–2%.

The morphology of the paclitaxel/PDLLA-PEG-PDLLA paste was investigated using scanning electron microscopy (SEM) (Hitachi F-2300). The sample was coated with 60% Au and 40% Pd (thickness 10–15 nm) using a Hummer instrument (Technics, USA).

D. In Vitro Release of Paclitaxel

A small pellet of 20% paclitaxel-loaded PDLLA:PCL paste (about 2 mg) or a cylinder (made by extruding molten paste through a syringe) of 20% paclitaxel-loaded PDLLA-PEG-PDLLA paste were placed into capped 14 ml glass tubes containing 10 ml phosphate buffered saline (pH 7.4) with 0.4 g/L albumin. The tube was incubated at 37° C. with gentle rotational mixing. The supernatant was withdrawn periodically for paclitaxel analysis and replaced with fresh PBS/albumin buffer. The supernatant (10 ml) was extracted with 1 ml methylene chloride. The water phase was decanted and the methylene chloride phase was dried under a stream of nitrogen at 60° C. The dried residue was reconstituted in a 40:60 water:acetonitrile mixture and centrifuged at 10,000 g for about 1 min. The amount of paclitaxel in the supernatant was then analyzed by HPLC. HPLC analysis was performed using a 110A pump and C-8 ultrasphere column (Beckman), and a SPD-6A UV detector set at 232 um, a SIL-9A autoinjector and a C-R3A integrator (Shimadzu). The injection volume was 20 μl and the flow rate was 1 ml/minute. The mobile phase was 58% acetonitrile, 5% methanol, and 37% distilled water.

E. Results and Discussion

Figure 30:
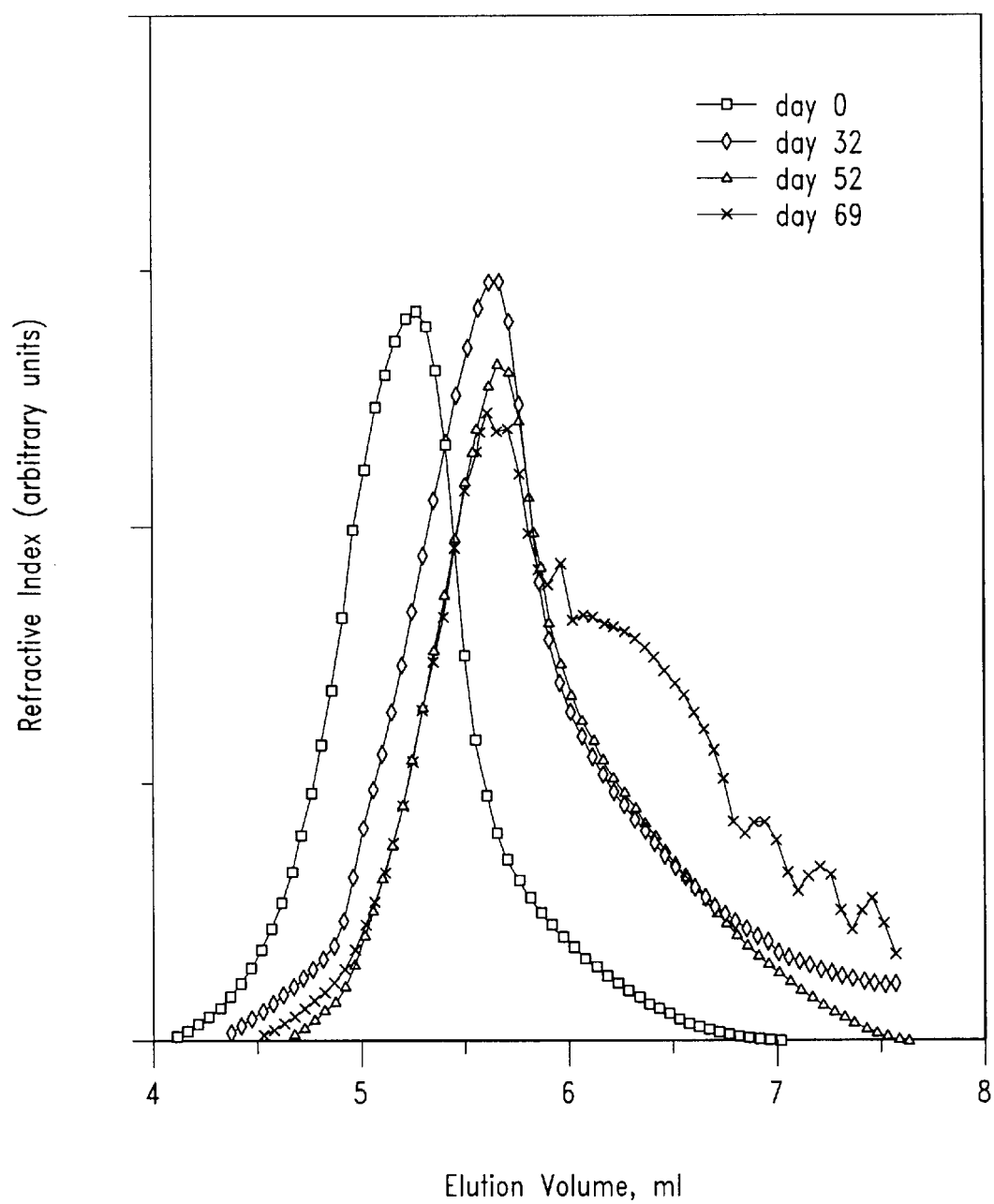
FIG. 30 is a graph which shows gel permeation chromatograms of PDLLA-PEG-PDLLA cylinders (20% PEG, 1 mm diameter) loaded with 20% paclitaxel during the release in PBS albumin buffer at 37° C.
Figure 31A:
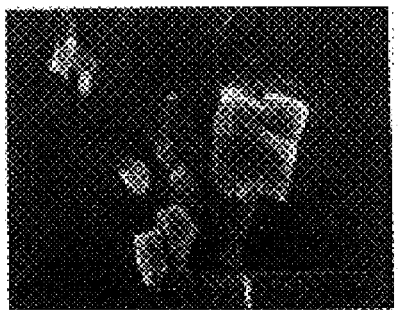
FIGS. 31A, 31B, 31C and 31D are SEMs of dried PDLLA-PEG-PDLLA cylinders (loaded with 20% paclitaxel, 1 mm in diameter) before and during paclitaxel release. A: 20% PEG, day 0; B: 30% PEG, day 0; C: 20% PEG, day 69; D: 30% PEG, day 69.
Figure 31B:
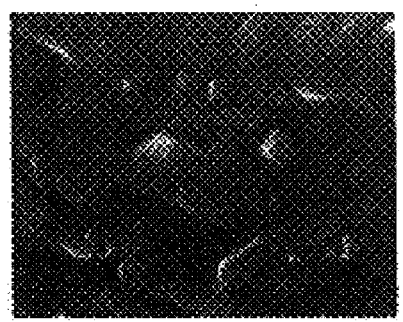
Figure 31C:
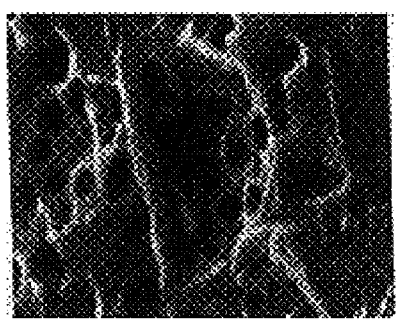
Figure 31D:

The molecular weight and molecular weight distribution of PDLLA-PEG-PDLLA, relative to polystyrene standards, were measured by GPC (FIG. 30). The intrinsic viscosity of the copolymer in $CHCl_3$ at 25° C. was determined using a Canon-Fenske viscometer. The molecular weight and intrinsic viscosity decreased with increasing PEG content. The polydispersities of PDLLA-PEG-PDLLA with PEG contents of 10%–40% were from 2.4 to 3.5. However, the copolymer with 70% PEG had a narrow molecular weight distribution with a polydispersity of 1.21. This might be due to a high PEG content reducing the chance of side reactions such as transesterfication which results in a wide distribution of polymer molecular weights. Alternatively, a coiled structure of the hydrophobic-hydrophilic block copolymers may result in an artificial low polydispersity value.

Figure 26:
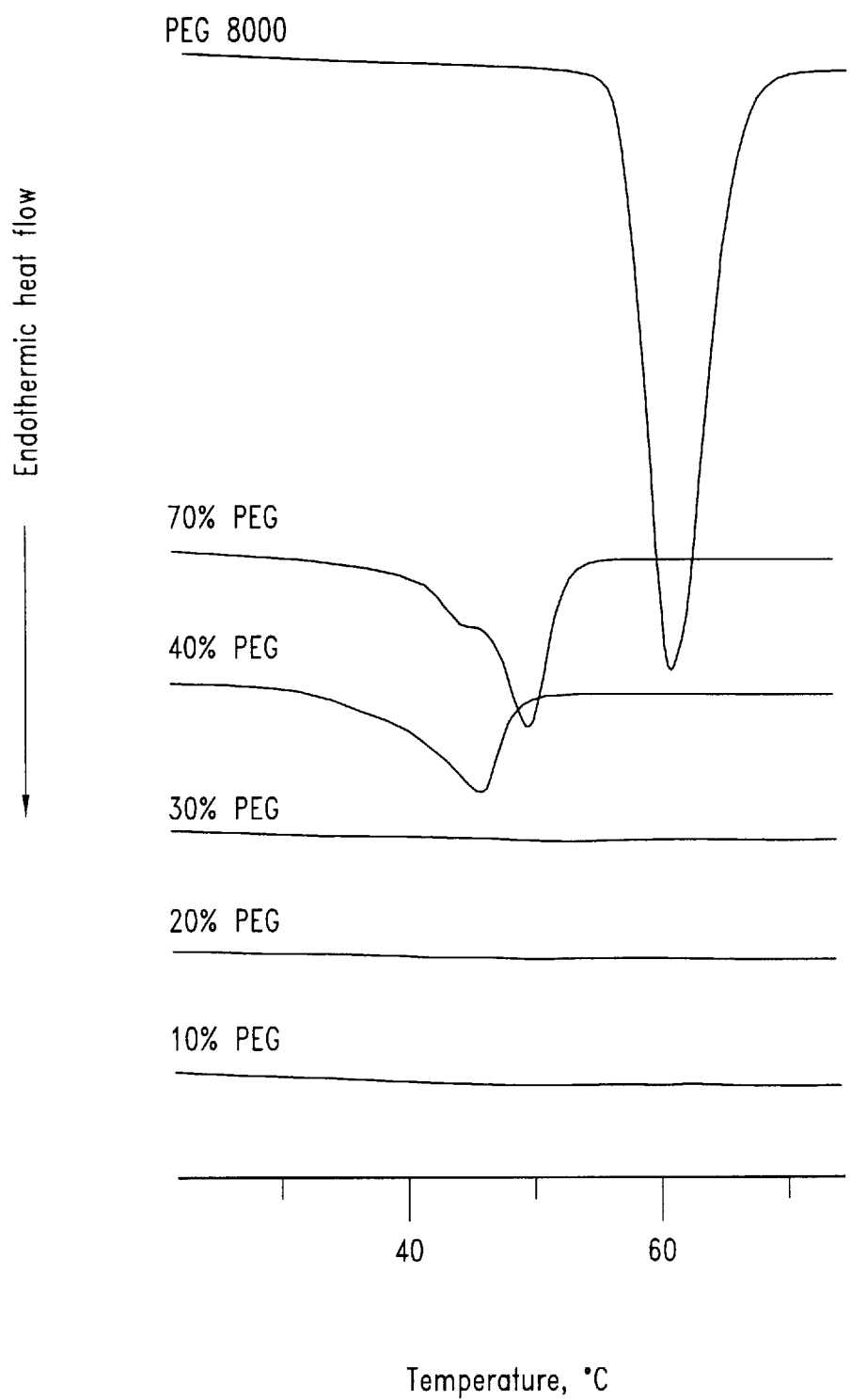
FIG. 26 is a graph which depicts DSC thermograms of PDLLA-PEG-PDLLA and PEG. The heating rate was 10° C./min. See FIG. 30 for melting temperatures and enthalpies.

DSC scans of pure PEG and PDLLA-PEG-PDLLA copolymers are given in FIGS. 25 and 26. The PEG and PDLLA-PEG-PDLLA with PEG contents of 70% and 40% showed endothermic peaks with decreasing enthalpy and temperature as the PEG content of the copolymer decreased. The endothermic peaks in the copolymers of 40% and 70% PEG were probably due to the melting of the PEG region, indicating the occurrence of phase separation. While pure PEG had a sharp melting peak, the copolymers of both 70% and 40% PEG showed broad peaks with a distinct shoulder in the case of 70% PEG. The broad melting peaks may have resulted from the interference of PDLLA with the crystallization of PEG. The shoulder in the case of 70% PEG might represent the glass transition of the PDLLA region. No thermal changes occurred in the copolymers with PEG contents of 10%, 20% and 30% in a temperature range of 10–250° C., indicating that no significant crystallization (therefore may be the phase separation) had occurred.

DSC thermograms of PDLLA:PCL (70:30, 80:20, 90:10) blends without paclitaxel or with 20% paclitaxel showed an endothermic peak at about 60° C., resulting from the melting of PCL. Due to the amorphous nature of the PDLLA and its low molecular weight (800), melting and glass transitions of PDLLA were not observed. No thermal changes due to the recrystallization or melting of paclitaxel was observed.

PDLLA-PEG-PDLLA copolymers of 20% and 30% PEG content were selected as optimum formulation materials for the paste for the following reasons: PDLLA-PEG-PDLLA of 10% PEG could not be melted at a temperature of about 60° C.; the copolymers of 40% and 70% PEG were readily melted at 60° C., send the 20% and 30% PEG copolymer became a viscous liquid between 50° C. to 60° C.; and the swelling of 40% and 70% PEG copolymers in water was very high resulting in rapid dispersion of the pastes in water.

Figure 27:
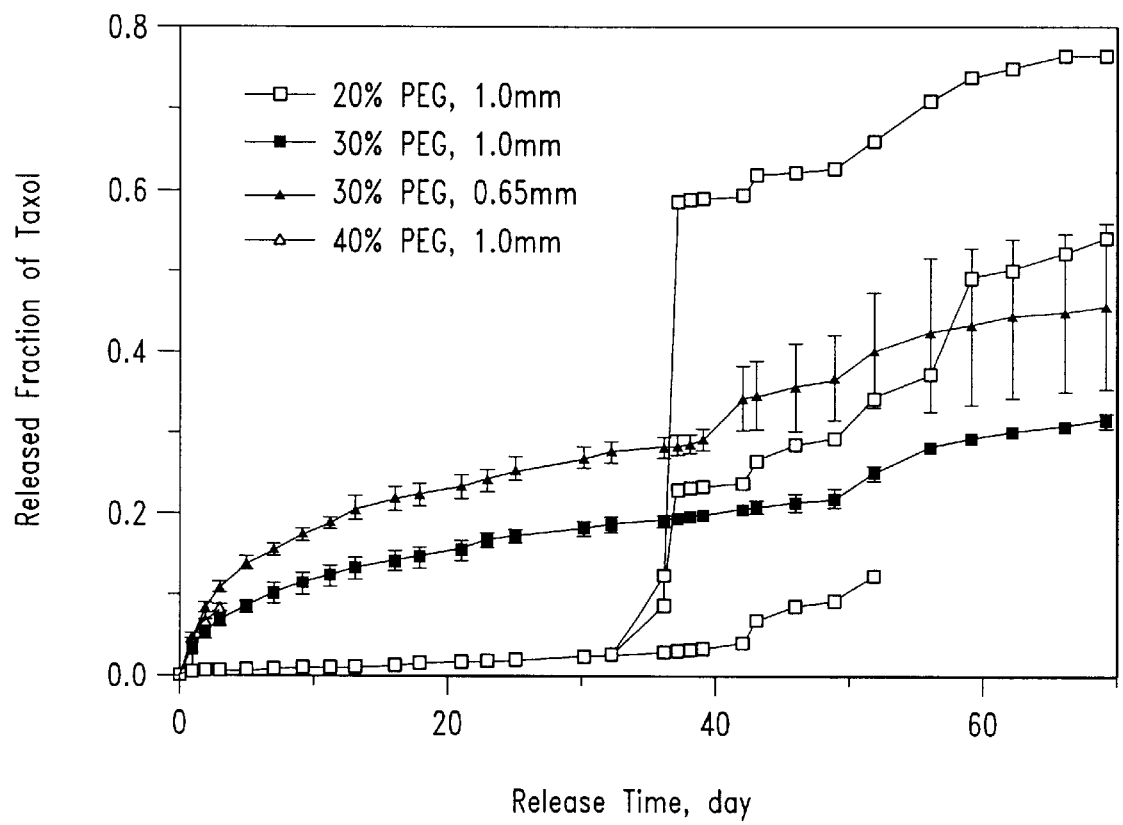
FIG. 27 is a graph which depicts the cumulative release of paclitaxel from 20% paclitaxel loaded PDLLA-PEG-PDLLA cylinders into PBS albumin buffer at 37° C. The error bars represent the standard deviation of 4 samples. Cylinders of 40% PEG were discontinued at 4 days due to disintegration.

The in vitro release profiles of paclitaxel from PDLLA-PEG-PDLLA cylinders are shown in FIG. 27. The experiment measuring release from the 40% PEG cylinders was terminated since the cylinders had a very high degree of swelling (about 200% water uptake within one day) and disintegrated in a few days The released fraction of paclitaxel from the 30% PEG cylinders gradually increased over 70 days. The released fraction from the 20% PEG cylinders slowly increased up to 30 days and then abruptly increased, followed by another period of gradual increase. A significant difference existed in the extent to which each individual cylinder (20% PEG content) showed the abrupt change in paclitaxel release. Before the abrupt increase, the release fraction of paclitaxel was lower for copolymers of lower PEG content at the same cylinder diameter (1 mm). The 40% and 30% PEG cylinders showed much higher paclitaxel release rates than the 20% PEG cylinders. For example, the cylinder of 30% PEG released 17% paclitaxel in 30 days compared to a 2% release from the 20% PEG cylinder. The cylinders with smaller diameters resulted in faster release rates (e.g., in 30 days the 30% PEG cylinders with 0.65 mm and 1 mm diameters released 26% and 17% paclitaxel, respectively (FIG. 27)).

The above observations may be explained by the release mechanisms of paclitaxel from the cylinders. Paclitaxel was dispersed in the polymer as crystals as observed by optical microscopy. The crystals began dissolving in the copolymer matrix at 170° C. and completely dissolved at 180° C. as observed by hot stage microscopy DSC thermograms of 20% paclitaxel-loaded PDLLA-PEG-PDLLA (30% PEG) paste revealed a small recrystallization exotherm (16 J/g, 190° C.) and a melting endotherm (6 J/g, 212° C.) for paclitaxel (FIG. 25) indicating the recrystallization of paclitaxel from the copolymer melt after 180° C. In this type of drug/polymer matrix, paclitaxel could be released via diffusion and/or polymer erosion.

In the diffusional controlled case, drug may be released by molecular diffusion in the polymer and/or through open channels formed by connected drug particles. Therefore at 20% loading, some particles of paclitaxel were isolated and paclitaxel may be released by dissolution in the copolymer followed by diffusion. Other particles of paclitaxel could form clusters connecting to the surface and be released through channel diffusion. In both cases, the cylinders with smaller dimension gave a faster drug release due to the shorter diffusion path (FIG. 27).

Figure 28A:
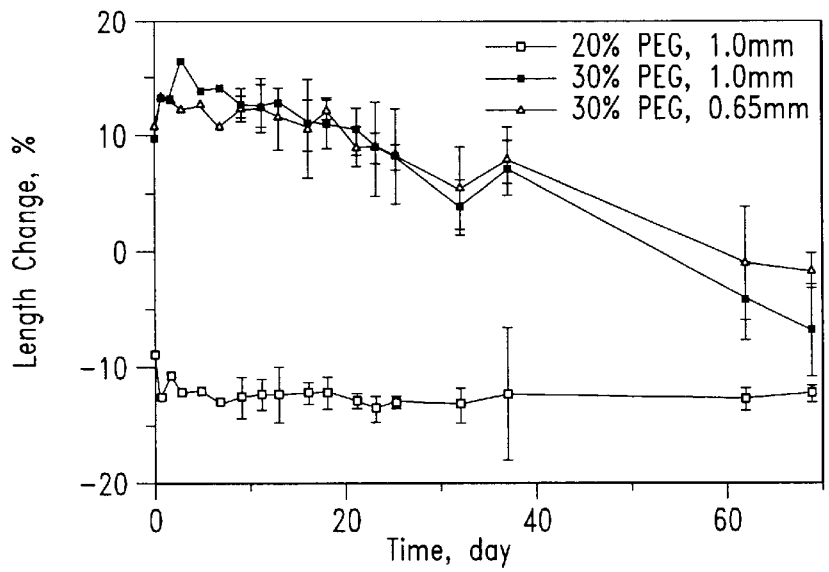
FIGS. 28A, 28B and 28C are graphs which depict the change in dimensions, length (A), diameter (B) and wet weight (C) of 20% paclitaxel loaded PDLLA-PEG-PDLLA cylinders during the in vitro release of paclitaxel at 37° C.
Figure 28B:
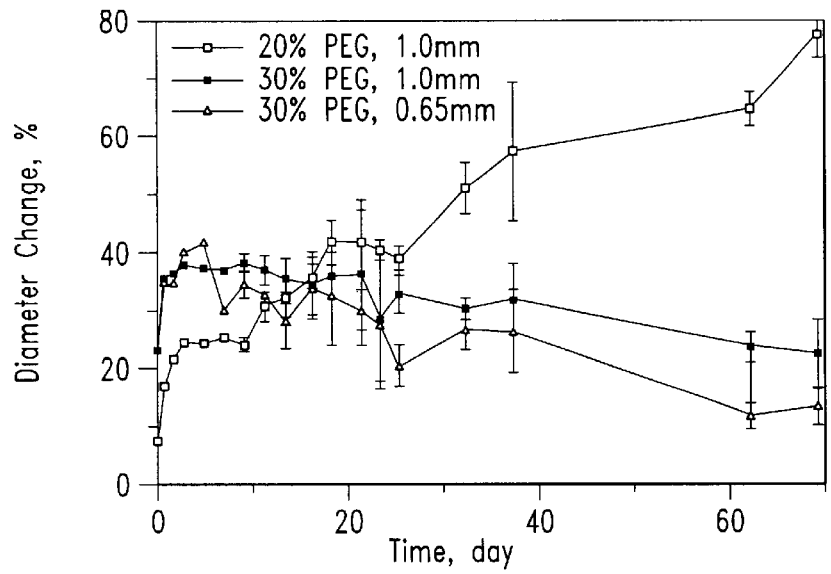
Figure 28C:
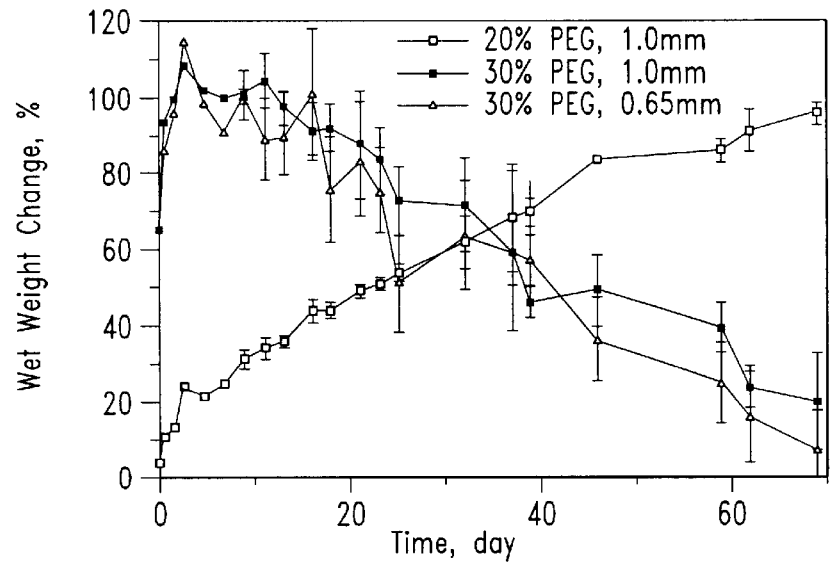

The dimension changes and water uptake of the cylinders were recorded during the release (FIG. 28). The changes in length, diameter and wet weight of the 30% PEG cylinders increased rapidly to a maximum within 2 days, remained unchanged for about 15 days, then decreased gradually. The initial diameter of the cylinder did not affect the swelling behavior. For the cylinder of 20% PEG, the length decreased by 10% in one day and leveled off, while the diameter and water uptake gradually increased over time. Since more PEG in the copolymer took up more water to facilitate the diffusion of paclitaxel, a faster release was observed (FIG. 27).

The copolymer molecular weight degradation of PDLLA-PEG-PDLLA paste was monitored by GPC. For the 20% PEG cylinder, the elution volume at the peak position increased with time indicating a reduced polymer molecular weight during the course of the release experiment (FIG. 30). A biphasic molecular weight distribution was observed at day 69. Polymer molecular weight was also decreased for 30% PEG cylinders (1 mm and 0.65 mm). However no biphasic distribution was observed.

NMR spectra revealed a PEG peak at 3.6 ppm and PDLLA peaks at 1.65 ppm and 5.1 ppm. The peak area of PEG relative to PDLLA in the copolymer decreased significantly after 69 days (FIG. 29), indicating the dissolution of PEG after its dissociation from PDLLA. The dry mass loss of the cylinders was also recorded (FIG. 29) and shows a degradation rate decreasing in the order 30% PEG-0.65 mm>30% PEG-1 mm>20% PEG-1 mm.

The morphological changes of the dried cylinders before and during paclitaxel release were observed using SEM (FIG. 31). Briefly, solid paclitaxel crystals and non-porous polymer matrices were seen before the release (FIGS. 31A and 31B). After 69 days of release, no paclitaxel crystals were observed and the matrices contained many pores due to polymer degradation and water uptake FIGS. 31C and 31D).

The 30% PEG cylinders showed extensive swelling after only two days in water (FIG. 28) and therefore the hindrance to diffusion of the detached water soluble PEG block and degraded PDLLA (i.e., DL-lactic acid oligomers) was reduced. Since the mass loss and degradation of the 30% PEG cylinders was continuous, the contribution of erosion release gradually increased resulting in a sustained release of paclitaxel without any abrupt change (FIG. 27). For the 20% PEG cylinders, the swelling was low initially (FIG. 28) resulting in a slow diffusion of the degradation products.

Therefore the degradation products in the interior region were primarily retained while there were fewer degradation products in the outer region due to the short diffusion path. The degradation products accelerated the degradation rate since the carboxylic acid end groups of the oligomers catalyzed the hydrolytic degradation. This resulted in a high molecular weight shell and a low molecular weight interior as indicated by the biphasic copolymer molecular weight distribution (FIG. 30, day 69). Since the shell rupture was dependent on factors such as the strength, thickness and defects of the shell and interior degradation products, the onset and the extent of the loss of interior degradation products were very variable. Because the shell rupture was not consistent and the drug in the polymer was not microscopically homogenous, the time point for the release burst and the extent of the burst were different for the 4 samples tested (FIG. 27).

Figure 32:
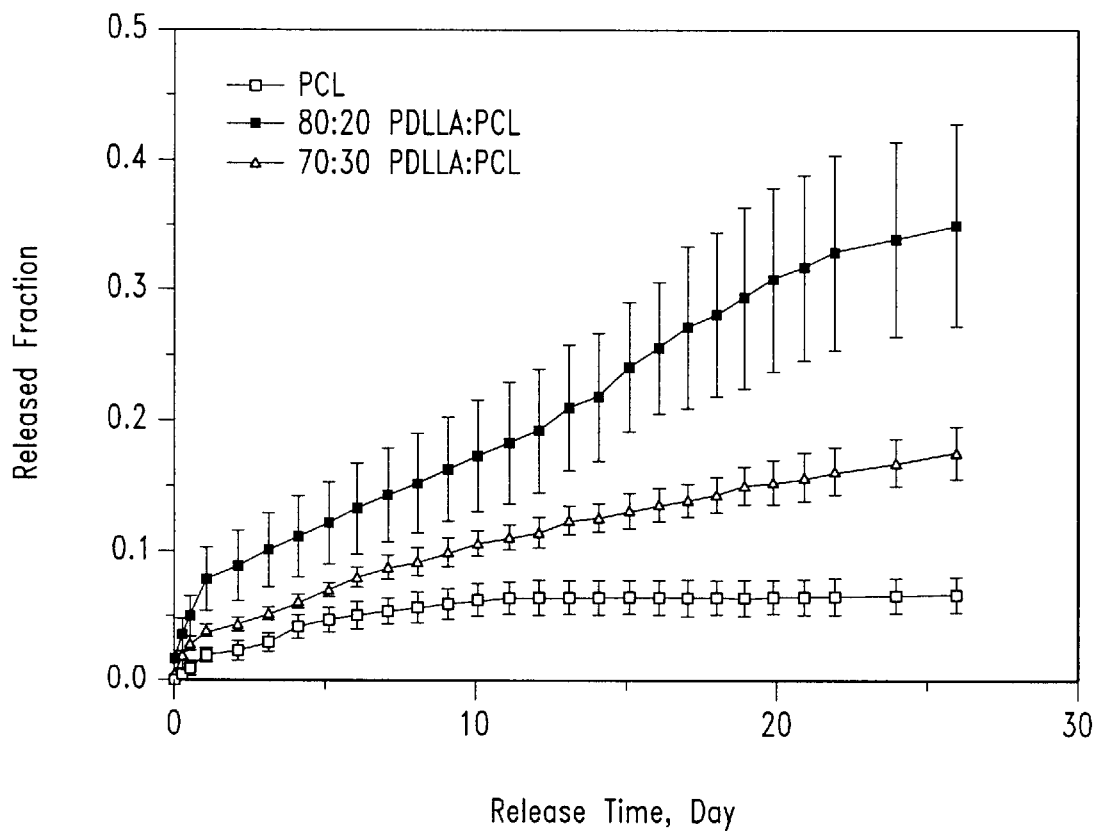
FIG. 32 is a graph which depicts the cumulative release of paclitaxel from 20% paclitaxel loaded PDLLA:PCL blends and PCL into PBS albumin buffer at 37° C. The error bars represent the standard deviations of 4 samples.

The release of paclitaxel from PDLLA and PCL blends and pure PCL are shown in FIG. 32. Briefly, the released fraction increased with PDLLA content in the blend. For example, within 10 days, the released paclitaxel from 80:20, 70:30, and 0:100 PDLLA:PCL were 17%, 11%, and 6%, respectively. After an initial burst in one day, approximately constant release was obtained from 80:20 PDLLA:PCL paste. No significant degree of swelling was observed during the release. For the PDLLA:PCL blends, since PDLLA had a very low molecular weight of about 800, it was hydrolyzed rapidly into water soluble products without a long delay in mass loss. PCL served as the "holding" material to keep the paste from rapidly disintegrating. Therefore the release rate increased with PDLLA content in the blend due to the enhanced degradation. The continuous erosion of the PDLLA controlled the release of paclitaxel and resulted in a constant release. The release of paclitaxel from pure PCL was probably diffusion controlled due to the slow degradation rate (in 1–2 years) of PCL.

Difficulties were encountered in the release study for 20% paclitaxel loaded 90:10 PDLLA:PCL paste due to the disintegration of the paste pellet within 24 hours of incubation. Briefly, during the first 12 hours of incubation, samples were taken every hour in order to ensure sink conditions for paclitaxel release. The released paclitaxel from the 90:10 paste was 25–35% within 10 hours.

Paste of 90:10 PDLLA:PCL containing 30% paclitaxel released more paclitaxel than 90:10 PDLLA:PCL paste containing 20% paclitaxel. Thus, modulation of the release rate of paclitaxel, which was regulated by the properties of the polymer and chemotherapeutic agents as well as the site of administration, was important in the development of local therapy.

Example 22

Preparation of Polymeric Compositions Containing Water Soluble Additives and Paclitaxel A. Preparation of Polymeric Compositions Microparticles of co-precipitates of paclitaxel/additive were prepared and subsequently added to PCL to form pastes. Briefly, paclitaxel (100 mg) was dissolved in 0.5 ml of ethanol (95%) and mixed with the additive (100 mg) previously dissolved or dispersed in 1.0 ml of distilled water. The mixture was triturated until a smooth paste was formed. The paste was spread on a Petri dish and air-dried overnight at 37° C. The dried mass was pulverized using a mortar and pestle and passed through a mesh #140 (106 µm) sieve (Endecotts Test Sieves Ltd., London, England). The microparticles (40%) were then incorporated into molten PCL (60%) at 65° C. corresponding to a 20% loading of paclitaxel. The additives used in the study were gelatin (Type B, 100 bloom, Fisher Scientific), methylcellulose, (British Drug Houses), dextran, T500 (Pharmacia, Sweden), albumin Fisher Scientific), and sodium chloride (Fisher Scientific). Microparticles of paclitaxel and gelatin or albumin were prepared as described above but were passed through a mesh #60 (270 μm) sieve (Endecotts Test Sieves Ltd., London, England) to evaluate the effect of microparticle size on the release of paclitaxel from the paste. Pastes were also prepared to contain 10, 20 or 30% gelatin and 20% paclitaxel in PCL to study the effect of the proportion of the additive on drug release. Unless otherwise specified, pastes containing 20% paclitaxel dispersed in PCL were prepared to serve as controls for the release rate studies.

B. Drug Release Studies

Approximately a 2.5 mg pellet of paclitaxel-loaded paste was suspended in 50 ml of 10 mM PBS (pH 7.4) in screw-capped tubes. The tubes were tumbled end-over-end at 37° C. and at given time intervals 49.5 ml of supernatant was removed, filtered through a 0.45 μm membrane filter and retained for paclitaxel analysis. An equal volume of PBS was replaced in each tube to maintain sink conditions throughout the study. For analysis, the filtrates were extracted with 3×1 ml dichloromethane (DCM), the DCM extracts evaporated to dryness under a stream of nitrogen and redissolved in 1 ml acetonitrile. The analysis was by HPLC using a mobile phase of water:methanol:acetonitrile (37:5:58:) at a flow rate of 1 ml/minute (Beckman Isocratic Pump), a C18 reverse phase column (Beckman), and UV detection (Shimadzu SPD A) at 232 nm.

C. Swelling Studies

Paclitaxel/additive/PCL pastes, prepared using paclitaxel-additive microparticles of mesh size #140 (and #60 for gelatin only), were extruded to form cylinders, pieces were cut, weighed and the diameter and length of each piece were measured using a micrometer (Mitutoyo Digimatic). The pieces were suspended in distilled water (10 ml) at 37° C. and at predetermined intervals the water was discarded and the diameter and the length of the cylindrical pieces were measured and the samples weighed. The morphology of the samples (before and after suspending in water) was examined using scanning electron microscopy (SEM) (Hitachi F-2300). The samples were coated with 60% Au and 40% Pd (thickness 10–15 nm) using a Hummer Instrument (Technics, USA).

D. Chick Embryo Chorioallantoic Membrane (CAM) Studies

Fertilized, domestic chick embryos were incubated for 4 days prior to shell-less culturing. The egg contents were incubated at 90% relative humidity and 3% $CO_2$ and on day 6 of incubation, 1 mg pieces of the paclitaxel-loaded paste (containing 6% paclitaxel, 24% gelatin and 70% PCL) or control (30% gelatin in PCL) pastes were placed directly on the CAM surface. After a 2-day exposure the vasculature was examined using a stereomicroscope interfaced with a video camera; the video signals were then displayed on a computer and video printed.

E. Results and Discussion

Microparticles of co-precipitated paclitaxel and gelatin or albumin were hard and brittle and were readily incorporated into PCL, while the other additives produced soft particles which showed a tendency to break up during the preparation of the paste.

Figure 33:
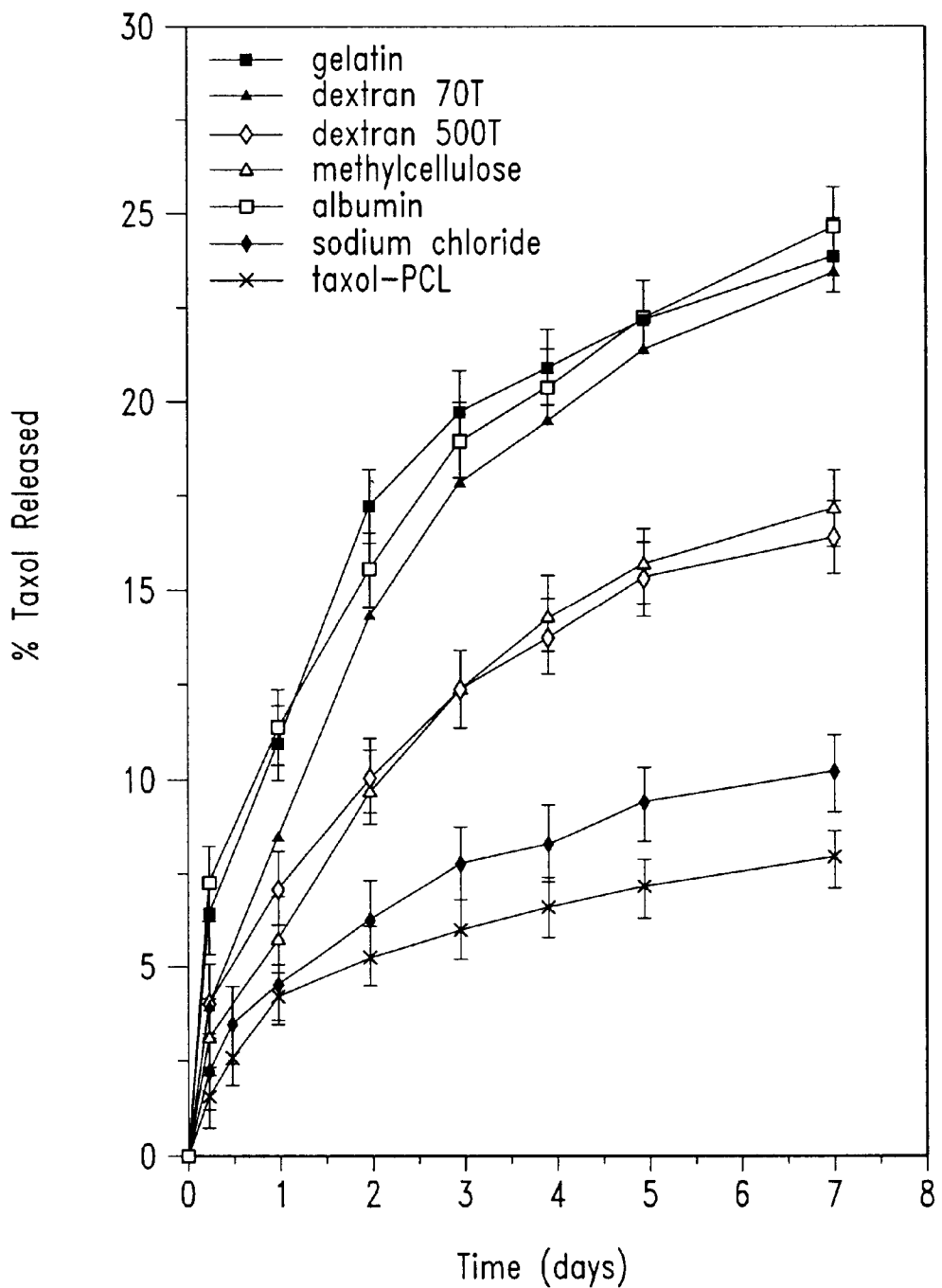
FIG. 33 is a graph which depicts, over a time course, the release of paclitaxel from PCL pastes into PBS at 37° C. The PCL pastes contain microparticles of paclitaxel and various additives prepared using mesh #140. The error bars represent the standard deviation of 3 samples.

FIG. 33 shows the time courses of paclitaxel release from pastes containing 20% paclitaxel in PCL or 20% paclitaxel, 20% additive and 60% PCL. The release of paclitaxel from PCL with or without additives followed a biphasic release pattern; initially, there was a faster drug release rate followed by a slower drug release of the drug. The initial period of faster release rate of paclitaxel from the pastes was thought to be due to dissolution of paclitaxel located on the surface or diffusion of paclitaxel from the superficial regions of the paste. The subsequent slower phase of the release profiles may be attributed to a decrease in the effective surface area of the drug particles in contact with the buffer, a slow ingress of the buffer into the polymer matrix or an increase in the mean diffusion paths of the drug through the polymer matrix.

Figure 34:
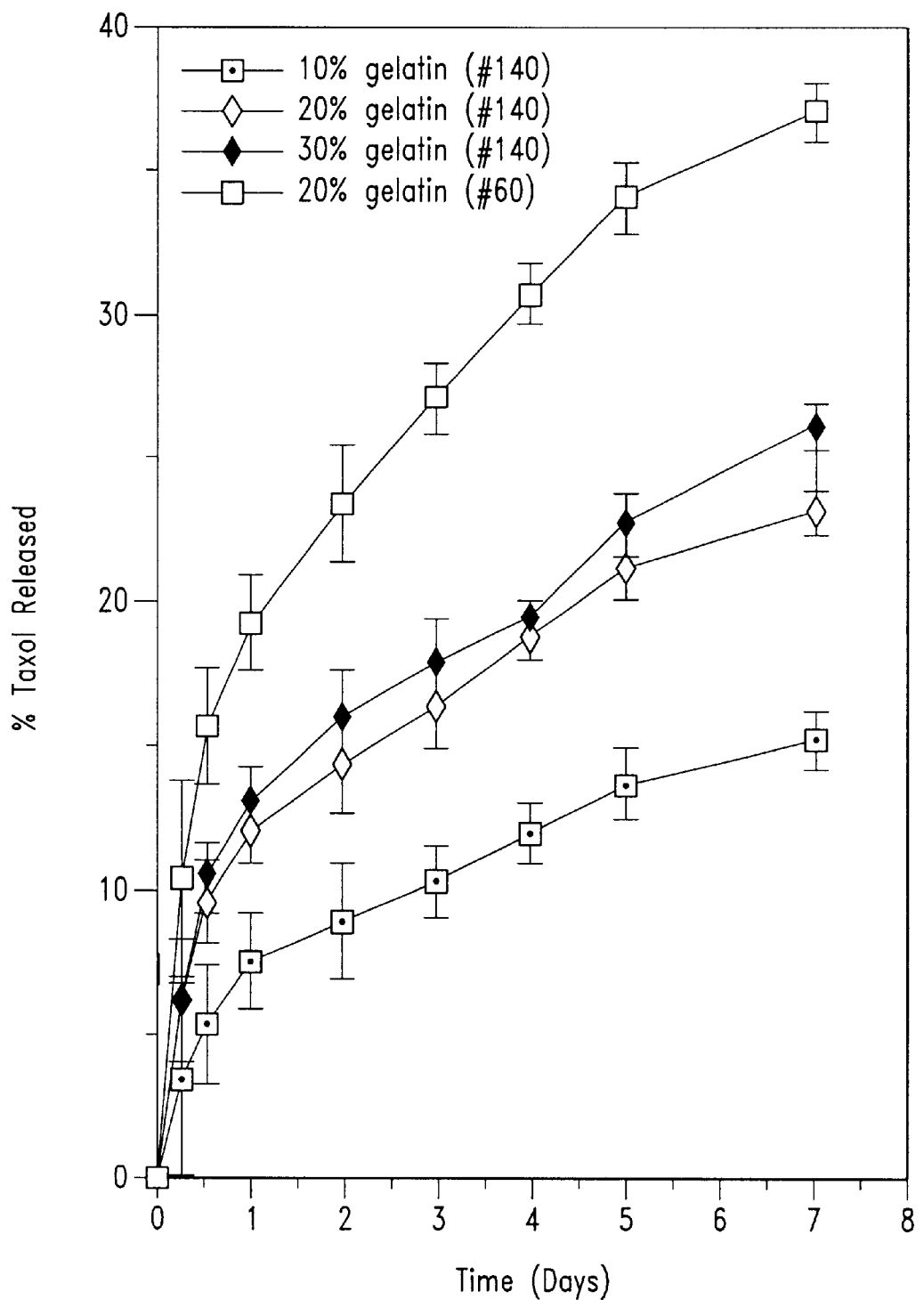
FIG. 34 is a graph which depicts time courses of paclitaxel release from paclitaxel-gelatin-PCL pastes into PBS at 37° C. This graph shows the effects of gelatin concentration (mesh #140) and the size of paclitaxel-gelatin (1:1) microparticles prepared using mesh #140 or mesh #60. The error bars represent the standard deviation of 3 samples.
Figure 35A:
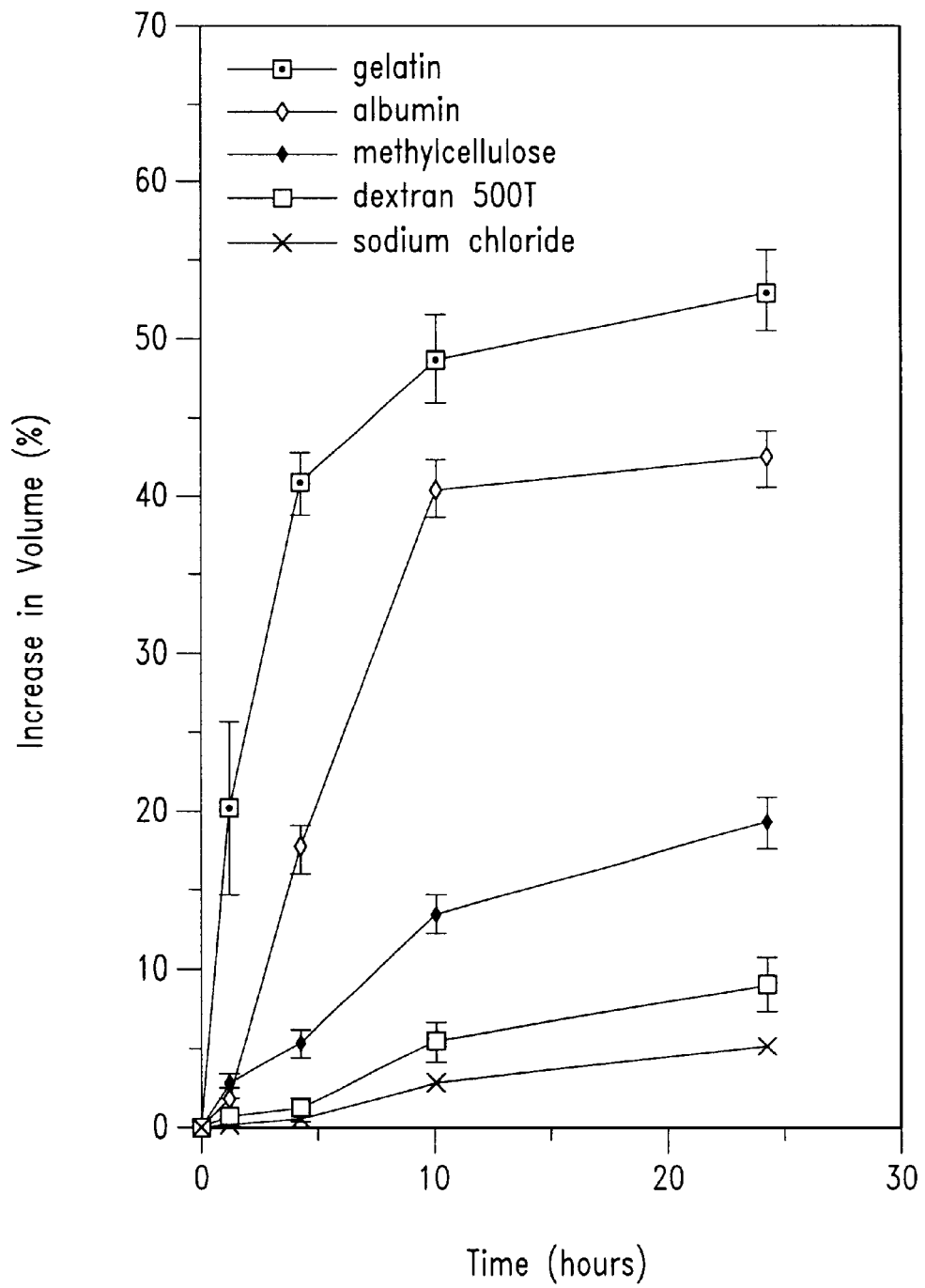
FIGS. 35A and 35B are graphs which depict the effect of additives (17A; mesh #140) and the size of microparticles (17B; mesh #140 or #60) and the proportion of the additive (mesh #140) on the swelling behavior of PCL pastes containing 20% paclitaxel following suspension in distilled water at 37° C. Measurements for the paste prepared with 270 $\mu$m microparticles in paclitaxel-gelatin and paste containing 30% gelatin were discontinued after 4 hours due to disintegration of the matrix. The error bars represent the standard deviation of 3 samples.
Figure 35B:
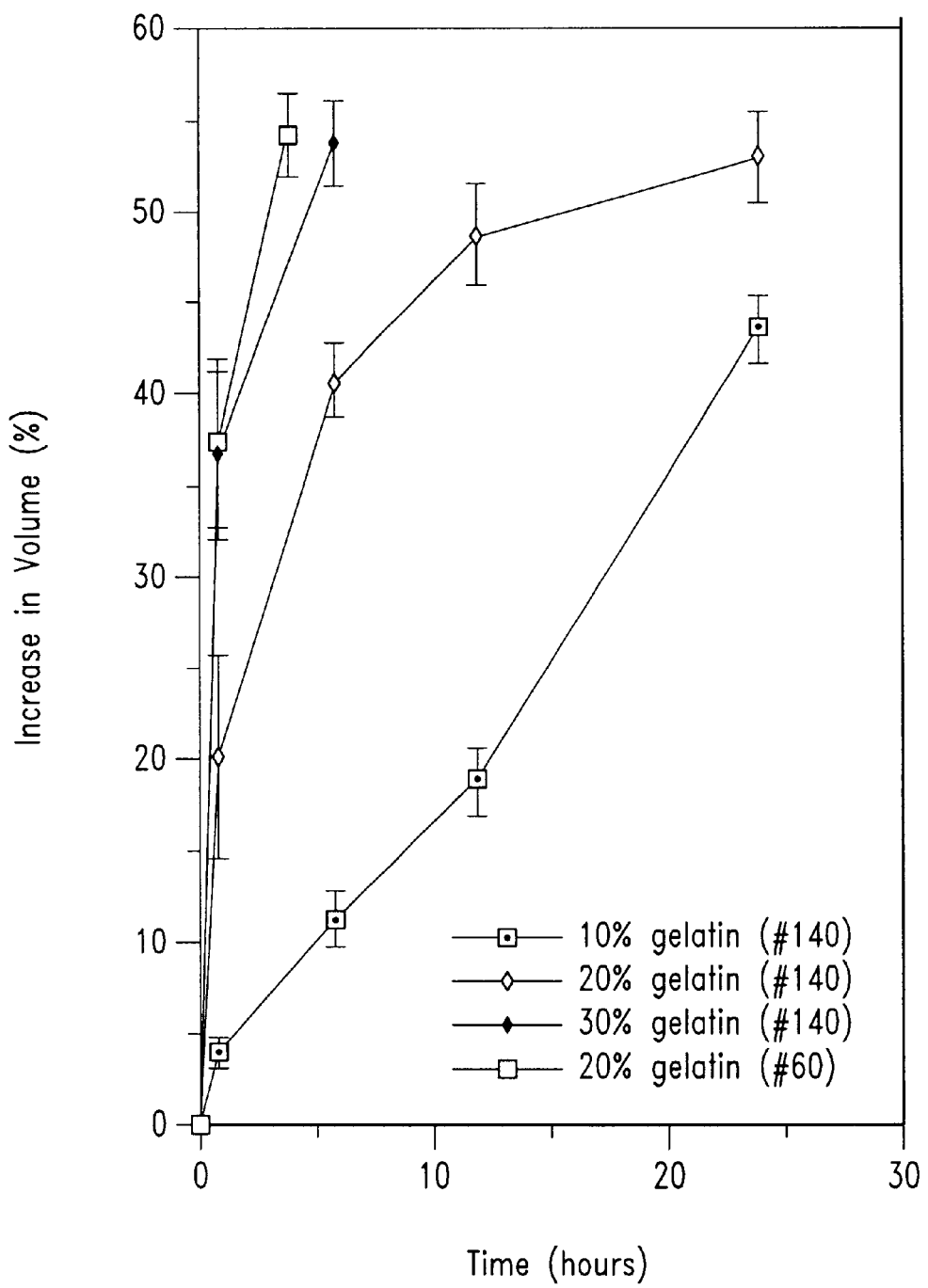
Figure 36A:
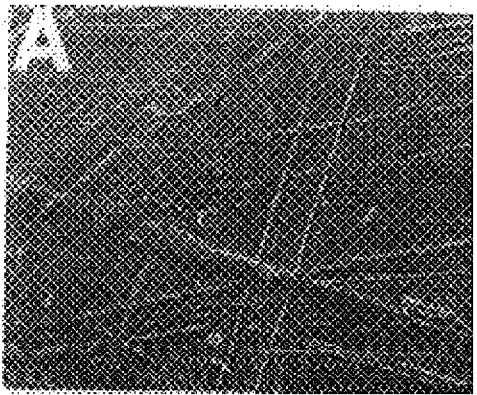
FIGS. 36A, 36B, 36C and 36D are representative scanning electron micrographs of paclitaxel-gelatin-PCL (20:20:60) pastes before (36A) and after (36B) suspending in distilled water at 37° C. for 6 hours. Micrographs 36C and 36D are higher magnifications of 36B, showing intimate association of paclitaxel (rod shaped) and gelatin matrix.
Figure 36B:
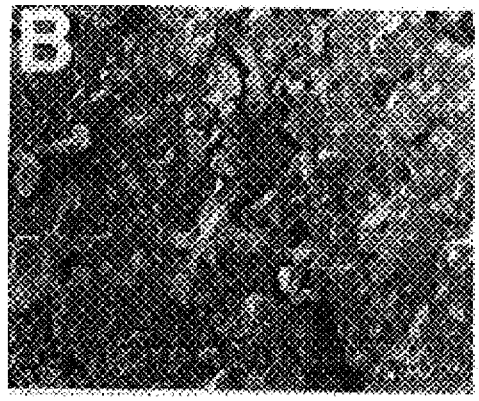
Figure 36C:
Figure 36D:
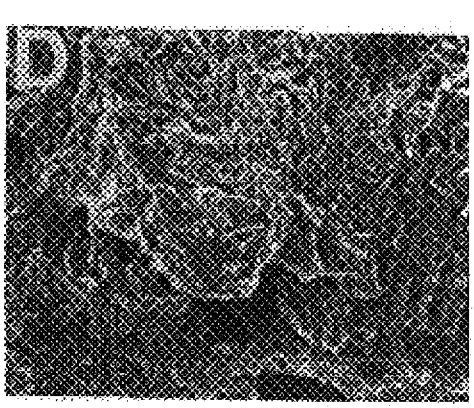

Both phases of the release profiles of paclitaxel from PCL increased in the presence of the hydrophilic additives with gelatin, albumin and methylcellulose producing the greatest increase in drug release rates (FIG. 33). There were further increases in the release of paclitaxel from the polymer matrix when larger paclitaxel-additive particles (270 μm) were used to prepare the paste compared with when the smaller paclitaxel-additive particles (106 μm) were used (FIG. 34). Increases in the amount of the additive (e.g., gelatin) produced a corresponding increase in drug release (FIG. 34). FIG. 35A shows the swelling behavior of pastes containing 20% paclitaxel, 20% additive and 60% PCL. The rate of swelling followed the order gelatin>albumin>methylcellulose>dextran>sodium chloride. In addition, the rate of swelling increased when a higher proportion of the water-soluble polymer was added to the paste (FIG. 35B). The pastes containing gelatin or albumin swelled rapidly within the first 8–10 hours and subsequently the rate of swelling decreased when the change in the volume of the sample was greater than 40%. The paste prepared using the larger (270 μm) paclitaxel-gelatin particles swelled at a faster rate than those prepared with the smaller (106 μm) paclitaxel-gelatin particles. All pastes disintegrated when the volume increased greater than 50%. The SEM studies showed that the swelling of the pastes was accompanied by the cracking of the matrix (FIG. 36). At high magnifications (FIGS. 36C and 36D) there was evidence of needle-or rod-shaped paclitaxel crystals on the surface of the paste and in close association with gelatin following swelling (FIGS. 36C and 36D).

Osmotic or swellable, hydrophilic agents embedded as discrete particles in the hydrophobic polymer resulted in drug release by a combination of matrix erosion, diffusion of drug through the polymer matrix, and/or diffusion and/or convective flow through pores created in the matrix by the dissolution of the water soluble additives. Osmotic agents and swellable polymers dispersed in a hydrophobic polymer would imbibe water (acting as wicking agents), dissolve or swell and exert a turgor pressure which could rupture the septa (the polymer layer) between adjacent particles, creating microchannels and thus facilitating the escape of the drug molecules into the surrounding media by diffusion or convective flow. The swelling and cracking of the paste matrix (FIG. 36) likely resulted in the formation of microchannels throughout the interior of the matrix. The different rates and extent of swelling of the polymers (FIG. 35) may account for the differences in the observed paclitaxel release rates (FIGS. 33 and 34).

Figure 37A:
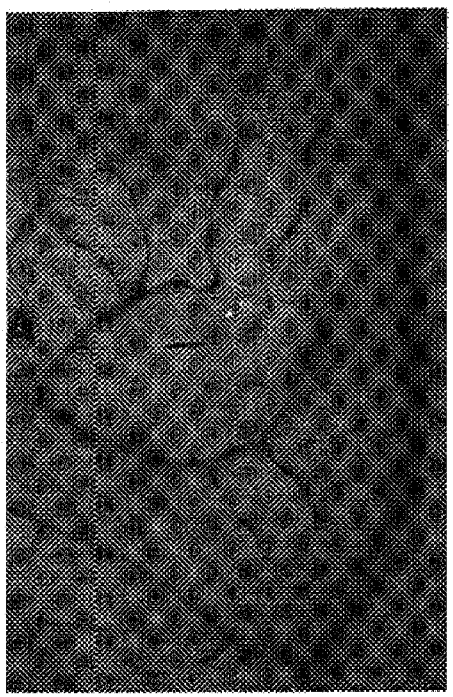
FIGS. 37A and 37B are representative photomicrographs of CAMs treated with gelatin-PCL (37A) and paclitaxel-gelatin-PCL (20:20:60; 37B) pastes showing zones of avascularity in the paclitaxel treated CAM.
Figure 37B:
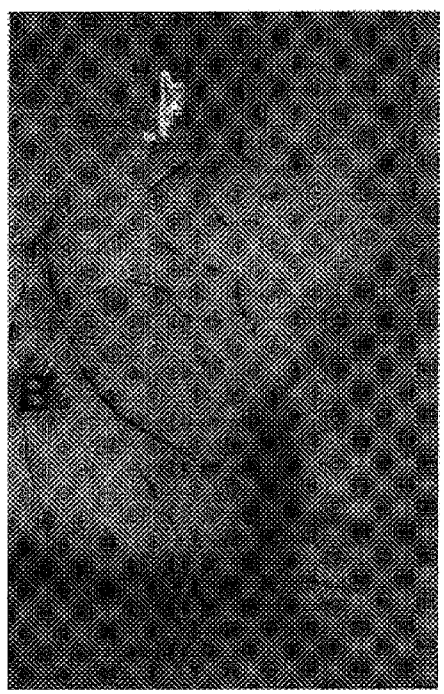

FIG. 37 shows CAMs treated with control gelatin-PCL paste (FIG. 37A) and 20% paclitaxel-gelatin-PCL paste (FIG. 37B). The paste on the surface of the CAMs are shown by the arrows in the figures. The CAM with the control paste shows a normal capillary network architecture. The CAMs treated with paclitaxel-PCL paste consistently showed vascular regression and zones which lacked a capillary network. Incorporation of additives in the paste markedly increased the diameter of the avascular zone (FIG. 37).

This study showed that the in vitro release of paclitaxel from PCL could be increased by the incorporation of paclitaxel/hydrophilic polymer microparticles into PCL matrix. In vivo studies evaluating the efficacy of the formulation in treating subcutaneous tumors in mice also showed that the paclitaxel/gelatin/PCL paste significantly reduced the tumor mass. Factors such as the type of water soluble agent, the microparticle size and the proportion of the additives were shown to influence the release characteristics of the drug.

Example 23

Procedure for Producing Nanopaste

Nanopaste is a suspension of microspheres in a hydrophilic gel. Within one aspect of the invention, the gel or paste can be smeared over tissue as a method of locating drug-loaded microspheres close to the target tissue. Being water based, the paste soon becomes diluted with bodily fluids causing a decrease in the stickiness of the paste and a tendency of the microspheres to be deposited on nearby tissue. A pool of microsphere encapsulated drug is thereby located close to the target tissue.

Reagents and equipment which were utilized within these experiments include glass beakers, Carbopol 925 (pharmaceutical grade, Goodyear Chemical Co.), distilled water, sodium hydroxide (1 M) in water solution, sodium hydroxide solution (5 M) in water solution, microspheres in the 0.1 lm to 3 lm size range suspended in water at 20% w/v (see previous).

1. Preparation of 5% w/v Carbopol Gel

A sufficient amount of carbopol was added to 1 M sodium hydroxide to achieve a 5% w/v solution. To dissolve the carbopol in the 1 M sodium hydroxide, the mixture was allowed to sit for approximately one hour. During this time period, the mixture was stirred and, after one hour, the pH was adjusted to 7.4 using 5 M sodium hydroxide until the carbopol was fully dissolved. Once a pH of 7.4 was achieved, the gel was covered and allowed to sit for 2 to 3 hours.

2. Procedure for Producing Nanopaste

A sufficient amount of 0.1 $\mu$m to 3 $\mu$m microspheres was added to water to produce a 20% suspension of the microspheres Carbopol gel (8 ml of the 5% w/v) was placed into a glass beaker and 2 ml of the 20% microsphere suspension was added. The mixture was stirred to thoroughly disperse the microspheres throughout the gel. This mixture was stored at 4° C.

EXAMPLE 24

Complexation of Paclitaxel with Cyclodextrinsins

A. Materials

Paclitaxel was obtained from Hauser Chemicals Inc. (Boulder, Colo.). Disodium phosphate (Fisher), citric acid (British Drug Houses), hydroxypropyl-$\beta$-cyclodextrin (HP$\beta$CD), $\gamma$-cyclodextrin ($\gamma$-CD) and hydroxypropyl-$\gamma$-cyclodextrin (HP$\gamma$CD) were obtained from American Maize-Products Company (Hammond, Ind.) and were used as received.

B. Methods

1. Solubility Studies

Excess amounts of paclitaxel (5 mg) were added to aqueous solutions containing various concentrations of $\gamma$-CD, HP$\gamma$-CD, or HP$\beta$-CD and tumbled gently for about 24 hours at 37° C. After equilibration, aliquots of the suspension were filtered through a 0.45 $\mu$m membrane filter (Millipore), suitably diluted and analyzed using HPLC. The mobile phase was composed of a mixture of acetonitrile, methanol and water (58:5:37) at a flow rate of 1.0 ml/minute. The solubility of paclitaxel in a solvent composed of 50:50 water and ethanol (95%) containing various concentrations, up to 10%, of HB$\beta$-CD was also investigated. In addition, dissolution rate profiles of paclitaxel were investigated by adding 2 mg of paclitaxel (as received) to 0, 5, 10 or 20% HP$\gamma$-CD solutions or 2 mg of previously hydrated paclitaxel (by suspending in water for 7 days) to pure water and tumbling gently at 37° C. Aliquots were taken at various time intervals and assayed for paclitaxel.

2. Stability Studies

The solutions containing 20% HP$\beta$CD or HP$\gamma$CD had pH values of 3.9 and 5.2, respectively. The stability of paclitaxel in cyclodextrin solutions was investigated by assaying paclitaxel in solutions (20 $\mu$g ml) containing 10 or 20% HP$\gamma$-CD or HP$\beta$-CD in either water or a 50:50 water-ethanol mixture at 37° C. or 55° C. at various time intervals. In addition, stability of paclitaxel in solutions (1 $\mu$g/ml) containing 1%, 2% or 5% HP$\beta$CD at 55° C. were determined.

C. Results

1. Solubility Studies

Figure 38:
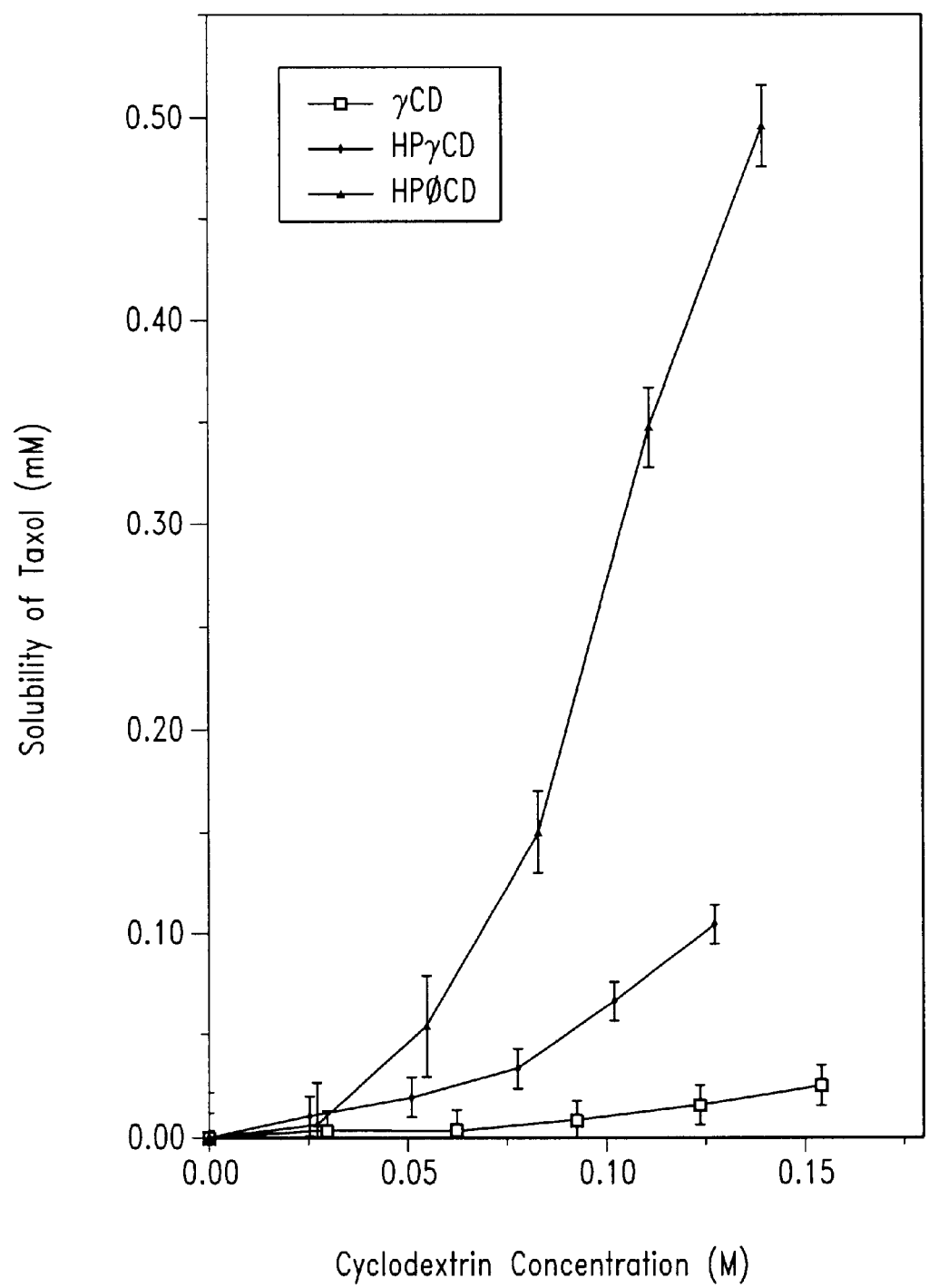
FIG. 38 is a graph which shows the phase solubility for cyclodextrins and paclitaxel in water at 37° C.
Figure 39:
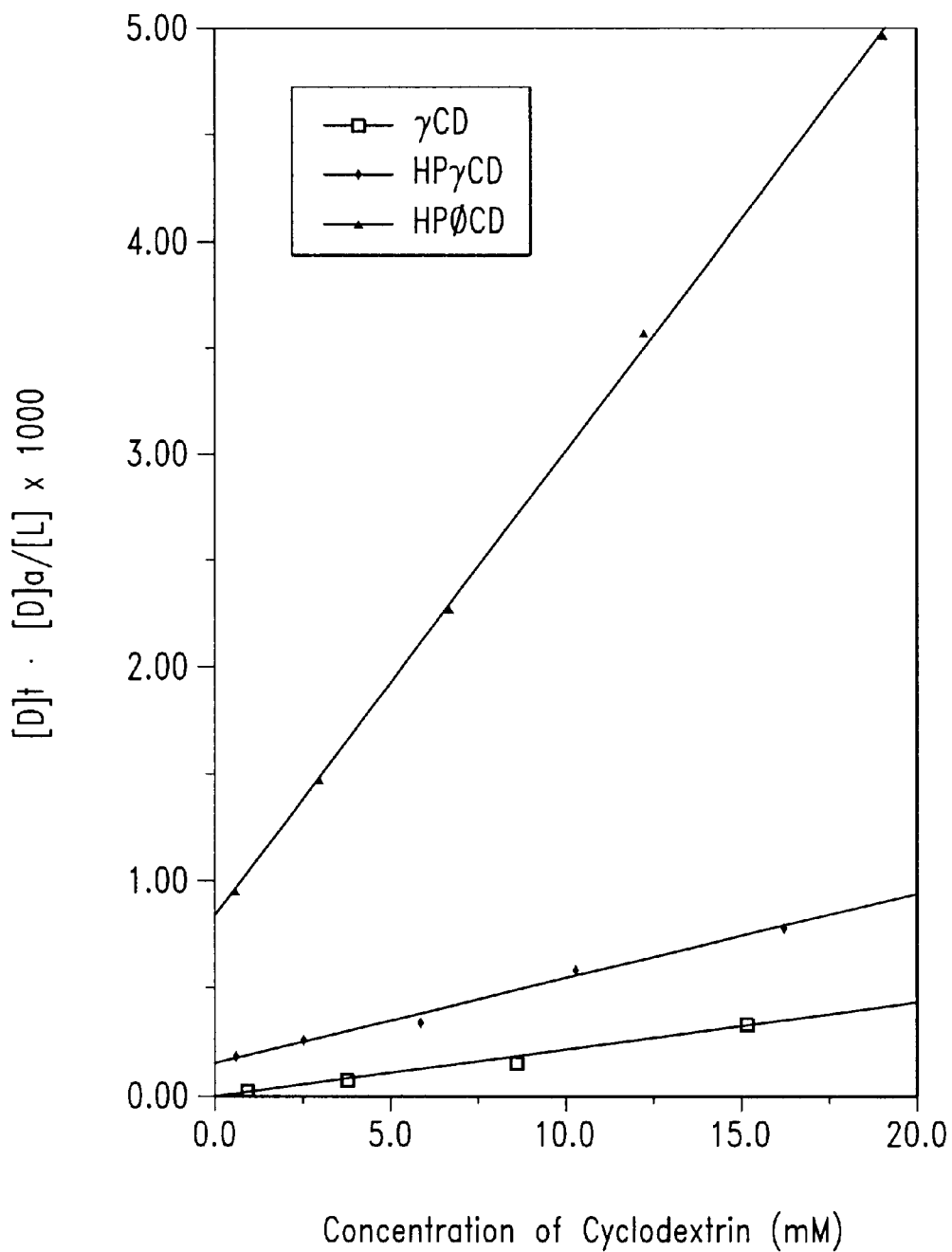
FIG. 39 is a graph which shows second order plots of the complexation of paclitaxel and γCD, HPβCD or HPγCD at 37° C.

The solubility of paclitaxel increased over the entire CD concentration range studied; HP$\beta$-CD producing the greatest increase in the solubility of paclitaxel (FIG. 38). The shape of the solubility curves suggests that the stoichiometries were of higher order than a 1:1 complex. Paclitaxel formed Type $A_p$ curves with both HP$\beta$-CD and HP$\gamma$-CD and Type $A_N$ curves with $\gamma$-CD. The solubility of paclitaxel in a 50% solution of HP$\beta$-CD in water was 3.2 mg/ml at 37° C. which was about a 2000-fold increase over the solubility of paclitaxel in water. The estimated stability constants (from FIG. 39) for first order complexes of paclitaxel-cyclodextrins were 3.1, 5.8 and 7.2 $M^{-1}$ for $\gamma$-CD, HP$\gamma$-CD and HP$\beta$-CD and those for second order complexes were $0.785 \times 10^3$, $1.886 \times 10^3$ and $7.965 \times 10^3$ $M^{-1}$ for $\gamma$-CD, HP$\gamma$-CD and HP$\beta$-CD, respectively. The values of the observed stability constants suggested that the inclusion complexes formed by paclitaxel with cyclodextrins were predominantly second order complexes.

Figure 40:
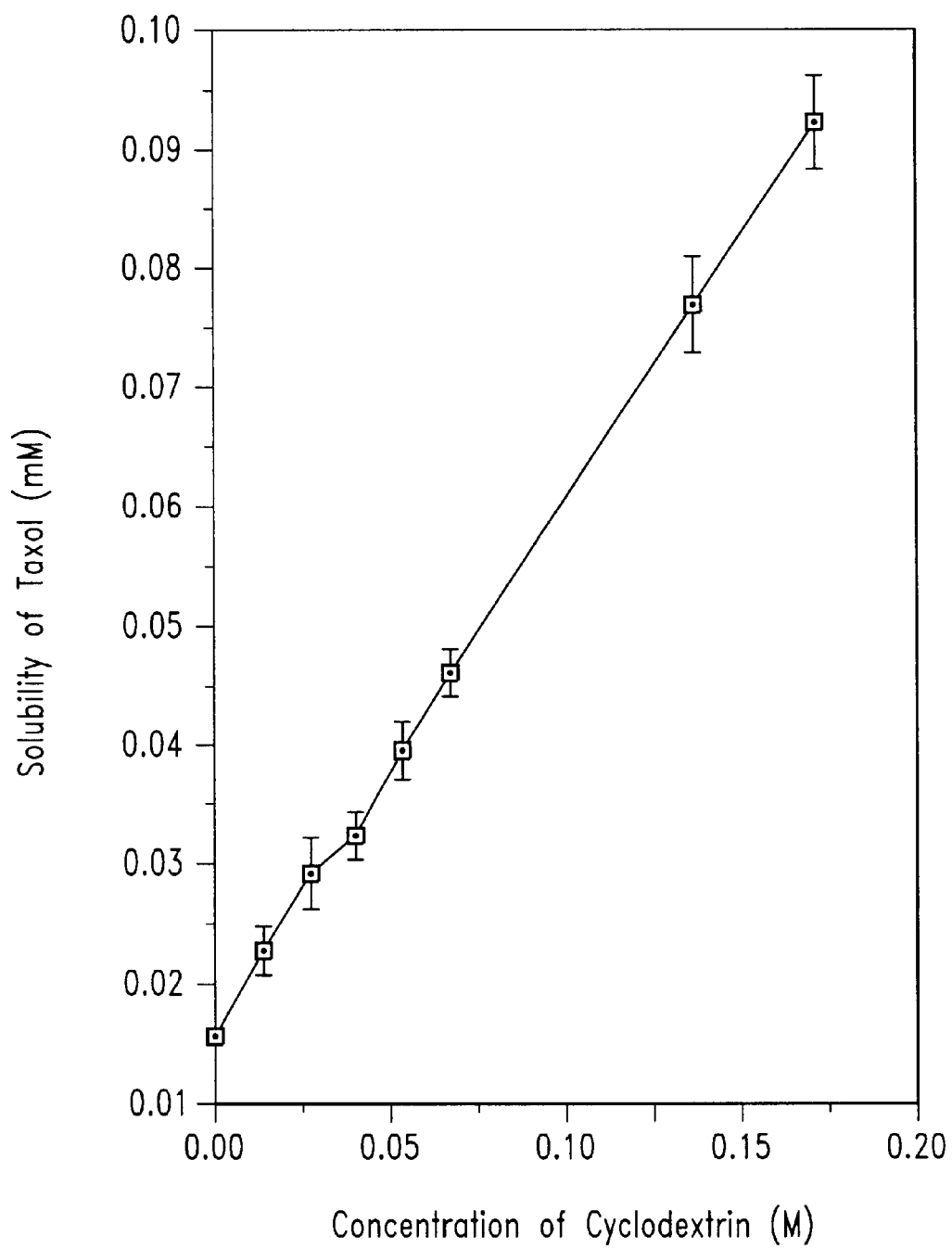
FIG. 40 is a graph which shows the phase solubility for paclitaxel at 37° C. and hydroxypropyl-β-cyclodextrin in 50:50 water:ethanol solutions.

The solubility of paclitaxel in 50:50 water ethanol mixture increased with an increase in the cyclodextrin concentration (FIG. 40) as observed for complexation in pure water. The apparent stability constant for the complexation of paclitaxel and HP$\beta$-CD in the presence of 50% ethanol (26.57 $M^{-1}$) was significantly lower (about 300 times) than the stability constant in the absence of ethanol. The lower stability constant may be attributed to a change in the dielectric constant or the polarity of the solvent in the presence of ethanol.

The dissolution profiles of paclitaxel in 0, 5, 10 and 20% $\gamma$-CD solutions (FIG. 41) illustrates the formation of a metastable solution of paclitaxel in pure water or the cyclodextrin solutions; the amount of paclitaxel in solution gradually increased, reached a maximum and subsequently decreased. Dissolution studies using paclitaxel samples which were previously hydrated by suspending in water for 48 hours did not show the formation of the metastable solution. In addition, DSC analysis of the hydrated paclitaxel (dried in a vacuum oven at room temperature) showed two broad endothermic peaks between 60 and 110° C. These peaks were accompanied by about 4.5% weight loss (determined by thermogravimetric analysis) indicating the presence of hydrate(s). A loss in weight of about 2.1% would suggest the formation of a paclitaxel monohydrate.

Figure 41:
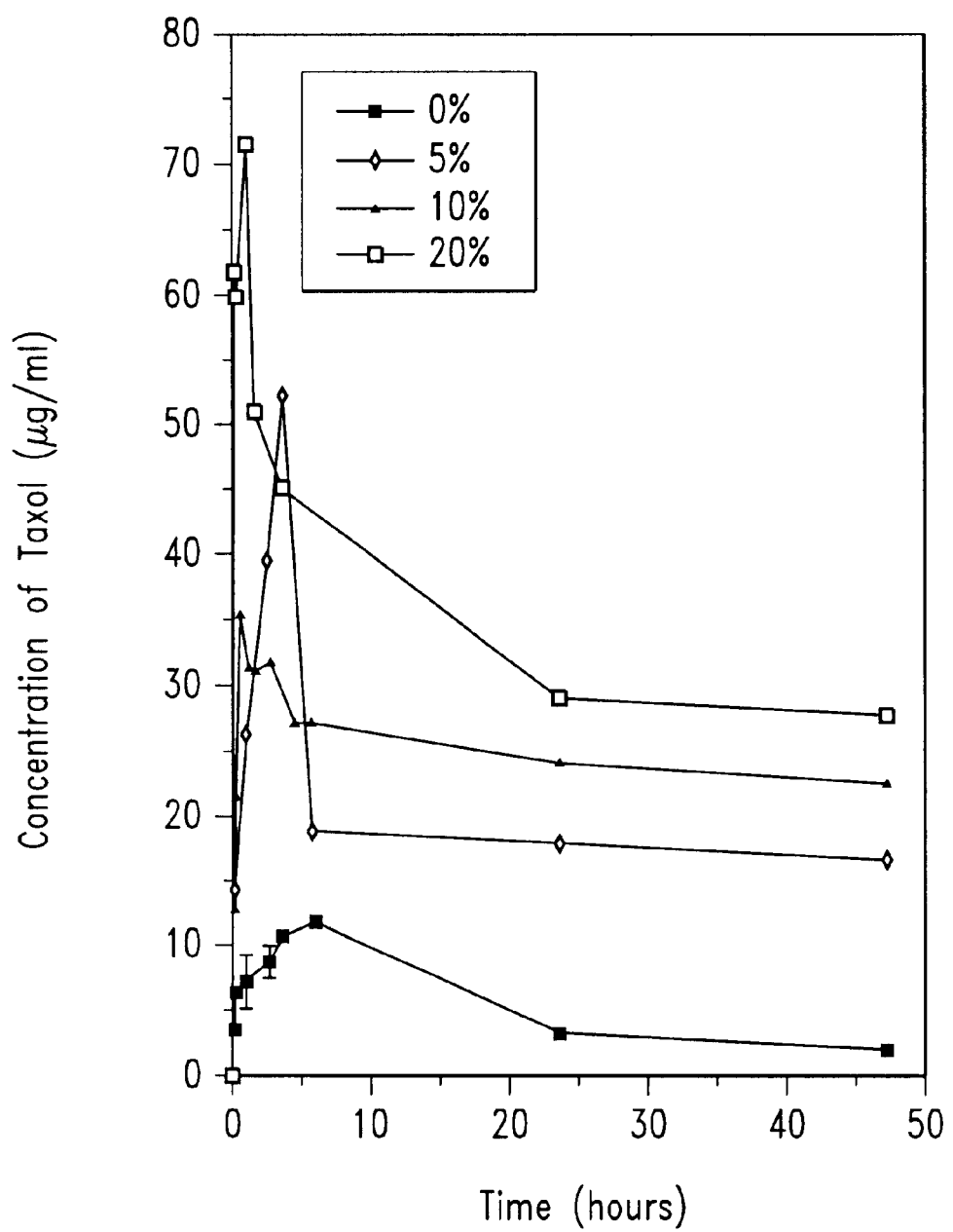
FIG. 41 is a graph which shows dissolution rate profiles of paclitaxel in 0, 5, 10 or 20% HPγCD solutions at 37° C.

Therefore, the occurrence of the DSC peaks between 60° C. and 110° C. and the loss in weight of about 4.5% suggests the presence of a dihydrate. There was no evidence of endothermic peak(s) between 60° C. and 110° C. (DSC results) or a weight loss (TGA results) for paclitaxel samples as received. Therefore, (as received) paclitaxel was anhydrous and on suspension in water it dissolved to form a supersaturated solution which recrystallized as a hydrate of lower solubility (FIG. 41).

2. Stability Studies

Figure 42:
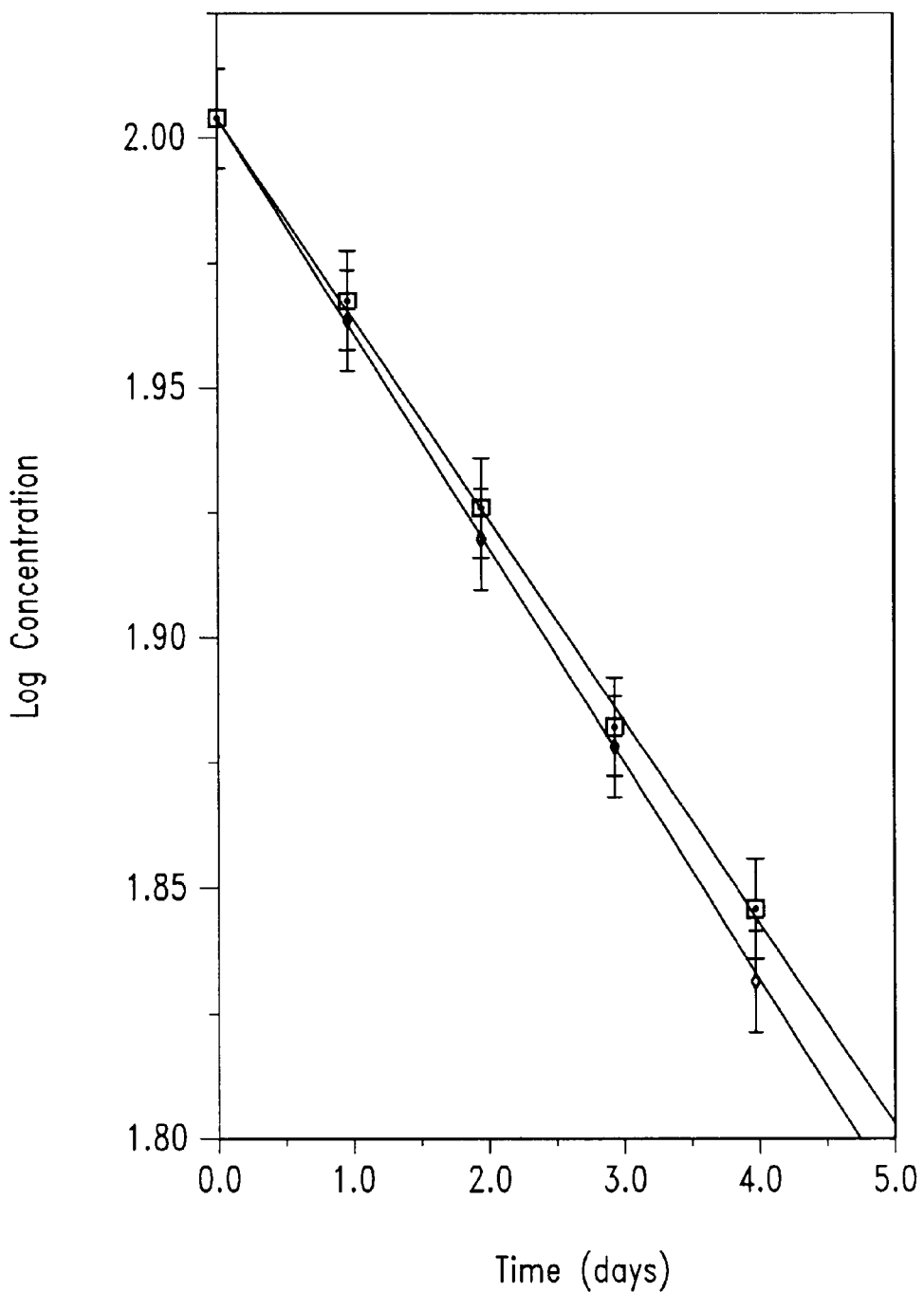
FIG. 42 is a graph which plots the observed pseudo first order kinetic degradation of paclitaxel (20 $\mu$g/ml) in 10% HPβCD and 10% HPγCD solutions at 37° C. and pH of 3.7 and 4.9, respectively.

Paclitaxel degradation depended on the concentration of the cyclodextrin and followed pseudo-first order degradation kinetics (e.g., FIG. 42). The rate of degradation of paclitaxel in solutions (1 µg/ml paclitaxel) containing 1% HPβ-CD at 55° C. faster ($k=3.38\times10^{-3}$ $h^{-1}$) than the rate at higher cyclodextrin concentrations. Degradation rate constants of $1.78\times10^{-3}$ and $0.96\times10^{-3}$ $h^{-1}$ were observed for paclitaxel in 10% HPβ-CD and HPγ-CD, respectively. Paclitaxel solutions (1 µg/ml) containing 2, 4, 6 or 8% BP, did not show any significant difference in the rate of degradation from that obtained with the 10 or 20% HPβ-CD solutions (20 µg/ml). The presence of ethanol did not adversely affect the stability of paclitaxel in the cyclodextrin solutions.

D. Conclusion

This study showed that the solubility of paclitaxel could be increased by complexation with cyclodextrins. These aqueous-based cyclodextrin formulations may be utilized in the treatment of various inflammatory diseases.

Example 25

Polymeric Compositions with Increased Concentrations of Paclitaxel

PDLLA-MePEG and PDLLA-PEG-PDLLA are block copolymers with hydrophobic (PDLLA) and hydrophilic (PEG or MePEG) regions. At appropriate molecular weights and chemical composition, they may form tiny aggregates of hydrophobic PDLLA core and hydrophilic MePEG shell. Paclitaxel can be loaded into the hydrophobic core, thereby providing paclitaxel with an increased "solubility".

A. Materials

D,L-lactide was purchased from Aldrich, Stannous octoate, poly (ethylene glycol) (mol. wt. 8,000), MePEG (mol. wt. 2,000 and 5,000) were from Sigma MePEG (mol. wt. 750) was from Union Carbide. The copolymers were synthesized by a ring opening polymerization procedure using stannous octoate as a catalyst (Deng et al., *J. Polym. Sci., Polym, Lett.* 28:411–416, 1990; Cohn et al., *J. Biomed, Mater. Res.* 22: 993–1009, 1988).

For synthesizing PDLLA-MePEG, a mixture of DL-lactide/MePEG/stannous octoate was added to a 10 milliliter glass ampoule. The ampoule was connected to a vacuum and sealed with flame. Polymerization was accomplished by incubating the ampoule in a 150° C. oil bath for 3 hours. For synthesizing PDLLA-PEG-PDLLA, a mixture of D,L-lactide/PEG/stannous octoate was transferred into a glass flask, sealed with a rubber stopper, and heated for 3 hours in a 150° C. oven. The starting compositions of the copolymers are given in Tables 1 and 2. In all the cases, the amount of stannous octoate was 0.5%–0.7%.

B. Methods

The polymers were dissolved in acetonitrile and centrifuged at 10,000 g for 5 minutes to discard any non-dissolvable impurities. Paclitaxel acetonitrile solution was then added to each polymer solution to give a solution with paclitaxel (paclitaxel+polymer) of 10% wt. The solvent acetonitrile was then removed to obtain a clear paclitaxel/PDLLA-MePEG matrix, under a stream of nitrogen and 60° C. warming. Distilled water, 0.9% NaCl saline, or 5% dextrose was added at four times weight of the matrix. The matrix was finally "dissolved" with the help of vortex mixing and periodic warming at 60° C. Clear solutions were obtained in all the cases. The particle sizes were all below 50 nm as determined by a submicron particle sizer (NICOMP Model 270). The formulations are given in Table 1.

TABLE 1

Formulations of Paclitaxel/PDLLA-MePEG*

| PDLLA-MePEG | Dissolving Media | Paclitaxel Loading (final paclitaxel concentrate) |
|---|---|---|
| 2000/50/50 | water | 10% (20 mg/ml) |
| 2000/40/60 | water | 10% (20 mg/ml) |
| 2000/50/50 | 0.9% saline | 5% (10 mg/ml) |
| 2000/50/50 | 0.9% saline | 10% (20 mg/ml) |
| 2000/50/50 | 5% dextrose | 10% (10 mg/ml) |
| 2000/50/50 | 5% dextrose | 10% (20 mg/ml) |

In the case of PDLLA-PEG-PDLLA (Table 2), since the copolymers cannot dissolve in water, paclitaxel and the polymer were co-dissolved in acetone. Water or a mixture of water/acetone was gradually added to this paclitaxel polymer solution to induce the formation of paclitaxel/polymer spheres.

TABLE 2

Composition of PDLLA-PEG-PDLLA

| Copolymer Name | Wt. of PEG (g) | Wt. of DL-lactide (g) |
|---|---|---|
| PDLLA-PEG-PDLLA 90/10 | 1 | 9 |
| PDLLA-PEG-PDLLA 80/20 | 2 | 8 |
| PDLLA-PEG-PDLLA 70/30 | 3 | 7 |
| PDLLA-PEG-PDLLA 60/40 | 4 | 6 |
| PDLLA-PEG-PDLLA 30-/70 | 14 | 6 |

*PEG molecular weight. 8,000.

C. Results

Many of the PDLLA-MePEG compositions form clear solutions in water, 0.9% saline, or 5% dextrose, indicating the formation of tiny aggregates in the range of nanometers. Paclitaxel was loaded into PDLLA-MePEG micelles successfully. For example, at % loading (this represents 10 mg paclitaxel in 1 ml paclitaxel/PDLLA-MePEG/aqueous system), a clear solution was obtained from 2000–50/50 and 2000–40/60. The particle size was about 60 nm.

Example 26

Manufacture of Micellar Paclitaxel

Poly(DL-lactide)-block-methoxypolyethylene gylcol (PDLLA-block-MePEG) with a MePEG molecular weight of 2000 and a PDLLA:MePEG weight ratio 40:60 is used as the micellar carrier for the solubilization of paclitaxel. PDLLA-MePEG 2000–40/60 (polymer) is an amphiphilic diblock copolymer that dissolves in aqueous solutions to form micelles with a hydrophobic PDLLA core and hydrophilic MePEG shell. Paclitaxel is physically trapped in the hydrophobic PDLLA core to achieve the solubilization.

The polymer was synthesized from the monomers methoxypolyethylene glycol and DL-lactide in the presence of 0.5% w/w stannous octoate through a ring opening polymerization. Stannous octoate acted as a catalyst and participated in the initiation of the polymerization reaction. Stannous octoate forms a number of catalytically reactive species which complex with the hydroxyl group of MePEG and provide an initiation site for the polymerization. The complex attacks the DL-lactide rings and the rings open up and are added to the chain, one-by-one, forming the polymer. The calculated molecular weight of the polymer is 3,333.

All reaction glassware was washed and rinsed with Sterile Water for Irrigation, USP, dried at 37° C., followed by depyrogenation at 250° C. for at least 1 hour. MePEG (240 g) and DL-lactide (160 g) were weighed and transferred to a round bottom glass flask using a stainless steel funnel. A 2 inch Teflon coated magnetic stir bar was added to the flask. The flask was sealed with a glass stopper and then immersed to the neck in a 140° C. oil bath. After the MePEG and DL-lactide melted, 2 ml of 95% stannous octoate (catalyst) was added to the flask. The flask was vigorously shaken immediately after the addition to ensure rapid mixing and then returned to the oil bath. The reaction was allowed to proceed for an additional 6 hours with heat and stirring. The liquid polymer was then poured into a stainless steel tray, covered and left in a chemical fume hood overnight (about 16 hours). The polymer solidified in the tray. The top of the tray was sealed using Parafilm. The sealed tray containing the polymer was placed in a freezer at −20±5° C. for at least 0.5 hour. The polymer was then removed from the freezer, broken up into pieces and transferred to glass storage bottles and stored refrigerated at 2 to 8° C.

Preparation of a 50 mg/m² Dose 4

Preparation of the bulk and filling of paclitaxel/polymer matrix was accomplished essentially as follows. Reaction glassware was washed and rinsed with Sterile Water for Irrigation USP, and dried at 37° C., followed by depyrogenation at 250° C. for at least 1 hour. First, a phosphate buffer (0.08 M, pH 7.6) was prepared. The buffer was dispensed at the volume of 10 ml per vial. The vials were heated for 2 hours at 90° C. to dry the buffer. The temperature was then raised to 160° C. and the vials dried for an additional 3 hours.

The polymer was dissolved in acetonitrile at 15% w/v concentration with stirring and heat. The polymer solution was then centrifuged at 3000 rpm for 30 minutes. The supernatant was poured off and set aside. Additional acetonitrile was added to the precipitate and centrifuged a second time at 3000 rpm for 30 minutes. The second supernatant was pooled with the first supernatant. Paclitaxel was weighed and then added to the supernatant pool. The solution was brought to the final desired volume with acetonitrile.

The paclitaxel/polymer matrix solution is dispensed into the vials containing previously dried phosphate buffer at a volume of 10 ml per vial. The vials are then vacuum dried to remove the acetonitrile. The paclitaxel/polymer matrix is then terminally sterilized by irradiation with at least 2.5 Mrad Cobalt-60 (Co-60) x-rays.

Example 27

Biocompatibility and Toxicology of Micelles

Studies were conducted to evaluate the toxicology and biocompatibility of PDLLA-MePEG micelles (Table 1).

TABLE 1

Biocompatibility Testing
Study Title

1. Hemolysis study—in vitro procedure
2. Genotoxicity: sister chromatid exchange study in mammalian cells
3. Genotoxicity: *Salmonella typhimurium* inverse mutation study
4. Cytotoxicity test using the iso elution method in the L-929 mouse fibroblast cell line
5. Acute intracutaneous reactivity study in the rabbit
6. Acute systemic toxicity study in the mouse
7. Subchronic (14 days) intravenous toxicity study in the rat In summary, the PDLLA-MePEG micelles provided the following results:

(i) PDLLA-MePEG micelles were found to be non-hemolytic in vitro;

(ii) The PDLLA-MePEG micelles were not genotoxic to Chinese Hamster Ovarian cells in the presence or absence of S9 metabolic activation;

(iii) The PDLLA-MePEG micelles were not mutagenic as demonstrated in vitro by a *Salmonella typhimurium* reverse mutation assay;

(iv) PDLLA-MePEG micelles showed evidence of cell lysis in L-929 mouse fibroblast cells, however, the concentration used and duration of exposure in cell culture far exceeded that expected to occur in the plasma of humans in the proposed clinical RA study;

(v) There was no evidence of significant irritation or toxicity from the PDLLA-MePEG micelles injected intracutaneously into rabbits; and (vi) There was no evidence of acute or subchronic systemic toxicity in vivo from the PDLLA-MePEG micelles.

A. Hemolysis Study—In Vitro Procedure

PDLLA-MePEG micelles were found to be nonhemolytic in vitro. Hemolysis assessment of the PDLLA-MePEG micelles was conducted by preparing the test article at the ratio of 2.0 mg/mL of micelles in phosphate buffered saline (PBS), which was warmed to 37° C. for 10 minutes. The resulting test article solution was evaluated to determine whether this solution would cause in vitro red blood cell hemolysis. Blood was obtained from rabbits, pooled, diluted and added to duplicate tubes of the test article solution. A PBS negative control and Purified Water, USP, positive control were similarly prepared. After gently mixing with the blood and 4 hours of incubation at 37° C., the suspensions were centrifuged and the resulting supernatant was added to Drabkin's reagent. The percent transmission of the test solution was spectrophotometrically measured at a wavelength of 540 nm. The negative and positive controls performed as anticipated. Under the conditions of this study, the mean hemolytic index for the test article solution was 1%. The test article solution was found to be non-hemolytic.

B. Genotoxicity: Sister Chromatid Exchange Study in Mammalian Cells

The PDLLA-MePEG micelles were not genotoxic to Chinese Hamster Ovarian cells in the presence or absence of S9 metabolic activation. Analysis of clastogenic changes in Chinese Hamster Ovarian cells was determined for PDLLA-MePEG micelles in a sister chromatid exchange study. The test was performed in the presence and absence of S9 metabolic activation. The sister chromatid exchange genotoxicity test employs Chinese Hamster Ovary cells to detect primary DNA effects. Detection was accomplished by observing the repaired chromosome, which has been differentially stained. To simulate clinical use, the test article was prepared based on the ratio of 2.0 mg/mL (mass of test article to volume of vehicle). The test article and the McCoy's 5A media were warmed to 37° C. for 20 minutes. After the warming stage was complete, the test article was vortexed with the vehicle until completely dissolved. Following preparation of the test solution, the pH was determined to be 7.3 and, therefore, the pH was not adjusted. Due to the acidic nature of the test article, a monolayer of Chinese Hamster Ovary cells was exposed to dilutions of the test article solution in triplicate cultures in the presence and absence of S9 metabolic activation. Parallel testing was also conducted with negative and positive controls. Culture medium was used as a negative control and the positive control was mitomycin C in the absence of S9 and cyclophosphomide in the presence of S9. It was determined that the 1:2 dilution of the test solution was not cytotoxic. Therefore, the cells were exposed to a fresh preparation of the undiluted test solution in the absence and presence of metabolic activation. Under the conditions of this assay, the undiluted test article solution was not considered genotoxic to Chinese Hamster Ovary cells in the presence or absence of S9 metabolic activation. The negative and positive controls performed as expected.

C. Genotoxicity: *Salmonella typhimurium* Reverse Mutation Study

The PDLLA-MePEG micelles were not mutagenic to *Salmonella typhimurium* tester strains in the presence or absence of S9 metabolic activation. A *Salmonella typhimurium* reverse mutation standard plate incorporation study was conducted to evaluate whether a PBS solution of PDLLA-MePEG micelles would cause mutagenic changes in histidine-dependent *Salmonella typhimurium* strains TA98, TA100, TA1535, TA1537 and TA1538 in the presence and absence of S9 metabolic activation. The PBS test article solution was found to be non-inhibitory to growth of tester strains TA98, TA100, TA1535, TA1537 and TA1538. Separate tubes containing 2 ml of molten top agar supplemented with histidine-biotin solution were inoculated with 0.1 ml of culture for each of five tester strains, and 0.1 ml of the PBS solution. A 0.5 ml aliquot of S9 homogenate stimulating metabolic activation was added when necessary. The mixture was poured across triplicate Minimal E plates. Parallel testing was also conducted with a negative control and four positive controls. The mean number of revertants of the triplicate test plates were compared to the mean number of revertants of the triplicate negative control plates for each of the five tester strains employed. The values (means) obtained for the positive controls were used as points of reference. Under the conditions of this assay, the PBS test article solution was not considered to be mutagenic to *Salmonella typhimurium* test strains TA98, TA100, TA1535, TA1537 and TA1538. The negative and positive controls performed as anticipated.

D. Cytotoxicity Test Using the Iso Elution Method in the L-929 Mouse Fibroblast Cell Line PDLLA-MePEG micelles showed evidence of cell lysis in L-929 mouse fibroblast cells, however, the concentration used and duration of exposure in cell culture far exceeded that expected to occur in the plasma of humans in the proposed clinical RA study. Cytotoxicity of the PDLLA-MePEG micelles was tested using the iso elution method in L-929 mouse fibroblasts. The test article was prepared in triplicate by extracting 4.0 g of PDLLA-MePEG micelles with 20 ml of minimum essential medium for 24 to 26 hours at 37° C. Each extract was placed onto separate confluent monolayers of L-929 mouse fibroblast cells which were then examined microscopically at 48 hours to determine any change in cell morphology. The PDLLA-MePEG extracts showed evidence of cell lysis and were graded as severely cytotoxic. The amount of micelles used for this test (4.0 g) is not representative of the anticipated systemic exposure during clinical evaluation (maximum initial dose of 50 mg paclitaxel/$m^2$ is represented by 150 mg of paclitaxel and 1350 mg of PDLLA-MePEG micelles).

E. Acute Intracutaneous Reactivity Study in the Rabbit

There was no evidence of significant irritation or toxicity from the PDLLA-MePEG micelles injected intracutaneously into rabbits. To evaluate the irritation and sensitization of PDLLA-MePEG micelles for intracutaneous reactivity in rabbits, two test article solutions of the control micelles were prepared. The first test article was prepared by dissolving PDLLA-MePEG micelles in PBS at a concentration of 2 mg/mL of solution. This solution was warmed to 37° C. for 10 minutes and then vortexed to thoroughly mix. The second test article was prepared by dissolving PDLLA-MePEG micelles in Cottonseed Oil, NF. Each test article solution at a dose of 0.2 ml was injected by the intracutaneous route into 5 separate sites on the right side of the back of each rabbit. Similarly, the corresponding reagent control was injected on the left side of the back of each rabbit. These rabbits were used for each pair of solutions. The injection sites were observed immediately after injection. Observations for erythema and edema were conducted at 24, 48 and 72 hours after injection. Under the conditions of this study, there was no evidence of significant irritation or toxicity from the solutions injected intracutaneously into rabbits. The Primary Irritation Index Characterization for both the PBS and Cottonseed Oil test article solutions was negligible.

F. Acute Systemic Toxicity Study in the Mouse

There was no evidence of acute systemic toxicity in vivo from the PDLLA-MePEG micelles. In this study, two test article solutions of the PDLLA-MePEG micelles were prepared. The first test article was prepared by dissolving PDLLA-MePEG micelles in PBS at a concentration of 2 mg/mL of solution. This solution was warmed to 37° C. for 10 minutes and then vortexed to mix thoroughly. The second test article was prepared by dissolving PDLLA-MePEG micelles in Cottonseed Oil, NF. Both test article solutions were evaluated for systemic toxicity. The PBS test article was injected IV while the Cottonseed Oil test article was administered via the intraperitoneal route. Each test article was evaluated in 5 mice which were weighed, injected with the test solution at a dose of 50 mL/kg, and returned to their cages. All mice were observed for adverse reactions immediately after dosing and at 4, 24, 48 and 72 hours. Under the conditions of this study, there was no mortality or evidence of significant systemic toxicity from the test solutions. Under the conditions of this study, the test article solutions would not be considered as systemically toxic to the mouse at the prescribed dosage. Both test article solutions met the ISO requirements.

G. Subchronic (14 Days) Intravenous Toxicity Study in the Rat

There was no evidence of subchronic systemic toxicity in vivo from the PDLLA-MePEG micelles following repeated IV injection. In this study, PDLLA-MePEG micelles were prepared in PBS based on the ratio of 2.0 mg/mL of micelles in PBS, which was warmed to 37° C. for 10 minutes. This solution along with PBS control was evaluated for subchronic IV toxicity in the rat. Twelve rats received daily IV injections of the test article solution at 10 mL/kg of body weight over a two-week period. Twelve control rats were similarly injected with the control PBS, prepared without the test article. Rats were observed immediately after injection for signs of behavioral change or toxicity. General health observations were conducted daily. Body weights were recorded on Days 0, 7 and 14. At termination, blood specimens were collected for complete blood cell count evaluation and serum chemistries. A gross visceral necropsy and histologic analysis were conducted on tissues including liver, lung, bone marrow, injection site, kidney, brain, heart, adrenals and gross lesions. Body weight and clinical pathology parameters were analyzed statistically. Under the conditions of this study, there was no significant evidence of systemic toxicity from the solution injected. Daily clinical observations, body weights, necropsy findings, histopathology findings and clinical pathology parameters were judged to be within acceptable limits for both the test and control treat These studies assessing the biocompatibility and toxicology of PDLLA-MePEG micelles demonstrate that the micelles are suitable and safe for clinical use in humans.

Example 28

Procedure for Producing Film

The term film refers to a polymer formed into one of many geometric shapes. The film may be a thin, elastic sheet of polymer or a 2 mm thick disc of polymer, either of which may be applied to the tissue surface to prevent subsequent scarring and adhesion formation. This film was designed to be placed on exposed tissue so that any encapsulated drug can be released from the polymer over a long period of time at the tissue site. Films may be made by several processes, including for example, by casting, and by spraying.

In the casting technique, the polymer was either melted and poured into a shape or dissolved in dichloromethane and poured into a shape. The polymer then either solidified as it cooled or solidified as the solvent evaporated, respectively. In the spraying technique, the polymer was dissolved in solvent and sprayed onto glass, as the solvent evaporated the polymer solidified on the glass. Repeated spraying enabled a build up of polymer into a film that can be peeled from the glass.

Reagents and equipment which were utilized within these experiments include a small beaker, Corning hot plate stirrer, casting moulds (e.g. 50 ml centrifuge tube caps) and mould holding apparatus, 20 ml glass scintillation vial with cap (Plastic insert type), TLC atomizer, nitrogen gas tank, polycaprolactone ("PCL"—mol. wt. 10,000 to 20,000; Polysciences), paclitaxel (Sigma 95% purity), ethanol, "washed" (see previous) ethylene vinyl acetate ("EVA"), poly(DL)lactic acid ("PLA"—mol. wt. 15,000 to 25,000; Polysciences), DCM (HPLC grade; Fisher Scientific).

1. Procedure for Producing Films—Melt Casting

A small glass beaker with a known weight of PCL was placed into a larger beaker containing water (to act as a water bath) and placed onto a hot plate at 70° C. until the polymer was fully melted. A known weight of drug was added to the melted polymer and the mixture sired thoroughly. The melted polymer was poured into a mould and allowed to cool.

2. Procedure for Producing Films—Solvent Casting

A known weight of PCL was weighed directly into a 20 ml glass scintillation vial and sufficient DCM to achieve a 10% w/v solution was added. The solution was mixed followed by the addition of sufficient paclitaxel to achieve the desired final paclitaxel concentration. The solution was vortexed to dissolve the paclitaxel, allowed to sit for one hour (to diminish the presence of air bubbles) and then poured slowly into a mould. The mould was placed in the fume hood overnight allowing the DCM to evaporate.

3. Procedure for Producing Films—Sprayed

A sufficient amount of polymer was weighed directly into a 20 ml glass scintillation vial and sufficient DCM added to achieve a 2% w/v solution. The solution was mixed to dissolve the polymer. Using an automatic pipette, a suitable volume (minimum 5 ml) of the 2% polymer solution was transferred to a separate 20 ml glass scintillation vial. Sufficient paclitaxel was added to the solution and dissolved by shaking the capped vial. To prepare for spraying, the cap of the vial was removed and the barrel of the TLC atomizer dipped into the polymer solution.

The nitrogen tank was connected to the gas inlet of the atomizer and the pressure gradually increased until atomization and spraying began. The moulds were sprayed using 5 second oscillating sprays with a 15 second dry time between sprays. Spraying was continued until a suitable thickness of polymer was deposited on the mould.

Example 29

Therapeutic Agent-Loaded Polymeric Films Composed of Ethylene Vinyl Acetate and a Surfactant Two types of films were investigated within this example: pure EVA films loaded with paclitaxel and EVA/surfactant blend films loaded with paclitaxel.

The surfactants being examined are two hydrophobic surfactants (Span 80 and Pluronic L101) and one hydrophilic surfactant (Pluronic F127). The Pluronic surfactants were themselves polymers which was an attractive property since they can be blended with EVA to optimize various drug delivery properties. Span 80 is a smaller molecule which disperses in the polymer matrix, and does not form a blend.

Figure 43A:
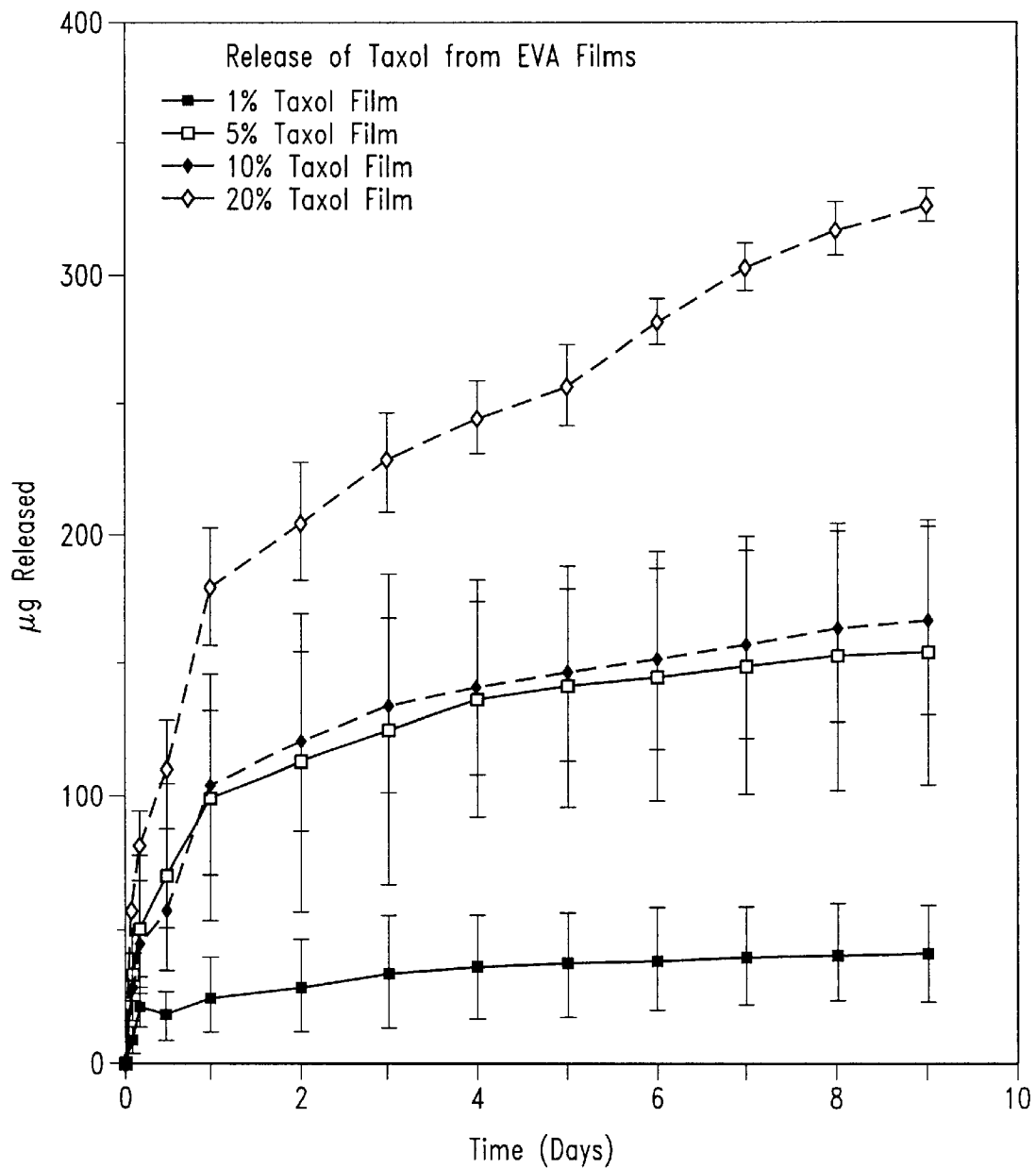
FIGS. 43A and 43B, respectively, are two graphs which show the release of paclitaxel from EVA films, and the percent paclitaxel remaining in those same films over time.
Figure 43B:
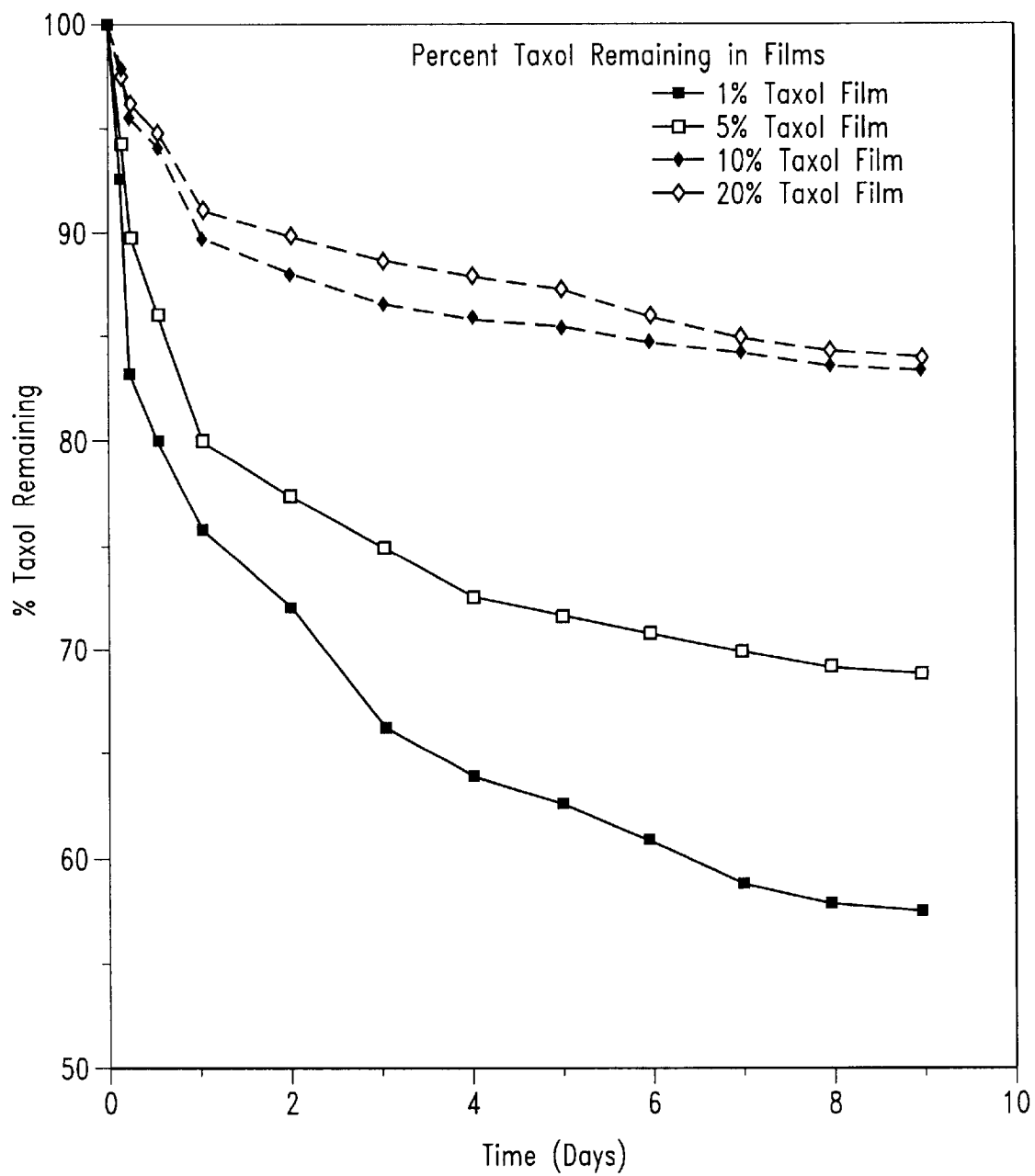
Figure 43C:
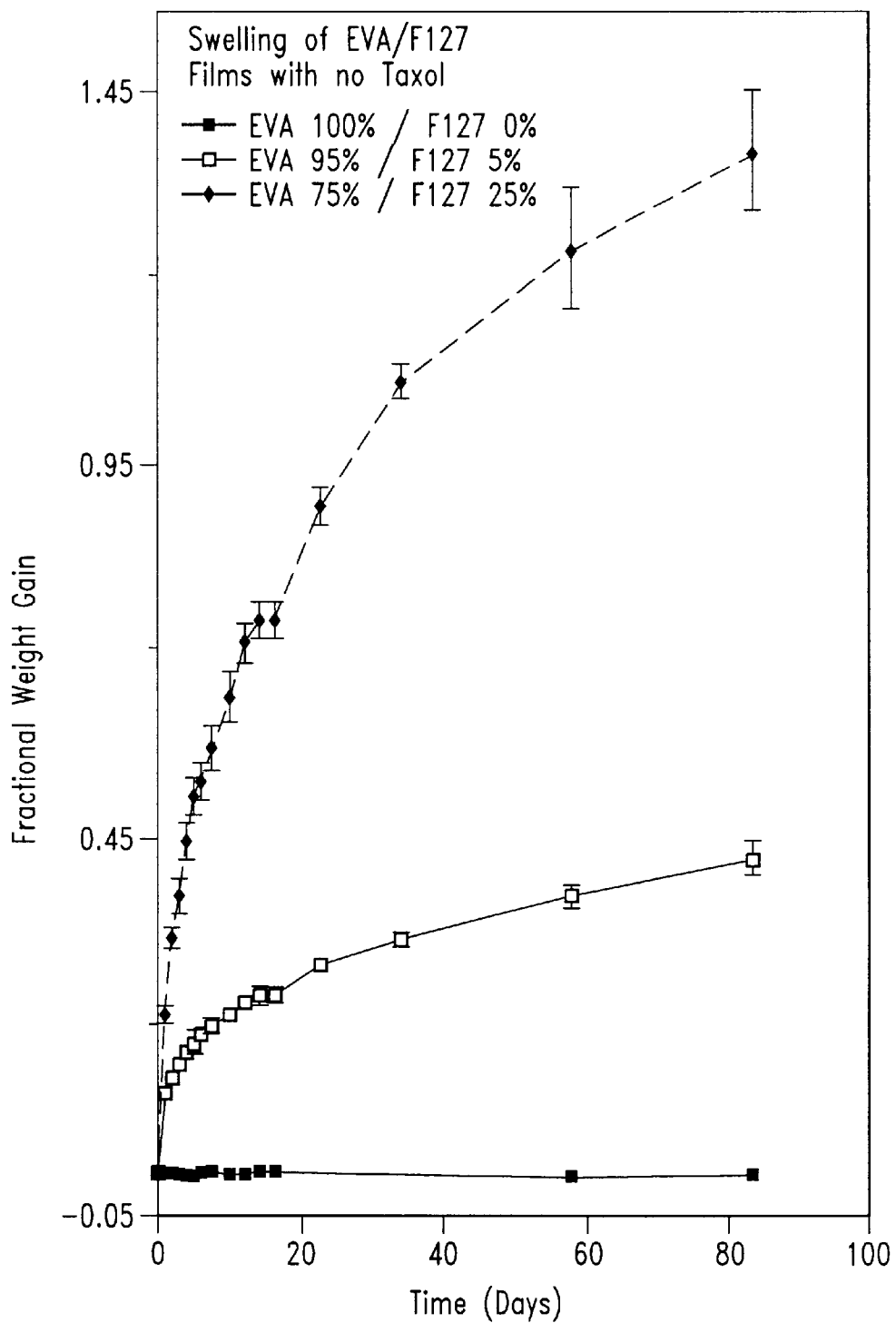
FIG. 43C is a graph which shows the swelling of EVA/F127 films with no paclitaxel over time.
Figure 43D:
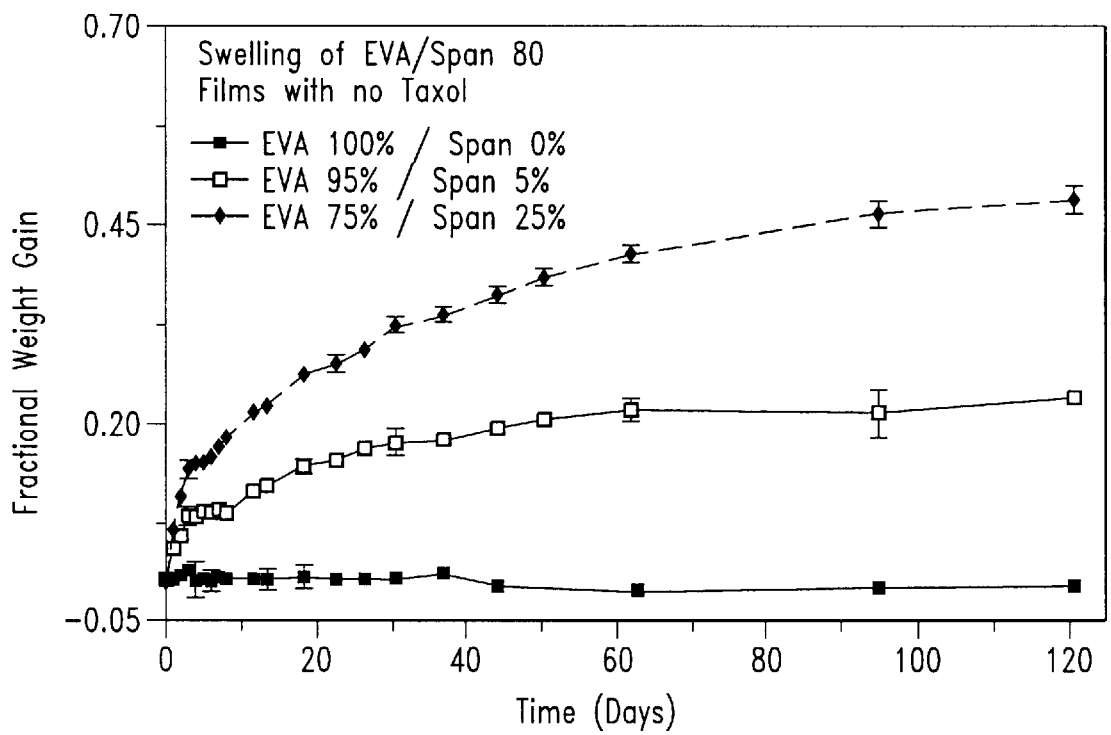
FIG. 43D is a graph which shows the swelling of EVA/Span 80 films with no paclitaxel over time.

Surfactants were useful in modulating the release rates of paclitaxel from films and optimizing certain physical parameters of the films. One aspect of the surfactant blend films which indicated that drug release rates can be controlled was the ability to vary the rate and extent to which the compound swelled in water. Diffusion of water into a polymer-drug matrix was critical to the release of drug from the carrier. FIGS. 43C and 43D shows the degree of swelling of the films as the level of surfactant in the blend was altered. Pure EVA films did not swell to any significant extent in over 2 months. However, by increasing the level of surfactant added to the EVA it was possible to increase the degree of swelling of the compound, and by increasing hydrophilicity swelling was increased.

Results of experiments with these films are shown below in FIGS. 43A–E. Briefly, FIG. 43A shows paclitaxel release (in mg) over time from pure EVA films. FIG. 43B shows the percentage of drug remaining for the same films. As can be seen from these two figures, as paclitaxel loading increased (i.e., percentage of paclitaxel by weight increased), drug release rates increased, showing the expected concentration dependence. As paclitaxel loading was increased, the percent paclitaxel remaining in the film also increased, indicating that higher loading may be more attractive for long-term release formulations.

Figure 43E:
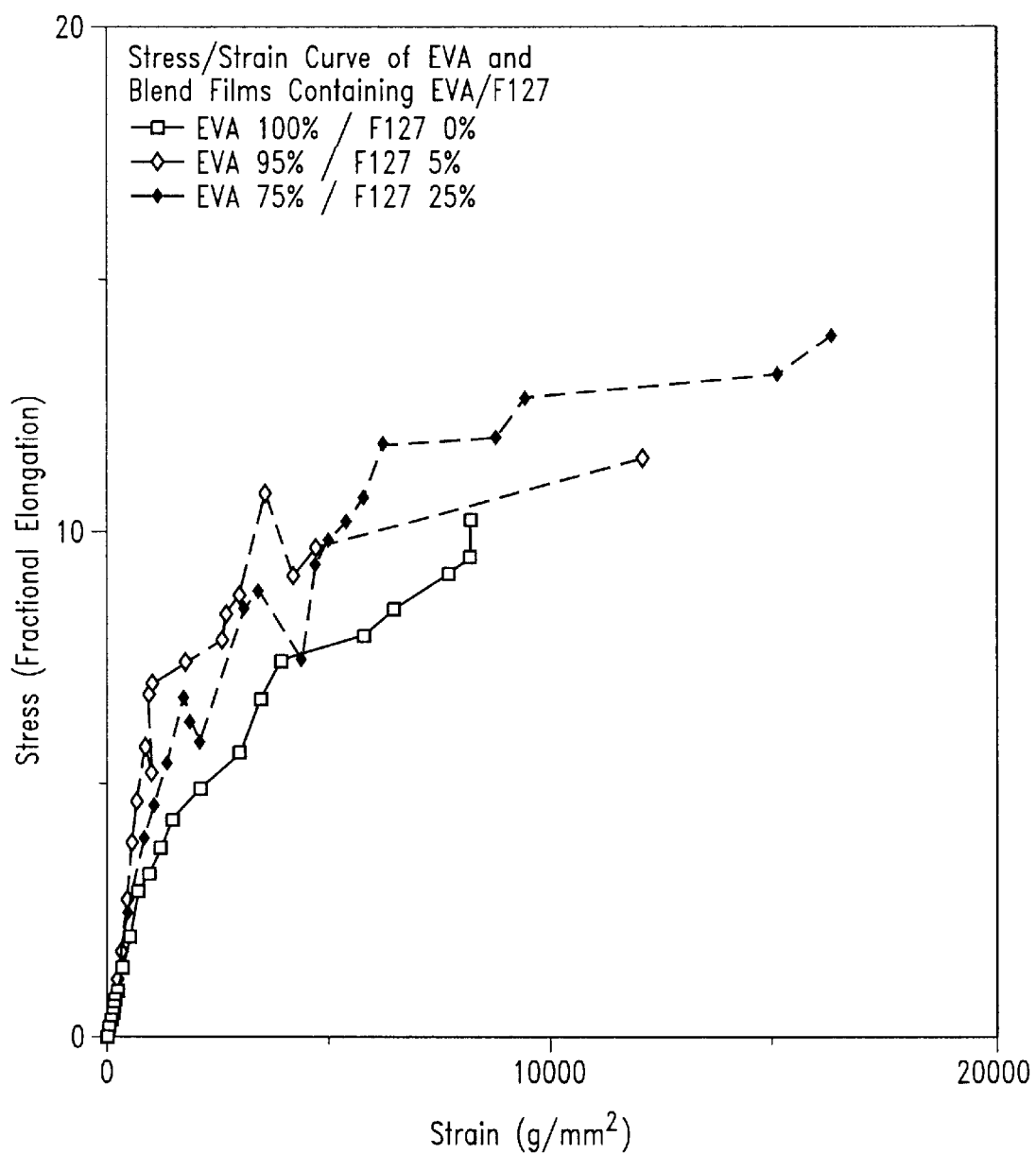
FIG. 43E is a graph which depicts a stress vs. strain curve for various EVA/F127 blends.

Physical strength and elasticity of the films was assessed and is presented in FIG. 43E. Briefly, FIG. 43E shows stress/strain curves for pure EVA and EVA/surfactant blend films. This crude measurement of stress demonstrated that the elasticity of films was increased with the addition of Pluronic F127, and that the tensile strength (stress on breaking) was increased in a concentration dependent manner with the addition of Pluronic F127. Elasticity and strength are important considerations in designing a film which must be manipulated for particular clinical applications without causing permanent deformation of the compound.

The above data demonstrates the ability of certain surfactant additives to control drug release rates and to alter the physical characteristics of the vehicle.

Example 30

Therapeutic Agent-Loaded Polymeric Films Composed of Cellulose for the Treatment of Surgical Adhesions Five grams of hydroxypropyl cellulose (Spectrum: M.W.= 95,000, 75–150 CPS)/ethyl cellulose (Spectrum: 10 CPS) was dissolved in 100 ml of HPLC grade acetone (or acetone/methanol at 80/20 or acetonitrile/methanol at 70/30). The ratio of hydroxypropyl cellulose and ethyl cellulose could be differed from 70:30 to 80:20 depending on the site of application and texture strength requirement. The mixture was stirred at 600 rpm at low temperature (5 to 25° C.) until the cellulose was completely dissolved.

50 mg of paclitaxel (1.0% paclitaxel loaded relatively to the total weight of the cellulose) was added into the above solution and the solution was continued to be stirred at room temperature until the paclitaxel was completely dissolved in the cellulose solution. With a 10 ml syringe or dispenser, 10 ml each of above resulted solution was transferred into a 100×15 mm PTFE PDA petri dish. The sample was first dried in the fumehood by rotating the petri dish slowly. Film was formed after drying for 90 minutes, carefully removed from the petri-dish and transferred into a container (with hole). The film was dried again under vacuum conditions (−90 KPa) for at least 24 hours at room temperature.

Example 31

Therapeutic Agent-Loaded NAOH-Treated Polymeric Films Composed of Chitosan for the Treatment of Surgical Adhesions 5 g of chitosan (Aldrich)/glycerol (Aldrich) was dissolved in 100 ml of 5% aqueous acetic acid solution. The ratio between chitosan and glycerol was 70:30. The solution was stirred at 600 rpm until the chitosan/glycerol was completely dissolved. 50 mg of paclitaxel was added into the above solution. The chitosan solution was continuously stirred until the paclitaxel was completely dissolved. Each 2 ml of resulted solution was transferred into a 50×9 polystyrene petri dish. The chitosan/glycerol film was formed by evaporating the water completely in a fumehood overnight. The resulted film was soaked in 0. IN NaOH solution for one minute and redried. The film was dried again under vacuum condition (−90 KPa) for at least 24 hours at room temperature.

Example 32

Therapeutic Agent-Loaded Cross-Linked Polymeric Films Composed of Chitosan for the Treatment of Surgical Adhesions Five grams of chitosan (Aldrich)/glycerol (Aldrich) was dissolved in 100 ml of 5% aqueous acetic acid solution. The ratio used for chitosan and glycerol was 70:30. The solution was stirred at 600 rpm until the chitosan/glycerol was completely dissolved. 50 mg of paclitaxel was added into the above solution and continuously stirred until the paclitaxel was completely dissolved in the chitosan solution. 0.5 ml of 1.0% glutaraldehyde (0.1% in weight percentage relatively to the total sample weight) was then added into the above solution. The solution was further mixed by a stirrer bar at 600 rpm for 30 minutes. Each 2 ml of resulted solution was transferred into a 50×9 polystyrene petri dish. The chitosan/glycerol film was formed by evaporating the water completely in fumehood overnight The film was dried again under vacuum conditions (−90 KPa) for at least 24 hours at room temperature.

Example 33

Therapeutic Agent-Loaded Cross-Linked Polymeric Films Composed of Hyaluronic Acid for the Treatment of Surgical Adhesions Five grams of hyaluronic acid/glycerol was dissolved in 100 ml distilled water. The ratio used for hyaluronic acid and glycerol was 90:10. Once the hyaluronic acid and glycerol was completely dissolved, a clear 5% solution was obtained. 50 mg of paclitaxel was added into the above solution and continuously stirred until paclitaxel was completely dissolved in above solution. Then, 0.5 ml of 20% EDA carbodimide solution (equivalent to 2% in weight percentage relatively to total sample weight) was added into the above solution and the solution was further stirred at 600 rpm for 30 minutes. Each 2 ml of resulted solution was placed into a 50×9 polystyrene petri dish and the film was formed by evaporating the water completely in the fumehood overnight. The film was dried again under vacuum conditions (−90 KPa) for at least 24 hours at room temperature.

Example 34

Therapeutic Agent-Loaded Polymeric Films Composed of Cellulose for Perivascular Application Similar to the film made above (Example 28), 5 g of hydroxypropyl cellulose (Spectrum: M.W.=95,000, 75–150 CPS)/ethyl cellulose (Spectrum: 10 CPS) was dissolved in 100 ml of HPLC grade acetone (or acetone/methanol at 80/20 or acetonitrile/methanol at 70/30). The ratio of hydroxypropyl cellulose and ethyl cellulose was from 50:50 to 80:20 depending on the site of application and texture strength requirement. The mixture was stirred at 600 rpm at low temperature (5 to 25° C.) until the cellulose was completely dissolved. Then, 50 mg of paclitaxel (1.0% paclitaxel loaded relatively to the total weight of the cellulose) was added into the above solution and the solution was continued to be stirred at room temperature until the paclitaxel was completely dissolved in the cellulose solution 10 ml each of above resulted solution was transferred into the 100×15 mm PTFE PDA petri dish with a syringe or dispenser. The sample was first dried in the fumehood by rotating the petri dish slowly. Film was formed after dried for 90 minutes. Removed the film from the petri-ish and transferred it into the container (with hole). The film was dried again under vacuum conditions (−90 KPa) for at least 24 hours at room temperature.

Example 35

Therapeutic Agent-Loaded Polymeric Films Composed of Polyurethane for Perivascular Application Polyurethane is a unique class of segmented thermoplastic elastomers composed of alternating rigid and flexible segments. With a range of molecular weights and chemical structures available, a broad range of physical properties can be achieved with polyurethane, ranging from rigid structural components to soft compliant elastomers.

0.5 g of polyether-based polyurethane with a molecular weight less than 1 million was dissolved in 10 ml of dichloromethane. 0.5 ml of above solution was applied to the surface of a precleaned microscope slide glass. The film was formed when the dichloromethane was completely evaporated. The film was further dried under vacuum condition (−90 KPa) for at least 24 hours at room temperature.

Example 36

Therapeutic Agent Direct Dip Stents

Known weight of paclitaxel was dissolved in a HPLC grade ethanol. Stent was dipped into the above solution and dried. The stent was further dried under vacuum conditions (−90 KPa) for at least 24 hours at room temperature.

Example 37

Therapeutic Agent-Loaded Polyurethane Stent Coating

The polyether-based polyurethane is known to be susceptible to microcracking due to biological peroxidation of the ether linkage. A second generation of polyurethane is based on a polycarbonate diol that appears biostable. Many researchers have reported minimal or no microcracking of polyurethane coating on a stent in the 60 days implantation period.

0.5 g of polycarbonate-based polyurethane with a molecular weight from 5 to 25 millions was dissolved in 10 ml of dichloromethane. The above solution was applied to a stent by spraying the solution evenly to its surface. The polyurethane coated-stent was formed by evaporating the dichloromethane completely. The coated stent was further dried under vacuum conditions (−90 KPa) for at least 24 hours at room temperature.

Example 38

Procedure for Producing Nanospray

Nanospray is a suspension of small microspheres in saline. If the microspheres are very small (i.e., under 1 $\mu$m in diameter) they form a colloid so that the suspension will not sediment under gravity. As is described in more detail below, a suspension of 0.1 $\mu$m to 1 $\mu$m microparticles may be created suitable for aerosolized deposition onto tissue directly at the time of surgery (e.g. for vascular adhesions), via laproscopic intervention, or through a finger pumped aerosol (e.g., to be delivered topically). Equipment and materials which was utilized to produce nanospray include 200 ml water jacketed beaker (Kimax or Pyrex), Haake circulating water bath, overhead stirrer and controller with 2 inch diameter (4 blade, propeller type stainless steel stirrer, Fisher brand), 500 ml glass beaker, hot plate/stirrer (Corning brand), 4×50 ml polypropylene centrifuge tubes (Nalgene), glass scintillation vials with plastic insert caps, table top centrifuge (Beckman), high speed centrifuge—floor model (JS 21 Beckman), Mettler analytical balance (AJ 100, 0.1 mg), Mettler digital top loading balance (AE 163, 0.01 mg), automatic pipetter (Gilson), sterile pipette tips, pump action aerosol (Pfeiffer pharmaceuticals) 20 ml, laminar flow hood, PCL (mol. wt. 10,000 to 20,000; Polysciences, Warrington, Pa. USA), "washed" (see previous) EVA, PLA (mol. wt. 15,000 to 25,000; polysciences), polyvinyl alcohol ("PVA"—mol. wt. 124,000 to 186,000; 99% hydrolyzed; Aldrich Chemical Co., Milwaukee, Wis. USA), DCM or "methylene chloride"; HPLC grade Fisher scientific), distilled water, sterile saline (Becton and Dickenson or equivalent)

1. Preparation of 5% (w/v) Polymer Solutions

Depending on the polymer solution being prepared, the following were weighed directly into a 20 ml glass scintillation vial: 1.00 g of PCL or PLA or 0.50 g each of PLA and washed EVA. Using a measuring cylinder, 20 ml of DCM was added and the vial tightly capped. The vial was allowed to sit at room temperature (25° C.) until all the polymer had dissolved.

2. Preparation of 3.5% (w/v) Stock Solution of PVA

The solution was prepared by following the procedure given below, or by diluting the 5% (w/v) PVA stock solution prepared for production of microspheres (see Example 28). Briefly, 17.5 g of PVA was weighed directly into a 600 ml glass beaker, and 500 ml of distilled water added. The beaker was covered and placed into a 2000 ml glass beaker containing 300 ml of water. The PVA was stirred at 300 rpm at 85° C. until fully dissolved.

3. Procedure for Producing Nanospray

Briefly, 100 ml of the 3.5% PVA solution was placed in the 200 ml water jacketed beaker with a connected Haake water bath. The contents of the beaker were stirred at 3000 rpm and 10 ml of polymer solution (polymer solution used based on type of nanospray being produced) was dipped into the stirring PVA over a period of 2 minutes using a 5 ml automatic pipetter. After 3 minutes, the stir speed was adjusted to 2500 rpm (+/−200 rpm) for 2.5 hours. After 2.5 hours, the stirring blade was removed from the nanospray preparation and rinsed with 10 ml of distilled water allowing the rinse solution to go into the nanospray preparation.

The microsphere preparation was poured into a 500 ml beaker. The jacketed water bath was washed with 70 ml of distilled water allowing the 70 ml rinse solution to go into the microsphere preparation. The 180 ml microsphere preparation was stirred with a glass rod and poured equally into four polypropylene 50 ml centrifuge tubes which were centrifuged at 10,000 g (+/−1000 g) for 10 minutes. The PVA solution was drawn off of each microsphere pellet and discarded. Distilled water (5 ml) was added to each centrifuge tube and vortexed. The four microsphere suspensions were pooled into one centrifuge tube using 20 ml of distilled water and centrifuged for 10 minutes at 10,000 g (+1−1000 g). The supernatant was drawn off of the microsphere pellet and 40 ml of distilled water was added and the microsphere preparation was vortexed (this process was repeated 3x). The microsphere preparation was then transferred into a preweighed glass scintillation vial.

The vial was allowed to sit for 1 hour at room temperature (25° C.) to allow the 2 $\mu$m and 3 $\mu$m diameter microspheres to sediment out under gravity. After 1 hour, the top 9 ml of suspension was drawn off, placed into a sterile capped 50 ml centrifuge tube, and centrifuged at 10,000 g (+/−1000 g) for 10 minutes. The supernatant was discarded and the pellet was resuspended in 20 ml of sterile saline by centrifuging the suspension at 10,000 g (+/−1000 g) for 10 minutes. The supernatant was discarded and the pellet was resuspended in sterile saline. The quantity of saline used was dependent on the final required suspension concentration (usually 10% w/v). The nanospray suspension was added to the aerosol.

Example 39

Manufacture of Microspheres

The equipment used for the manufacture of microspheres include: 200 ml water jacketed beaker (Kimax or Pyrex), Haake circulating water bath, overhead stirrer and controller with 2 inch diameter (4 blade, propeller type stainless steel stirrer-Fisher brand), 500 ml glass beaker, hot plate/stirrer (Corning brand), 4×50 ml polypropylene centrifuge tubes (Nalgene), glass scintillation vials with plastic insert caps, table top centrifuge (GPR Beckman), high speed centrifuge-floor model (JS 21 Beckman), Mettler analytical balance (AJ 100, 0.1 mg), Mettler digital top loading balance (AE 163, 0.01 mg), automatic pipetter (Gilson). Reagents include PCL (mol. wt. 10,000 to 20,000; Polysciences, Warrington, Pa., USA), "washed" (see later method of "washing") EVA, PLA (mol. wt. 15,000 to 25,000; Polysciences), polyvinyl alcohol ("PVA"—mol. wt. 124,000 to 186,000; 99% hydrolyzed; Aldrich Chemical Co., Milwaukee, Wis., USA), DCM or "methylene chloride"; HPLC grade Fisher scientific, and distilled water.

A. Preparation of 5% (w/v) Polymer Solutions

DCL (1.00 g) or PLA, or 0.50 g each of PLA and washed EVA was weighed directly into a 20 ml glass scintillation vial. Twenty milliliters of DCM was then added. The vial was capped and stored at room temperature (25° C.) for one hour (occasional shaking may be used), or until all the polymer was dissolved. The solution may be stored at room temperature for at least two weeks.

B. Preparation of 5% (w/v) Stock Solution of PVA

Twenty-five grams of PVA was weighed directly into a 600 ml glass beaker and 500 ml of distilled water was added, along with a 3 inch Teflon coated stir bar. The beaker was covered with glass to decrease evaporation losses, and placed into a 2000 ml glass beaker containing 300 ml of water. The PVA was stirred at 300 rpm at 85° C. (Corning hot plate/stirrer) for 2 hours or until fully dissolved. Dissolution of the PVA was determined by a visual check; the solution should be clear. The solution was then transferred to a glass screw top storage container and stored at 4° C. for a maximum of two months. The solution, however must be warmed to room temperature before use or dilution.

C. Procedure for Producing Microspheres

Based on the size of microspheres being made (see Table 1), 100 ml of the PVA solution (concentrations given in Table 1) was placed into the 200 ml water jacketed beaker. Haake circulating water bath was connected to this beaker and the contents were allowed to equilibrate at 27° C. (+/−1° C.) for 10 minutes. Based on the size of microspheres being made (see Table I), the start speed of the overhead stirrer was set, and the blade of the overhead stirrer placed half way down in the PVA solution. The stirrer was then started, and 10 ml of polymer solution (polymer solution used based on type of microspheres being produced) was then dripped into the stirring PVA over a period of 2 minutes using a 5 ml automatic pipetter. After 3 minutes the stir speed was adjusted (see Table 1), and the solution stirred for an additional 2.5 hours. The stirring blade was then removed from the microsphere preparation, and rinsed with 10 ml of distilled water so that the rinse solution drained into the microsphere preparation. The microsphere preparation was then poured into a 500 ml beaker, and the jacketed water bath washed with 70 ml of distilled water, which was also allowed to drain into the microsphere preparation. The 180 ml microsphere preparation was then stirred with a glass rod, and equal amounts were poured into four polypropylene 50 ml centrifuge tubes. The tubes were then capped, and centrifuged for 10 minutes (force given in Table 1). Forty-five milliliters of the PVA solution was drawn off of each microsphere pellet.

TABLE 1

PVA concentrations, stir speeds, and centrifugal force requirements for each diameter range of microspheres.

| PRODUCTION STAGE | MICROSPHERE DIAMETER RANGES | | |
|---|---|---|---|
| | 30 μm to 100 μm | 10 μm to 30 μm | 0.1 μm to 3 μm |
| PVA concentration | 2.5% (w/v) (i.e., dilute 5% stock with distilled water) | 5% (w/v) (i.e., undiluted stock) | 3.5% (w/v) (i.e., dilute 5% stock with distilled water) |
| Starting Stir Speed | 500 rpm +/− 50 rpm | 500 rpm +/− 50 rpm | 3000 rpm +/− 200 rpm |
| Adjusted Stir Speed | 500 rpm +/− 50 rpm | 500 rpm +/− 50 rpm | 2500 rpm +/− 200 rpm |
| Centrifuge Force | 1000 g +/− 100 g (Table top model) | 1000 g +/− 100 g (Table top model) | 10000 g +/− 1000 g (High speed model) |

Five milliliters of distilled water was then added to each centrifuge tube and vortexed to resuspend the microspheres. The four microsphere suspensions were then pooled into one centrifuge tube along with 20 ml of distilled water, and centrifuged for another 10 minutes (force given in Table 1). This process was repeated two additional times for a total of three washes. The microspheres were then centrifuged a final time, and resuspended in 10 ml of distilled water. After the final wash, the microsphere preparation was transferred into a preweighed glass scintillation vial. The vial was capped, and left overnight at room temperature (25° C.) in order to allow the microspheres to sediment out under gravity. Since microspheres which fall in the size range of 0.1 um to 3 um do not sediment out under gravity, they were left in the 10 ml suspension.

D. Drying of 10 μm to 30 μm or 30 μm to 100 μm Diameter Microspheres

After the microspheres sat at room temperature overnight, the supernatant was drawn off of the sedimented microspheres. The microspheres were allowed to dry in the uncapped vial in a drawer for a period of one week or until they were fully dry (vial at constant weight). Faster drying may be accomplished by leaving the uncapped vial under a slow stream of nitrogen gas (flow approx. 10 ml/minute.) in the fume hood. When fully dry (vial at constant weight), the vial was weighed and capped. The labeled, capped vial was stored at room temperature in a drawer. Microspheres were normally stored no longer than 3 months.

E. Determining the Concentration of 0.1 μm to 3 μm Diameter Microsphere Suspension This size range of microspheres did not sediment out, so they were left in suspension at 4° C. for a maximum of four weeks. To determine the concentration of microspheres in the 10 ml suspension, a 200 μl sample of the suspension was pipetted into a 1.5 ml preweighed microfuge tube. The tube was then centrifuged at 10,000 g (Eppendorf table top microfuge), the supernatant removed, and the tube allowed to dry at 50° C. overnight. The tube was then reweighed in order to determine the weight of dried microspheres within the tube.

F. Manufacture of Paclitaxel Loaded Microsphere

In order to prepare paclitaxel containing microspheres, an appropriate amount of weighed paclitaxel (based upon the percentage of paclitaxel to be encapsulated) was placed directly into a 20 ml glass scintillation vial. Ten milliliters of an appropriate polymer solution was then added to the vial containing the paclitaxel, which was then vortexed until the paclitaxel dissolved.

Microspheres containing paclitaxel may then be produced essentially as described above in steps (C) through (E).

Example 40

Surfactant Coated Microspheres

A. Materials and Methods

Microspheres were manufactured from poly (DL) lactic acid (PLA), poly methylmethacrylate (PMMA), polycaprolactone (PCL) and 50:50 Ethylene vinyl acetate (EVA):PLA essentially as described above. Size ranged from 10 to 100 um with a mean diameter 45 um.

Human blood was obtained from healthy volunteers. Neutrophils (white blood cells) were separated from the blood using dextran sedimentation and Ficoll Hypaque centrifugation techniques. Neutrophils were suspended at 5 million cells per ml in HBSS.

Neutrophil activation levels were determined by the generation of reactive oxygen species as determined by chemiluminescence. In particular, chemiluminescence was determined by using an LKB luminometer with 1 uM luminol enhancer. Plasma precoating (or opsonization) of microspheres was performed by suspending 10 mg of microspheres in 0.5 ml of plasma and tumbling at 37° C. for 30 minutes.

Microspheres were then washed in 1 ml of HBSS and the centrifuged microsphere pellet added to the neutrophil suspension at 37° C. at time t=0. Microsphere surfaces were modified using a surfactant called Pluronic F127 (BASF) by suspending 10 mg of microspheres in 0.5 ml of 2% w/w solution of F127 in HBSS for 30 minutes at 37° C. Microspheres were then washed twice in 1 ml of HBSS before adding to neutrophils or to plasma for further precoating.

B. Results

Figure 44:
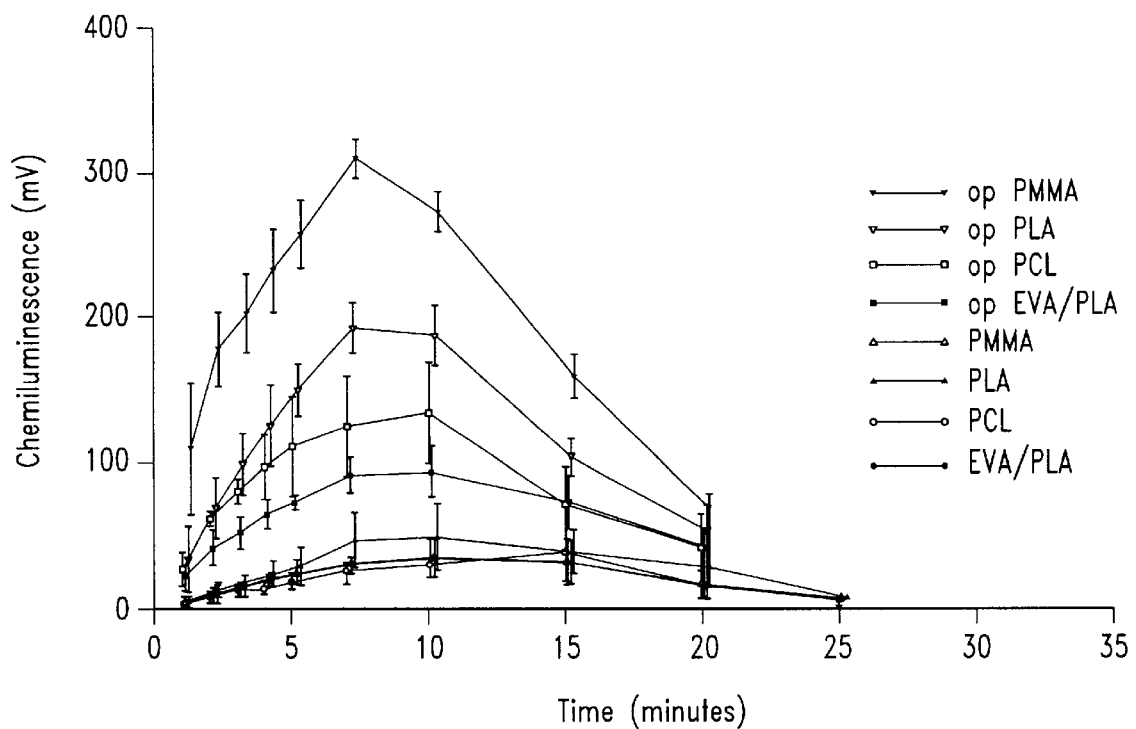
FIG. 44 is a graph which shows the effect of plasma opsonization of polymeric microspheres on the chemiluminescence response of neutrophils (20 mg/ml microspheres in 0.5 ml of cells (conc. 5×10$^6$ cells/ml)) to PCL microspheres.
Figure 45:
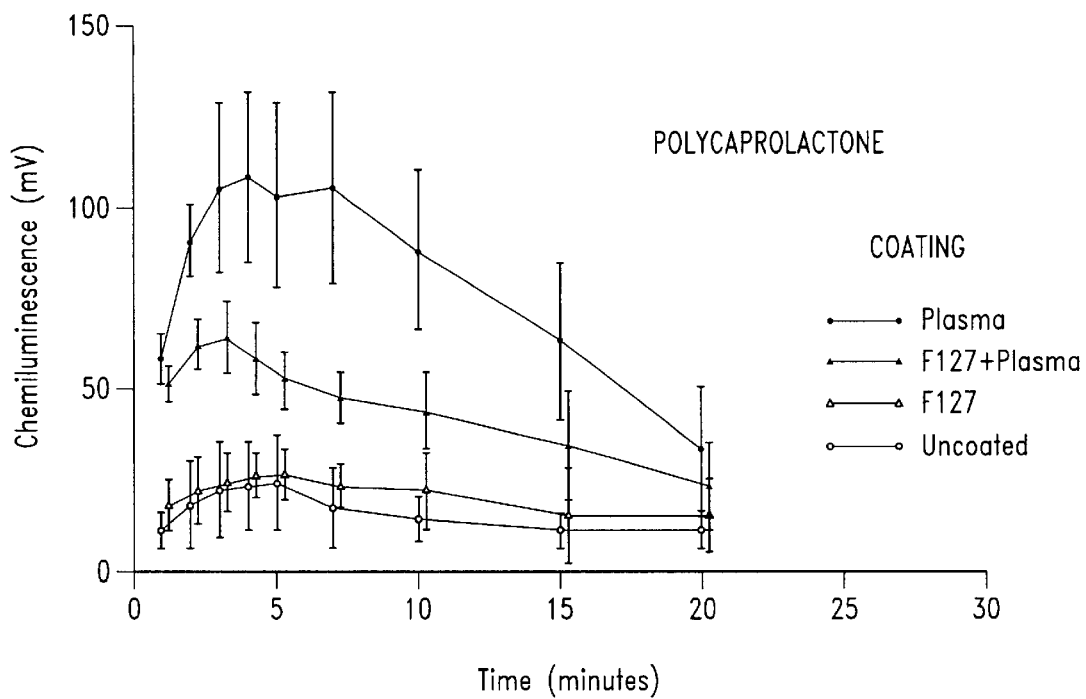
FIG. 45 is a graph which shows the effect of precoating plasma +/−2% Pluronic F127 on the chemiluminescence response of neutrophils (5×10$^6$ cells/ml) to PCL microspheres.
Figure 46:
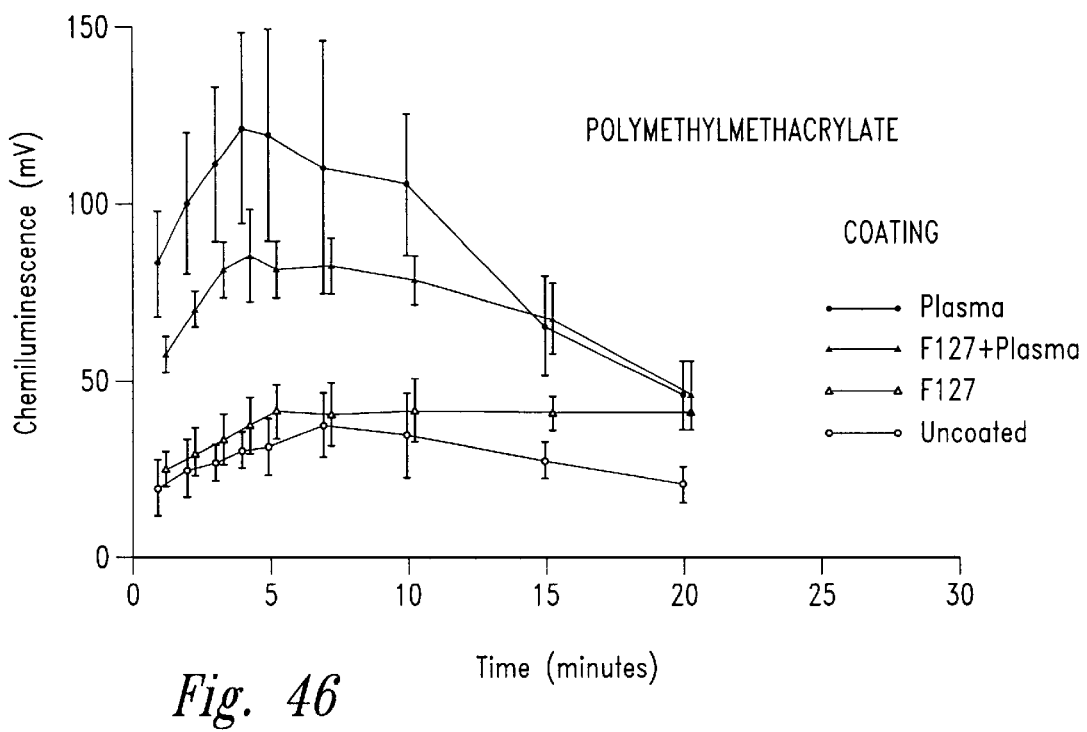
FIG. 46 is a graph which shows the effect of precoating plasma +/−2% Pluronic F127 on the chemiluminescence response of neutrophils (5×10$^6$ cells/ml) to PMMA microspheres.
Figure 47:
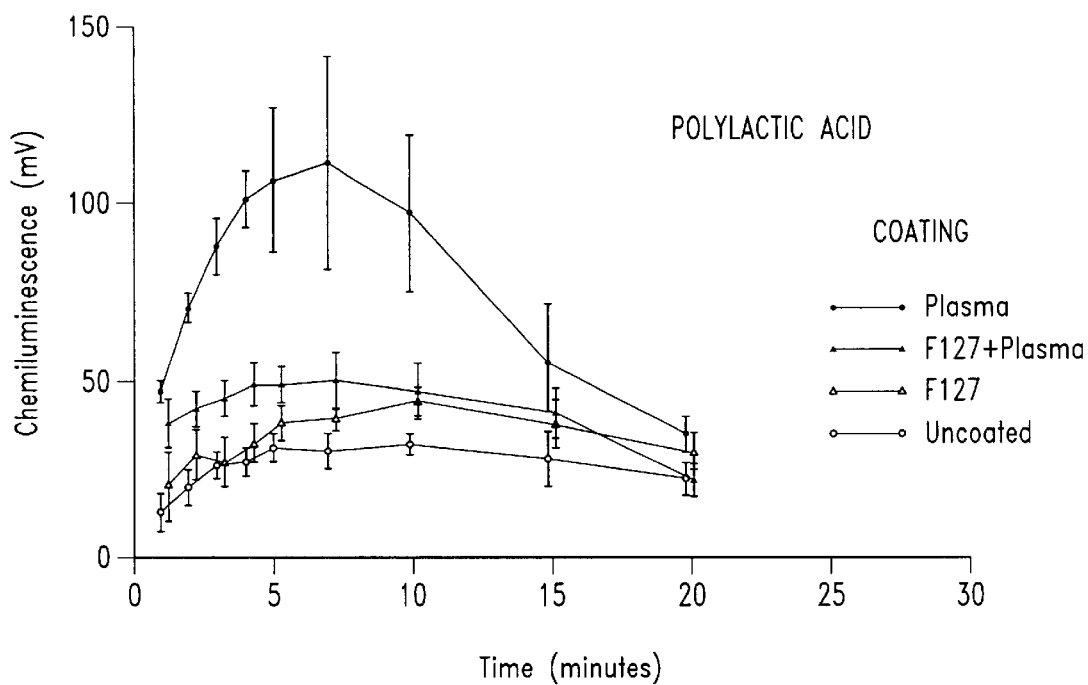
FIG. 47 is a graph which shows the effect of precoating plasma +/−2% Pluronic F127 on the chemiluminescence response of neutrophils (5×10$^6$ cells/ml) to PLA microspheres.
Figure 48:
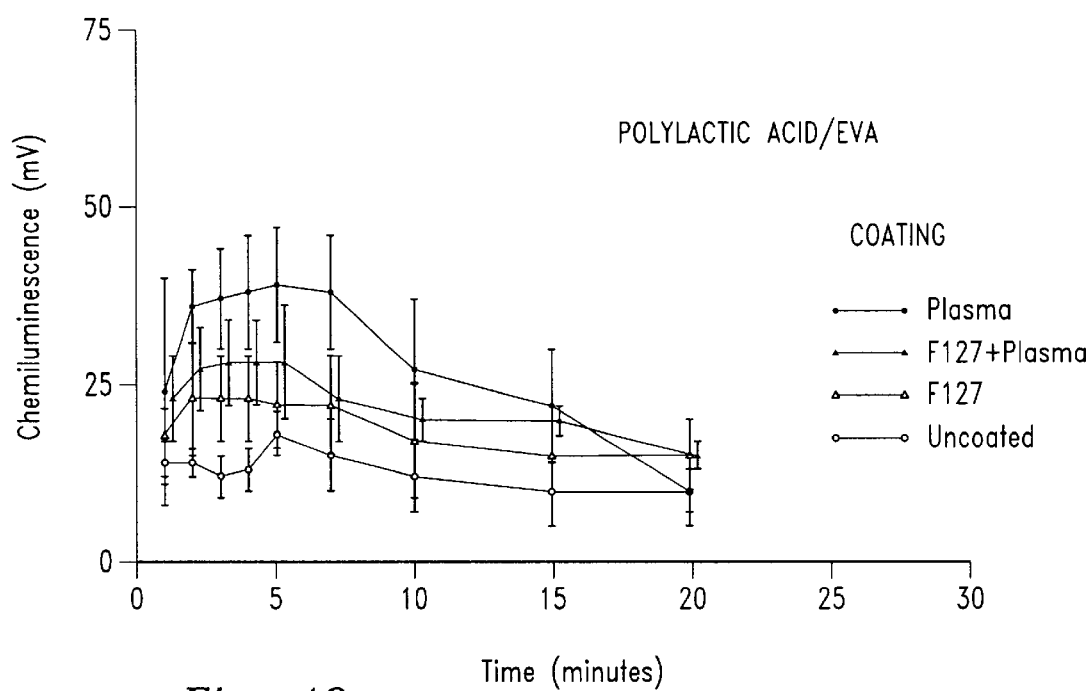
FIG. 48 is a graph which shows the effect of precoating plasma +/–2% Pluronic F127 on the chemiluminescence response of neutrophils ($5 \times 10^6$ cells/ml) to EVA:PLA microspheres.
Figure 49:
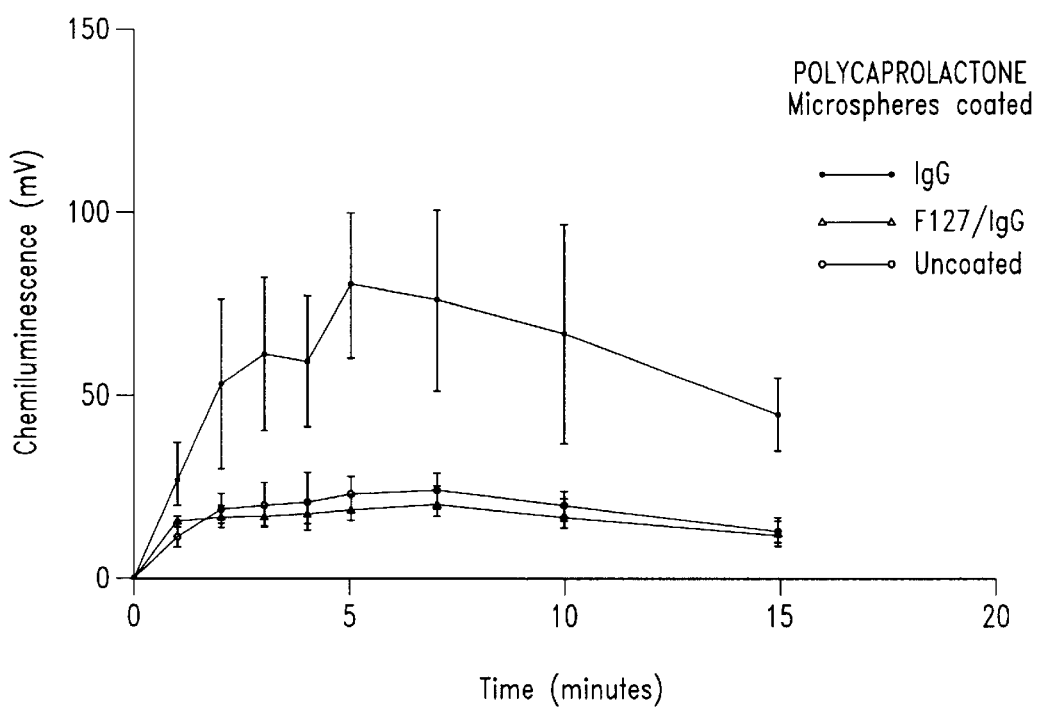
FIG. 49 is a graph which shows the effect of precoating IgG (2 mg/ml), or 2% Pluronic F127 then IgG (2 mg/ml) on the chemiluminescence response of neutrophils to PCL microspheres.
Figure 50:
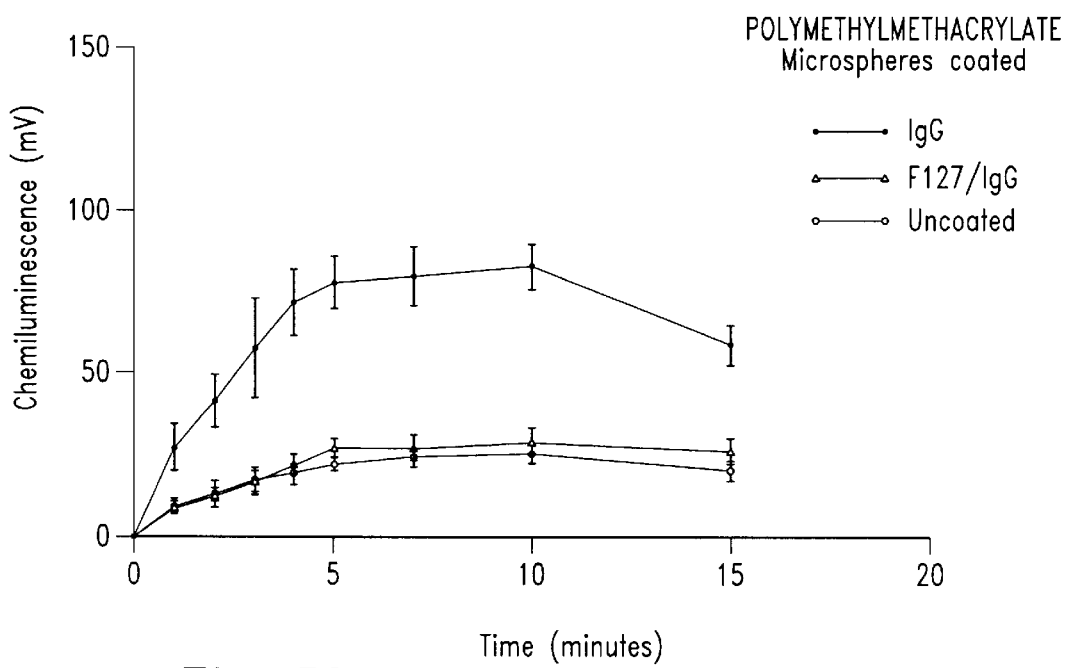
FIG. 50 is a graph which shows the effect of precoating IgG (2 mg/ml), or 2% Pluronic F127 then IgG (2 mg/ml) on the chemiluminescence response of neutrophils to PMMA microspheres.
Figure 51:
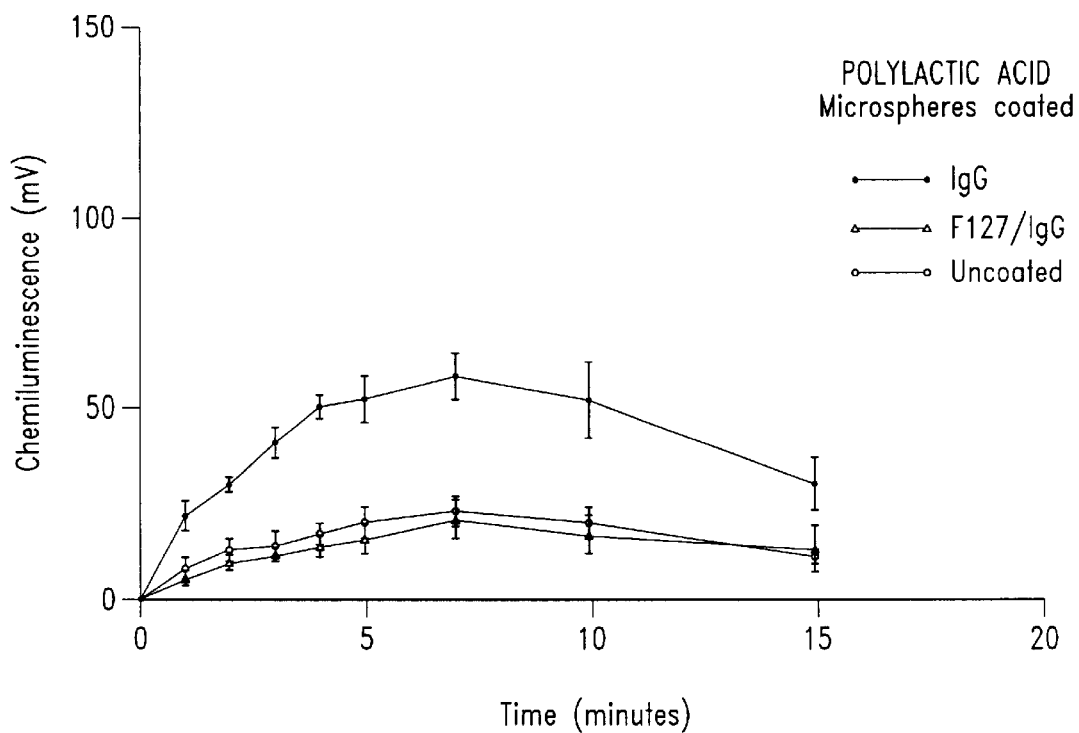
FIG. 51 is a graph which shows the effect of precoating IgG (2 mg/ml), or 2% Pluronic F127 then IgG (2 mg/ml) on the chemiluminescence response of neutrophils to PVA microspheres.
Figure 52:
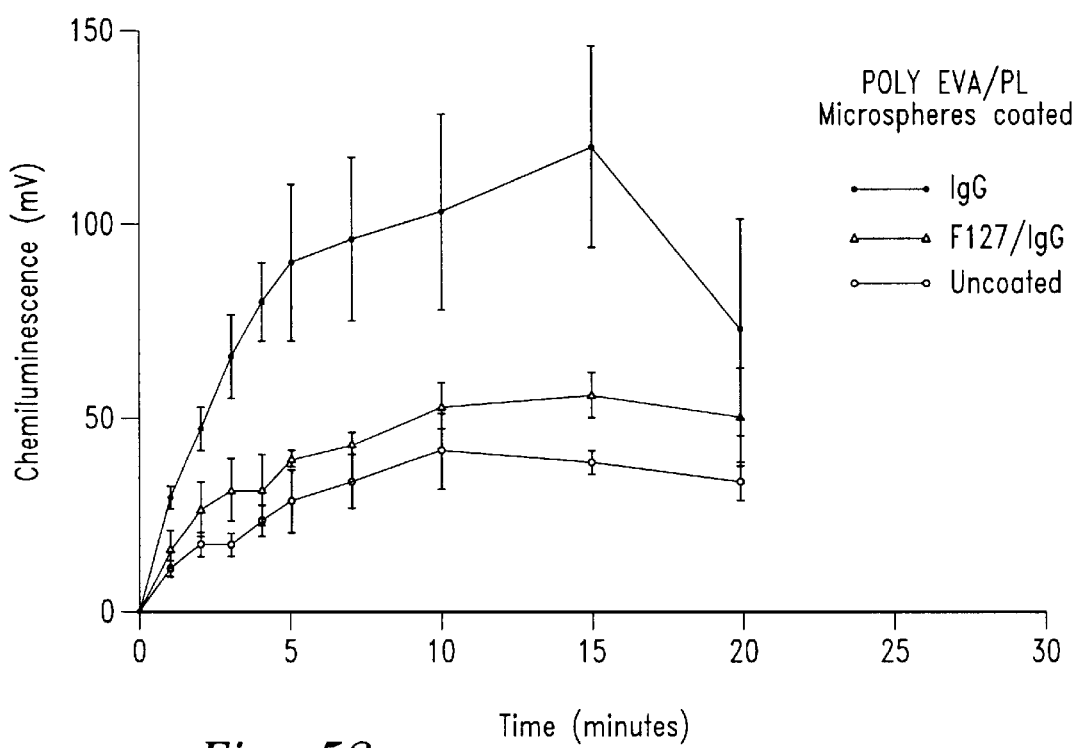
FIG. 52 is a graph which shows the effect of precoating IgG (2 mg/ml), or 2% Pluronic F127 then IgG (2 mg/ml) on the chemiluminescence response of neutrophils to EVA:PLA microspheres.

FIG. 44 shows that the untreated microspheres give chemiluminescence values less than 50 mV. These values represent low levels of neutrophil activation. By way of comparison, inflammatory microcrystals might give values close to 1000 mV, soluble chemical activators might give values close to 5000 mV. However, when the microspheres are precoated with plasma, all chemiluminescence values are amplified to the 100 to 300 mV range (FIG. 44). These levels of neutrophil response or activation can be considered mildly inflammatory. PMMA gave the biggest response and could be regarded as the most inflammatory. PLA and PCL both become three to four times more potent in activating neutrophils after plasma pretreatment (or opsonization) but there is little difference between the two polymers in this regard. EVA:PLA is not likely to be used in angiogenesis formulations since the microspheres are difficult to dry and resuspend in aqueous buffer. This effect of plasma is termed opsonization and results from the adsorption of antibodies or complement molecules onto the surface. These adsorbed species interact with receptors on white blood cells and cause an amplified cell activation.

FIGS. 45–48 describe the effects of plasma precoating of PCL, PMMA, PLA and EVA:PLA respectively as well as showing the effect of Pluronic F127 precoating prior to plasma precoating of microspheres. These figures all show the same effect: (1) plasma precoating amplifies the response; (2) Pluronic F127 precoating has no effect on its own; (3) the amplified neutrophil response caused by plasma precoating can be strongly inhibited by pretreating the microsphere surface with 2% Pluronic F127.

The nature of the adsorbed protein species from plasma was also studied by electrophoresis. Using this method, it was shown that pretreating the polymeric surface with Pluronic F127 inhibited the adsorption of antibodies to the polymeric surface.

FIGS. 49–52 likewise show the effect of precoating PCL, PMMA, PLA or EVA:PLA microspheres (respectively) with either IgG (2 mg/ml) or 2% Pluronic F127 then IgG (2 mg/ml). As can be seen from these figures, the amplified response caused by precoating microspheres with IgG can be inhibited by treatment with Pluronic F127.

This result shows that by pretreating the polymeric surface of all four types of microspheres with Pluronic F127, the "inflammatory" response of neutrophils to microspheres may be inhibited.

Example 41

Therapeutic Agent Encapsulation in Poly(E-caprolactone) Microspheres Inhibition of Angiogenesis on the CAM Assay by Paclitaxel-Loaded Microspheres This example evaluates the in vitro release rate profile of paclitaxel from biodegradable microspheres of poly($\epsilon$-caprolactone) (PCL) and demonstrates the in vivo anti-angiogenic activity of paclitaxel released from these microspheres when placed on the CAM.

Reagents which were utilized in these experiments include: PCL (molecular weight 35,000–45,000; purchased from Polysciences (Warrington, Pa.)); DCM from Fisher Scientific Co., Canada; polyvinyl alcohol (PVP) (molecular weight 12,000–18,000, 99% hydrolysed) from Aldrich Chemical Co. (Milwaukee, Wis.), and paclitaxel from Sigma Chemical Co. (St. Louis, Mo.). Unless otherwise stated all chemicals and reagents are used as supplied. Distilled water is used throughout.

A. Preparation of Microspheres

Microspheres were prepared essentially as described in Example 28 utilizing the solvent evaporation method. Briefly, 5% w/w paclitaxel-loaded microspheres were prepared by dissolving 10 mg of paclitaxel and 190 mg of PCL in 2 ml of DCM, adding to 100 ml of 1% PVP aqueous solution and stirring at 1000 rpm at 25° C. for 2 hours. The suspension of microspheres was centrifuged at 1000×g for 10 minutes (Beckman GPR), the supernatant removed and the microspheres washed three times with water. The washed microspheres were air-dried overnight and stored at room temperature. Control microspheres (paclitaxel absent) were prepared as described above. Microspheres containing 1% and 2% paclitaxel were also prepared. Microspheres were sized using an optical microscope with a stage micrometer.

B. Encapsulation Efficiency

A known weight of drug-loaded microspheres (about 5 mg) was dissolved in 8 ml of acetonitrile and 2 ml distilled water was added to precipitate the polymer. The mixture was centrifuged at 1000 g for 10 minutes and the amount of paclitaxel encapsulated was calculated from the absorbance of the supernatant measured in a UV spectrophotometer (Hewlett-Packard 8452A Diode Array Spectrophotometer) at 232 nm.

C. Drug Release Studies

About 10 mg of paclitaxel-loaded microspheres were suspended in 20 ml of 10 mM PBS (H 7.4) in screw-capped tubes. The tubes were tumbled end-over-end at 37° C. and at given time intervals 19.5 ml of supernatant was removed (after allowing the microspheres to settle at the bottom), filtered through a 0.45 $\mu$m membrane filter and retained for paclitaxel analysis. An equal volume of PBS was replaced in each tube to maintain sink conditions throughout the study. The filtrates were extracted with 3×1 ml DCM, the DCM extracts evaporated to dryness under a stream of nitrogen, redissolved in 1 ml acetonitrile and analyzed by HPLC using a mobile phase of water:methanol:acetonitrile (37:5:58) at a flow rate of 1 ml/minute (Beckman Isocratic Pump), a C8 reverse phase column (Beckman), and UV detection (Shimadzu SPD A) at 232 nm.

D. CAM Studies

Fertilized, domestic chick embryos were incubated for 4 days prior to shell-less culturing. On day 6 of incubation, 1 mg aliquots of 5% paclitaxel-loaded or control (paclitaxel-free) microspheres were placed directly on the CAM surface. After a 2-day exposure the vasculature was examined using a stereomicroscope interfaced with a video camera; the video signals were then displayed on a computer and video printed E. Scanning Electron Microscopy Microspheres were placed on sample holders, sputter-coated with gold and then placed in a Philips 501B SEM operating at 15 kV.

F. Results

The size range for the microsphere samples was between 30–100 µm, although there was evidence in all paclitaxel-loaded or control microsphere batches of some microspheres falling outside this range. The efficiency of loading PCL microspheres with paclitaxel was always greater than 95% for all drug loadings studied. Scanning electron microscopy demonstrated that the microspheres were all spherical and many showed a rough or pitted surface morphology. There appeared to be no evidence of solid drug on the surface of the microspheres.

Figure 53A:
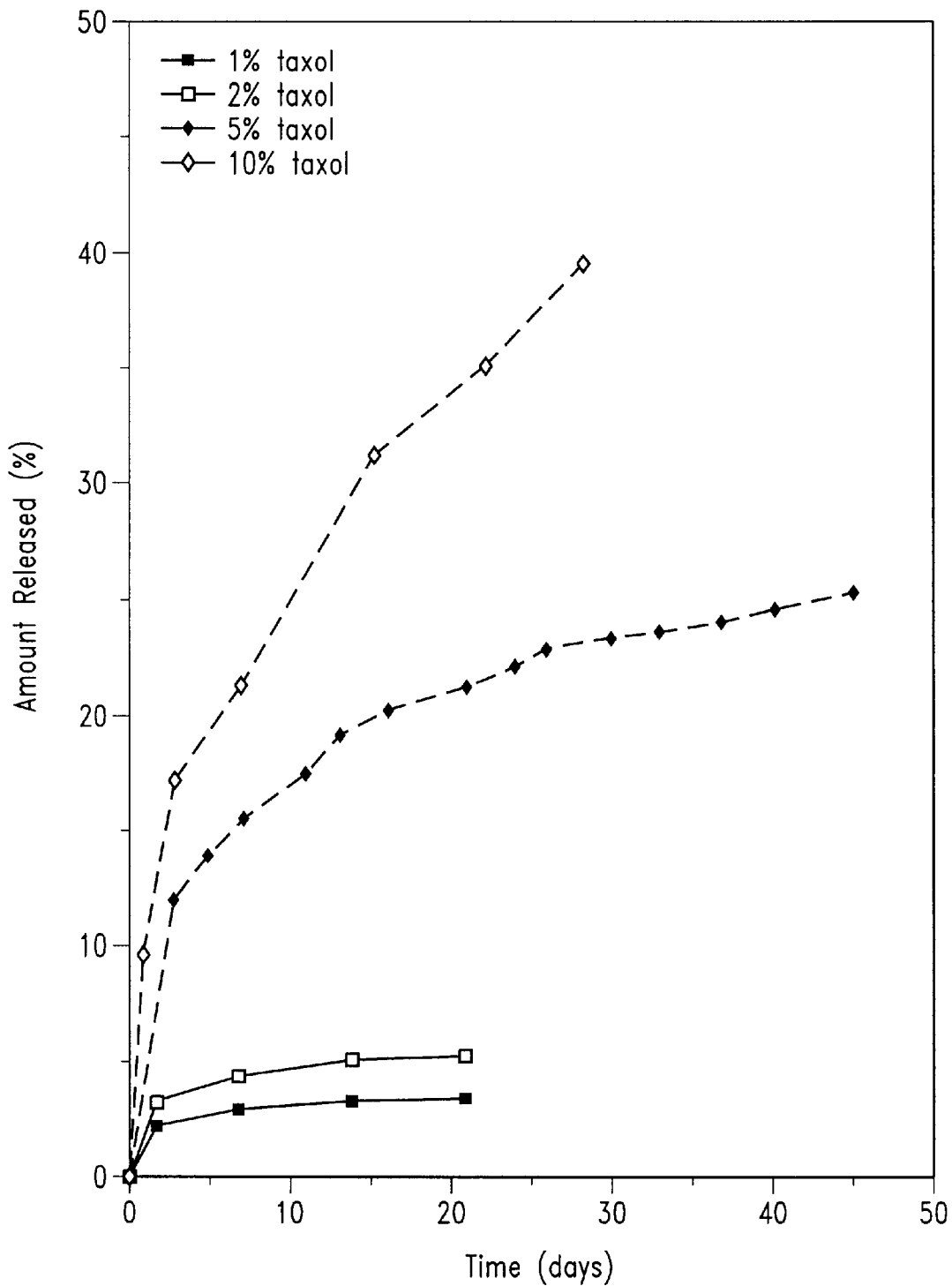
FIG. 53A is a graph which shows release rate profiles from polycaprolactone microspheres containing 1%, 2%, 5% or 10% paclitaxel into phosphate buffered saline at 37° C.

The time courses of paclitaxel release from 1%, 2% and 5% loaded PCL microspheres are shown in FIG. 53A. The release rate profiles were biphasic. There was an initial rapid release of paclitaxel or "burst phase" at all drug loadings. The burst phase occurred over 1–2 days at 1% and 2% paclitaxel loading and over 34 days for 5% loaded microspheres. The initial phase of rapid release was followed by a phase of significantly slower drug release. For microspheres containing 1% or 2% paclitaxel there was no further drug release after 21 days. At 5% paclitaxel loading, the microspheres had released about 20% of the total drug content after 21 days.

Figure 53B:
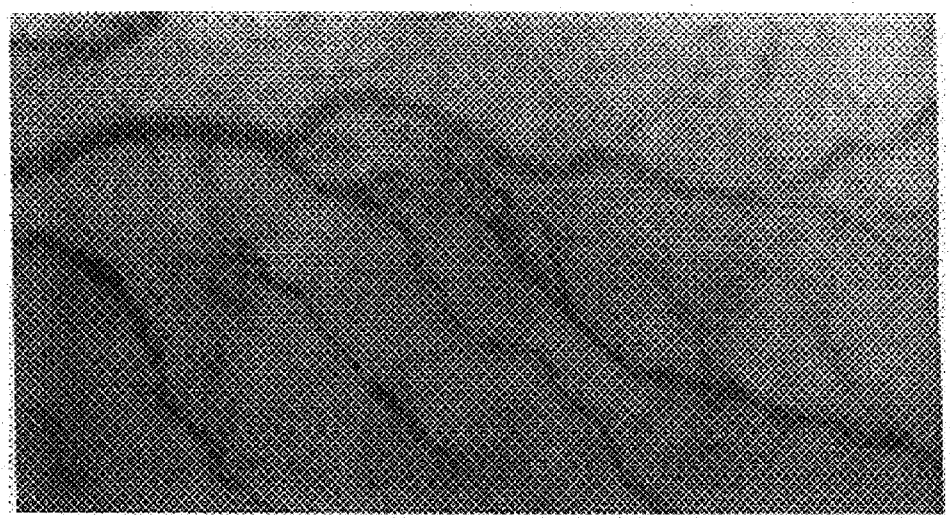
FIG. 53B is a photograph which shows a CAM treated with control microspheres.
Figure 53C:
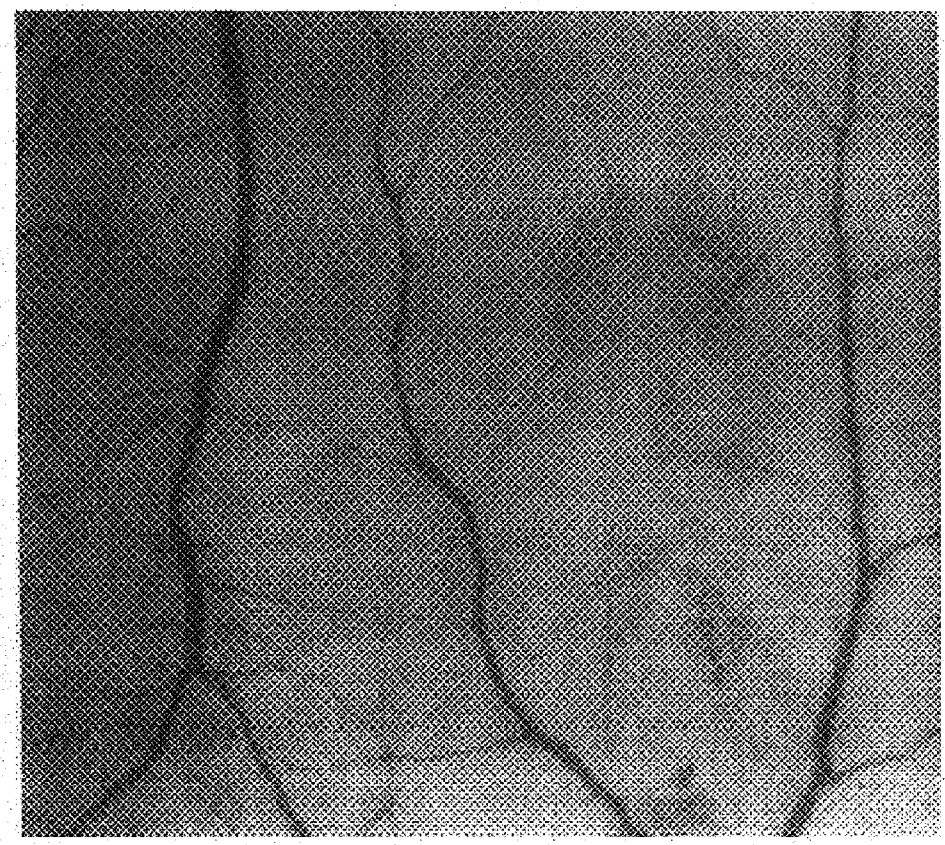
FIG. 53C is a photograph which shows a CAM treated with 5% paclitaxel loaded microspheres.
Figure 54:
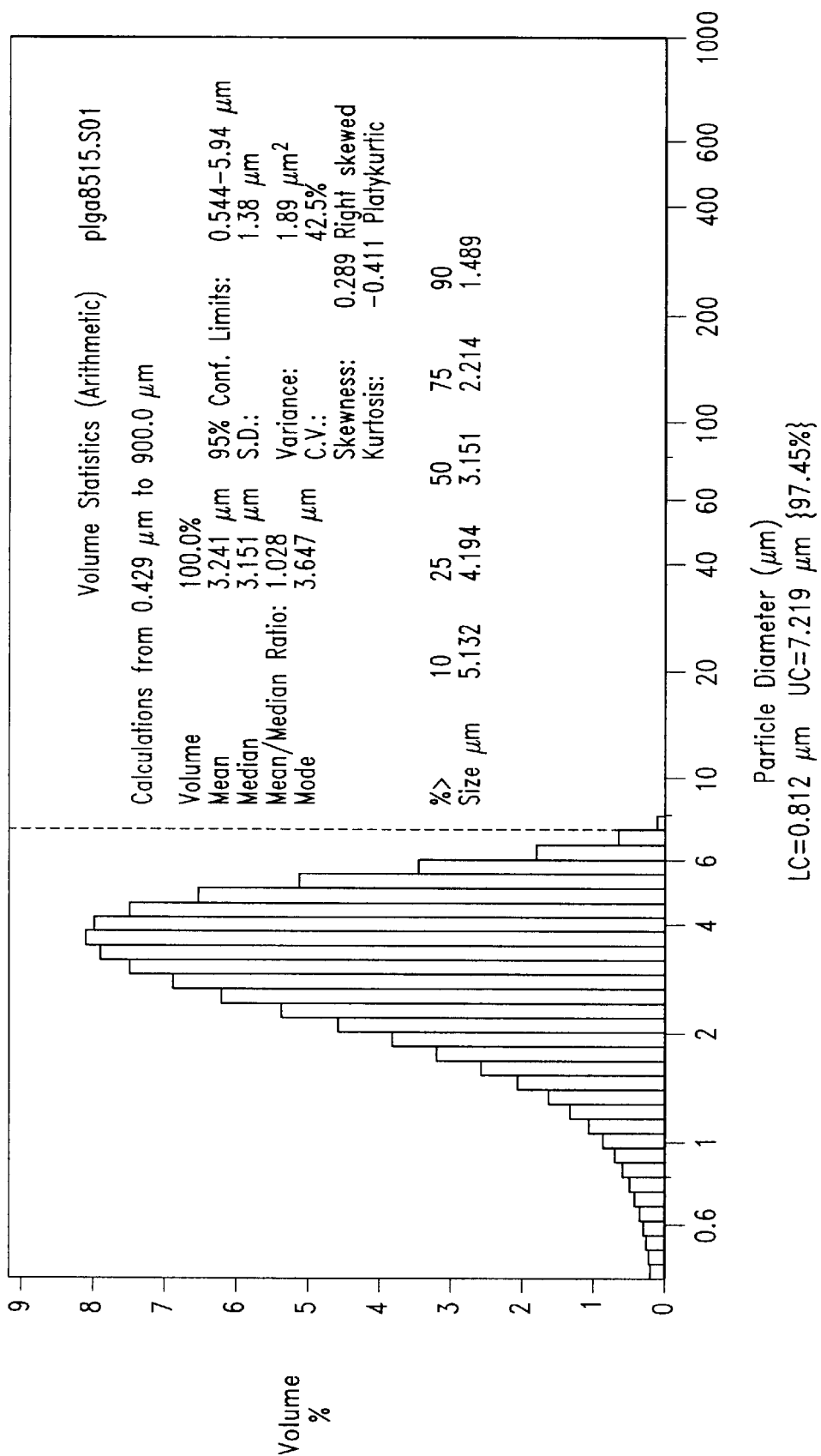
FIG. 54 is a graph which depicts the range of particle sizes for control microspheres (PLLA:GA-85:15).
Figure 55:
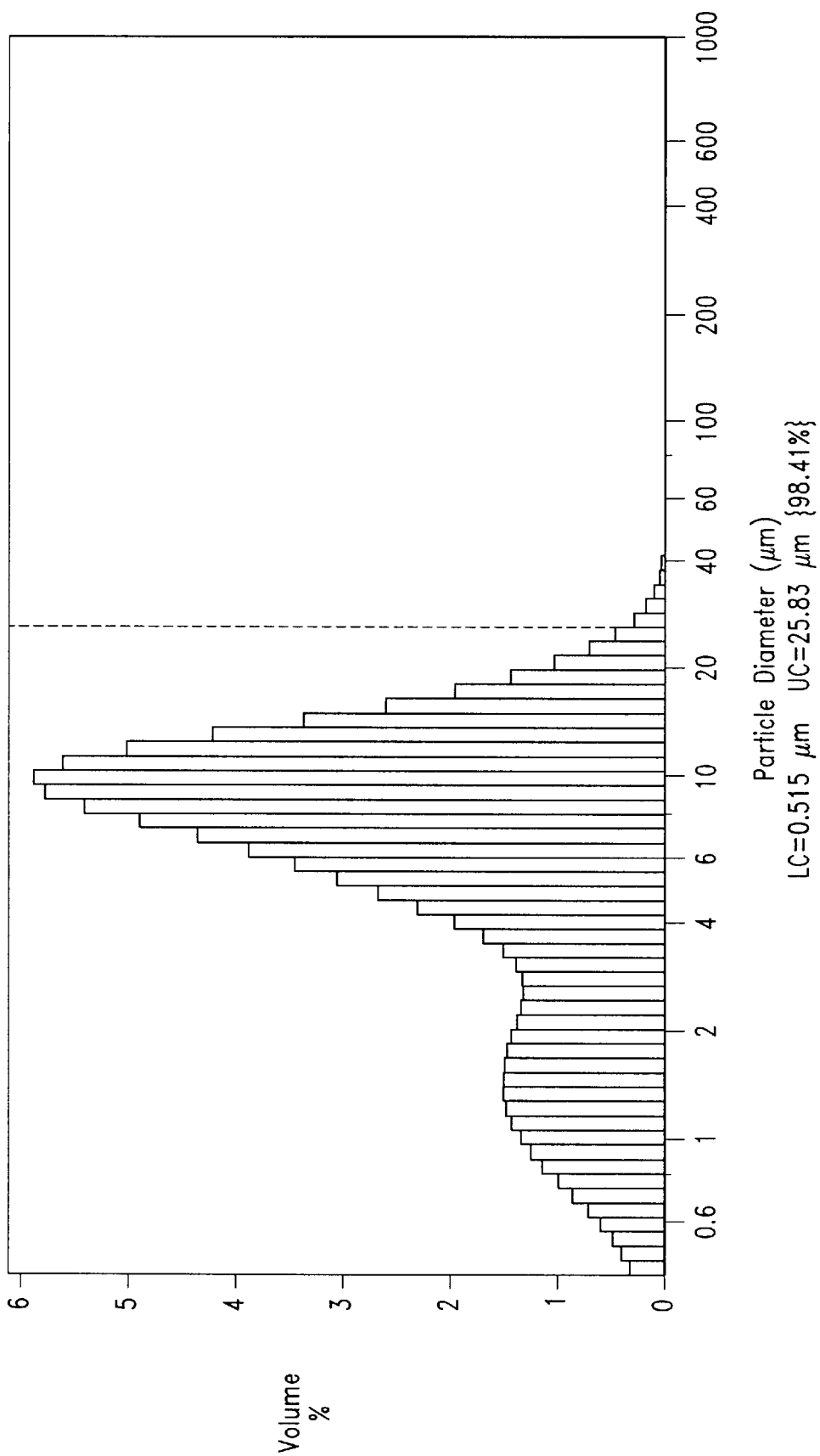
FIG. 55 is a graph which depicts the range of particle sizes for 20% paclitaxel loaded microspheres (PLLA:GA-85:15).
Figure 56:
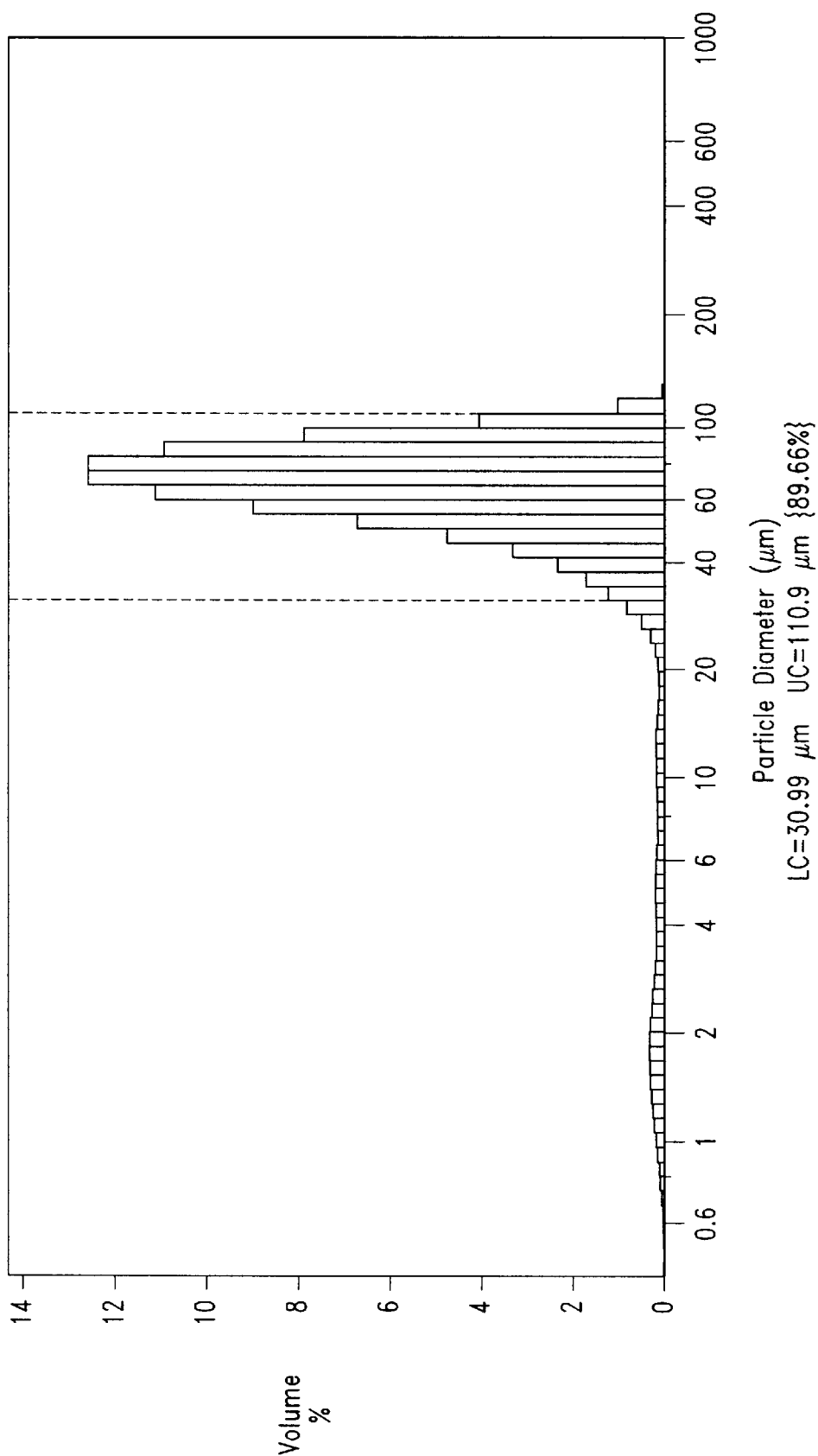
FIG. 56 is a graph which depicts the range of particle sizes for control microspheres (PLLA:GA-85:15).
Figure 57:
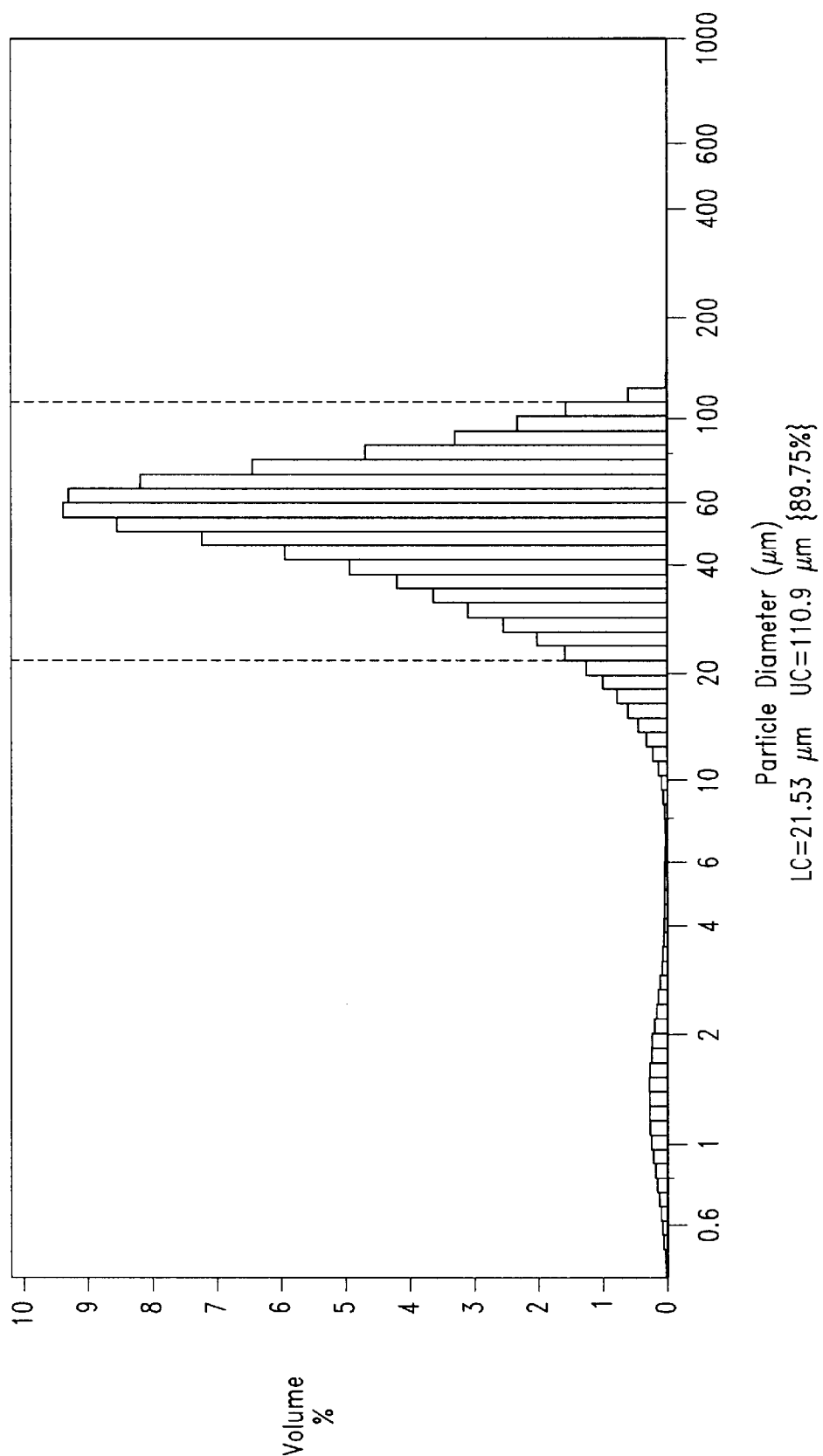
FIG. 57 is a graph which depicts the range of particle sizes for 20% paclitaxel loaded microspheres (PLLA:GA-85:15).
Figure 58A:
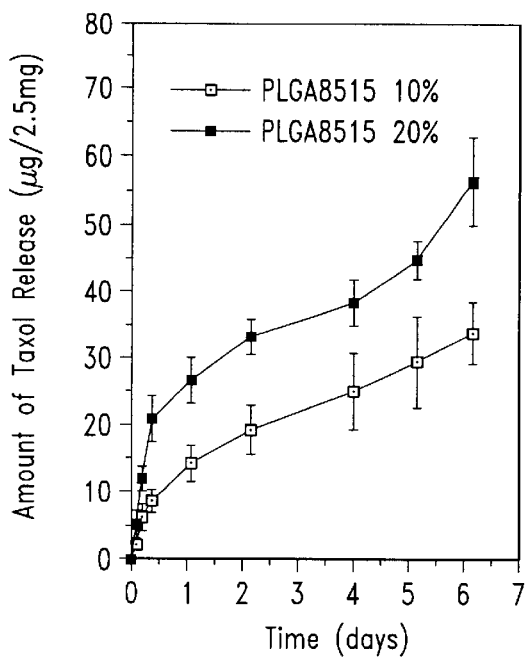
FIGS. 58A, 58B and 58C are graphs which show the release rate profiles of paclitaxel from varying ranges of microsphere size and various ratios of PLLA and GA.
Figure 58B:
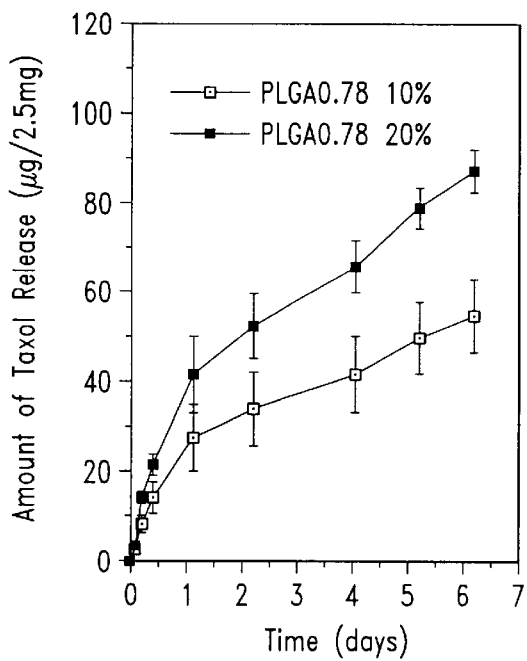
Figure 58C:
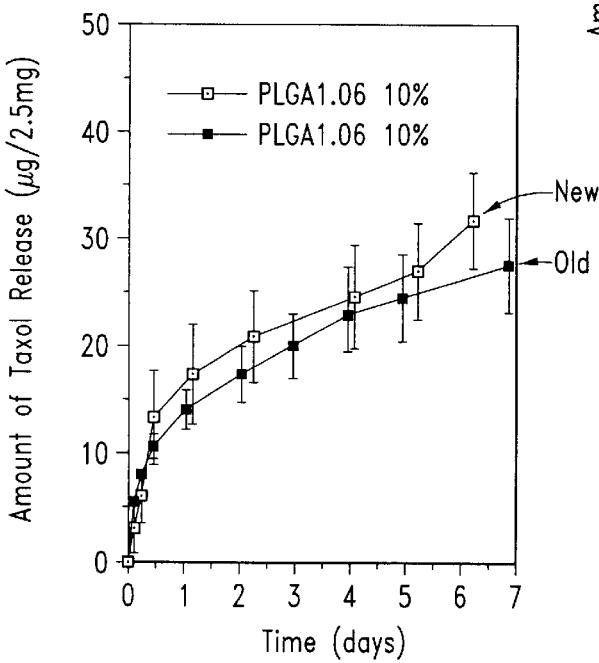
Figure 59A:
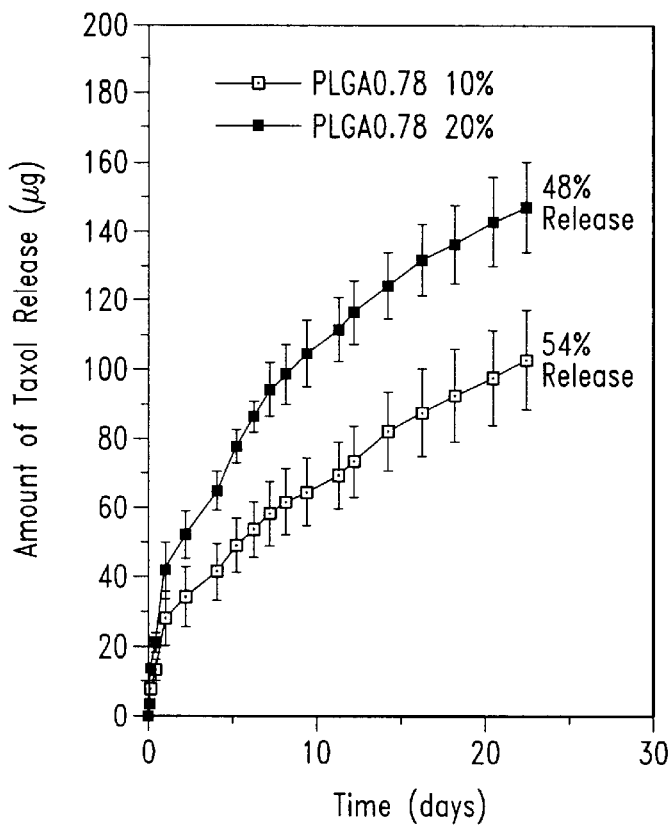
FIGS. 59A and 59B are graphs which show the release rate profiles of paclitaxel from microspheres with various ratios of PLLA and GA.
Figure 59B:
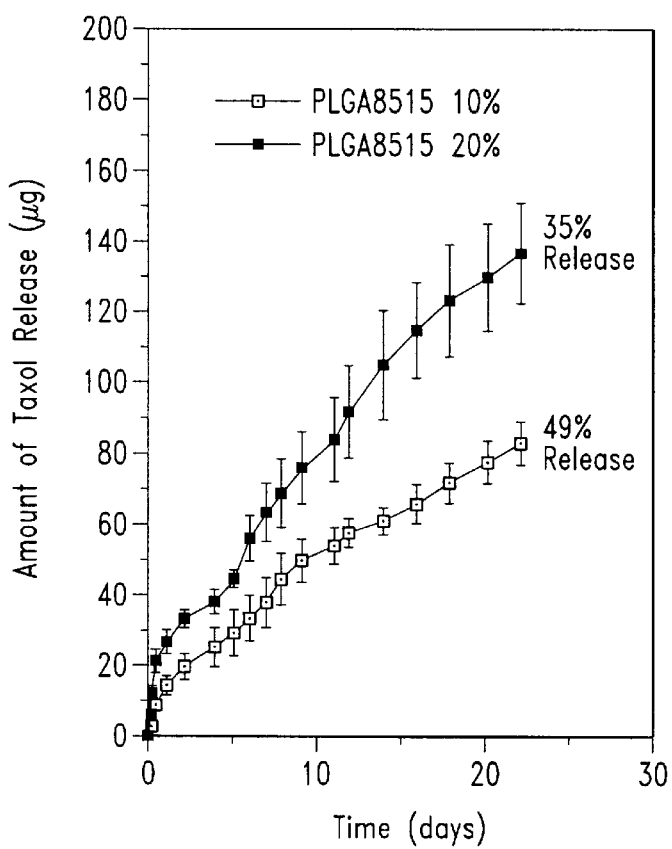
Figure 60A:
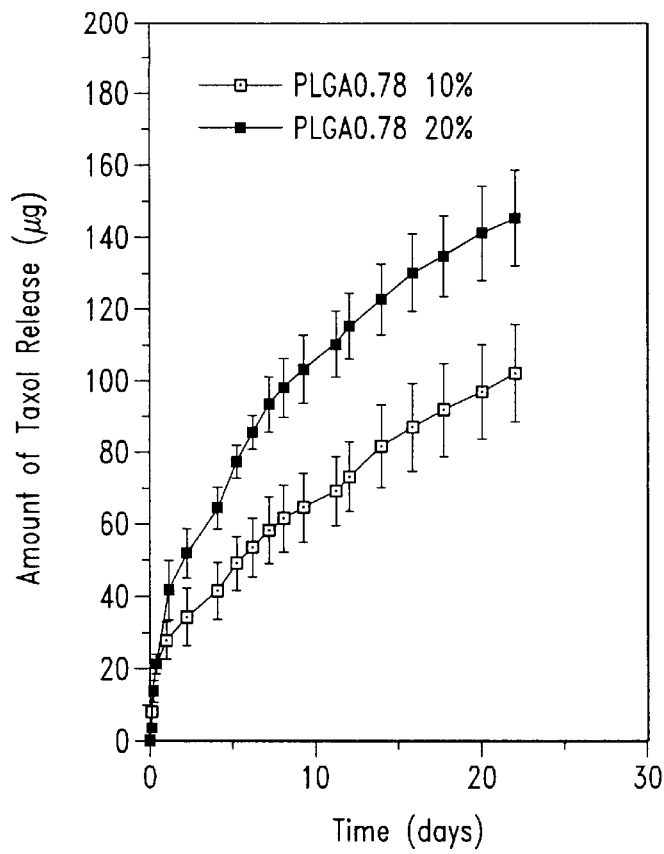
FIGS. 60A and 60B are graphs which show the release rate profiles of paclitaxel from microspheres with various ratios of PLLA and GA.
Figure 60B:
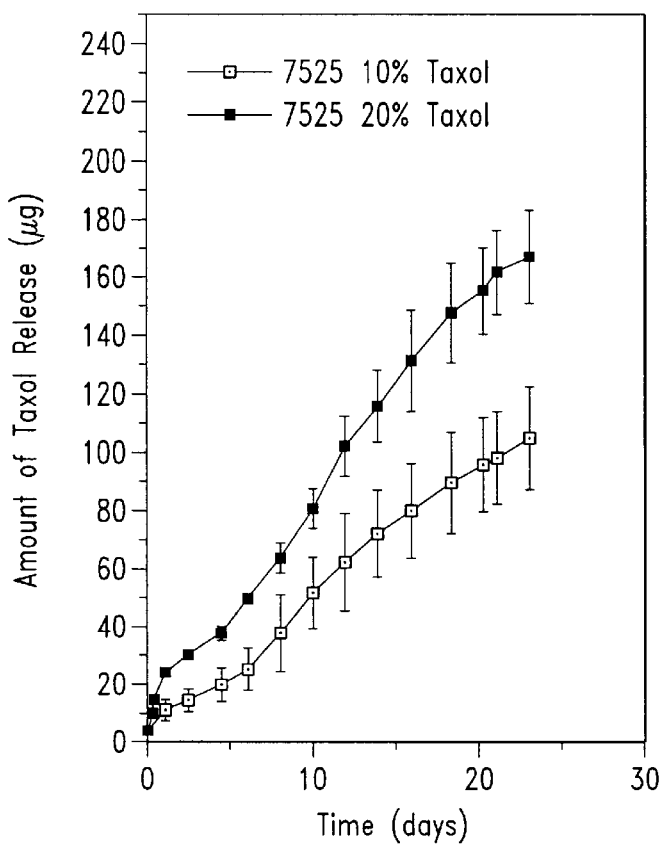
Figure 61A:
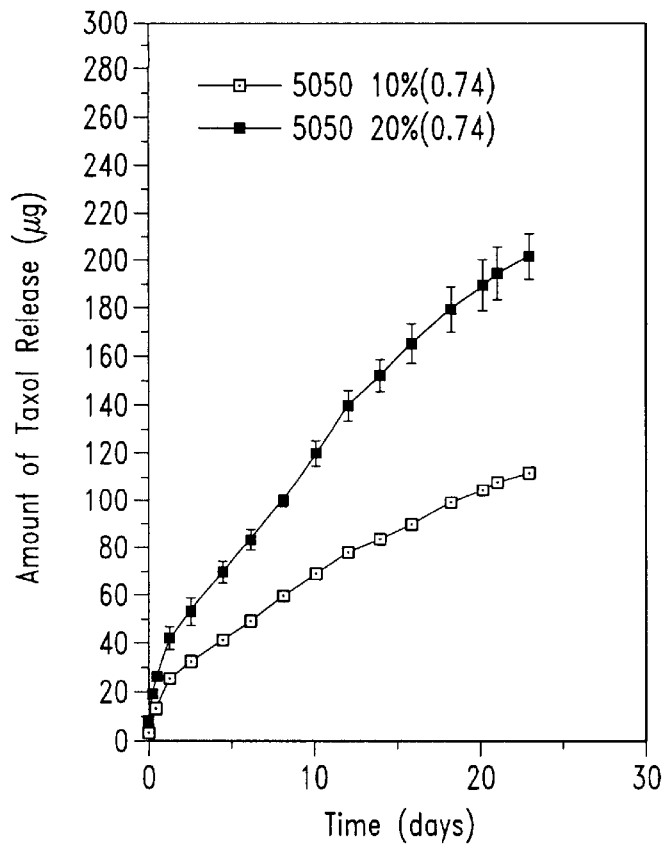
FIGS. 61A, 61B and 61C are graphs which show the release rate profiles of paclitaxel from microspheres of varying size and various ratios of PLLA and GA.
Figure 61B:
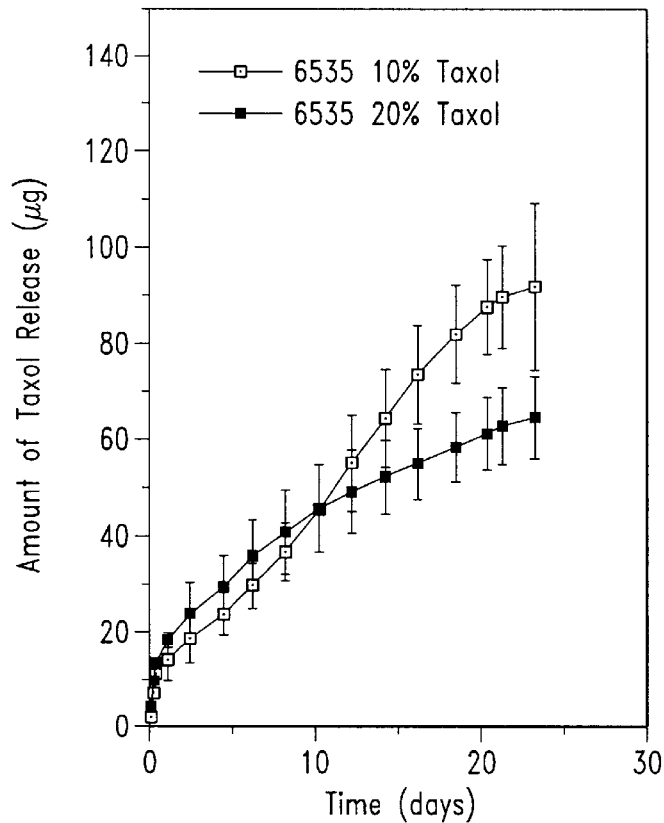
Figure 61C:
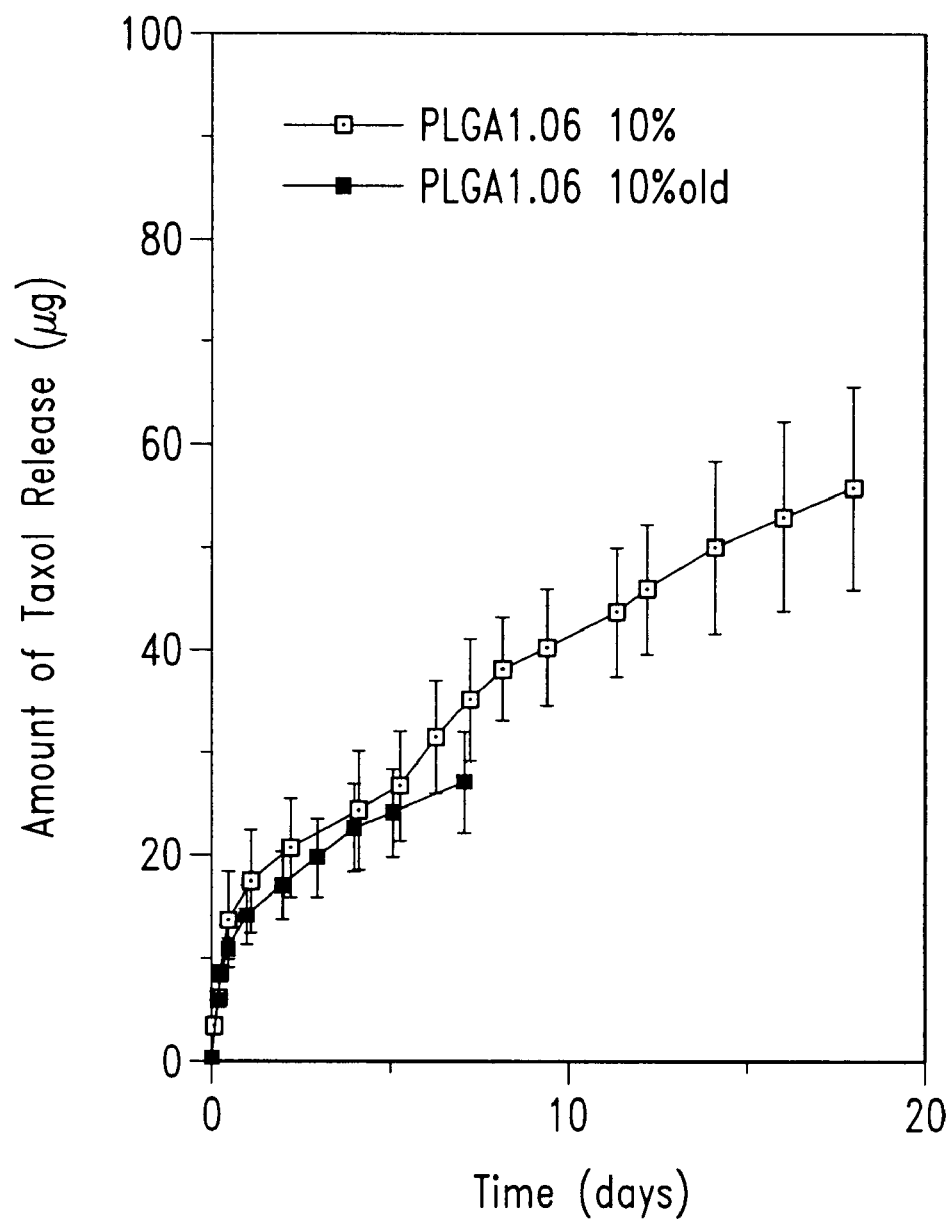

FIG. 53B shows CAMs treated with control PCL microspheres, and FIG. 53C shows treatment with 5% paclitaxel loaded microspheres. The CAM with the control microspheres showed a normal capillary network architecture. The CAM treated with paclitaxel-PCL microspheres showed marked vascular regression and zones which were devoid of a capillary network.

G. Discussion

The solvent evaporation method of manufacturing paclitaxel-loaded microspheres produced very high paclitaxel encapsulation efficiencies of between 95–100%. This was due to the poor water solubility of paclitaxel and its hydrophobic nature favoring partitioning in the organic solvent phase containing the polymer.

The biphasic release profile for paclitaxel was typical of the release pattern for many drugs from biodegradable polymer matrices. Poly(ε-caprolactone) is an aliphatic polyester which can be degraded by hydrolysis under physiological conditions and it is non-toxic and tissue compatible. The degradation of PCL is significantly slower than that of the extensively investigated polymers and copolymers of lactic and glycolic acids and is therefore suitable for the design of long-term drug delivery systems. The initial rapid or burst phase of paclitaxel release was thought to be due to diffusional release of the drug from the superficial region of the microspheres (close to the microsphere surface). Release of paclitaxel in the second (slower) phase of the release profiles was not likely due to degradation or erosion of PCL because studies have shown that under in vitro conditions in water there was no significant weight loss or surface erosion of PCL over a 7.5-week period. The slower phase of paclitaxel release was probably due to dissolution of the drug within fluid-filled pores in the polymer matrix and diffusion through the pores. The greater release rate at higher paclitaxel loading was probably a result of a more extensive pore network within the polymer matrix.

Paclitaxel microspheres with 5% loading have been shown to release sufficient drug to produce extensive inhibition of angiogenesis when placed on the CAM. The inhibition of blood vessel growth resulted in an avascular zone as shown in FIG. 53C.

Example 42

Manufacture of PLGA Microspheres

Microspheres were manufactured from lactic acid-glycolic acid copolymers (PLGA).

A. Method

Microspheres were manufactured in the size ranges 0.5 to 10 µm, 10–20 µm and 30–100 µm using standard methods (polymer was dissolved in dichloromethane and emulsified in a polyvinyl alcohol solution with stirring as previously described in PCL or PDLLA microspheres manufacture methods). Various ratios of PLLA to GA were used as the polymers with different molecular weights (given as Intrinsic Viscosity (I.V.))

B. Result

Microspheres were manufactured successfully from the following starting polymers:

| PLLA | GA | I.V. |
|------|------|------|
| 50 | 50 | 0.74 |
| 50 | 50 | 0.78 |
| 50 | 50 | 1.06 |
| 65 | 35 | 0.55 |
| 75 | 25 | 0.55 |
| 85 | 15 | 0.56 |

Paclitaxel at 10% or 20% loadings was successfully incorporated into all these microspheres. Examples of size distributions for one starting polymer (85:15, IV=0.56) are given in FIGS. 54–57. Paclitaxel release experiments were performed using microspheres of various sizes and various compositions. Release rates are shown in FIGS. 58–61.

Example 43

Encapsulation of Paclitaxel in Nylon Microcapsules

Therapeutic agents may also be encapsulated in a wide variety of carriers which may be formed into a selected form or device. For example, as described in more detail below, paclitaxel may be incorporated into nylon microcapsules which may be formulated into artificial heart valves, vascular grafts, surgical meshes, or sutures.

A. Preparation of Paclitaxel-Loaded Microcapsules

Paclitaxel was encapsulated into nylon microcapsules using the interfacial polymerization techniques. Briefly, 100 mg of paclitaxel and 100 mg of Pluronic F-127 was dissolved in 1 ml of DCM and 0.4 ml (about 500 mg) of adipoyl chloride (ADC) was added. This solution was homogenized into 2% PVA solution using the Polytron homogenizer (1 setting) for 15 seconds. A solution of 1,6-hexane-diamine (HMD) in 5 ml of distilled water was added dropwise while homogenizing. The mixture was homogenized for a further 10 seconds after the addition of HMD solution. The mixture was transferred to a beaker and stirred with a magnetic stirrer for 3 hours. The mixture was centrifuged, collected and resuspended in 1 ml distilled water.

B. Encapsulation Efficiency/Paclitaxel-Loading

About 0.5 ml of the suspension was filtered and the microspheres were dried. About 2.5 mg of the microcapsules was weighed and suspended in 10 ml of acetonitrile for 24 hours. The supernatant analyzed for paclitaxel and the result was expressed as a percentage of paclitaxel. Preliminary studies have shown that paclitaxel could be encapsulated in nylon microcapsules at a high loading (up to 60%) and high encapsulation efficiency (greater than 80%).

C. Paclitaxel Release Studies

Figure 62:
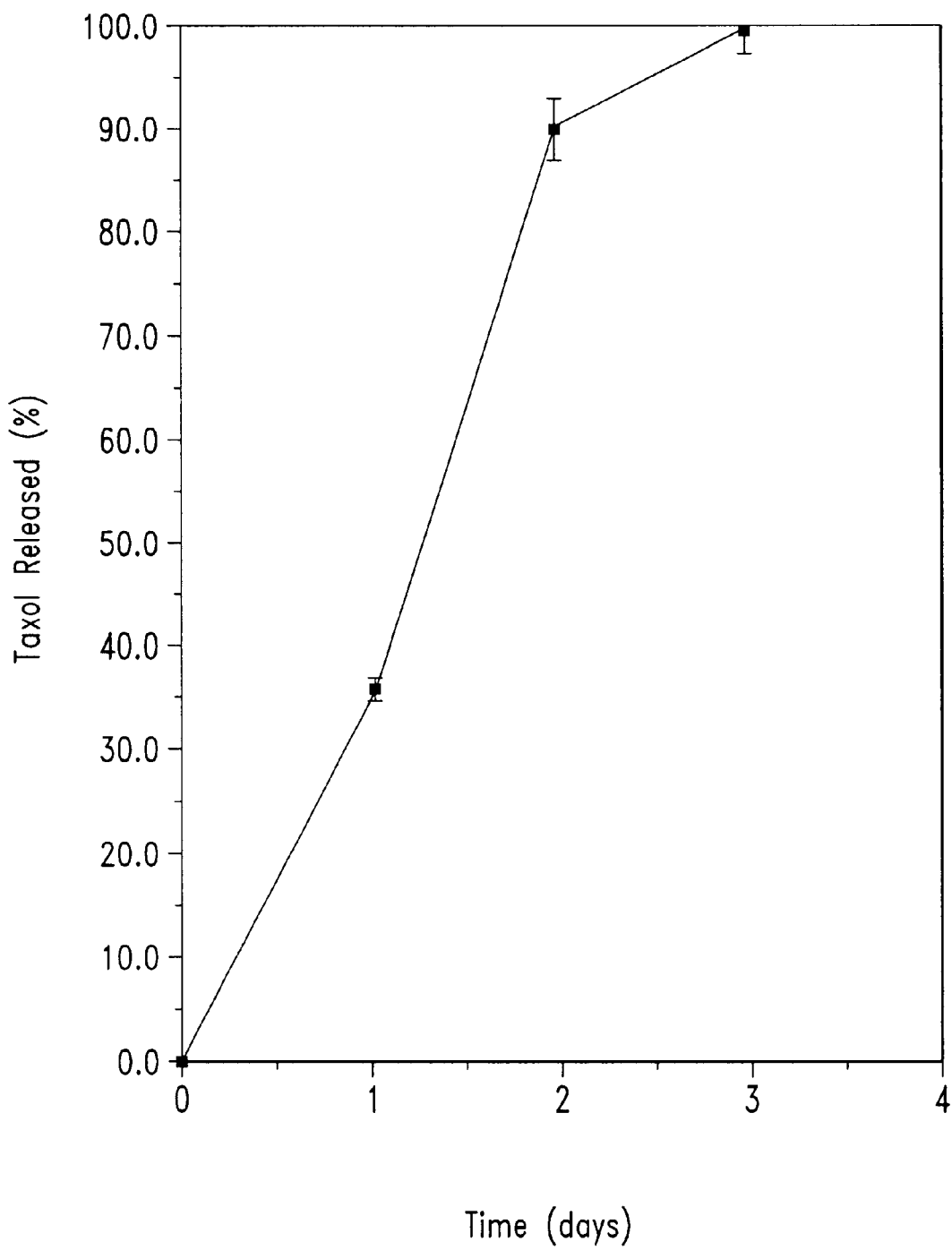
FIG. 62 is a graph which depicts paclitaxel release from paclitaxel-nylon microcapsules.

About 2.5 mg of the paclitaxel-nylon microspheres were suspended in 50 ml water containing 1 M each of sodium chloride and urea and analyzed periodically. Release of paclitaxel from the microcapsule was fast with more than 95% of the drug released after 72 hours (FIG. 62).

Example 44

Bioadhesive Microspheres

A. Preparation of Bioadhesive Microspheres

Microspheres were made from 100k g/mol PLLA with a particle diameter range of 10–60 µm. The microspheres were incubated in a sodium hydroxide solution to produce carboxylic acid groups on the surface by hydrolysis of the polyester. The reaction was characterized with respect to sodium hydroxide concentration and incubation time by measuring surface charge. The reaction reached completion after 45 minutes of incubation in 0.1 m sodium hydroxide. Following base treatment, the microspheres were coated with dimethylaminoproylcarbodiimide (DEC), a cross-linking agent, by suspending the microspheres in an alcoholic solution of DEC and allowing the mixture to dry into a dispersible powder. The weight ratio of microspheres to DEC was 9:1. After the microspheres were dried, they were dispersed with stirring into a 2% w/v solution of poly (acrylic acid) (PAA) and the DEC allowed to react with PAA to produce a water insoluble network of cross-linked PAA on the microspheres surface. Scanning electron microscopy was used to confirm the presence of PAA on the surface of the microspheres.

Differential scanning calorimetry of the microspheres before and after treatment with base revealed that no changes in bulk thermal properties (Tg, melting, and degree of crystallinity) were observed by SEM.

B. In Vitro Paclitaxel Release Rates

Paclitaxel-loaded microspheres (10% and 30% w/w loadings) with the same particle diameter size range were manufactured and in vitro release profiles for 10 days release in PBS. Release was proportional to drug loading, with 400 µg of paclitaxel released from 5 mg of 30% loaded microspheres in 10 days and 150 µg released from 10% loaded microspheres in the same period. The efficiency of encapsulation was about 80%. The paclitaxel-loaded microspheres were incubated in 0.1 M sodium hydroxide for 45 minutes and the zeta potential measured before and after incubation in sodium hydroxide. The surface charge of paclitaxel-loaded microspheres was lower than microspheres with no paclitaxel both before and after treatment with base.

Figure 63A:
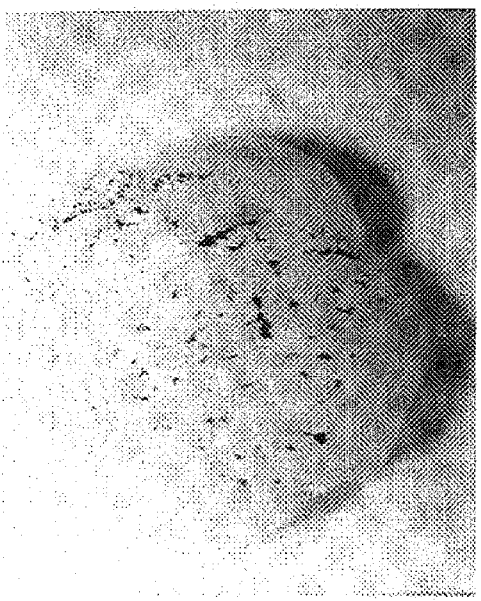
FIGS. 63A and 63B are photographs of fibronectin coated PLLA microspheres on bladder tissue (63A), and poly (L-lysine) microspheres on bladder tissue.
Figure 63B:
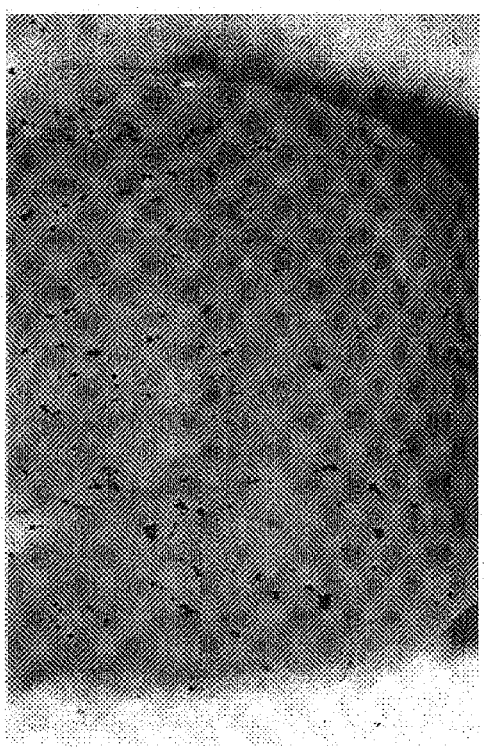

C. Preparation and In Vitro Evaluation of PLLA Coated with Either Poly-lysine or Fibronectin PLLA microspheres were prepared containing 1% sudan black (to color the microspheres). These spheres were suspended in a 2% (w/volume) solution of either poly-lysine (Sigma chemicals—Hydrobromell form) or fibronectin (Sigma) for 10 minutes. The microspheres were washed in buffer once and placed on the inner surface of freshly prepared bladders from rats. The bladder were left for 10 minutes then washed three times in buffer. Residual (bound) microspheres were present on the bladder wall after the process therefore showing bioadhesion had occurred (FIGS. 63A and 63B) for both fibronectin-and poly-1-lysine-coated micro spheres.

Example 45

Manufacture of Paclitaxel-Loaded Albumin Microspheres

Albumin microspheres were prepared by either heat denaturation or crosslinking with glutaraldehyde.

In the former method, 2 ml albumin solution (25%) in distilled water was stirred into 100 ml of light mineral oil and level 3 speed setting with a overhead propeller stirrer (Fisher Scientific). After stirring for 15 minutes, the mixture was heated to and maintained at 60 to 70° C. for 30 minutes and then heated to and maintained at 120° C. for 10 minutes (microspheres aggregated when the mixture was heated directly to 120° C.). The mixture was subsequently cooled to room temperature, mixed with 100 ml of petroleum ether and filtered using suction. The microspheres were washed under suction with 100 ml petroleum ether and then with 50 ml ethanol (100%). The microspheres (on the filter paper) were air-dried at 37° C. overnight, weighed and packaged.

In the second method, microspheres were prepared exactly as described above but after heating to 60 to 70° C. for 30 minutes, glutaraldehyde (0.1 ml of 25% solution) was added and stirred for a further 30 minutes. Washing and collecting were as described above.

Loading of paclitaxel into albumin microspheres: paclitaxel was loaded into albumin using the oil-in-water-in-oil (O/W/O) double emulsion technique. Briefly, 200 mg paclitaxel and 200 mg PEG (M.W.=20,000) were dissolved in 1 ml methylene chloride and emulsified into 2.4 ml of 25% albumin solution. This emulsion was subsequently added to 100 ml of light liquid paraffin and stirred at speed level 3 setting with the overhead propeller stirrer (Fisher Scientific). After stirring for 15 minutes, the mixture was heated to and maintained at 60 to 70° C. for 15 minutes, 0.1 ml glutaraldehyde was then added and stirring was continued for another 30 minutes. The mixture was cooled to room temperature and centrifuged at 1,500 rpm for 5 minutes. The liquid paraffin was discarded. Petroleum ether (20 ml) was added to the microspheres and the microspheres were filtered using suction. The microspheres subsequently washed with 60 ml of petroleum ether and then with 30 ml ethanol. The microspheres were dried and weighed.

Example 46

Manufacture of Paclitaxel-Loaded Polyethyleneglycol (PEG) Microspheres

Microspheres containing 10 or 20% paclitaxel in PEG (M.W.=20,000) were prepared by the solvent evaporation method. Briefly, the appropriate amounts of paclitaxel and 0.5 g PEG were dissolved in 3 ml of acetone. This solution was emulsified into 100 ml of light mineral oil containing 0.5 g of Span 80. The mixture was stirred until microspheres formed (about 1.5 hours). The mixture was centrifuged at 2,000 rpm for 5 minutes and the oil decanted. The microspheres were washed with petroleum ether and then with ethanol and subsequently dried The yield of microspheres was 94% and the encapsulation efficiency was 64%. The microspheres were then aged at 37° C. for three weeks.

Example 47

Manufacture of Paclitaxel-Loaded Star-Shaped Poly (Lactic Acid) (PLA) and Poly(Lactide-co-glycolic Acid) (PLGA) (PEG) Microspheres Microspheres containing 5, 10 or 20% paclitaxel in low molecular weight star-shaped PLA and PLGA (M.W.≈10, 000 by Gel Permeation Chromatography) were prepared by an oil-in-water emulsification technique. Briefly, the appropriate weights of the paclitaxel and 0.5 polymer were dissolved in 10 ml of dichloromethane and emulsified with a overhead propeller stirrer at the level of 3 (Fisher Scientific) into 100 ml 1% polyvinyl alcohol solution for about 3 hours. The formed microspheres were sieved and dried under vacuum at a temperature below 10° C. Yield of microspheres in the desired size range (53–90 μm) was about 50% and the encapsulation efficiency of paclitaxel in microspheres was about 98%.

Release studies were done by placing 2.5 mg of said microspheres in a 15 ml Teflon capped tube (with 10 ml phosphate buffer saline with albumin). Sampling daily (three sampling at the first day) to maintain the sink condition. Release study data showed that paclitaxel was released from the star-shaped microspheres 3 to 10 times faster than the conventional linear PLA and PLGA microspheres.

Example 48

Manufacture of Paclitaxel-Loaded Gelatin Microparticles

For a 5% paclitaxel loaded gelatin formulation, 50 mg of paclitaxel was mixed with 950 mg of gelatin. The mixture was gradually heated up to and maintained at 70° C. until the paclitaxel was completely dissolved in the molten gelatin. Mixed the solution for 30 minutes with a stirrer bar at 600 rpm. The resulted solution was cooled down to room temperature and became solidified. The solid gelatin-paclitaxel solution was ground into the micro-particles until the anticipated size ranges was achieved.

Example 49

Manufacture of Paclitaxel-Loaded Chitosan Microspheres

Fifty milliliters of paraffin oil (Fisher Scientific) was placed in a 100 ml beaker at 60° C. and 0.5 ml of Span 80 (Fisher Scientific) was added. The mixture was stirred at 700 rpm. In a separate vial, chitosan (Fluka, low molecular weight) was dissolved in a 2% acetic acid (Fisher Scientific) at 25 mg/ml by stirring for 2 hours. This solution was diluted to 12.5 mg/ml with water. 6.25 mg of paclitaxel was then added into 5 ml of the 12.5 mg/ml chitosan solution (10% w/w paclitaxel to chitosan) together with 25 μl of Tween 40 (Fisher Scientific) and the suspension was homogenized using a polytron set at "mark 2" for 30 seconds. The chitosan-paclitaxel suspension was poured slowly into the paraffin and stirred for 5 hours. The microspheres were then washed three times in hexane and air-dried.

The encapsulation efficiency of paclitaxel in the chitosan microspheres was determined by dissolution of 10 mg microspheres in 10 ml of 2% acetic acid followed by extraction and phase separation of paclitaxel in 1 ml of dichloromethane.

The release rate of paclitaxel in the chitosan microspheres was measured by adding 10 mg of the microspheres to a 15 ml Teflon capped tube followed by 10 ml of phosphate buffer saline (pH=7.4). The tube was tumbled at 8 rpm at 37° C. for specified times. The tube was then centrifuged at 1000×g and the supernatant was collected for analysis of released drug. 10 ml of fresh phosphate buffer saline was added back to the tubes to retain sink condition in the release study.

Example 50

Manufacture of Paclitaxel-Loaded Chitosan Films for Pulverization into Microparticles To increase the encapsulation efficiency of paclitaxel in chitosan, the following method was utilized to cast a chitosan film which was pulverized into microparticles. A 20% (w/w) solution of chitosan (high molecular weight from Fluka) was made in 2% acetic acid. Ten grams of this solution was poured onto an 8 cm diameter Teflon watch glass. 50 mg of paclitaxel (dissolved in 1.5 ml of 100% ethanol with vigorous spatula mixing) was added to this viscous solution. The suspension was then dried in an oven at 37° C. overnight to form a film. The resulted film was pulverized for 30 minutes to grind the film to microparticles. Microparticles formed by this method was good, based on the ease of manufacturing and full encapsulation of paclitaxel. Paclitaxel crystal could be visualized within the chitosan. The microparticles would swell and became a gel when contacting with water.

Example 51

Manufacture of Paclitaxel-Loaded Hyaluronic Acid Microspheres

Two hundred milligrams of hyaluronic acid (sodium salt) was dissolved in 10 ml of distilled water overnight. 3.3 mg of paclitaxel (Hauser Chemical Company, Boulder, Colo.) was placed in a 2 ml homogenizer and 1 ml of water was added. The paclitaxel was hand homogenized for 2 minutes to reduce the particle size. Immediately before the experiment, the homogenized paclitaxel was added to 3.3 ml of hyaluronic acid solution and mixed together using a spatula 50 ml of light paraffin oil (Fisher Scientific) containing 250 μl of span 80 (Fisher Scientific) was stirred at 600 rpm at 50° C. using a propeller type overhead stirrer (Fisher Scientific) in a 100 ml beaker on a heating block The hyaluronic acid-paclitaxel solution was added to the paraffin and allowed to stir for 5 hours at 50° C. The contents were allowed to settle under-gravity and then washed three times with hexane. The resulted hyaluronic acid-paclitaxel microspheres (10 to 100 sum) contained 0.7% paclitaxel by weight.

Example 52

Manufacture of Paclitaxel-Loaded Crosslinked Hyaluronic Acid Microspheres

Two hundred milligrams of hyaluronic acid (sodium salt) was dissolved in 10 ml of distilled water overnight. 3.3 mg of paclitaxel (Hauser Chemical Company, Boulder, Colo.) was placed in a 2 ml homogenizer and 1 ml of water was added. The paclitaxel was hand homogenized for 2 minutes to reduce the particle size. Immediately before the experiment, the homogenized paclitaxel was added into 3.3 ml of hyaluronic acid solution and mixed together using a spatula 50 ml of light paraffin oil (Fisher Scientific) containing 250 μl of Span 80 (Fisher Scientific) was stirred at 600 rpm at 50° C. using a propeller type overhead stirrer (Fisher Scientific) in a 100 ml beaker on a heating block. The hyaluronic acid-paclitaxel solution was added to the paraffin and allowed to stir for one hours at 50° C. Then, 200 μl of a 0.02% EDA carbodimide (Aldrich) was added to the oil to initiate cross-linking of the hyaluronic acid. The hyaluronic acid microspheres were allowed to form over the next four hours. The microspheres (10 to 100 μm) were then allowed to settle under gravity and then washed three times with hexane.

Example 53

Manufacture of Paclitaxel-Loaded Hyaluronic Acid and Chemically Crosslinked Gelatin Microspheres Microspheres made with hyaluronic acid which is blended with a water soluble protein retain the biocompatibility and mucoadhesive features of hyaluronic acid in a reinforced matrix of cross-linked gelatin.

Briefly, 200 mg of hyaluronic acid was dissolved in 10 ml of water overnight at 50° C. Twenty milligrams of gelatin (bloom strength 60, Sigma) was then dissolved in this hyaluronic acid solution at 50° C. Twenty milligrams of homogenized paclitaxel was blended into the hyaluronic acid solution (as described above). One hundred milliliters of paraffin (Fisher Scientific) containing 500 μl of span 80 (Fisher Scientific) was stirred at 600 rpm at 50° C. using an overhead propeller. Five milliliters of the hyaluronic acid solution was added to the paraffin and mixture was left for 3 hours until microspheres were well formed. At this time, 300 gl of 25% glutaraldehyde was added into the stirring mixture in order to cross-link the microspheres.

Example 54

Prevention of Arthritis Onset by Paclitaxel in the CIA Rat Model

A. Materials and Methods

Syngeneic female Louvain rats weighing 120 to 150 grams were injected intradermally with 0.5 mg of native chick collagen II (Genzyme, Boston, Mass.) solubilized in 0.1 M acetic acid and emulsified in FIA (Difco, Detroit, Mich.). Approximately 9 days after immunization, animals developed a polyarthritis with histologic changes of pannus formation and bone/cartilage erosions. A total of 45 rats in 4 protocols were used: a control group (n=17) that received vehicle alone and 3 paclitaxel treatment groups consisting of a prevention and 2 suppression protocols. In order to evaluate the effect of paclitaxel, paclitaxel (solubilized in 1:1 dilution of ethanol and Cremophor®EL (Sigma) and added to saline for a final concentration of 4.8 mg/ml paclitaxel in 5% w/v ethanol and Cremophor®EL) was administered intraperitoneally (i.p.) beginning on day 2 after immunization (prevention protocol) or at arthritis onset on day 9 (suppression protocol). For the prevention protocol (n=8), paclitaxel was given at a concentration of 1 mg/kg body weight starting on day 2 with 5 subsequent doses on days 5, 7, 9, 12 and 14. For the high dose suppression protocol (n=10), paclitaxel (1 mg/kg body weight) was given on alternate days starting on day 9. In the low dose suppression protocol (n=10), paclitaxel was given at 1 mg/kg body weight on days 9, 11 and 13 and then at 75% of this does level (0.75 mg/kg body weight) on alternate days through to day 21. The control and experimental animals were evaluated for disease severity both clinically and radiographically by individuals blinded to treatment groups.

The severity of inflammation for each limb was evaluated daily and scored based on standardized levels of swelling and periarticular erythema (0 being normal and 4 severe). Animals were evaluated radiographically on day 28 of the experiment. The radiographs of both hind limbs were graded by the degree of soft tissue swelling, joint space narrowing, bone destruction, and periosteal new bone formation. A scale of 0–3 was used to quantify each limb (0=normal, 1=soft tissue swelling, 2=early erosions of bone, 3=severe bone destruction and/or ankylosis). Histological assessment of the joints was completed at the conclusion of the experiment.

Delayed-type hypersensitivity (DTH) to CII was determined by a radiometric ear assay completed on day 28. Radiometric ear indices $\geq 1.4$ represent a significant response to CII. The presence of anti-CII IgG antibodies was determined by enzyme-linked immunosorbent assay (ELISA). Serum samples obtained on day 26 were diluted to 1:2,560, and the results were expressed as the mean optical density at 490 nm, in quadruplicate aliquots. Background levels in normal rat serum at this dilution are 0 and are readily distinguishable from collagen-immunized rat serum.

B. Results

In this model, paclitaxel treatment instituted prior to arthritis onset completely precluded development of the disease in all rats treated (even after the discontinuation of paclitaxel treatment) compared with the vehicle control group.

In control animals there was a progressive increase in clinical symptoms of disease until deformity and loss of joint function occurred. Animals that received both low- and high-dose paclitaxel after the onset of arthritis demonstrated significant clinical improvement. On average, the clinical scores were equivalent to those seen at the initiation of treatment, indicating an ability of paclitaxel to prevent clinical progression of the disease.

Animals receiving paclitaxel were able to weight bear and ambulate and demonstrated few, if any toxic effects of the treatment. Wound healing and hair regrowth at the vaccination site was observed in treated animals. Paclitaxel-treated animals gained weight relative to controls.

None of the rats in the paclitaxel arthritis prevention protocol manifested any radiographic changes or clinical arthritis. Both the high- and low-dose paclitaxel groups had significantly less radiographic disease compared with control group. Further histological assessment revealed that control group rats demonstrated marked pannus, with bone and cartilage erosions, however, paclitaxel-treated rats had minimal if any pannus, with preservation of articular cartilage.

Using an ELISA assay, IgG antibodies to type II collagen were significantly lower in paclitaxel-treated rats as compared to control group; rats in the prevention protocol had significantly lower IgG antibodies when compared to the rats in the high and low paclitaxel dose suppression protocols.

C. Discussion

Paclitaxel is a viable treatment for arthritis and potentially other types of autoimmune disease since it blocks the disease process when administered after immunization but prior to arthritis onset. The results indicate that paclitaxel could completely abrogate arthritis onset if initiated 2 days after CII immunization. With paclitaxel treatment in the suppression protocol, the severity of arthritis continued to decrease throughout the duration of paclitaxel administration but began to rise within 4 days after the cessation of treatment in both suppression protocols. However, early intervention with paclitaxel appeared to attenuate the need for continuous therapy.

Example 55

Regression of Collagen-Induced Arthritis with Intraperitoneal Micellar Paclitaxel Administration Paclitaxel demonstrated disease-modifying effects in the CIA model when administered systemically in a micellar formulation. In order to evaluate the potential disease-modifying effect of paclitaxel, micellar (Cremophor-free) paclitaxel was administered intraperitoneally (i.p.), every four days (q.o.d.) at 5 mg/kg (group 1) or 10 mg/kg (group 2) to immunized animals at the onset of clinically detectable arthritis (day 9). Paclitaxel was administered throughout the evaluation period. As a comparison with standard therapy, a third group received methotrexate at 0.3 mg/kg i.p. (human equivalent dose) on days 0, 5 and 10 post-arthritis onset. A fourth group received methotrexate (0.3 mg/kg) and micellar paclitaxel (10 mg/kg) combination therapy. The control (group 5) and experimental animals were evaluated for disease severity both clinically and radiographically by individuals blinded to treatment groups.

The severity of inflammation for each limb was evaluated daily and scored based on standardized levels of swelling and periarticular erythema (0 being normal and 4 severe). Animals were evaluated radiographically on day 28 of the experiment. The radiographs of both hind limbs were graded by the degree of soft tissue swelling, joint space narrowing, bone destruction and periosteal new bone formation; a scale of 0 to 3 was used to quantify each hind limb (0=normal, 1=soft tissue swelling, 2=early erosions of bone, 3=severe bone destruction and/or ankylosis) (Brahn et al., *Arthritis Rheum.* 37: 839–845, 1994; Oliver et al., *Cell. Immunol.*, 157: 291–299, 1994). Histological assessment of the joints was completed at the conclusion of the experiment.

Figure 64:
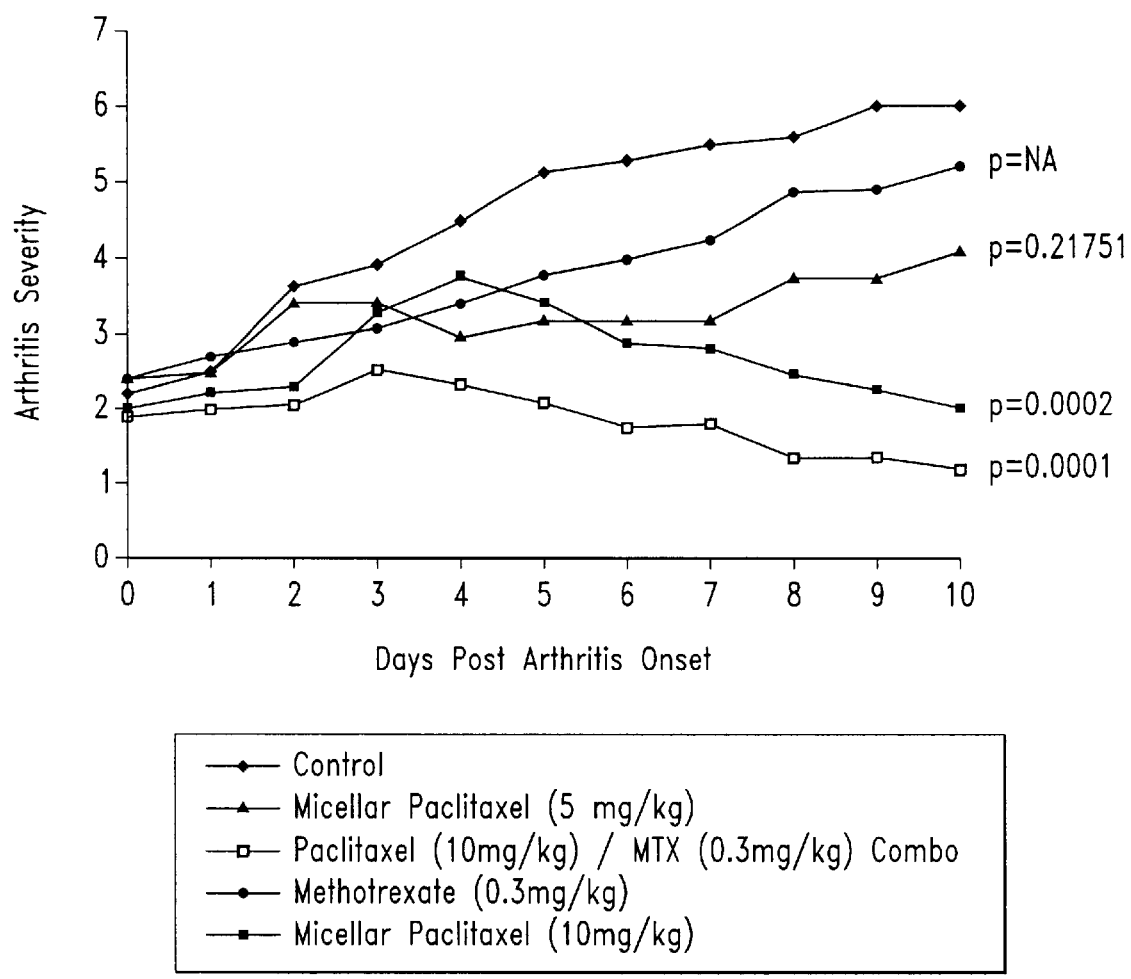
FIG. 64 is a graph which shows that micellar paclitaxel improves the daily mean arthritis scores in the collagen-induced arthritis rat model.

In this model, micellar paclitaxel treatment instituted prior to arthritis onset completely precluded development of the disease even after the discontinuance of paclitaxel treatment. In control animals, there was a progressive increase in clinical symptoms of disease (FIG. 64) until deformity and loss of joint function occurred Animals receiving methotrexate therapy were not statistically improved as compared to controls FIG. 64 & Table 1). Animals that received low dose micellar paclitaxel (5 mg/kg) after the onset of arthritis demonstrated some improvement, but animals that received doses of micellar paclitaxel at 10 mg/kg demonstrated a highly significant (p=0.0002) clinical improvement (FIG. 64). On average, the clinical scores were equivalent to those seen at the initiation of treatment, indicating an ability of micellar paclitaxel to prevent clinical progression of the disease (Table 1).

TABLE 1

Micellar Paclitaxel Improves Clinical Indices
in the Collagen-Induced Arthritis Rat Model

|  | Arthritic Index on Day 10 | Maximum Mean Arthritis Score | Antibody to Collagenase II |
|---|---|---|---|
| Arthritic Controls (n = 11) | 6.1 ± 0.6 | 6.4 ± 0.5 | 0.199 ± 0.0042 |
| Methotrexate (0.3 mg/kg) (n = 5) | 5.4 ± 0.6 (p = NS) | 5.7 ± 0.6 (p = NS) | 0.182 ± 0.0034 (p < 0.03) |
| Micellar Paclitaxel (5 mg/kg) (n = 4) | 4.3 ± 1.8 (p = NS) | 4.3 ± 1.8 (p = NS) | 0.176 ± 0.0042 (p < 0.01) |
| Micellar Paclitaxel (10 mg/kg) (n = 5) | 2.0 ± 0.7 (p = 0.0002) | 3.8 ± 0.7 (p = 0.0002) | 0.162 ± 0.0194 (p < 0.02) |
| Micellar Paclitaxel (10 mg/kg)/ Methotrexate (0.3 mg/kg) Combo (n = 7) | 1.1 ± 0.5 (p = 0.0001) | 3.6 ± 0.9 (p ≤ 0.0001) | 0.164 ± 0.0090 (p < 0.001) |

The arthritic index quantified levels of swelling and periarticular erythema, with 0 representing normal and 4 representing severe, and maximum possible score of 8 for the sum of the hind limbs. T-tests compared drug-treated rats to control collagen-induced arthritis rats at day 10 post-arthritis onset.

TABLE 1-continued

Micellar Paclitaxel Improves Clinical Indices
in the Collagen-Induced Arthritis Rat Model

|  | Arthritic Index on Day 10 | Maximum Mean Arthritis Score | Antibody to Collagenase II |
|---|---|---|---|

Clinical scores of the paclitaxel-treated animals were significantly lower than control animals and were equivalent to those seen at the initiation of treatment, indicating an ability to prevent progression of disease.
NS = not significant Animals receiving micellar paclitaxel were able to bear weight and ambulate and did not show any toxic effects of the treatment. Wound healing and hair regrowth at the vaccination site was observed in treated animals. Micellar paclitaxel-treated animals gained weight relative to untreated controls. Animals receiving both micellar paclitaxel and methotrexate tolerated the therapy well and showed impressive clinical improvement (p<0.0001), relative to controls (FIG. 64). Using an enzyme linked immunosorbant antibody (ELISA) assay, IgG antibodies to type II collagen were lower in paclitaxel and combination (MTX/paclitaxel)-treated rats as compared to controls.

Figure 65:
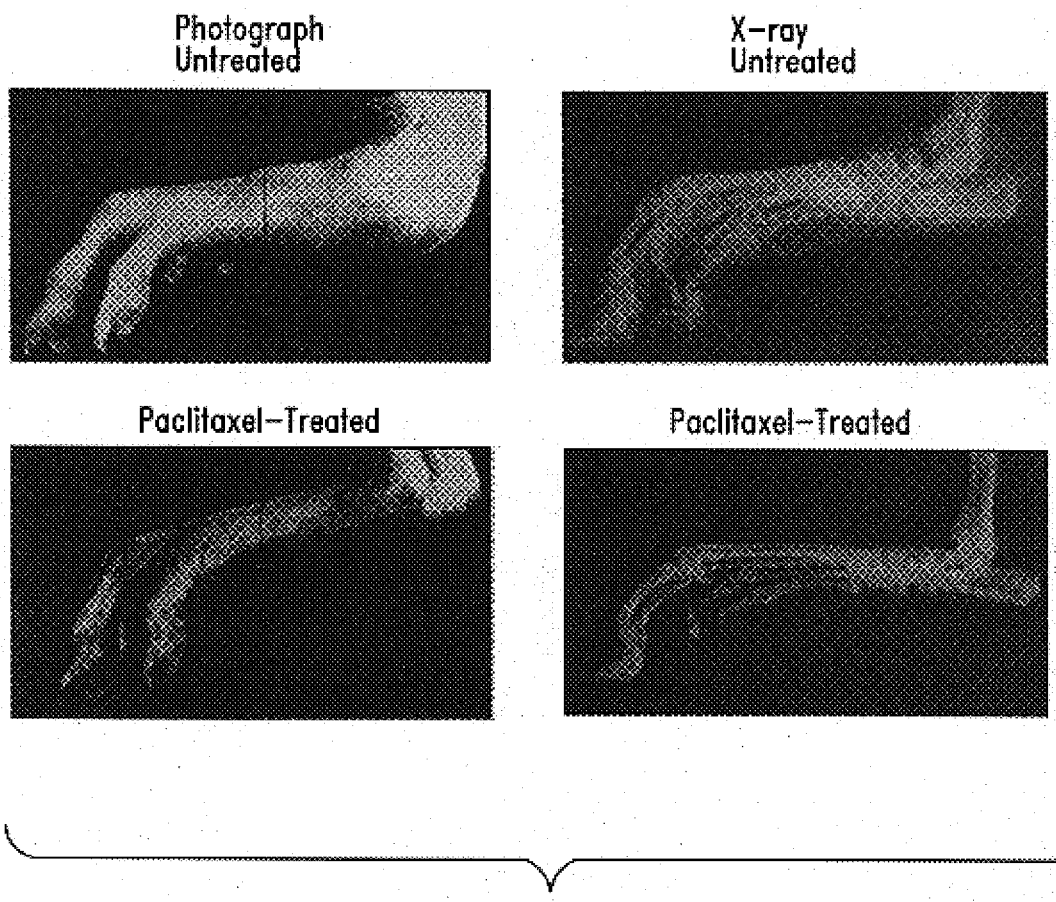
FIGS. 65A–65D are a series of x-rays which show the effect of micellar paclitaxel in the collagen-induced arthritis rat model.

Radiographic studies also demonstrated a significant improvement with paclitaxel therapy. While control and methotrexate-treated animals displayed radiographic evidence of soft tissue swelling, joint space narrowing, bone destruction and periosteal new bone formation, paclitaxel-treated animals had almost normal joint features on x-ray (FIG. 65).

In fact, only a small percentage (17 to 18%) of animals receiving micellar paclitaxel alone (10 mg/kg) or in combination with methotrexate developed cartilage erosions. Cartilage erosions, an important indicator of disease progression/outcome, occur four times more frequently in control animals (72%) or those receiving methotrexate alone than in animals receiving micellar paclitaxel therapy (Table 2).

TABLE 2

Micellar Paclitaxel Improves Radiographic
Indices in Collagen-Induced Arthritis Rats

|  | Percentage of Animals with Erosions | Radiographic Score |
|---|---|---|
| Arthritic Controls (n = 32) | 72% | 4.31 ± 0.45 |
| Methotrexate (0.3 mg/kg) (n = 17) | 76% (p = NS) | 4.25 ± 0.64 (p = NS) |
| Micellar Paclitaxel (5 mg/kg) (n = 8) | 50% (p = NS) | 3.25 ± 1.60 (p = NS) |
| Micellar Paclitaxel (10 mg/kg) (n = 18) | 17% (p = 0.0005) | 1.78 ± 0.60 (p < 0.003) |
| Micellar Paclitaxel (10 mg/kg)/ Methotrexate (0.3 mg/kg) Combo (n = 22) | 18% (p = 0.0003) | 1.45 ± 0.39 (p < 0.0001) |

Radiographs of both hind limbs, of collagen-induced arthritis (CIA) rats, were graded by the degree of soft tissue swelling, joint space narrowing, bone destruction and periosteal new bone formation. An integer scale of 0 to 3 was used to quantify each limb, with a maximum possible score of 6 from the sum of both limbs.
The presence of cartilage erosions, an important indicator of disease progression/outcome, occurs four times more frequently in control animals (72%) than in animals receiving micellar paclitaxel therapy (18%).

Figure 66A:
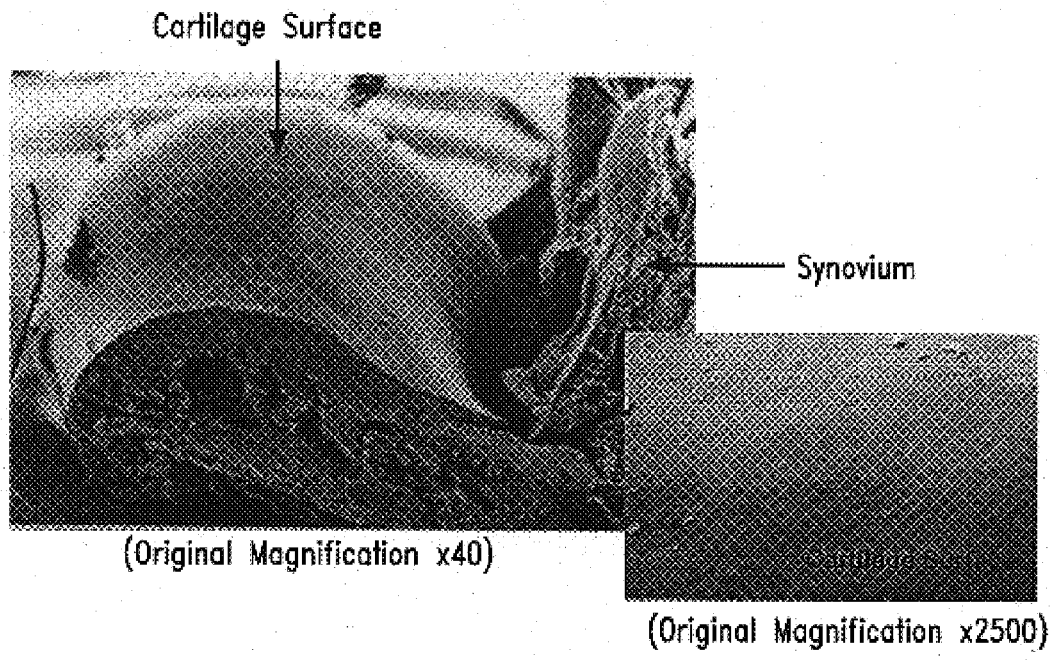
FIGS. 66A–66C are scanning electron micrographs of a rat ankle joint.
Figure 66B:
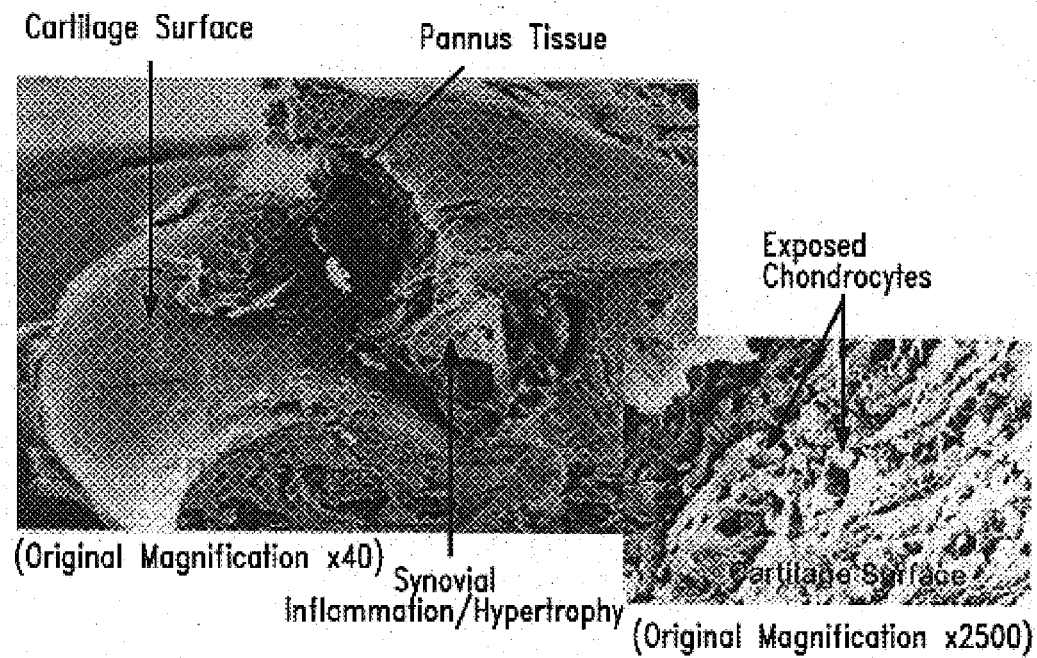
Figure 66C:
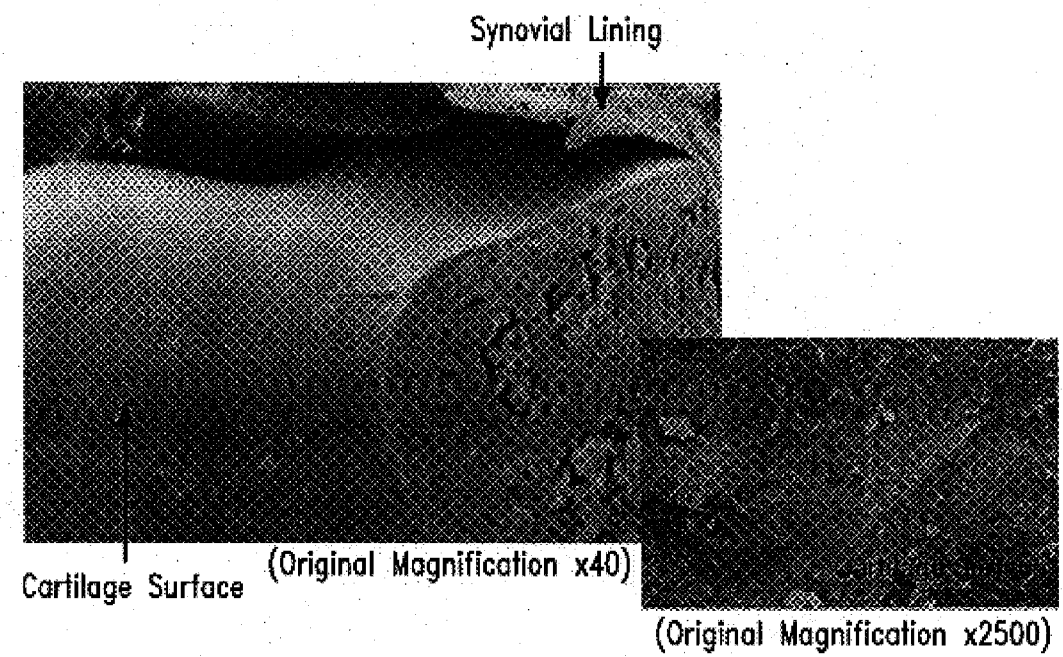

Scanning electron micrographs illustrate the chondroprotective effects of paclitaxel therapy in vivo. The normal articular surface is characterized by a smooth intact cartilage matrix surrounded by a thin synovial lining (FIG. 66A). In CIA, the cartilage surface is eroded by MMP produced by pannus tissue and an inflamed synovium (FIG. 66B). The superficial cartilage matrix is digested, exposing chondrocytes or the empty lacunae they once occupied FIG. 66B inset). In animals with CIA that received paclitaxel treatment after the onset of clinical arthritis, the joint surface remained intact (FIG. 66C) and the cartilage matrix appeared largely normal, even at high magnification (FIG. 66C inset). Pannus tissue formation and synovial hypertrophy was not seen in paclitaxel-treated groups.

Figure 67:
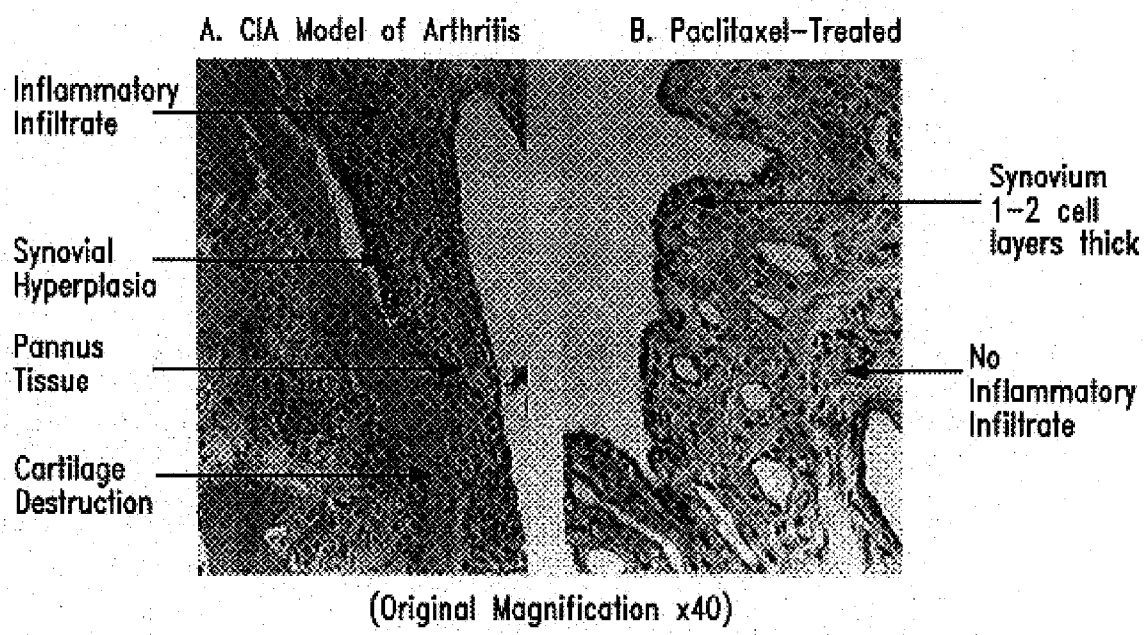
FIG. 67 is a magnified view which shows the histopathology in the collagen-induced arthritis rat model.

Histologically, CIA is characterized by marked synovial hypertrophy, inflammatory cell infiltration of the synovium and cartilage destruction (FIG. 67A). In paclitaxel-treated animals, the synovium appeared normal, with only 1–2 layers of synoviocytes and no inflammatory cell infiltrate (FIG. 67B).

Figure 68A:
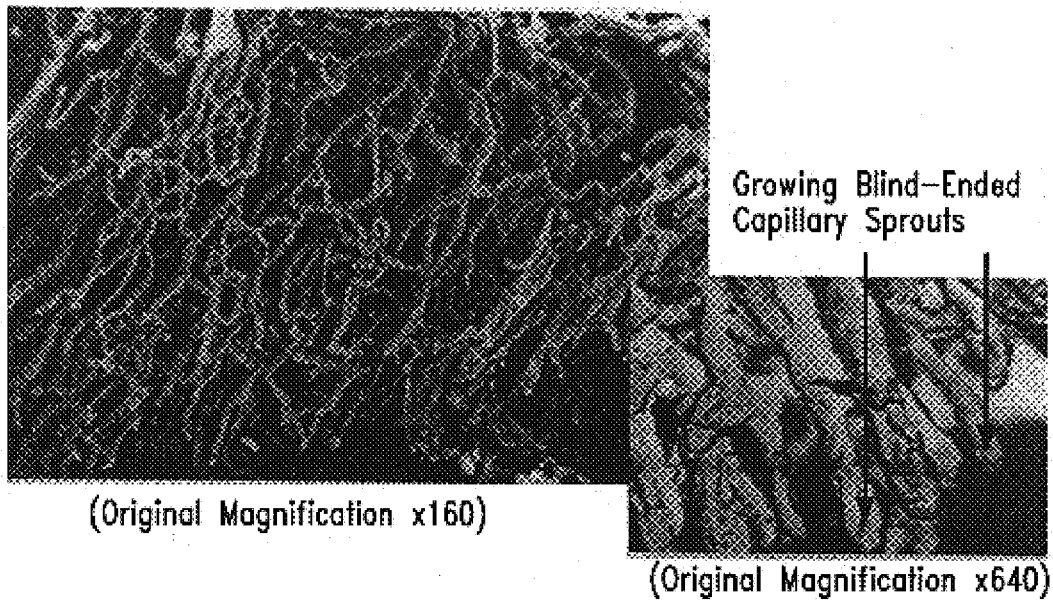
FIGS. 68A and 68B are magnified views of the synovial vasculature in the collagen-induced arthritis rat model.
Figure 68B:
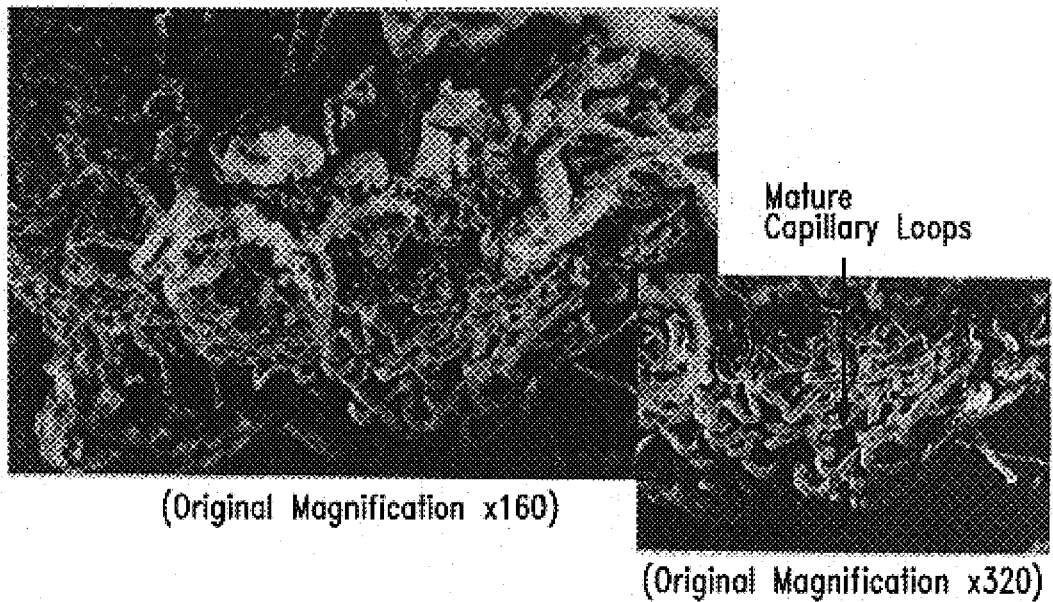

Corrosion casts were also evaluated to determine if paclitaxel was capable of blocking angiogenesis in the synovium of animals with CIA. Mercox polymer was infused into the femoral artery of sacrificed animals at a pressure of 100 mmHg, allowed to solidify in situ and the tissues subsequently digested to produce a cast of the lower limb vasculature. Scanning electron micrographs of casts of the synovial vasculature in animals with CIA revealed blind-ended capillary sprouts projecting inwards towards the joint space (FIG. 68A). These vessels appeared morphologically similar to growing angiogenic vessels described in solid tumors and other angiogenic conditions (FIG. 68A inset). In contrast, the synovial vessels of paclitaxel-treated animals were arranged in capillary loops (FIG. 68B) with no evidence of neovascular sprouts.

There was involution of vessel proliferation and morphologic vascular structures in paclitaxel/MTX recipients similar to that found in naive controls. These studies suggest that micellar paclitaxel and combination paclitaxel/methotrexate therapy, can regress neovascularization, inhibit inflammatory processes, involute established synovitis and prevent joint destruction.

It has been demonstrated that systemic administration of paclitaxel is a viable treatment for arthritis. The natural course of the disease is to flare and remit, with each successive flare resulting in additive damage which ultimately leads to joint destruction. The potential exists for short-term, higher dose, systemic therapy to be used to induce remission of the disease or sustained low dose therapy to maintain disease control. Alternative methods of delivering paclitaxel include direct intra-articular injection of the drug into afflicted joints in patients with 1 or 2 joint predominant disease.

Example 56

Regression of Collagen-Induced Arthritis with Intravenous Micellar Paclitaxel Administration A. Materials and Methods Arthritis was induced in rats under anesthesia through intradermal injection of 0.5 mg of native chick CII (Genzyme, Boston, Mass.) solubilized in 0.1 M acetic acid and emulsified in Freund's incomplete adjuvant CIA, Difco, Detroit, Mich.). Using this protocol, rats begin to develop synovitis in the hind limbs by approximately Day 9 post-immunization.

Micellar paclitaxel was constituted with 2.1 mL of 0.9% Sodium Chloride Injection, USP with heating in a water bath, to a final paclitaxel concentration of 5 mg/mL. Sufficient formulation was drawn into a 1 ml, syringe with a 26 or 28 gauge needle to deliver a volume adjusted to 0.6 ml to 0.7 ml (maximum of 2 mg/ml paclitaxel) with 0.9% Sodium Chloride Injection, USP. The entire dose was administered as a slow infusion over approximately 1 minute. CIA rats were divided into three groups consisting of a control and two micellar paclitaxel dose level groups. Both micellar paclitaxel-treated groups were dosed at 10 mg/kg on Days 0, 2 and 4. On Days 6, 9, 12 and 15, the two micellar paclitaxel-treated groups were dosed at either 5.0 mg/kg (Dose Level I, N=8) or 7.5 mg/kg (Dose Level II, N=9). The Control group (N=7) was administered control micelles equivalent to that used for the Dose Level II group. Animals were terminated on Day 18 following clinical assessment of arthritis.

The incidence and severity of arthritis in the hind limbs were quantified on a daily basis as CIA typically affects only the hind limbs. Incidence was determined according to the number of rats with clinical evidence of joint inflammation during the study. For clinical evaluation, the severity of inflammation of each hind limb ankle joint was assessed daily by an investigator blinded to the study groups, using an integer scale ranging from 0 to 4. This quantification method is based on standardized levels of swelling and periarticular erythema, with a score of 0 representing normal and 4 representing severe arthritis. The sum of the scores for the limbs (maximum number 8) is the arthritis index. An index score between 6 and 8 is considered to represent severe disease.

Hind limb radiographs were obtained on Day 18 and graded according to the extent of soft tissue swelling, joint space narrowing, bone destruction and periosteal new bone formation. An investigator who was blinded to the treatment protocol assigned radiographic scores. An integer scale of 0 to 3 was used to quantify each limb (0=normal, 1=soft tissue swelling, 2=early erosions of bone, 3=severe bone destruction and/or ankylosis). The radiographic joint index was calculated as the sum of both hind limb scores for each rat (maximum possible score of 6).

Following termination of the animals on Day 18, brain, heart, liver, kidneys, spleen, thymus, lungs and hind limbs were removed from three animals in each of the three groups and stored in formalin for histologic assessment. The samples were labeled to ensure blinded evaluation and then shipped to Pathology Associates International (P.A.I., Frederick, Md.) where they were trimmed, processed, paraffin-embedded and sectioned (5 $\mu$m thickness). Sections were stained with hematoxylin and eosin (H&E) and evaluated microscopically for tissue changes. Bone marrow was harvested from the hind limb upon arrival at P.A.I. John M. Pletcher, DVM, MPH, DACVP, analyzed all the tissue samples except the joint. A specialist in hard tissue, Rogerly Boyce, Ph.D., DVM, DACVP, analyzed the joint tissue. The final report is appended (Appendix A).

IgG antibodies to CII were measured in quadruplicate aliquots from serum obtained on Day 18 using an enzyme-linked immunosorbant assay (ELISA). Antibody titers were expressed as the absorbance at 490 nm of a 1:2560 dilution of serum normalized against a standardized curve.

The Student's t-test was used to analyze group means of continuous variables. Results were considered significant at $p<0.05$.

B. Results

There were no treatment-related deaths or episodes of diarrhea throughout the treatment period. Rats in the control and Dose Level I groups gained weight throughout the period, while the mean weight of rats in the Dose Level II group was not significantly increased at the end of the study (Table 1).

TABLE 1

Weights of Rats Treated with Micellar Paclitaxel of Control Micelles

|  | Initial Weight (g) | Final Weight (g) | Weight Change (g) | Weight Change (%) | Mean Weight Over Treatment Period (g) |
|---|---|---|---|---|---|
| Control Group (N = 7) | 122.2 ± 3.5 | 129.9 ± 2.9 | 7.8 ± 3.5 | 6.7 ± 2.9 | 126.1 ± 2.7 |
| Dose Level I Group (N = 8) | 126.0 ± 1.6 | 138.6 ± 2.0 | 12.5 ± 1.5 | 10.0 ± 1.2 | 132.3 ± 1.6 |
| Dose Level II Group (N = 9) | 127.2 ± 4.3 | 115.3 ± 13.0 | −11.9 ± 5.7 | −8.7 ± 4.1 | 121.3 ± 3.3 |

*Values are mean ± SEM

A significant reduction in arthritis severity ($p<0.05$) occurred in both micellar paclitaxel-treated groups in comparison to the control group (FIG. 82A). The significant reduction in the mean arthritis scores first occurred on Day 5 ($p<0.05$) and was maintained through to the termination of the study on Day 18 ($p<0.001$). The higher micellar paclitaxel dose regimen (Dose Level II), however, did not result in additional improvement in the daily mean arthritis score when compared to the lower dose regimen (Dose Level I).

Mean blinded radiographic scores of the rat hind limbs in the micellar paclitaxel-treated groups taken at the termination of the study were significantly reduced compared to control group ($p<0.001$, FIG. 82B). In fact, all rats in Dose Level I had radiographic scores of 0, indicating no radiographic evidence of arthritis-induced damage to the joints following the treatment protocol.

Sensitization to CII, as measured by anti-CII IgG antibodies, was evident in all treated and control groups by Day 18 (Table 2). However, the mean anti-CII antibody titer was significantly higher in the control group compared with the micellar paclitaxel-treated groups.

TABLE 2

Micellar Paclitaxel Reduces Mean Anti-CII Antibody Titer in the Collagen-Induced Arthritis Rat Model

|  | Antibody Titer to CII[a] |
|---|---|
| Control Group (N = 7) | 0.241 ± 0.005 |
| Dose Level I Group (N = 8) | 0.133 ± 0.005[b] |
| Dose Level II Group (N = 9) | 0.091 ± 0.009[b] |

[a]Mean absorbance at 490 nm of a 1:2560 dilution of serum. Values are mean ± SEM.

[b]Student's t-test was used to compare group means with control micelles ($p < 0.001$).

Blood cell indices measured at the termination of the study showed no changes in WBC count or mean cell volume; but a significant reduction in hematocrit was noted for the animals in the higher dose micellar paclitaxel group (Table 3).

TABLE 3

Micellar Paclitaxel Reduces Blood Indices in the Collagen-Induced Arthritis Rat Model

| Group | White Blood Cells (mm × $10^{-3}$) | Hematocrit (%) | Mean Corpuscular Volume (FL) |
|---|---|---|---|
| Control Group | 5.00 | 35.33 | 60.00 |
| Dose Level I Group | 3.83 | 28.23 | 65.33 |
| Dose Level II Group | 3.83 | 24.43[a] | 60.33 |

[a]Student's t-test was used to compare group means with control micelles ($p < 0.01$).

A summary of the histopathological findings is shown in Table 4. The animals in the control group showed marked inflammation involving the joint capsule, cartilage and bone, characteristic of arthritis, while the animals in the micellar is paclitaxel-treated groups did not have lesions involving their ankle joints.

TABLE 4

Histopathological Assessment of Tissues from Arthritic Rats Treated with Micellar Paclitaxel

|  | Control Group (Animal #'s 1, 2, 6) | | | Dose Level I Group (Animal #'s 8, 10, 14) | | | Dose Level II Group (Animal #'s 16, 23, 24) | | |
|---|---|---|---|---|---|---|---|---|---|
| Liver | N | N | N | HCP 1 | N | N | Inflam 2 | HCP 1 | N |
| Spleen | N | N | HCP 3 | HCP 3 | HCP 3 | HCP 3 | HCP 3 | HCP 3 | HCP 3 |
| Lung | N | Inflam 1 | Inflam 1 | N | N | Inflam 3 | Inflam 1 | Inflam 1 | Granulo 1 |
| Heart | N | N | N | N | N | N | N | N | N |
| Thymus | N | N | N | Atroph 2 | Atroph 2 | Atroph 2 | Atroph 3 | Atroph 3 | Atroph 3 |

TABLE 4-continued

Histopathological Assessment of Tissues from Arthritic
Rats Treated with Micellar Paclitaxel

|  | Control Group (Animal #'s 1, 2, 6) | | | Dose Level I Group (Animal #'s 8, 10, 14) | | | Dose Level II Group (Animal #'s 16, 23, 24) | | |
| --- | --- | --- | --- | --- | --- | --- | --- | --- | --- |
| Muscle | N | N | N | N | N | N | N | N | N |
| Kidneys | N | N | N | N | N | N | N | N | N |
| Brain | N | N | N | N | N | N | N | N | N |
| Femur | N | N | N | N | N | N | N | N | N |
| Bone Marrow | N | Hyperpl 2 | N | Hyperpl 2 | Hyperpl 2 | Hyperpl 2 | N | N | N |
| Ankle Joint | A3 | A4 | A4 | N | N | N | N | N | N |

1 = minimal; 2 = mild; 3 = moderate; 4 = marked. 'HCP' Hematopoietic cellular proliferation; 'Inflam' Inflammation; 'Atroph' Atrophied; 'Granulo' Granulocytes; 'N' normal; 'A' arthritis; 'Hyperpl' Hyperplasia.

The following is a description of the ankle lesions found in the control rats. In the control animals, the proximal joints were the most severely affected, while the more distal joints were unaffected or only minimally involved. In the proximal joints, synovial tissue was moderately to severely thickened by pockets of inflammatory cells (macrophages and neutrophils) and fibroblasts surrounded by mature collagen fibers of an eosinophilic matrix. This chronic inflammatory process continued into the adjacent tendon sheaths, periosteal tissue and, in focally extensive areas, bone and articular cartilage, which were destroyed in the process. In some areas, focal collections of neutrophils formed small abscesses within the thickened, inflamed synovial tissues. Thrombosed vessels were not readily apparent. Mitotic figures were present but appeared to be in dividing macrophages or fibroblasts. Articular cartilage appeared relatively normal in areas unaffected by chronic inflammation.

Since hematopoietic cell proliferation (HCP) is a common finding in rat spleens, its absence in the control animals is more significant than its presence in the micellar paclitaxel-treated groups. The thymic atrophy observed in the micellar paclitaxel treatment groups is characterized by a decrease in the normal number of thymic lymphocytes. Inflammation in the lungs is considered incidental, possibly related to a pulmonary pathogen within the colony. The mild bone marrow hyperplasia observed in one control and three micellar paclitaxel-treated animals is also considered incidental.

The control rats had moderate to marked arthritis in the hind limb ankle joint and no HCP in their spleens (this is a normal finding in young rats). The micellar paclitaxel-treated groups, which had no evidence of arthritis, showed mild or moderate atrophy of the thymus characterized by a reduction in the number of thymic lymphocytes present in the thymic cortex. The other lesions observed were considered to be incidental.

This study demonstrates a significant reduction of established CIA by the administration of micellar paclitaxel, as indicated by clinical, radiographic and histologic criteria.

Example 57

Evaluation of Paclitaxel Formulations in Animal Models of Psoriasis

A. Skin Angiogenesis Model

A novel animal model is used to investigate skin-specific angiogenesis. Immunuodeficient SCID mice are used as recipients for surface transplants of human keratinocyte lines transfected with vascular endothelial growth factor (VEGF) in sense or antisense orientation. Keratinocytes are transplanted via use of modified silicone transplantation chamber assay onto the skin of recipient mice. Keratinocytes are allowed to differentiate and to induce skin angiogenesis. Paclitaxel is then given either systemically or topically (cream, ointment, lotion, gel), and morphometric measurements of vessel numbers and sizes are performed in untreated and treated groups.

B. Mouse Model for Cutaneous Delayed-Type Hypersensitivity Reactions

Figure 69:
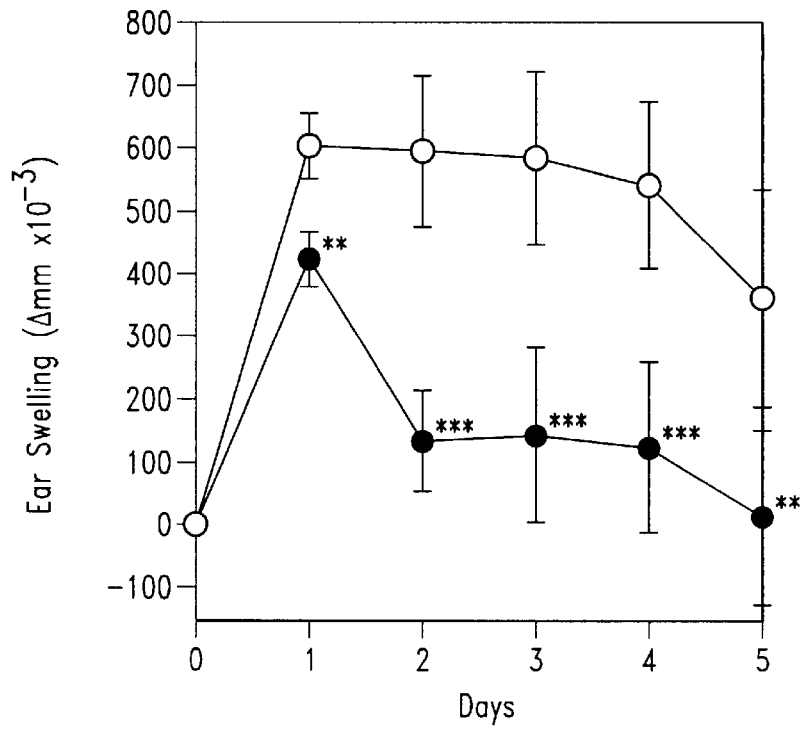
FIG. 69 is a graph which depicts the induction of contact hypersensitivity reaction in mouse ears by oxazolone. Treatment with 1% paclitaxel gel or vehicle at the time of antigen challenge and then once daily. Skin inflammation was quantitated by measurements of ear swelling as compared to pre-challenge ear thickness. Data represent means values +/–SD (n=5). $p<0.01$; * $p<0.001$.
Figure 70:
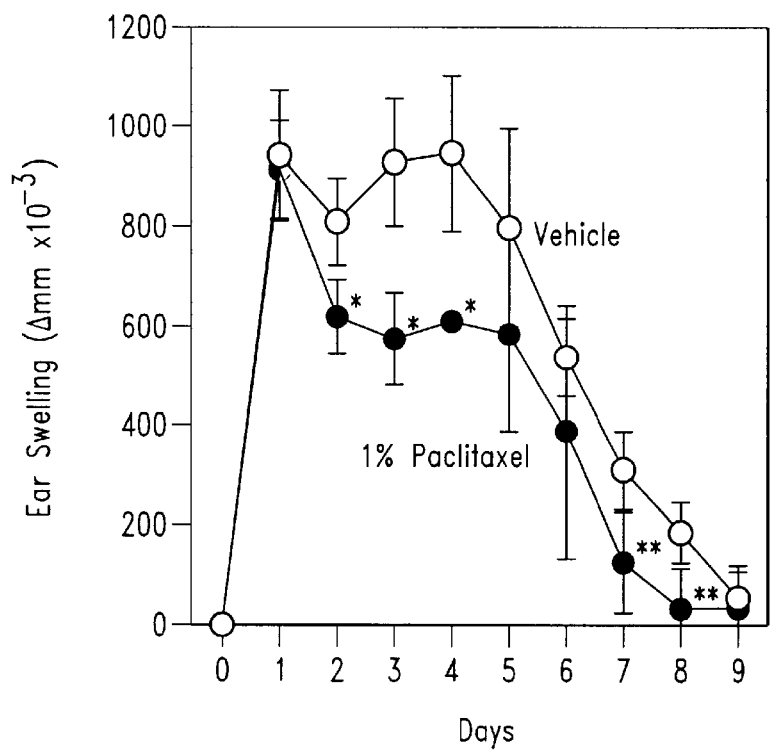
FIG. 70 is a graph which depicts the induction of contact hypersensitivity reaction in mouse ears by oxazolone. Initial treatment with 1% paclitaxel gel or vehicle at 24 hours after antigen challenge and thereafter once daily. Skin inflammation was quantitated by measurements of ear swelling as compared to pre-challenge ear thickness. Data represent mean values +/–SD (n=5). *$p<0.05$; **$p<0.01$.

The mouse model for cutaneous delayed type hypersensitivity reactions was used to investigate the effects of paclitaxel on induced skin inflammation. Briefly, mice were sensitized to oxazolone by topical application of the compound onto the skin. Five days later, mice were challenged with oxazolone by topical application onto the ear skin (left ear: oxazolone, right ear: vehicle alone), resulting in a cutaneous inflammatory, "delayed-type hypersensitivity" reaction. The extent of inflammation was quantified by measurements of the resulting ear swelling over a period of 48 hours (see FIGS. 69 and 70). Epon-embedded, Giesma-stained, 1 $\mu$m tissue sections were evaluated for the presence of inflammatory cells, for the presence of tissue mast cells and their state of activation, and for the degree of epidermal hyperplasia. Paclitaxel was given topically (formulation described in Example 18) to quantitate its effect-on the cutaneous inflammatory reaction in this in vivo model.

C. Results

Figure 71:
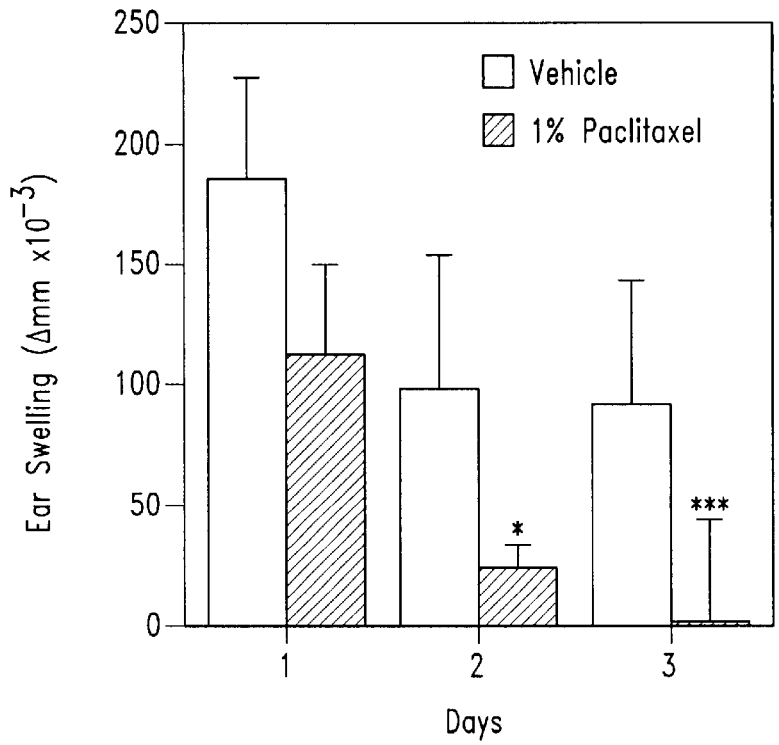
FIG. 71 is a graph which depicts the induction of skin inflammation in mouse ears by topical application of PMA. Initial treatment with 1% paclitaxel gel or vehicle at 1 hour after PMA application and thereafter once daily. Skin inflammation was quantitated by measurements of ear swelling as compared to pre-challenge ear thickness. Data represent mean values +/–SD (n=5). *$p<0.05$; *** $p<0.001$.
Figure 72:
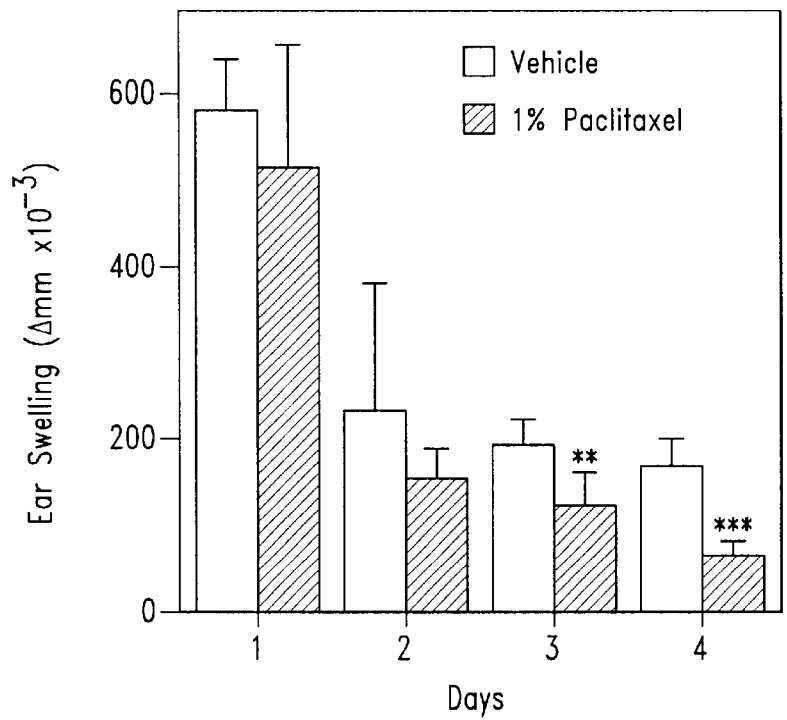
FIG. 72 is a graph which depicts the induction of skin inflammation in mouse ears by topical application of PMA. Initial treatment with 1% paclitaxel gel or vehicle at 24 hours after PMA application and thereafter once daily. Skin inflammation was quantitated by measurements of ear swelling as compared to pre-challenge ear thickness. Data represent mean values +/–SD (n=5). $p<0.01$; * $p<0.001$.
Figure 73:
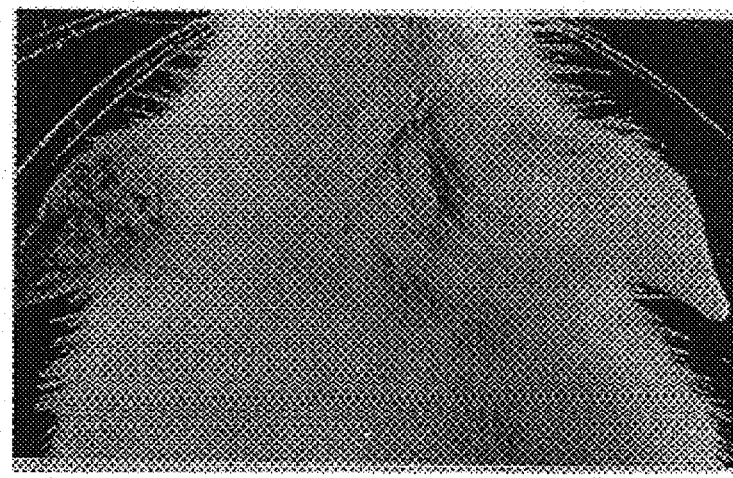
FIG. 73 illustrates induction of skin inflammation in mouse ears by topical application of PMA. Pre-treatment with 1% paclitaxel gel (right ear) or vehicle (left ear). Image was taken at 48 hours after PMA application. Note redness and dilated blood vessels of vehicle-treated left ears, as compared to paclitaxel-treated right ears. Similar results were obtained in a total of 5 mice.

These studies have shown that topical administration of 1% paclitaxel versus vehicle alone in the treatment of experimentally-induced skin inflammation in mice revealed that paclitaxel exerts inhibitory effects on skin inflammation. In experimentally-induced delayed-type hypersensitivity reactions, there was a significant decrease in ear swelling in the ears treated topically with 1% paclitaxel versus vehicle alone. Topical application of 1% paclitaxel formulation significantly inhibited ear swelling and skin erythema (redness) induced by topical application of PMA (phorbol 12-myristol 13-acetate) (see FIGS. 71 and 72). As illustrated in FIG. 73, the paclitaxel treated ear (right ear) was normal in appearance when compared to controls (left ear). Similar results were obtained in a total of 5 mice.

To assess the skin irritation of 1% paclitaxel versus vehicle alone, application of these two formulations were applied daily at 20 $\mu$l to each side of the ears for 8 days. After 8 days, there was no detection of skin irritation after application of either vehicle alone or 1% paclitaxel formulation onto normal or inflamed mouse ear skin.

Example 58

Evaluation of Chronic Rejection in an Animal Model

An accelerated form of atherosclerosis develops in the majority of cardiac transplant recipients and limits long-term graft survival. The Lewis-F344 heterotopic rat cardiac transplantation model of chronic rejection is a useful experimental model because it produces atherosclerotic lesions in stages, in medium and long-term surviving allografts. The advantages of the Lewis-F344 model are that: (i) the incidence and severity of atherosclerotic lesions in long-surviving grafts is quite high; and (ii) an inflammatory stage of lesion development is easily recognized since this system does not require immunosuppression.

Adult male Lewis rats serve as donors and F-344 rats as recipients. Twenty heterotopic abdominal cardiac allografts are transplanted by making a long midline abdominal incision in anesthetized recipients to expose the aorta and inferior vena cava. The two vessels are separated from each other and from the surrounding connective tissue and small clamps are placed on the vessels. Longitudinal incisions (2 to 3 mm) are made in each vessel at the site of anastomosis.

The abdomen of anesthetized donor rat is opened for injection of 300 units of aqueous heparin into the inferior vena cava. The chest wall is opened to expose the heart. Venae cavae are ligated, followed by the transection of the ascending aorta and main pulmonary artery, with vessel origins 2 to 3 mm in length left attached to the heart. Venae cavae distal to the ligatures are divided and the ligature placed around the mass of the left atrium and pulmonary veins. Vessels on the lung side of the ligatures are divided and the heart is removed.

The donor heart is placed in the abdominal cavity of the recipient and the aortae are sutured together at the site of incision on the recipient vessel. Similarly, the pulmonary artery is connected to the incision site on the inferior vena cava in a similar manner. Vessel clamps are released (proximal vena cava, distal cava and aorta, and proximal aorta) to minimize bleeding from the needle holes.

Following transplantation, paclitaxel (33%) in polycaprolactone (PCL) paste (n=10) or PCL paste alone (n=10) is injected through the epicardium over a length of the outer surface of a coronary artery in 10 rats, such that the artery area embedded in the myocardium remains untreated.

All recipients receive a single intramuscular injection of penicillin G (100,000 units) at the time of grafting. Allografts are followed by daily palpation and their function assessed on a scale of 1 to 4, with 4 representing a normal heartbeat and 0 the absence of mechanical activity. Five rats from each group are sacrificed at 14 days and the final five at 28 days. The rats are observed for weight loss and other signs of systemic illness. After 14 or 28 days, the animals are anesthetized and the heart exposed in the manner of the initial experiment. Coated and uncoated coronary arteries are isolated, fixed in 10% buffered formaldehyde and examined for histology.

The initial experiment can be modified for the use of paclitaxel/EVA film or coated stents in the coronary arteries following transplantation. The EVA film is applied to the extraluminal surface of the coronary artery in a similar manner as above, while the coated stent is placed intraluminally.

In addition, these investigations can be further extended to include other organ transplants as well as graft transplants (e.g., vein, skin).

Example 59

Effects of Paclitaxel in a Transgenic Animal Model of MS

The ability of paclitaxel micelles to inhibit the progression of MS symptoms and pathogenesis in a demyelinating transgenic mouse model (Mastronardi et al., *J. Neurosci. Res.* 36:315–324, 1993) was examined. These transgenic mice contain 70 copies of the transgene DM20, a myelin proteolipid. Clinically, the animals appear normal up to 3 months of age. After 3 months, evidence of neurological pathology, such as seizures, shaking, hind limb mobility, unsteadiness of gait, limp tail, wobbly gait and reduction in the degree of activity, appear and progressively increase in severity until the animals die between 6 and 8 months of age. Clinical signs correlate histologically with demyelination and increased fibrous astrocyte proliferation in the brain (Mastronardi et al., *J. Neurosci. Res.* 36:315–324, 1993).

A. Materials and Methods

Two animal studies were carried out using the ND4 transgenic mouse model: (i) a low dose micellar paclitaxel [subcutaneous (SC) administration] protocol (2.5 mg/kg; 3 times per week; total of 7 injections) and (ii) a high dose, "pulse" micellar paclitaxel [intraperitoneal (I) injection] protocol (20 mg/kg; once weekly; total of 4 injections). For both of these sets of experiments, dosing was initiated at the clinical onset of disease (approximately 3 to 4 months of age).

In the first study, a total of 10 mice [6 trasgenics, 4 normal mice (normal compliment of DM-20)] were used for the low dose protocol (2.5 mg/kg; 3 times per week; total of 7 injections) and divided into the following groups: (i) five transgenic animals received micellar paclitaxel constituted in phosphate buffered saline (PBS) alone; (ii) one control transgenic received PBS (equivalent volume); (iii) three normal mice received micellar paclitaxel in PBS; and (iv) one control normal mouse received PBS (equivalent volume). Only one transgenic mouse was used as a control since the course of the disease has been well established in the laboratory and is highly reproducible (Mastronardi et al., 1993). Animals were injected with the first dose once the initial signs of MS had reached a score of 1+ for the symptom categories described. The clinical scores and body weight were determined on each injection day and continued three times a week until the end of the study period (6 months of age). Scoring was based on a 1+ to 4+ system, whereby 1+=slight but definite signs, 2+=increase in severity, 3+=signs worsened with limited movement and 4+=very severe signs with loss of motor control (moribund).

In the second study (high dose protocol), 6 transgenic mice were treated with 20 mg/kg of micellar paclitaxel (IP) once weekly for 4 weeks to mimic interval pulse chemotherapy (given monthly for breast and ovarian cancer) as is used in oncology patients. Three additional transgenic mice were used as controls and received an equivalent dose of PBS. At the onset of treatment, all transgenics had a clinical score of 1+ in the major symptom categories. Furthermore, four normal mice were used as controls and administered equivalent volumes of PBS.

B. Results

In the first study, the clinical indicators of MS, such as shaking, hind limb mobility, seizures, head tremors, unsteadiness of gait, limp tail and degree of activity, were monitored daily. At the onset of treatment, all animals had a score of 1+ in the major symptom categories. Control transgenic animals progressed from a 1+ to a 4+ scoring over the study period in a number of symptoms; 3+ was characterized by poor balance, one of the major features of the disease. In the micellar paclitaxel-treated group, all five animals remained at a score of 1+ over the same period in all of the symptoms monitored (Table 1).

TABLE 1

Low Dose Continuous Micellar Paclitaxel Treatment Inhibits the Progression of Multiple Sclerosis Symptoms in Transgenic Mice

|  | Seizures | Shaking | Hind Limb Paralysis | Head Tremors | Weight Change (%) |
|---|---|---|---|---|---|
| Normal Mice Control (n + 1) | 0 | 0 | 0 | 0 | 0 |
| Normal Mice Paclitaxel Treated (n + 3) | 0 | 0 | 0 | 0 | −0–5% |
| Transgenic Mice Control (n = 1) | 2+–3+ | 2+–3+ | 2+–4+ | 3+ | −30–5% |
| Transgenic Mice Paclitaxel Treated (n = 5) | 1+ | 1+ | 1+ | 1+ | +5–10% |

Mice (transgenic and normal) were given either micellar paclitaxel (2.5 mg/kg; 3 times per week; 7 injections) or equivalent volumes of PBS (control) and monitored for symptom severity until the termination of the study (6 months of age).
Control transgenic animals had severe symptoms at the end of the study period (as shown in the table), whereas micellar paclitaxel-treated mice had minimal neurological symptoms at this time.
A score of 1+ means definite but minimal signs; 4+ is moribund.

Figure 74:
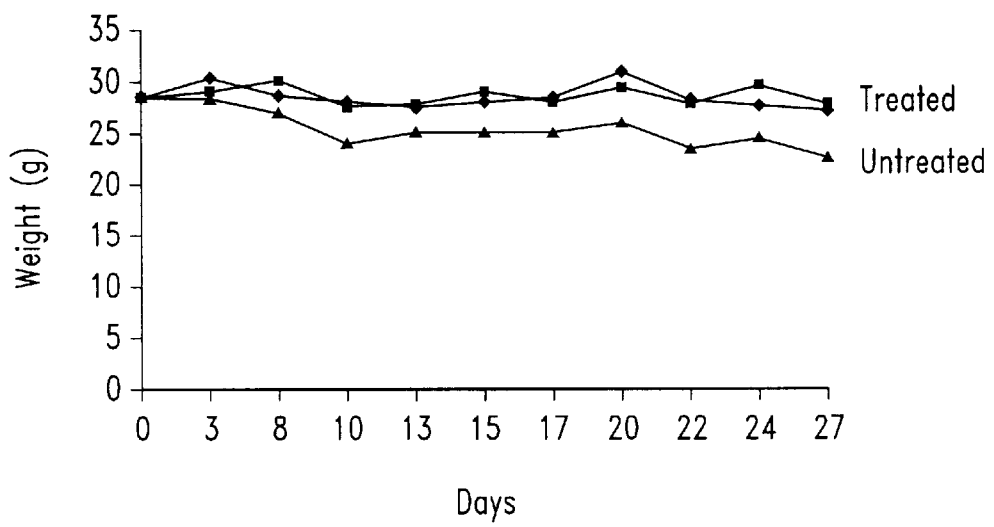
FIG. 74 is a graph which depicts the effect of paclitaxel on body weight of DM20 transgenic mice. Transgenic mice were treated with vehicle or paclitaxel (2.0 mg/kg) three times weekly for 24 days and then sacrificed on day 27. The results are for two animals treated with paclitaxel and one untreated animal. Paclitaxel treated animals demonstrated minimal weight loss, whereas control animals showed a 30% decrease in body weight, from 29 g to 22 g.

The five transgenic animals that received micellar paclitaxel did not lose any weight and, in fact, gained an average of 5% to 10%. However, the untreated transgenic mouse showed a 30% decrease in body weight, from 29 g to 22 g FIG. 74), as is normally associated with progression of the disease. At the conclusion of the study period (6 months of age), brain tissue was removed from each mouse and processed according to the protocol for the evaluation to be conducted (i.e., measurement of enzyme activity, electron microscopy and protein staining).

Figure 75:
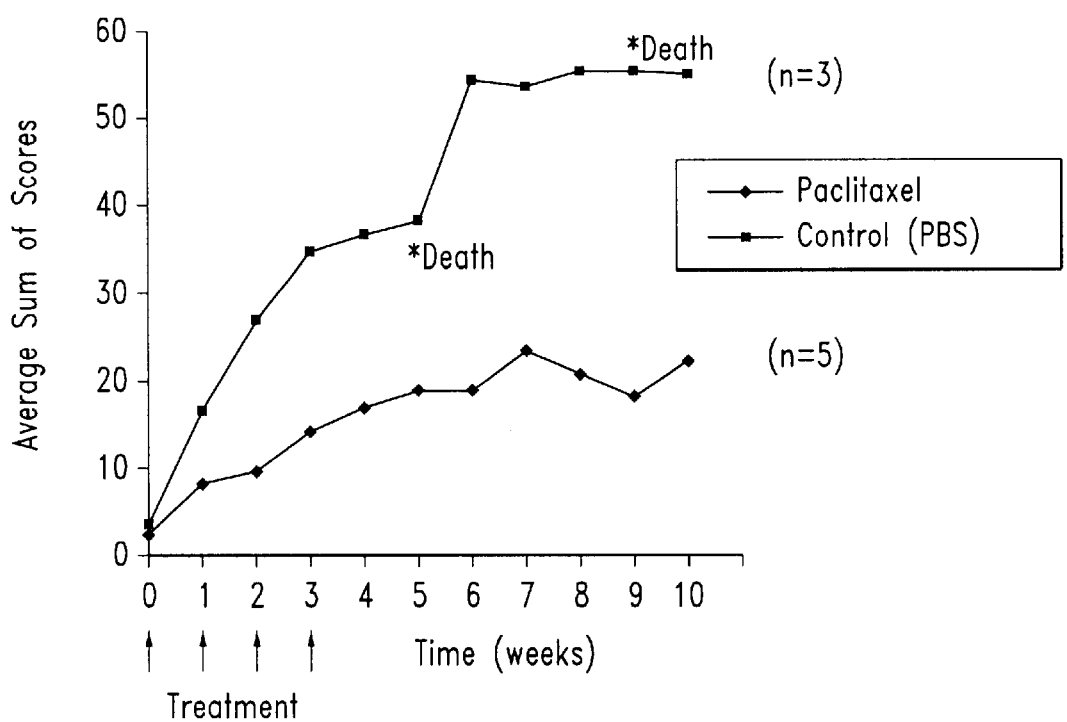
FIG. 75 is a graph which depicts the effect of high dose interval paclitaxel therapy on the progression of clinical symptoms in transgenic mice. Transgenic mice were treated with 20 mg/kg paclitaxel once weekly for 4 weeks (week 0, 1, 2 and 3) and monitored for 10 weeks, every two days, with scores determined for each symptom. The data represents the average score (cumulative for all symptoms) for paclitaxel treated transgenic mice (n=5) and control mice (n=3). Paclitaxel treatment reduced the deterioration caused by overexpression of DM20 in transgenics, whereas control mice deteriorated very rapidly with 2 out of 3 animals not surviving to the end of the experimental protocol (as indicated).

In the second study, the animals were monitored until six months of age, three times per week, and scores determined for each symptom. In the three control transgenic animals, neurological symptoms progressed rapidly and two of the mice died (on week 5 and week 9) before the termination of the study; the third animal had severe clinical symptoms. In the six transgenic animals receiving micellar paclitaxel treatment, there was a reduction in MS scores relative to controls after the first week of treatment and, thereafter, further neurological deterioration was not observed In these animals, disease progression was not observed and the animals remained clinically in remission both during therapy (weeks 0 to 3) and subsequent to cessation of micellar paclitaxel administration (weeks 4 to 10) (FIG. 75).

C. Conclusions

Micellar paclitaxel prevented the rapid progression of neurological symptoms observed in this demyelinating transgenic animal model with both subcutaneous low dose administration and intraperitoneal high dose, pulse therapy. These data suggest that micellar paclitaxel would be an effective treatment of human demyelinating diseases, such as MS.

Example 60

Effects of Paclitaxel in an Experimental Autoimmune Encephalomyelitis (EAE) Animal Model of MS Active EAE was induced in female Lewis rats (250 g) of 7 to 8 weeks of age by subcutaneous injection into the hind footpad. Each rat was injected with 50 μg of guinea pig myelin basic protein (GPMBP) peptide, GP68–88, emulsified in complete Freund's adjuvant (CFA) containing 4 mg/ml mycobacterium tuberculosis H37RA (Difco, Detroit, Mich.). The animals were weighed daily and observed for clinical indices which typically peak at Day 12 to 14 post-immunization. The severity of EAE was scored according to the following clinical scale: 0, no clinical signs; 1+, mild tail weakness; 2+, complete loss of tail movement and/or hind limb paresis; 3+, moderate hind limb paralysis; 4+, total hind limb paralysis; 5+, moribund or death.

Micellar paclitaxel was constituted with 2.1 ml of 0.9% Sodium Chloride Injection, USP, with heating in a water bath to produce a final paclitaxel concentration of 5 mg/ml. The dose (10 mg/kg) was administered as a bolus i.p. on Days 6 and 8 after EAE induction to 2 rats while 4 rats received PBS as control. The rats were evaluated on Day 14 (time of peak disease clinical index in control EAE-induced animals.)

All animals survived the treatment protocol. Micellar paclitaxel-treated animals had minimal weight loss during the study relative to PBS-treated controls (Table 1, FIG. 83A).

TABLE 1

Micellar Paclitaxel Prevents Weight Loss in Rats Induced with Active Experimental Autoimmune Encephalomyelitis

|  | Initial Weight (g) | Day 14 Weight (g) | Weight Change (%) |
|---|---|---|---|
| Active EAE Rats Control (N = 4) | 249.7 ± 10.6 | 223.2 ± 9.7 | −10.6 ± 0.4 |
| Active EAE Rats Micellar Paclitaxel-Treated (N = 2) | 252.0 ± 22.0 | 244.0 ± 18.0 | −3.1 ± 1.3 |

Myolin basic protein peptide (50 μg) was subcutaneously injected into rats to induce active experimental autoimmune encephalomyelitis (EAE).
Micellar paclitaxel (10 mg/kg) was administered intraperitoneally (Days 6 and 8) to 2 rats while 4 rats were treated with PBS alone (control).
Values are mean ± SEM.
Micellar paclitaxel-treated rats had minimal weight loss whereas rats in the control group suffered more severe weight loss. Weight loss as represented on the day of maximal clinical score.

Figure 83A:
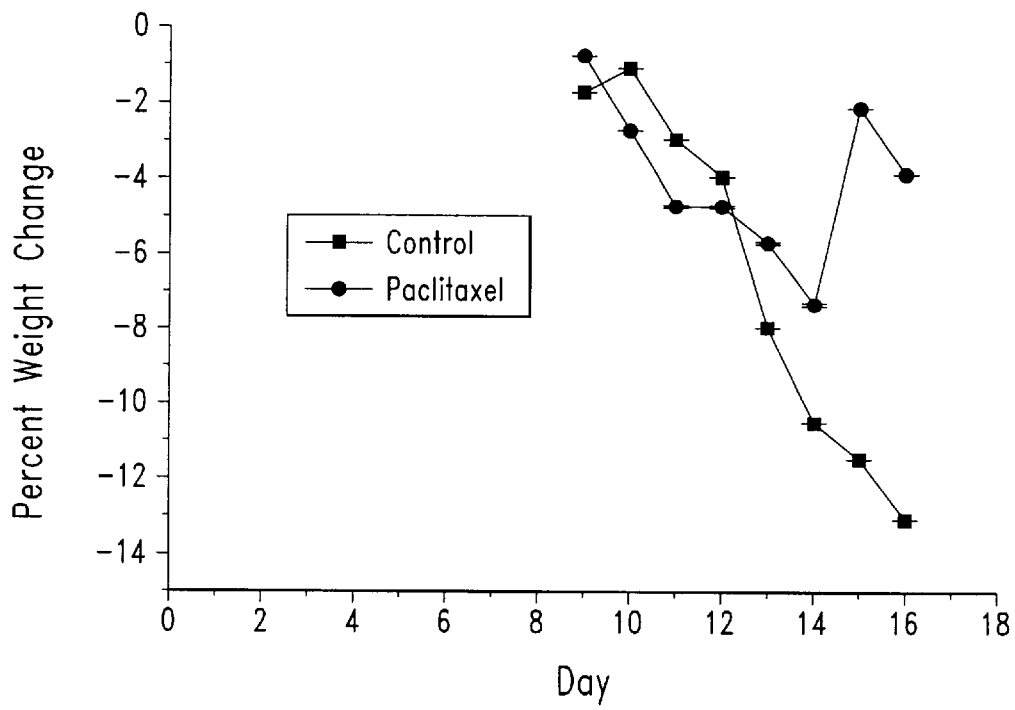
Figure 83B:
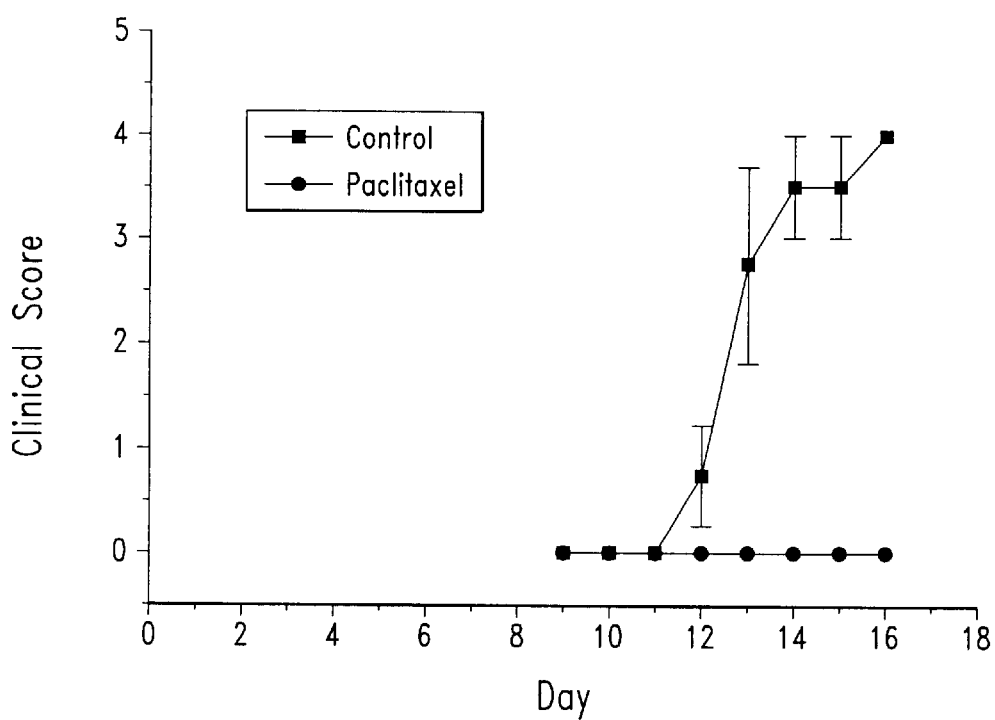
Figure 83C:
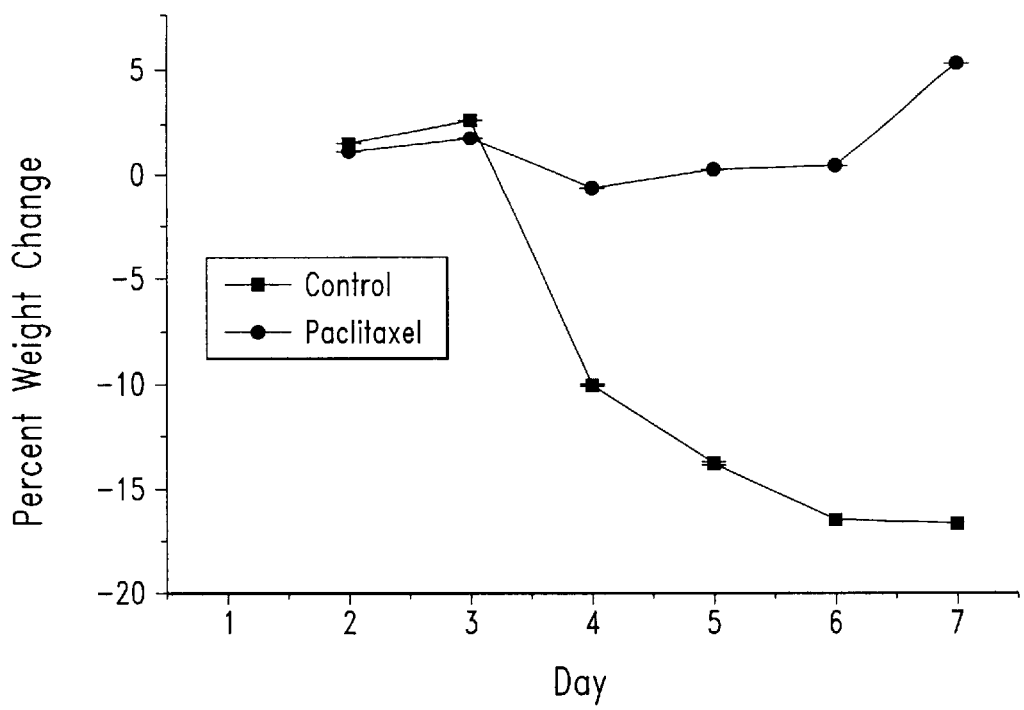

Comparison of the clinical score between the two groups showed a dramatic increase in clinical score involving significant hind limb paralysis through the study in the control group. The micellar paclitaxel-treated animals had a clinical score of 0, and thus prevented the development of MS symptoms in this model (FIG. 83B).

To induce passive transfer of EAE to recipient rats, a GPMBP specific T cell line (LR88L1) was stimulated with GPMBP (20 μg/ml) for 3 days in the presence of irradiated syngeneic thymocytes. Activated T cells were isolated and each recipient rat received 5×10⁶ T cells i.p. suspended in PBS. In this model, clinical indices typically peak at Days 5 to 6 post-immunization. Micellar paclitaxel (10 mg/kg) was administered i.p. on Days 1 (24 hours after injection of T cells) and 3 after EAE induction to 3 rats while an additional 3 rats received PBS as control. Rats were evaluated on Day 7 and clinical scores assigned.

The control animals lost weight through the study. In fact, control rats suffered fulminating disease and two animals died on Day 7 post-immunization. There was no corresponding weight loss in the micellar paclitaxel-treated group (Table 2, FIG. 83C).

TABLE 2

Paclitaxel Suppresses Weight Loss in Passively Transferred Experimental Autoimmune Encephalomyelitis Rats

|  | Initial Weight (g) | Day 7 Weight (g) |
|---|---|---|
| Passive EAE Rats Control (N = 3) | 159.7 ± 3.2 | 133* |
| Passive EAE Rats Micellar Paclitaxel-Treated (N = 3) | 158.0 ± 4.3 | 166 ± 4.0 |

Myelin basic protein-activated T cells (5 × 10$^6$) were injected intraperitoneally into rats to passively induce experimental autoimmune encephalomyelitis (EAE). EAE animals were administered 10 mg/kg (IP; Days 1 and 3) micellar paclitaxel or PBS.
Values are mean ± SEM.
*Two animals died on Day 7.

Figure 83D:
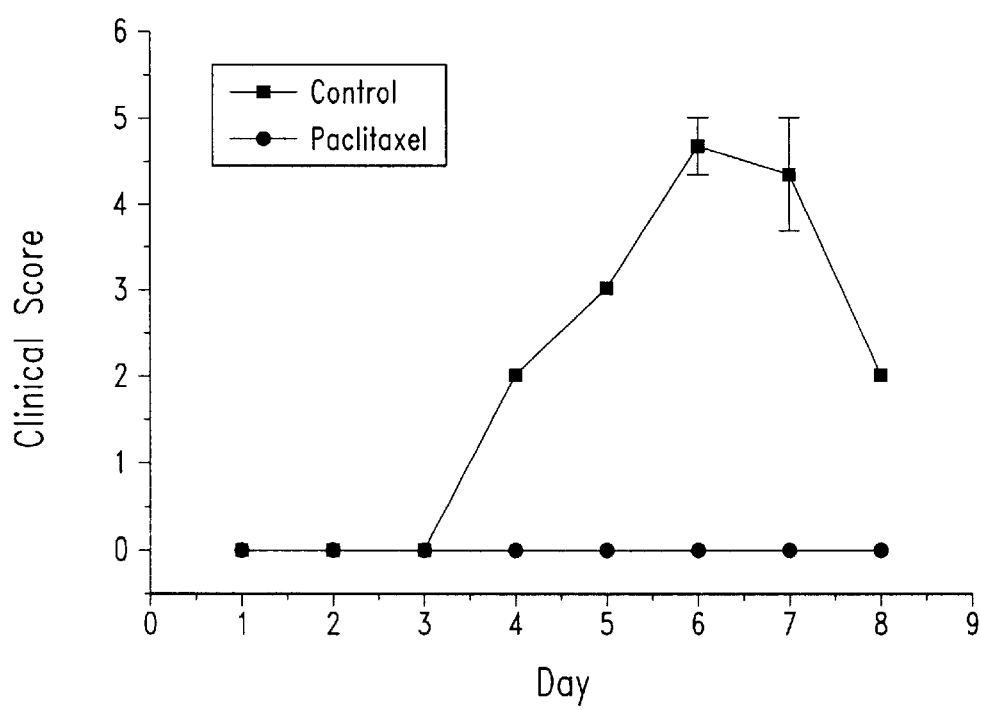

The clinical scores of the control group increased rapidly through to Day 7 while micellar paclitaxel prevented the onset of clinical symptoms (FIG. 83D).

In summary, these studies demonstrate that treatment with micellar paclitaxel suppresses the progression of clinical symptoms associated with demyelination and thus provides support for the use of micellar paclitaxel in the treatment of MS in patients.

Example 61

Evaluation of Paclitaxel and Other Microtubule Stabilizing Agents for the Treatment of Nasal Polyps Epithelial cell cultures and/or nasal polyp tissue cultures are used to evaluate the efficacy of formulations containing paclitaxel or other agents in the treatment of nasal polyps. This approach is based on the premise that epithelial cells release cytokines and contribute to chronic inflammation detected in nasal polyposis as well as in rhinitis and asthma and that a prolonged release medication will prevent eosinophilia and inhibit cytokine gene expression.

Paclitaxel formulations including solutions (the use of cyclodextrins) or suspensions containing paclitaxel encapsulated into mucoadhesive polymers for use as nasal sprays, and/or micro-encapsulated paclitaxel in mucoadhesive polymers are used as insufflations. These formulations are used in the studies detailed below.

A. Effect of Paclitaxel In Vitro

Tissue handling—Normal nasal mucosal (NM) specimens are obtained from patients with no clinical evidence of rhinitis and negative skin-prick test during nasal reconstructive surgery. Nasal polyp (NP) specimens are obtained from patients with positive and negative skin-prick test undergoing nasal polypectomy. The nasal specimens are placed in Ham's F12 medium supplemented with 100 UI/ml penicillin, 100 µg/ml streptomycin and 2 µg/ml amphotericin B and immediately transported to the laboratory.

Epithelial cell culture—Nasal epithelial cells from NM and NP are isolated by protease digestion as follows. Tissue specimens are rinsed 2–3 times with Ham's F12 supplemented with 100 UI/ml penicillin, 100 µg/ml streptomycin and 2 µg/ml amphotericin B and then incubated in a 0.1% protease type XIV in Ham's F12 at 4° C. overnight. After incubation, 10% FBS is added to neutralize protease activity and epithelial cells are detached by gentle agitation. Cell suspensions are filtered through a 60 mesh cell dissociation sieve and centrifuged at 500 g for 10 minutes at room temperature. The cell pellet is then resuspended in hormonally defined Ham's F12 culture medium (Ham's HD) containing the following reagents: 100 UI/ml penicillin, 100 µg/ml streptomycin, 2 µg/ml amphotericin B, 150 µg/ml glutamine, 5 µg/ml transferin, 5 µg/ml insulin, 25 ng/ml epidermal growth factor, 15 gg/ml endothelial cell growth supplement, 200 pM triiodothryonine and 100 nM hydrocortisone. Cell suspensions (10$^5$ cells/well) are then plated on collagen coated wells in 2 ml of Ham's HD and cultured in a 5% $CO_2$ humidified atmosphere at 37° C. Culture medium is changed at day and subsequently every other day. Monolayer cell confluence is achieved after 6–10 days of culture.

Human epithelial conditioned media (HECM) generation—When epithelial cell cultures reached confluence, Ham's HD is switched to RPMI 1640 medium (Irvin, Scotland) supplemented with 100 UI/ml penicillin, 100 µg/ml streptomycin, 2 µg/ml amphotericin B, 150 µg/ml glutamine and 25 mM Hepes buffer (RPMI 10%). HECM which is generated after 48 hours of incubation with RPMI (10%) is harvested from cultures, centrifuged at 400 g for 10 minutes at room temperature (RT), sterilized by filtration through 0.22 µm filters and stored at −70° C. until used.

Eosinophil survival and effect of paclitaxel—Eosinophils are isolated from the peripheral blood and the effect of HECM from both NM and NP on eosinophil survival is determined in two different ways: time-course and dose response analyses. In time-course experiments, eosinophils at a concentration of approximately 250,000/ml are incubated in six well tissue cultures with or without (negative control) 50% HECM and survival index assessed at days 2, 4, 6 and 8. Other experiments are conducted with 1 to 50% HECM. In experiments where the effect of drugs (e.g., paclitaxel) on HECM-induced eosinophil survival is tested, the drug (paclitaxel) from 0.1 nM to 10 µM is incubated with eosinophils at 37° C. over 1 hour before the addition of HECM. In each experiment, negative control (culture media only) and positive control (culture media with HECM) wells are always assessed. To investigate whether the drugs have any toxic effect, the viability of eosinophils incubated with the drug (various concentrations) are compared with eosinophils cultured with RPMI 10% alone over 24 hour period.

B. Effect of Paclitaxel on Cytokine Gene Expression and Release From Epithelial Cells Epithelial cells obtained from nasal polyps and normal nasal mucosa are cultured to confluence, human epithelial cell conditioned media generated with or with paclitaxel (or other agents) and supernatants are measured by ELISA. Cytokine gene expression is investigated by reverse transcription-polymerase chain reaction (RT-PCR) as described by Mullol et al., *Clinical and Experimental Allergy* 25:607–615, 1995.

The results show whether paclitaxel modulates cytokine gene expression as a means of inhibiting eosinophil survival. The main disadvantage of using primary cell cultures is that it takes 10 days for the cells to reach confluence, dissociating cellular functions from local melieu as well as systemic effects, which would have led to the disease in the first place. However, this is an excellent in vitro/ex vivo model to study the growth factors regulating the function and proliferation of structural cells (e.g., epithelial cells) and thereby elucidate some aspects of mucosal inflammation.

C. Immunologic Release of Chemical Mediators from Human Nasal Polyps

Mediation by paclitaxel and other agents—Polyps are obtained at the time of resection and are washed 5 times with Tyrode's buffer and fragmented with fine scissors into replicates about 200 mg in wet weight. The replicates are suspended in 3 ml buffer containing various concentrations of paclitaxel at 37° C. and challenged (5 minutes later) with 0.2 µg/ml of antigen E. After 15 minutes incubation with the antigen, the diffusates are removed and the tissues boiled in fresh buffer for 10 minutes to extract the residual histamine. The histamine and SRS-A released are assayed using HPLC.

Example 62

Perivascular Administration of Agents that Disrupt Microtubule Function

Studies have been conducted to evaluate the efficacy of paclitaxel-camptothecin loaded surgical paste (PCL) and/or an EVA film as a perivascular treatment for restenosis.

A. Materials and Methods

WISTAR rats weighing 250 to 300 g were anesthetized by the intramuscular injection of Innovar (0.33 ml/kg). Once sedated they were then placed under Halothane anesthesia After general anesthesia was established, fur over the neck region was shaved, the skin clamped and swabbed with betadine. A vertical incision was made over the left carotid artery and the external carotid artery exposed. Two ligatures were placed around the external carotid artery and a transverse arteriotomy was made. A number 2 French Fogarty balloon catheter was then introduced into the carotid artery and passed into the left common carotid artery and the balloon inflated with saline. The endothelium was denuded by passing the inflated balloon up and down the carotid artery three times. The catheter was then removed and the ligature tied off on the left external carotid artery.

Rats were randomized into groups of 10 to receive no treatment, polymer alone (EVA film or PCL paste), or polymer plus 20% paclitaxel. The polymer mixture (2.5 mg) was placed in a circumferential manner around the carotid artery. The wound was then closed. Five rats from each group were sacrificed at 14 and the final five at 28 days. In the interim, the rats were observed for weight loss or other signs of system illness. After 14 or 28 days, the animals were anesthetized and the left carotid artery was isolated, fixed with 10% buffered formaldehyde and examined histologically.

As a preliminary study, two rats were treated with 10% camptothecin-loaded EVA film for 14 days to assess camptothecin's efficacy in this disease model.

B. Results

Figure 76A:
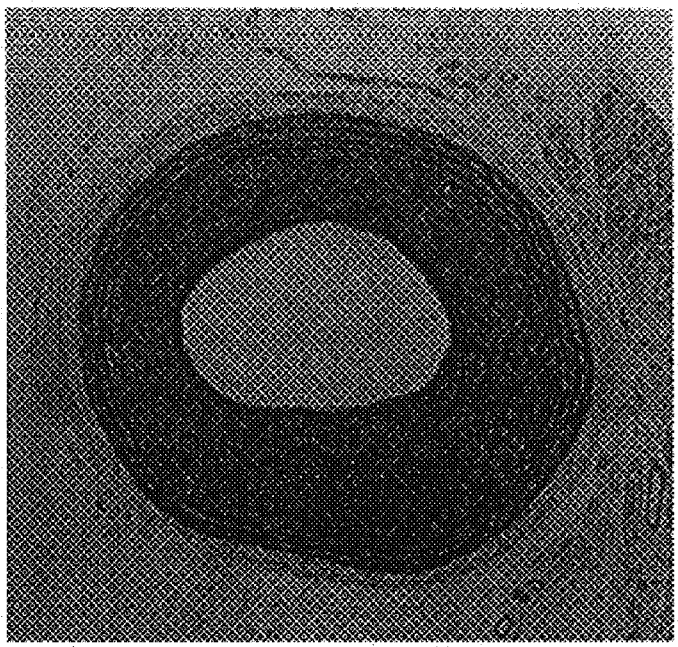
FIGS. 76A and 76B show paclitaxel paste applied perivascularly (to the adventitia of the blood vessel) in the rat carotid artery model. The adventitial surface of the left common carotid artery was treated with 2.5 mg of either control paste (76A) or 20% paclitaxel-loaded paste (76B). Control arteries displayed an increase in the thickness of the arterial wall due to smooth muscle cell hyperproliferation, whereas the artery treated with paclitaxel-loaded paste did not show evidence of intimal thickening.
Figure 76B:
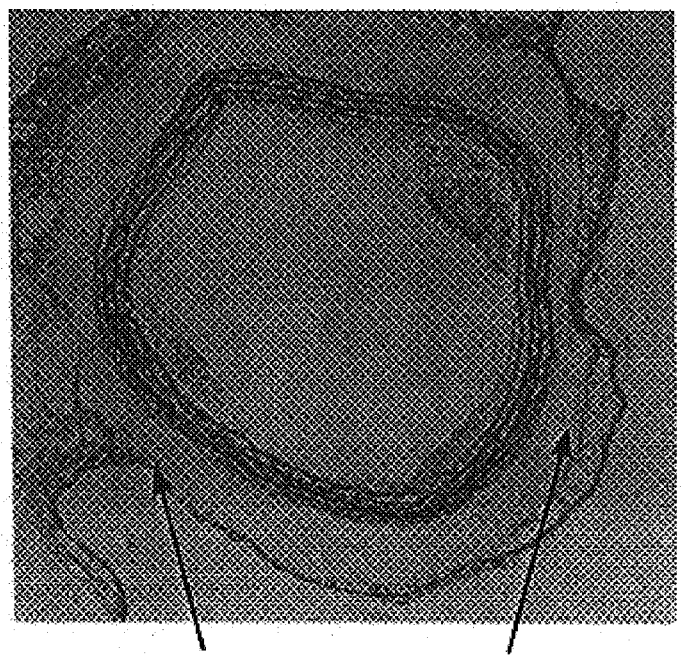

Results from these studies revealed that paclitaxel-loaded (20%) polymers completely prevented restenosis whereas the control animals and the animals receiving polymer alone developed between 28% and 55% luminal compromise at 14 and 28 days post-balloon injury (FIGS. 76A and 76B).

Figure 77:
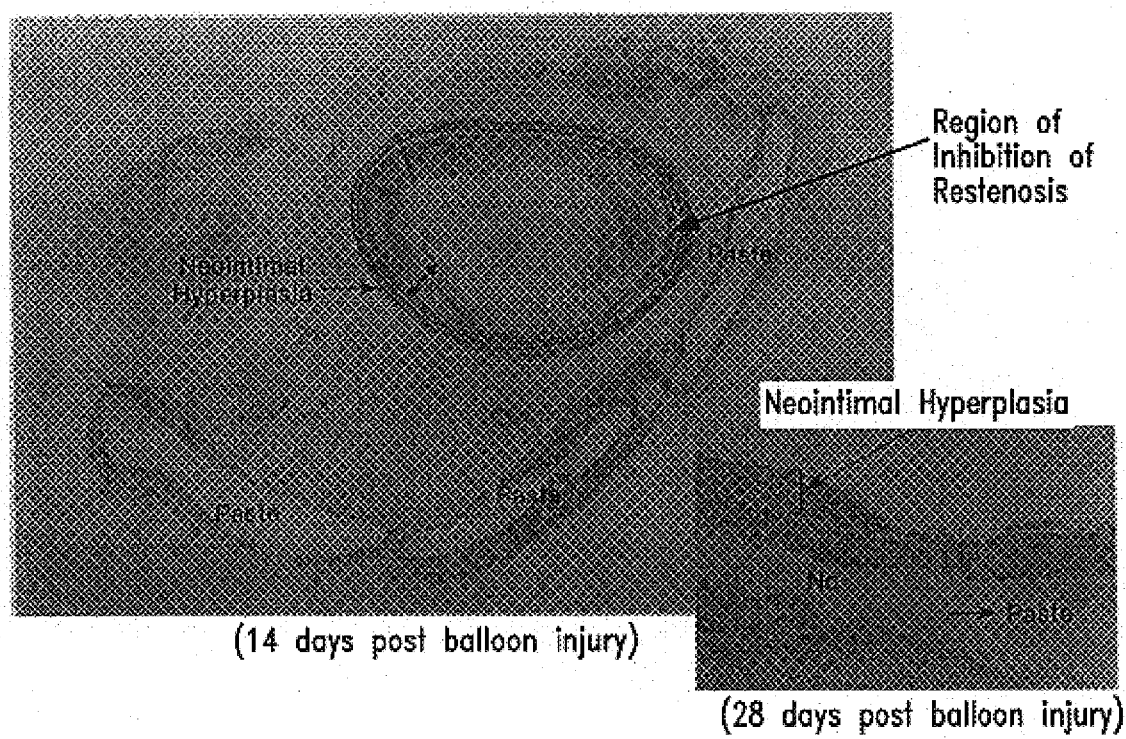
FIGS. 77A and 77B depict the proximity effect of perivascular paclitaxel paste in the rat carotid artery model.

There was an absolute inhibition of intimal hyperplasia where paclitaxel was in contact with the vessel wall. However, the effect was very local as evidenced by the uneven effect of paclitaxel where there was an inability to maintain the drug adjacent to the vessel wall (FIGS. 77A and 77B).

Preliminary data has shown that camptothecin-loaded EVA film was efficacious in preventing a restenotic response in this animal model of disease. Camptothecin completely inhibited intimal hyperplasia in the two animals tested.

Example 63

Effects of Paclitaxel in an Animal Model of Surgical Adhesions

The use of a paclitaxel-loaded PCL film to reduce adhesion formation is examined in the rabbit uterine horn model.

A. Methods

The rabbit uterine horn model was conducted essentially as described by Wiseman et al., 1992 (*Journal of Reproductive Medicine,* 37:766–770), with hemostasis. New Zealand female white rabbits were anesthetized and a midline incision made through the skin and the abdominal wall. Both uterine horns were located and exteriorized. Using a French Catheter Scale, the diameter of each uterine horn was measured and recorded. Only those rabbits with uterine horns measuring size 8 to 16, inclusive, on the French scale were used. Using a number 10 scalpel blade, 5 cm lengths of each uterine horn, approximately 1 cm from the uterine bifurcation, were scraped, 40 times per side, until punctuate bleeding. Hemostasis was achieved by tamponade.

Animals were randomized to receive: no treatment (Surgical Control); polymer Vehicle Control; paclitaxel (0.1% in vehicle); and paclitaxel (1% in vehicle). Test agent (0.4 to 2.5 ml) was applied over the horns via an 18 gauge needle. Uterine horns were replaced into the pelvis and the abdominal incision closed.

At 18, 31, 32, 33 and 60 days after surgery, animals were euthanized by intravenous injection of sodium pentobarbital (120 mg/ml; 1 ml/kg). Body weights of the animals were recorded. The abdomen was opened and the surgical site inspected. Adhesions were graded by a blinded observer as follows:

Extent of Adhesions

The total length (cm) of each uterine horn involved with adhesions was estimated and recorded.

Tenacity (Seventy) of Adhesions

Adhesions were grades as 0 (absent), 1.0 (filmy adhesions) and 2.0 (tenacious, requiring sharp dissection).

Degree of Uterine Convolution

The degree of uterine convolution was recorded according to the following scale:

No convolution: Straight lengths of adherent or non-adherent horns which are clearly discerned.

Party convoluted: Horns have adhesions and 50%–75% of the horn length is entangled preventing discernment of straight portions.

Completely convoluted: It is impossible to discern uterine anatomy because the horn is completely entangled.

B. Results

All animals maintained or gained weight during the study period. By inspection, there appeared to be no differences in average weight gain between the groups.

By inspection the extent of adhesion formation did not appear to vary with the time, in each group. Thus data for each group have been pooled. Adhesions formed in surgical controls to an extent consistent with historical data for this model. Paclitaxel exhibited a dose-dependent reduction in the extent of adhesions from 4.781±0.219 cm in the Vehicle Control Group (N=8) to 2.925±0.338 cm (p<0.05) and 2.028±0.374 cm (p<0.01) in the 0.1% (N=10) and 1% (=9) paclitaxel groups, respectively (Table 1).

TABLE 1

Effect of Paclitaxel on Adhesion Formulation in a Rabbit Uterine Horn Model

| Group | Extent[1] | Adhesion-Free[2] | Convolution[3] | N |
|---|---|---|---|---|
| B. Vehicle Control | 4.781 (0.219) | 0/16 | 3/6/7 | 8 |
| D. 0.1% paclitaxel | 2.925 (0.338)* | 0/20 | 16/2/2† | 10 |
| A. 1% paclitaxel | 2.028 (0.374)** | 0/18 | 18/0/0‡ | 9 |

TABLE 1-continued

Effect of Paclitaxel on Adhesion Formulation
in a Rabbit Uterine Horn Model

| Group | Extent[1] | Adhesion-Free[2] | Convolution[3] | N |
|---|---|---|---|---|
| C. Surgical Control | 2.700 (0.407)** | 0/20 | 16/2/2† | 10 |

[1]Length of uterine horn with adhesions, cm (± Standard Error of the Mean)
[2]Number of uterine horns free of adhesions/total
[3]Number of uterine horns with no convolution/partial convolution/full convolution
*p < 0.05 (Dunnett's test); p < 0.01 *Student's t-test) vs Vehicle Control unequal variance
**p < 0.01 (Dunnett's test), vs Vehicle Control
†p = 0.0031 (Fisher's Exact Test), vs Vehicle Control. Convolution classed as Present/Absent $x^2$ = 8.251
‡p = <0.0001 (Fisher's Exact Test), vs Vehicle Control, Convolution classed as Present/Absent $x^2$ = 17.07

The degree of uterine convolution was also reduced in the 0.1% paclitaxel (p=0.0031) and 1% paclitaxel (p<0.0001) groups.

Example 64

Micellar Paclitaxel in the Treatment of Inflammatory Bowel Disease (IBD)

Inflammatory bowel disease (IBD), namely Crohn's disease and ulcerative colitis, is characterized by periods of relapse and remission. The best available model of IBD is produced in the rat by the intracolonic injection of 2,4,6-trinitrobenzene sulphonic acid (TNF) in a solution of ethanol and saline (Morris et al., Gastroenterology 96:795–803, 1989). A single administration initiates an acute and chronic inflammation that persists for several weeks. However, pharmacologically, the rabbit colon has been shown to resemble the human colon more so than does the rat (Gastroenterology 99:13424–1332, 1990).

Female New Zealand white rabbits are used in all experiments. The animals are anesthetized intravenously (i.v.) with pentobarbitol. An infants' feeding tube is inserted rectally, so that the tip is 20 cm proximal to the anus, for injection of the TNF (0.6 ml; 40 mg in 25% ethanol in saline). One week following TNF administration, the rabbits are randomized into 3 treatment groups. At this time, the animals receive either no treatment, micelles alone (i.v.) or micellar paclitaxel (i.v.). This is repeated every 4 days for a total of 4 treatments.

During the course of the study, rabbits are examined weekly by endoscopy using a pediatric bronchoscope under general anesthesia, induced as above. Damage is scored by an endoscopist (blinded) according to the following scale: 0, no abnormality; 1, inflammation, but no ulceration; 2, inflammation and ulceration at 1 site (<1 cm); 3, two or more sites of inflammation and ulceration or one major site of inflammation and ulceration (>1 cm) along the length of the colon.

Following the last treatment, the rabbits are sacrificed with Euthanol at 24 hours and 1, 2, 4 and 6 weeks. The entire colon is isolated, resected and opened along the anti-mesenteric border, washed with saline and placed in Hank's balanced salt solution containing antibiotics. The colon is examined with a stereomicroscope and scored according to the same criteria as at endoscopy. As well, specimens of colon are selected at autopsy, both from obviously inflamed and ulcerated regions and from normal colon throughout the entire length from anus to ascending colon. The tissues are fixed in 10% formaldehyde and processed for embedding in paraffin; 5 (m sections are cut and stained with hemotoxylin and eosin. The slides are examined for the presence or absence of IBD histopathology.

The initial experiment can be modified for the use of oral paclitaxel following induction of colitis in rabbits by the intracolonic injection of TNF. The animals are randomized into 3 groups receiving no treatment, vehicle alone or orally formulated paclitaxel.

Example 65

Effect of Paclitaxel in an Animal Model of Systemic Lupus Erythematosus

Paclitaxel's efficacy in systemic lupus erythematosus is determined by treating female NZB/NZW $F_1$ mice (B/W) with micellar paclitaxel. This strain of mice develops disease similar to human SLE. At one month of age, these mice have an elevated level of spleen B-cells spontaneously secreting immunoglobulin compared to normal mice. High levels of anti-ssDNA antibody occurs at 2 months of age. At five months of age, immunoglobulin accumulates along glomerular capillary walls. Severe glomerulonephritis evolves and by 9 months of age, 50% of B/W mice are dead.

A. Materials and Methods

Female B/W mice are purchased from The Jackson Laboratory (Bar Harbor, Me., USA). Five-month-old female B/W mice are randomly assigned into treatment and control groups. Treatment groups receive either a low dose continuous micellar paclitaxel (2.0 mg/kg; 3 times per week, total of 10 injections) or a high dose "pulse" micellar paclitaxel (20 mg/kg; four times, once weekly). The control group receives control micelles.

At predetermined time intervals, paclitaxel treated and untreated control B/W mice of comparable age are sacrificed, their spleens removed aseptically and single cell suspensions are prepared for lymphocyte counts. To identify spleen lymphocyte subpopulations, fluorescence analysis is conducted. The number of cells/million spleen B-cells spontaneously secreting immunoglobulin (IgG, IgM, total immunoglobulin) or anti-ssDNA antibody is determined using ELISA.

Example 66

Clinical Study to Assess the Safety and Tolerability of Micellar Paclitaxel for the Treatment of Multiple Sclerosis A. Study Design Fifteen patients will be studied first at the low dose of micellar paclitaxel (25 mg/m$^2$) and fifteen at the higher dose of micellar paclitaxel (50 mg/m) for a total of 30 patients. Patients will receive a dose of 25 or 50 mg/m$^2$ infused over 1 to 2 hours, at monthly intervals for a total of 6 treatments.

Prior to the treatment of micellar paclitaxel, each patient will be treated with a premedication regimen of 100 mg hydrocortisone (i.v.), 50 mg diphenylhydramine (i.v.) and 300 mg cimetidine or 50 mg ranitidine (i.v.) 30 to 60 minutes before treatment with micellar paclitaxel. As the dose to be used in the study will be ⅕ to ⅒ of the dose of paclitaxel that can be used in cancer chemotherapy, and as the frequency of dosing will be every 30 days as opposed to 21 days, a correspondingly lower incidence of side effects is expected. If necessary, the dose can be decreased by one-half according to tolerance of the patient and at the discretion of the treating oncologist, although this is to be avoided as much as possible as it will constitute a protocol deviation.

Concomitant therapies will be permitted. If a patient develops a superimposed relapse, treatment with 1000 mg methylprednisolone (i.v.) for 4 days will be performed. A tapering two week course of oral prednisone is also permitted. Other temporary medications will be allowed except those affecting immune system function.

B. Evaluation and Testing

At the pre-enrollment visit, patients will have a laboratory examination to assess haematology, clinical chemistry and urinalysis. A baseline MRI with galolinium, multimodal evoked potentials, ECG and chest x-ray will also be done prior to initiation of the treatment phase of the study. At the pre-enrollment visit, a medical history and physical examination including comprehensive neurologic exam will be completed for each patient. Women of child-bearing age must have a negative serum pregnancy test prior to study enrollment. Functional and neurological testing, including 9BPT, timed 25 foot walk, PASAT, neurologic rating score (NRS), FS and EDSS will also be completed for each patient. The patient will also be questioned if he/she has any known allergies, if he/she has any symptoms of concurrent disease and if he/she takes any concomitant medication.

At each monthly follow up, patients will have laboratory examination to assess for safety and tolerability which will consist of haematology, clinical chemistry and urinalysis. A CBC will be obtained 2 weeks after all treatments and reviewed by the oncologist. The oncologist who infuses the drug will obtain blood test results prior to micellar paclitaxel infusion. The drug will not be infused if significant neutropenia (<2000), leukopenia (<4000), thrombocytopenia (<100,000), anaemia (<11 g/dl) or any other significant illness is present which in the judgment of the oncologist could worsen with micellar paclitaxel administration.

During the treatment phase of the study, patients will return monthly for a total of 6 months. At each return visit, clinical chemistry, haematology, urinalysis and pregnancy test will be performed.

The study nurse will review the study treatment, adverse events, use of concomitant medication and have the pharmacology activity assessment forms, such as the quality of life instrument filled out. The oncologist will monitor and treat adverse events. The neurologist will perform FS, EDSS and NRS, and manage neurologic symptoms. The study nurse will perform the timed ambulation, 9 hole peg test and PASAT (Functional testing).

The termination visit will occur 24 months after treatment onset (18 months after the patient completes the 6 month treatment phase). Patients will be seen monthly for the first 6 months (treatment phase) and then followed-up at Months 7, 9, 12, 15, 18, 21 and 24. Clinical and lab examinations identical to the treatment phase will be performed at each post-treatment visit. If a patient develops a life-threatening side effect, or persistent significant haematologic abnormalities, treatment will be discontinued although they will continue to come for all scheduled visits and tests.

At 6, 12, 18 and 24 months, MRI studies will be performed. If an interim analysis on the data at 9 months does not suggest a hint of efficacy in terms of suppression of gadolinium enhancement of MS lesions, than the patient will not complete the MRI studies scheduled after Month 6. ECG and chest X-ray is mandatory at enrolment and termination. ECG, chest x-ray and other tests will be performed whenever needed for investigation of suspected side effects. Multimodal evoked potentials will be performed at baseline, the end of year 1 and year 2.

C. Enrollment

Patients between the ages of 18–65 will be eligible for enrollment in this study if they present with secondary, progressive MS with progression over the last 18 months. The patients must have a EDSS between 3 and 6.5 inclusive and have evidence of MS on the enrolment cranial MRI according to the Fazekas or Paty criteria. Patients must be willing to undergo repeated cranial MRI studies during the course of the study.

Patients must not be enrolled in this study if they present with primary progressive MS or if they have a MS relapse within 30 days before the pre enrolment visit or between pre-enrolment and enrolment visits. If the patient is treated with chronic therapies primarily acting on the immune system within 90 days of the pre-enrolment visit (chronic high dose steroids, Methotrexate, Colchicine, Cyclophosphamide, Cyclosporin, Interferon-beta, Copolymer 1, IVIG) or between pre-enrolment and enrolment visits, the patient must not be enrolled in this study. For Cladribine, the exclusion is permanent. Patients must not be receiving treatment with any other investigational drug during this study. If the patient has received prior treatment with total radiation or treatment with plasma exchange within 90 days of the pre enrolment visit or between pre-enrolment and enrolment visits, the patient cannot be enrolled in this study. Also, patients having received temporary steroid therapy within 30 days of their pre-enrolment visit cannot receive micellar paclitaxel. Patients expected to remain on treatment with any contraindicated medication (chronic Prednisone) can also not receive micellar paclitaxel. Also, if patients have a known hypersensitivity to Gadolinium-DTPA or Taxol, they must not be treated with micellar paclitaxel.

Patients with prior history of severe immune suppression or current neutropenia (<1500 cells/cc) or thrombocytopenia (<100,000/cc) must not receive micellar paclitaxel. If patients have serious intercurrent illness, including neurologic disease other than MS which could interfere with the assessment of treatment effect, such as Sjögren's syndrome or stroke, they must not be enrolled in this study.

Women that are pregnant, currently breast feeding a baby, or are unwilling to practice reliable methods of contraception, including use of oral contraceptives, IUD or sterilization, and women unwilling to subject themselves to regular pregnancy testing must not be enrolled in this study.

Example 67

Clinical Study to Assess Safety and Tolerability of Micellar Paclitaxel for the Treatment of Rheumatoid Arthritis A. Study Design Patients with a diagnosis of RA who have failed at least one DMARD will be eligible for participation in the study. Fifteen patients will be randomized into the following groups: 4 Controls (control micelles and premedication) with the option to be crossed-over to Dose Level I at the end of the third treatment or thereafter if disease is stable or progressing as defined by ACR criteria N=4 maximum); 6 Dose Level I (25 mg/m$^2$) with the option to be crossed-over to Dose Level II at the end of the third treatment if the disease is stable or progressing (N=3 maximum); and 5 Dose Level II (50 mg/m$^2$). All patients will be premedicated with hydrocortisone, diphenhydramine and cimetidine or ranitidine. The clinical investigator and study coordinator, who will conduct and monitor clinical scoring, will be blinded to the study. Treatment of patients in the Dose Level I group and Dose Level II group will consist of 6 monthly 1 hour infusions of micellar paclitaxel. Patients on NSAID must have been on a stable regimen for at least 1 month prior to entry, and should remain on stable NSAID for at least 1 month post-infusions as well. Otherwise, patients will receive the standard of medical care in the investigator's opinion. Patients will be monitored for study endpoints at defined intervals in the study.

All patients will be pretreated with hydrocortisone, diphenhydramine and cimetidine or ranitidine approximately 1 hour prior to treatment with either control micelles or micellar paclitaxel. Treatment must be given 30 to 60 minutes prior to initiation of treatment infusion. The following regimen is required:

Hydrocortisone: 100 mg (i.v.), 30 to 60 minutes prior to test article

Diphenhydramine: 50 mg (i.v.), 30 to 60 minutes prior to test article

Cimetidine at 300 mg (i.v.) OR Ranitidine at 50 mg (i.v.), 30 to 60 minutes prior to test article.

At each treatment day (Day 0, Months 1, 2, 3, 4 and 5) and each follow-up visit (Months 6 and 12), 5.0 ml of blood and 20 ml of urine will be collected and stored frozen. These samples will be used to assay markers of disease activity and/or progression by measuring cytokine, adhesion molecule and/or growth factor levels.

Dosing schedule may vary by ±5 days and laboratory testing schedules may vary by ±5 days. After conclusion of treatment, follow-up evaluation visits may occur within ±7 days of the targeted day. The following is a list of samples to be collected from patients for both routine and specialized laboratory tests:

Baseline #1
  (i) Chemistry, Hematology, Urinalysis
  (ii) ESR
  (iii) CRP
  (iv) Serum pregnancy test (bHCG)
  (v) Radiographs
  (vi) Plasma/Serum and Urine Sample
  (vii) Each Treatment Day (Day 0, Months 1, 2, 3, 4 and 5)
  (viii) Chemistry, Hematology
  (ix) ESR
  (x) CRP
  (xi) Tender joint count
  (xii) Swollen joint count
  (xiii) Duration of morning stiffness
  (xiv) Physician and Patient Global Assessment
  (xv) Visual Analog Pain Scale
  (xvi) SF-36
  (xvii) HAQ
  (xviii) AIMS
  (xix) Plasma/Serum and Urine Sample B. Evaluation and Testing Baseline visit #1 will occur at least 28 days prior to the first infusion to allow for the necessary 1 month washout period if the patient is on a DMARD regimen. If the patient is not on a DMARD regimen, then baseline visit #1 will occur at least 10 days prior to the first infusion of the test article. A complete medical history and physical examination will be obtained as well as urinalysis and screening blood tests, which include: blood chemistries (including liver function tests and creatinine) and hematology (CBC, differential, platelets, Westergren ESR and CRP). An ECG and chest x-ray is required prior to treatment. Women of childbearing potential must have a negative serum pregnancy test prior to treatment, and should be apprised of the potential risks. Patients whose clinical and laboratory findings fulfill the inclusion criteria will be notified and infusion scheduled.

At baseline visit #1, a physical examination and complete medical history of the patients will be done. Interim history and a relevant physical examination of the patients will be completed at each treatment day and at 6 and 12 months. At Day 0, all patients will have a tender joint count, swollen joint count, patient's assessment of pain, patient's global assessment of disease activity and physician's global assessment of disease (ACR Disease Activity Measures). At Day 0 and Months 6 and 12, radiographs of affected joints (hands and feet) will be obtained. Vital signs will be obtained prior to dosing. Treatment vital sign monitoring will be done at 15 minute intervals during infusion and, if stable, at 30 minute intervals during post-infusion observation. Patients will be treated on Day 0, Months 1, 2, 3, 4 and 5, and follow up visits will occur at Months 6 and 12. In addition, the patients will be monitored for safety at 7 days post-infusion. Assessments will be completed for both safety and clinical response criteria at each treatment visit and follow-up visit, as defined below.

(i) Chemistry, Hematology
  (ii) ESR
  (iii) CRP
  (iv) Tender joint count
  (v) Swollen joint count
  (vi) Duration of morning stiffness
  (vii) Physician and Patient Global Assessment
  (viii) Visual Analog Pain Scale
  (ix) SF-36
  (x) HAQ
  (xi) AIMS The patient must be assessed carefully during the first 30 minutes of infusion as well as 1 hour post-infusion. Vital signs need to be taken at 15 minute intervals during infusion and, if stable, at 30 minute intervals during post-infusion observation.

Adverse events will be tabulated and frequencies of events will be determined, overall and by dosing group. All events with a WHO Grading of Acute and Subacute Toxicity of Grade 3 or above will be tabulated by event, as well as tabulations for all events that have been determined to be possibly or probably related to the test article. Laboratory analyses (chemistries, hematology) will consist of measurements of change from baseline over time by patient and overall, with plots of actual values compared to normal values for patients by dose group. Logarithmic transformations may be applied as necessary. Group means and standard errors will be calculated for the various laboratory parameters. The various Visual Analog Scales will be analyzed by computing change from baseline and over time to determine any potential degradation in overall function. Concurrent illnesses will be listed and examined as possible confounders in the treatment response relationship. Concurrent medications will also be listed. Effects from premedications and effects of previous treatments for RA and any potential related side effects will be analyzed and discussed.

Response has been defined by a series of measures related to RA defined to be consistent with the ACR 20% improvement criteria for RA, consisting of the following measures: joint tenderness count, joint swelling count, ESR, CRP, morning stiffness, Patient global assessment scale, Physician global assessment scale, Visual Analog Pain Scale, HAQ and AIMS. Changes in pain scale, morning stiffness, joint tenderness count and joint swelling count over time will be calculated as change from baseline by dose group and overall. Trend analysis may also be used to assess various parameters over time. Correlations of various measures will be performed to determine important and significant responses.

C. Enrollment

Patients enrolled in this study must have RA fulfilling 1987 ACR revised criteria and have an ACR revised 1991 Functional Class I to III. Patients must have active RA as defined by 10 swollen and $\geq 12$ tender joints, ESR=28 or CRP=0.8 mg/dL or morning stiffness>45 minutes. Patients enrolled in this study must be aged between 21 to 65 years and have failed treatment with at least one DMARD. Patients will be eligible for this study if they have no major concurrent illness or laboratory abnormalities and their WBC count>5,000/mm$^3$; Neutrophils>2,500/mm$^3$; Platelet count$\geq$125,000/mm$^3$; hemoglobin$\geq$10 mg/dL; creatinine $\leq$1.4; <2×elevated liver function tests; normal clotting time. Patients must have stable non-steroidal regimen for 1 month prior to study and must discontinue all DMARD regimens 1 month prior to study entry. If patients are taking any intra-articular corticosteroids, they must discontinue 1 month prior to study. Also, if taking prednisone, the patient must have stable regimen (=10 mg) for minimum of 1 month prior to study entry. If the patient is a women of child-bearing age, the patient must have a negative serum pregnancy test, and if pre-menopausal and sexually active, using an effective contraceptive.

If the patient has had prior/current treatment with Taxol®, colchicine, alkylating agents or radiation, the patient must not be treated with micellar paclitaxel. Prior malignancy, major organ allograft, or uncontrolled cardiac, hepatic, pulmonary, renal or central nervous system disease, known clotting deficiency or any illness that increases undue risk to patient will exclude them from this study. Also, if the patient has been treated with an experimental anti-rheumatic drug within 90 days of enrollment, the patient must not be treated with micellar paclitaxel.

Example 68

Clinical Study to Assess the Safety and Tolerability of Topical Paclitaxel Gel for the Treatment of Psoriasis A. Study Design Twenty patients will enter into the study with mild to moderate plaque-type psoriasis for more than 12 months prior to the study. Twenty patients will be randomized to receive two of the following gel formulations: (i) control gel, (ii) 0.01% topical paclitaxel gel, (iii) 0.1% topical paclitaxel gel, or (iv) 1% topical paclitaxel gel. Two well-defined psoriatic plaques measuring at least 5 cm in diameter will be identified on each patient for treatment. The two plaques will be treated twice per day (0.55 ml per application) for 8 weeks, with each plaque receiving a different dose as assigned by the randomization procedure. Patients will be monitored for study endpoints at defined intervals in the study. The study is estimated to last up to 12 weeks (8 weeks of treatment and 4 weeks of follow-up).

Each patient will be assigned two 30 ml pump vials of different paclitaxel dose levels (control, 0.01, 0.1 or 1%). Patients will apply 0.55 ml of each gel to the assigned psoriatic plaque twice daily for 8 weeks. The investigator will assign each pump vial to a specific psoriatic plaque on the patient. The patient will then be instructed on how to apply the gel to the psoriatic lesion. Before the topical study gel is applied to the psoriatic plaques, both psoriatic lesions will be photographed.

The patient's sun exposure should be limited during the entire study and psoriatic areas being treated with the topical study gel shall not be exposed to direct sunlight during the study. Patients must be instructed not to use any other emollients, creams, ointments or gels on the psoriatic lesions being treated with the topical study gel. In addition, patients must be instructed to apply the gel to the same psoriatic lesion every 12 hours during the treatment phase of the study. When the patient applies the topical study gel to the psoriatic lesion, the area should not be covered with dressings or articles of clothing until the gel dries (approximately 20 minutes). During this drying period, the patient may experience a soothing, cooling effect at the application site.

Concomitant therapies are permitted. All concomitant medications must be reported to the study coordinator. Patients must not receive treatment with another investigational drug or approved therapy for investigational use, with retinoids or any other systemic immunosuppressant agent at any time during study participation. Topical emollients, creams, ointments and gels must not be used on the psoriatic lesions being treated with the topical study gel. Topical corticosteroids, including keratolytics, coal tar, calcipotriol, must not be used on any psoriatic lesions during the treatment phase of the study, unless permitted by the investigator and Angiotech (e.g., less frequent applications of topical corticosteroids could be used for maintenance treatment of extreme itching, burning or stinging of psoriatic lesions not treated with the topical study gel).

B. Evaluation and Testing

The pre-enrollment visit will occur at least one week prior to the first topical gel application. The study objectives and procedures will be explained during the visit and each patient will sign the Informed Consent Form. A complete medical history and physical examination will be obtained as well as urinalysis and screening blood tests, which include: blood chemistries (including liver function tests and creatine) and hematology (CBC, differential and platelets). Women of child-bearing potential must have a negative serum pregnancy test prior to treatment, and should be apprised of the potential risks. At the pre-enrollment visit, two psoriatic plaques measuring approximately 5 cm in diameter will be identified for the treatment phase of the study. Patients whose clinical and laboratory findings fulfill the inclusion criteria will be notified for study enrollment.

During the treatment phase of the study, patients will be seen clinically every week for the first 4 weeks (Week 0, 1, 2, 3, and 4) and then once every 2 weeks during the second 4 weeks (Week 6 and 8) of the study. Once the treatment phase of the study is completed (Week 8), the patient will be scheduled for one follow-up visit at Week 12.

At each visit during the treatment phase of the study (Week 0, 1, 2, 3, 4, 6, and 8) and at the follow-up visit (Week 12), concomitant medications and adverse events are to be recorded. Patients will be evaluated for safety and efficacy at each visit by assessing the following:

(i) Interim History and Relevant Physical Examination, including body weight and vital signs (temperature, heart rate, respiration rate and blood pressure);
(ii) Chemistry, Hematology and Urinalysis;
(iii) Target Skin Lesion Assessment; and
(iv) Global Assessment of Efficacy.

At the end of the treatment schedule (Week 8), and at the follow-up visit (Week 12), both psoriatic lesions well be examined and photographed. The analysis will be mostly descriptive in nature.

Adverse events will be tabulated and frequencies of events will be determined, overall and by dosing group.

Laboratory analyses (chemistries, hematology) will consist of measurements of change from baseline over time by patient and overall, with plots of actual values compared to normal values for patients by dose group. Group means and standard errors will be calculated for the various laboratory parameters. Concurrent illnesses will be listed and examined as possible confounders in the treatment response relationship. Concurrent medications will also be listed. Effects from previous treatments for psoriasis and any potential related side effects will be analyzed and discussed.

Clinical response has been defined by a series of measures related to psoriasis, consisting of changes in the diameter of the psoriatic plaque, erythema, redness, swelling and overall visual examination. These measures will be calculated as change from baseline by dose group and overall. Trend analysis may also be used to assess various parameters over time. Correlations of various measures will be performed to determine important and significant responses.

C. Enrollment

Patients (male or female) between 18 to 65 years of age will be eligible for enrollment in this study if they are diagnosed with mild to moderate psoriasis for a period of greater than 12 months prior to first dose of study drug. Patient must have at least two well-defined plaques of psoriasis measuring 5 cm in diameter, and must be on no current prescription medications other than oral contraceptives. Patients must have normal renal function, hematologic function within normal range and normal serum electrolytes. No other underlying active skin disease may be present at the test site at the time of administration.

Patients will be excluded from the study if they have received prior treatment with Taxol®. If the patient is treated with another investigational drug or approved therapy for investigational use, or with systemic retinoids or any systemic immunosuppressant agent (e.g., methotrexate, cyclosporine or azathiprine) within 4 weeks prior to the first application of the study drug, they must not be enrolled in this study. Patients must not have received oral prednisone >25 mg (or its equivalent), or topical corticosteroids, including keratolytics, coal tar or calcipotriol within two weeks prior to applying the first dose of the topical study gel. Patients will be excused if they received treatment with UV therapy within two weeks of receiving first dose of topical study gel, or anticipate need for UV therapy during study participation.

Patients that present clinically significant abnormal laboratory values for hematocrit, hemoglobin, platelets, serum creatinine and bilirubin will not be admitted into the study. As well, patients must have alanine transaminase (ALT) and aspartate transaminase (AST) levels greater than three times the upper limit of normal standards.

Those patients that demonstrate active or history of clinically significant cardiac, endocrinologic, renal, hematologic, hepatic, immunologic, metabolic, urologic, pulmonary, neurologic, psychiatric and/or any other major disease (other than psoriasis) will not be able to receive topical paclitaxel gel, as well as those that are diagnosed with erythrodermic, guttate, palmar, or plantar pustular, or generalized pustular psoriasis. Patients with a history of anaphylactic reactions, or those that have tested positive for hepatitis will not be entered into the study.

Women will not be entered into the study unless post-menopausal for at least one year or surgically sterile, or are unwilling to practice effective contraception during the study. Women planning to become pregnant, are currently pregnant or lactating are to be excluded.

History of drug or alcohol abuse, or an unwillingness or inability to restrict alcohol or drug use during study participation as required by the protocol, will eliminate patients from the study.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for treating or preventing surgical adhesions, comprising administering to a patient in need thereof a therapeutically effective amount of an anti-microtubule compound-containing, pharmaceutically acceptable composition, wherein said anti-microtubule compound is paclitaxel.

2. The method according to claim 1 wherein said paclitaxel-containing composition comprises paclitaxel and a polymer or a copolymer.

3. The method according to claim 2 wherein said composition contains a copolymer of lactic acid and glycolic acid.

4. The method according to claim 2 wherein said polymer is poly(caprolactone).

5. The method according to claim 2 wherein said polymer is poly(lactic acid).

6. The method according to claim 2 wherein said composition contains a copolymer of poly(lactic acid) and poly(caprolactone).

7. The method according to claim 2 wherein said polymer is polyethyleneglycol.

8. The method according to claim 2 wherein said copolymer is ethylene vinyl acetate.

9. The method according to claim 1 wherein said paclitaxel-containing composition comprises paclitaxel and isopropyl myristate.

10. The method according to claim 1 wherein said paclitaxel-containing composition comprises paclitaxel and a glycol.

11. The method according to claim 10 wherein said glycol is ethoxydiglycol.

12. The method according to claim 2 wherein said copolymer is a diblock or triblock copolymer.

13. The method according to claim 2 wherein said composition contains 0.5% to 20% paclitaxel by weight.

14. The method according to claim 2 wherein said composition is delivered as a paste, a film, or a wrap.

15. The method according to claim 2 wherein said composition is delivered as a spray.

16. The method according to claim 2 wherein said composition is applied to the surface of a surgical implant.

* * * * *

UNITED STATES PATENT AND TRADEMARK OFFICE
CERTIFICATE OF CORRECTION

PATENT NO. : 6,689,803 B2 Page 1 of 1
DATED : February 10, 2004
INVENTOR(S) : William L. Hutner It is certified that error appears in the above-identified patent and that said Letters Patent is hereby corrected as shown below:

<u>Title page,</u>
Item [56], References Cited, U.S. PATENT DOCUMENTS, add:
-- 5,627,207    05/06/1997    Hupe et al. --.

Signed and Sealed this

Ninth Day of May, 2006

JON W. DUDAS
*Director of the United States Patent and Trademark Office*